United States Patent
Sosin et al.

(10) Patent No.: US 9,999,600 B2
(45) Date of Patent: *Jun. 19, 2018

(54) NANOPARTICLE COMPOSITIONS

(71) Applicant: N-Fold LLC, Fairfield, CT (US)

(72) Inventors: Howard B. Sosin, Southport, CT (US); Michael J. Caplan, Woodbridge, CT (US)

(73) Assignee: N-Fold LLC, Fairfield, CT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/362,476

(22) Filed: Nov. 28, 2016

(65) Prior Publication Data

US 2017/0071867 A1 Mar. 16, 2017

Related U.S. Application Data

(63) Continuation of application No. 14/782,285, filed as application No. PCT/US2014/032838 on Apr. 3, 2014, now Pat. No. 9,539,217.

(60) Provisional application No. 61/808,118, filed on Apr. 3, 2013.

(51) Int. Cl.
| | |
|---|---|
| A61K 9/51 | (2006.01) |
| A61K 39/35 | (2006.01) |
| A61K 9/50 | (2006.01) |
| A61K 39/02 | (2006.01) |
| A61K 39/145 | (2006.01) |
| A61K 39/39 | (2006.01) |
| C12N 7/00 | (2006.01) |
| A61K 39/108 | (2006.01) |
| A61K 39/00 | (2006.01) |

(52) U.S. Cl.
CPC .......... *A61K 9/5153* (2013.01); *A61K 9/5031* (2013.01); *A61K 9/5176* (2013.01); *A61K 39/025* (2013.01); *A61K 39/0258* (2013.01); *A61K 39/145* (2013.01); *A61K 39/35* (2013.01); *A61K 39/39* (2013.01); *C12N 7/00* (2013.01); *A61K 2039/5258* (2013.01); *A61K 2039/54* (2013.01); *A61K 2039/542* (2013.01); *A61K 2039/545* (2013.01); *A61K 2039/55511* (2013.01); *A61K 2039/55516* (2013.01); *A61K 2039/55555* (2013.01); *A61K 2039/55561* (2013.01); *A61K 2039/55566* (2013.01); *A61K 2039/55594* (2013.01); *A61K 2039/57* (2013.01); *C12N 2760/16034* (2013.01)

(58) Field of Classification Search
None
See application file for complete search history.

(56) References Cited

U.S. PATENT DOCUMENTS

| | | | |
|---|---|---|---|
| 3,977,794 | A | 8/1976 | Liedholz |
| 4,191,743 | A | 3/1980 | Klemm et al. |
| 4,270,537 | A | 6/1981 | Romaine |
| 4,316,885 | A | 2/1982 | Rakhit |
| 4,384,996 | A | 5/1983 | Bollinger et al. |
| 4,596,556 | A | 6/1986 | Morrow et al. |
| 4,650,803 | A | 3/1987 | Stella et al. |
| D296,006 | S | 5/1988 | Asche |
| 4,790,824 | A | 12/1988 | Morrow et al. |
| 4,798,823 | A | 1/1989 | Witzel |
| 4,886,499 | A | 12/1989 | Cirelli et al. |
| 4,894,366 | A | 1/1990 | Okuhara et al. |
| 4,929,611 | A | 5/1990 | Okuhara et al. |
| 4,940,460 | A | 7/1990 | Casey, I. et al. |
| 4,941,880 | A | 7/1990 | Burns |
| 4,956,352 | A | 9/1990 | Okuhara et al. |
| 5,008,110 | A | 4/1991 | Benecke et al. |
| 5,015,235 | A | 5/1991 | Crossman |
| 5,064,413 | A | 11/1991 | McKinnon et al. |
| 5,100,883 | A | 3/1992 | Schiehser |
| 5,118,678 | A | 6/1992 | Kao et al. |
| 5,120,725 | A | 6/1992 | Kao et al. |
| 5,120,727 | A | 6/1992 | Kao et al. |
| 5,120,842 | A | 6/1992 | Failli et al. |
| 5,122,511 | A | 6/1992 | Patchett et al. |
| 5,141,496 | A | 8/1992 | Dalto et al. |
| 5,143,918 | A | 9/1992 | Bochis et al. |
| 5,151,413 | A | 9/1992 | Caufield et al. |
| 5,162,334 | A | 11/1992 | Goulet et al. |
| 5,169,851 | A | 12/1992 | Hughes et al. |
| 5,189,042 | A | 2/1993 | Goulet et al. |
| 5,190,521 | A | 3/1993 | Hubbard et al. |
| 5,202,332 | A | 4/1993 | Hughes et al. |
| 5,208,228 | A | 5/1993 | Ok et al. |
| 5,208,241 | A | 5/1993 | Ok et al. |

(Continued)

FOREIGN PATENT DOCUMENTS

| | | |
|---|---|---|
| EP | 1752151 A1 | 2/2007 |
| JP | 2003-535122 A | 11/2003 |

(Continued)

OTHER PUBLICATIONS

Aguado et al., Controlled-release vaccines—biodegradable polylactide/polyglycolide (PL/PG) microspheres as antigen vehicles, Immunobiology, 184(2-3): 113-25 (1992).

(Continued)

*Primary Examiner* — Robert A Wax
*Assistant Examiner* — Quanglong N Truong
(74) *Attorney, Agent, or Firm* — Choate, Hall & Stewart LLP; Brenda Herschbach Jarrell; Brian E. Reese

(57) ABSTRACT

The present invention provides, among other things, nanoparticle compositions including a plurality of nanoparticles, each of which is comprised of a biodegradable or biocompatible polymer arranged in a nanoparticle structure defining an internal lumen and an external surface and one or more of a preparation of hydrophilic cellular components and a preparation of hydrophobic cellular components. In some embodiments, the preparation of hydrophilic cellular components is encapsulated within the internal lumen and the preparation of hydrophobic cellular components is associated with the external surface. Various methods of making and using disclosed nanoparticle compositions are also provided.

9 Claims, 29 Drawing Sheets

(56) References Cited

U.S. PATENT DOCUMENTS

| | | |
|---|---|---|
| 5,225,194 A | 7/1993 | Suer |
| 5,227,467 A | 7/1993 | Durette et al. |
| 5,250,678 A | 10/1993 | Goulet et al. |
| 5,254,562 A | 10/1993 | Okuhara et al. |
| 5,258,389 A | 11/1993 | Goulet et al. |
| 5,262,533 A | 11/1993 | Sinclair et al. |
| 5,284,826 A | 2/1994 | Eberle |
| 5,284,840 A | 2/1994 | Rupprecht et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,504,091 A | 4/1996 | Molnar-Kimber et al. |
| 5,520,639 A | 5/1996 | Peterson et al. |
| 5,527,288 A | 6/1996 | Gross et al. |
| 5,532,248 A | 7/1996 | Goulet et al. |
| 5,543,158 A | 8/1996 | Gref et al. |
| 5,558,869 A | 9/1996 | Burks, Jr. et al. |
| 5,569,189 A | 10/1996 | Parsons |
| 5,591,767 A | 1/1997 | Mohr et al. |
| 5,599,302 A | 2/1997 | Lilley et al. |
| 5,649,912 A | 7/1997 | Peterson |
| 5,683,712 A | 11/1997 | Cavazza |
| 5,693,648 A | 12/1997 | Goulet et al. |
| 5,704,911 A | 1/1998 | Parsons |
| 5,709,797 A | 1/1998 | Bocchiola et al. |
| 5,739,432 A | 4/1998 | Sinha |
| 5,753,234 A | 5/1998 | Lee et al. |
| 5,774,209 A | 6/1998 | Shestock |
| 5,830,877 A | 11/1998 | Carson et al. |
| 5,893,397 A | 4/1999 | Peterson et al. |
| 5,948,433 A | 9/1999 | Burton et al. |
| 5,962,566 A | 10/1999 | Grandfils et al. |
| 5,965,154 A | 10/1999 | Haralambopoulos |
| 5,972,366 A | 10/1999 | Haynes et al. |
| 5,973,121 A | 10/1999 | Burks, Jr. et al. |
| 5,993,412 A | 11/1999 | Deily et al. |
| 6,007,845 A | 12/1999 | Domb et al. |
| 6,010,715 A | 1/2000 | Wick et al. |
| 6,126,936 A | 10/2000 | Lanza et al. |
| 6,136,357 A | 10/2000 | Dietl |
| 6,238,925 B1 | 5/2001 | Sampson |
| 6,475,995 B1 | 11/2002 | Roy et al. |
| 6,486,311 B1 | 11/2002 | Burks, Jr. et al. |
| 6,503,921 B2 | 1/2003 | Naicker et al. |
| 6,544,543 B1 | 4/2003 | Mandrusov et al. |
| 6,551,990 B2 | 4/2003 | Giachelli et al. |
| 6,628,382 B2 | 9/2003 | Robertson |
| 6,676,963 B1 | 1/2004 | Lanza et al. |
| 6,793,938 B2 | 9/2004 | Sankaram |
| 6,809,826 B2 | 10/2004 | Robertson |
| 6,835,824 B1 | 12/2004 | Burks, Jr. et al. |
| 7,081,489 B2 | 7/2006 | Chen et al. |
| 7,397,036 B2 | 7/2008 | Robertson et al. |
| 7,485,708 B2 | 2/2009 | Burks, Jr. et al. |
| 7,534,448 B2 | 5/2009 | Saltzman et al. |
| 7,534,449 B2 | 5/2009 | Saltzman et al. |
| 7,550,154 B2 | 6/2009 | Saltzman et al. |
| 8,629,098 B2 | 1/2014 | Fahmy et al. |
| 8,802,375 B2 | 8/2014 | Sampson et al. |
| 8,815,251 B2 | 8/2014 | Caplan et al. |
| 8,889,117 B2 | 11/2014 | Mellman et al. |
| 9,522,180 B2 | 12/2016 | Shea et al. |
| 9,539,217 B2 | 1/2017 | Sosin et al. |
| 9,597,385 B2 | 3/2017 | Caplan |
| 9,616,113 B2 | 4/2017 | Shea et al. |
| 9,913,883 B2 | 3/2018 | Getts |
| 2001/0051155 A1 | 12/2001 | Sosin et al. |
| 2002/0009452 A1 | 1/2002 | Caplan |
| 2002/0044959 A1 | 4/2002 | Goetz et al. |
| 2002/0076420 A1 | 6/2002 | Caplan et al. |
| 2002/0132763 A1 | 9/2002 | Naicker et al. |
| 2002/0155607 A1 | 10/2002 | Boutin |
| 2003/0003591 A1 | 1/2003 | LaCourt et al. |
| 2003/0035810 A1 | 2/2003 | Caplan |
| 2003/0153044 A1 | 8/2003 | Liljedahl et al. |
| 2003/0202980 A1 | 10/2003 | Caplan et al. |
| 2003/0235619 A1 | 12/2003 | Allen et al. |
| 2004/0022840 A1 | 2/2004 | Nagy et al. |
| 2004/0023897 A1 | 2/2004 | Caplan |
| 2004/0156821 A1 | 8/2004 | Bottomly et al. |
| 2004/0208894 A1 | 10/2004 | Caplan |
| 2004/0234548 A1 | 11/2004 | Caplan |
| 2004/0247579 A1 | 12/2004 | Sykes |
| 2006/0002852 A1 | 1/2006 | Saltzman et al. |
| 2006/0002971 A1 | 1/2006 | Saltzman et al. |
| 2006/0051426 A1 | 3/2006 | Golomb et al. |
| 2006/0077390 A1 | 4/2006 | Kralik |
| 2006/0087650 A1 | 4/2006 | Shen |
| 2006/0109468 A1 | 5/2006 | Evans |
| 2006/0147428 A1 | 7/2006 | Sachs |
| 2006/0246139 A1 | 11/2006 | Miyaji et al. |
| 2007/0092575 A1 | 4/2007 | Balaban et al. |
| 2007/0148074 A1 | 6/2007 | Sadoqi et al. |
| 2007/0184068 A1 | 8/2007 | Renner et al. |
| 2007/0213507 A1 | 9/2007 | Burks et al. |
| 2007/0224225 A1 | 9/2007 | Irache Garreta et al. |
| 2008/0014144 A1 | 1/2008 | Saltzman et al. |
| 2008/0031899 A1 | 2/2008 | Reddy et al. |
| 2008/0249014 A1 | 10/2008 | Tauer et al. |
| 2009/0011993 A1 | 1/2009 | Murthy et al. |
| 2009/0239789 A1 | 9/2009 | Saltzman et al. |
| 2009/0269397 A1 | 10/2009 | Saltzman et al. |
| 2010/0031262 A1 | 2/2010 | Baird-Gent |
| 2010/0055189 A1 | 3/2010 | Hubbell et al. |
| 2010/0104503 A1 | 4/2010 | Mellman et al. |
| 2010/0151436 A1 | 6/2010 | Fong et al. |
| 2010/0166802 A1 | 7/2010 | Caplan et al. |
| 2010/0233251 A1* | 9/2010 | Von Andrian ......... A61K 39/00 424/450 |
| 2010/0233521 A1 | 9/2010 | Byun et al. |
| 2010/0284965 A1 | 11/2010 | Fahmy et al. |
| 2011/0027298 A1 | 2/2011 | Caplan et al. |
| 2011/0218396 A1 | 9/2011 | Williams et al. |
| 2011/0293705 A1 | 12/2011 | Irvine et al. |
| 2012/0076831 A1 | 3/2012 | Miller et al. |
| 2012/0276156 A1 | 11/2012 | Fraser et al. |
| 2013/0302409 A1 | 11/2013 | Fuchs et al. |
| 2013/0323319 A1 | 12/2013 | Getts et al. |
| 2015/0118318 A1 | 4/2015 | Fahmy et al. |
| 2015/0125384 A1 | 5/2015 | Mellman et al. |
| 2015/0150996 A1 | 6/2015 | Miller et al. |
| 2015/0153358 A1 | 6/2015 | Ayuso et al. |
| 2015/0174155 A1 | 6/2015 | Getts et al. |
| 2015/0174225 A1 | 6/2015 | Caplan |
| 2015/0209293 A1 | 7/2015 | Shea et al. |
| 2015/0231266 A1 | 8/2015 | Metcalfe et al. |
| 2015/0366994 A1 | 12/2015 | Metcalfe et al. |
| 2016/0054315 A1 | 2/2016 | Fahmy et al. |
| 2016/0113881 A1 | 4/2016 | Sosin et al. |
| 2016/0166664 A1 | 6/2016 | Miller et al. |
| 2016/0213761 A1 | 7/2016 | Fahmy et al. |
| 2016/0228521 A1 | 8/2016 | Sosin et al. |
| 2016/0346382 A1 | 12/2016 | Bryce et al. |
| 2017/0258880 A1 | 9/2017 | Shea et al. |
| 2017/0312349 A1 | 11/2017 | Shea et al. |

FOREIGN PATENT DOCUMENTS

| | | |
|---|---|---|
| JP | 2011-500569 A | 1/2011 |
| WO | WO-92/05179 A1 | 4/1992 |
| WO | WO-95/03356 A1 | 2/1995 |
| WO | WO-95/03357 A1 | 2/1995 |
| WO | WO-96/02555 A1 | 2/1996 |
| WO | WO-96/20698 A2 | 7/1996 |
| WO | WO-97/13537 A1 | 4/1997 |
| WO | WO-97/37705 A1 | 10/1997 |
| WO | WO-98/16247 A1 | 4/1998 |
| WO | WO-98/18810 A1 | 5/1998 |

(56) References Cited

FOREIGN PATENT DOCUMENTS

| | | |
|---|---|---|
| WO | WO-98/40100 A1 | 9/1998 |
| WO | WO-99/34850 A1 | 7/1999 |
| WO | WO-99/52550 A1 | 10/1999 |
| WO | WO-00/029043 A1 | 5/2000 |
| WO | WO-00/037067 A2 | 6/2000 |
| WO | WO-00/054803 A2 | 9/2000 |
| WO | WO-01/039800 A2 | 6/2001 |
| WO | WO-01/093835 A1 | 12/2001 |
| WO | WO-02/067849 A2 | 9/2002 |
| WO | WO-02/076441 A1 | 10/2002 |
| WO | WO-03/087021 A2 | 10/2003 |
| WO | WO-2004/071493 A1 | 8/2004 |
| WO | WO-2005/021730 A2 | 3/2005 |
| WO | WO-2006/037979 A2 | 4/2006 |
| WO | WO-2006/050170 A2 | 5/2006 |
| WO | WO-2006/052285 A2 | 5/2006 |
| WO | WO-2006/080951 A8 | 8/2006 |
| WO | WO-2008/109347 A2 | 9/2008 |
| WO | WO-2008/115641 A2 | 9/2008 |
| WO | WO-2008/121949 A1 | 10/2008 |
| WO | WO-2009/038591 A1 | 3/2009 |
| WO | WO-2009/051837 A2 | 4/2009 |
| WO | WO-2009/094273 A2 | 7/2009 |
| WO | WO-2010/003009 A2 | 1/2010 |
| WO | WO-2010/042870 A1 | 4/2010 |
| WO | WO-2010085509 A1 | 7/2010 |
| WO | WO-2011/150235 A1 | 12/2011 |
| WO | WO-2012065153 A2 | 5/2012 |
| WO | WO-2012/167261 A2 | 12/2012 |
| WO | WO-2013/003157 A1 | 1/2013 |
| WO | WO-2013184976 A2 | 12/2013 |
| WO | WO-2013192532 A2 | 12/2013 |
| WO | WO-2014160465 A2 | 10/2014 |
| WO | WO-2015023796 A2 | 2/2015 |
| WO | WO-2015/066535 A1 | 5/2015 |
| WO | WO-2015/175597 A1 | 11/2015 |
| WO | WO-2016057909 A1 | 4/2016 |
| WO | WO-2016191723 A1 | 12/2016 |
| WO | WO-2017075053 A1 | 5/2017 |
| WO | WO-2017112899 A1 | 6/2017 |
| WO | WO-2017120222 A1 | 7/2017 |
| WO | WO-2017139498 A1 | 8/2017 |
| WO | WO-2017143346 A1 | 8/2017 |

OTHER PUBLICATIONS

Almería, B. et al., A multiplexed electrospray process for single-step synthesis of stabilized polymer particles for drug delivery, J. Control. Release, 154(2): 203-210 (2011).
Almería, B. et al., Controlling the morphology of electrospray-generated PLGA microparticles for drug delivery, J Colloid Interface Sci., 343(1): 125-133 (2010).
Anderson and Shive, et al., Biodegradation and biocompatibility of PLA and PLGA microspheres, Adv Drug Deliv Rev, 28(1):5-24 (1997).
Apostolopoulos, V. et al., Structural implications for the design of molecular vaccines, Curr. Opin. Mol. Ther., 2(1): 29-36 (2000).
Aziz et al., Oral Vaccines: New Needs, New Possibilities, BioEssays, 29(6): 591-604 (2007).
Bandyopadhyay, A. et al., The impact of nanoparticle ligand density on dendritic-cell targeted vaccines, Biomaterials, 32(11): 3094-3105 (2011).
Blanchette et al., Cellular evaluation of oral chemotherapy carriers, J. Biomed. Mater. Res. A, 72(4): 381-388 (2005).
Blanchette et al., Oral chemotherapeutic delivery: design and cellular response, Ann. Biomed. Eng., 33(2): 142-149 (2005).
Bonifaz, L. et al., Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance, The Journal of Experimental Medicine, 196(12):1627-1638 (2002).
Bonifaz, L. et al., In Vivo Targeting of Antigens to Maturing Dendritic Cells via the DEC-205 Receptor Improves T Cell Vaccination, The Journal of Experimental Medicine, 199(6):815-824 (2004).
Bourges et al., Ocular drug delivery targeting the retina and retinal pigment epithelium using polylactide nanoparticles, Invest Ophthalmol Vis Sci, 44:3562-3569 (2003).
Bourla et al., Age-related macular degeneration: a practical approach to a challenging disease, J. Am. Geriatr. Soc., 54: 1130-1135 (2006).
Bramwell et al., Particulate delivery systems for biodefense subunit vaccines, Adv. Drug Deliv. Rev. 57(9): 1247-1265 (2005).
Bramwell et al., The rational design of vaccines, Drug Discovery Today, 10(22): 1527-1534 (2005).
Brigger et al., Nanoparticles in cancer therapy and diagnosis, Adv Drug Deliv Rev, 54:631-651 (2002).
Brunner et al., pH and osmotic pressure inside biodegradable microspheres during erosion, Pharm Res, 16(6):847-53 (1999).
Bryniarski, K. et al., Antigen-specific, antibody-coated, exosome-like nanovesicles deliver suppressor T-cell microRNA-150 to effector T cells to inhibit contact sensitivity, J. Allergy Clin. Immunol., 132(1)170-181 (2013).
Calvo et al., Chitosan and chitosan/ethylene oxide-propylene oxide block copolymer nanoparticles as novel carriers for proteins and vaccines. Pharm. Res., 14(10): 1431-1436 (1997).
Cannizzaro, et al., A novel biotinylated degradable polymer for cell-interactive applications, Biotech Bioeng., 58(5): 529-535 (1998).
Cao et al., Production and surface modification of polylactide-based polymeric scaffolds for soft-tissue engineering, Methods Mol. Biol., 238:87-112 (2004).
Caponetti et al., Microparticles of novel branched copolymers of lactic acid and amino acids: preparation and characterization, J Pharm Sci, 88(1):136-41 (1999).
Capurso, N.A. and Fahmy, T.M, Development of a pH-responsive particulate drug delivery vehicle for localized biologic therapy in inflammatory bowel disease, Yale J. Biol. Med., 84(3): 285-288 (2011).
Capurso, N.A. et al., Development of a nanoparticulate formulation of retinoic acid that suppresses Th17 cells and upregulates regulatory T cells, Self Nonself., 1(4): 335-340 (2010).
Cartiera, M.S. et al., Partial correction of cystic fibrosis defects with PLGA nanoparticles encapsulating curcumin, Mol. Pharm., 7(1): 86-93 (2010).
Cartiera, M.S. et al., The uptake and intracellular fate of PLGA nanoparticles in epithelial cells, Biomaterials, 30(14): 2790-2798. pp. 1-22 (2009).
Challacombe et al., Enhanced secretory IgA and systemic IgG antibody responses after oral immunization with biodegradable microparticles containing antigen, Immunology, 76(1): 164-168 (1992).
Cho et al., Receptor-mediated delivery of all trans-retinoic acid to hepatocyte using poly(L-lactic acid) nanoparticles coated with galactose-carrying polystyrene, J Control Release, 77:7-15 (2001).
Corradetti, B. et al., Paracrine signalling events in embryonic stem cell renewal mediated by affinity targeted nanoparticles, Biomaterials, 33(28): 6634-6643 (2012).
Cremaschi et al., Different kinds of polypeptides and polypeptide-coated nanoparticles are accepted by the selective transcytosis shown in the rabbit nasal mucosa, Biochim. Biophys. Acta, 1416(1-2): 31-38 (1999).
Cremaschi et al., Further analysis of transcytosis of free polypeptides and polypeptide-coated nanobeads in rabbit nasal mucosa, J. Appl. Physiol., 91(1): 211-217 (2001).
Criscione J.M. et al., Self-assembly of pH-responsive fluorinated dendrimer-based particulates for drug delivery and noninvasive imaging, Biomaterials, 30(23-24): 3946-3955 (2009).
Criscione, J.M. et al., Development and application of a multimodal contrast agent for SPECT/CT hybrid imaging, Bioconjug. Chem., 22(9): 1784-1792 (2011).

(56) References Cited

OTHER PUBLICATIONS

Croll et al., Controllable surface modification of poly(lactic-co-glycolic acid) (PLGA) by hydrolysis or aminolysis 1: physical, chemical, and theoretical aspects, Biomacromolecules, 5(2):463-73 (2004).
Cu, Y. et al., Ligand-modified gene carriers increased uptake in target cells but reduced DNA release and transfection efficiency, Nanomedicine, 6(2): 334-343 (2010).
Cui et al., Intradermal immunization with novel plasmid DNA-coated nanoparticles via a needle-free injection device, J. Biotechnology, 102(2): 105-115 2003).
De Kozak et al., Intraocular injection of tamoxifen-loaded nanoparticles: a new treatment of experimental autoimmune uveoretinitis, Eur J Immunol, 34:3702-3712 (2004).
De Souza Reboucas, J. et al., Nanoparticulate Adjuvants and Delivery Systems for Allergen Immunotherapy, Journal of Biomedicine and Biotechnology, 2012: 1-13 (2012).
Demento et al., Inflammasome-activating nanoparticles as modular systems for optimizing vaccine efficacy, Vaccine, 27(23): 3013-3021 (2009).
Demento et al., TLR9-Targeted Biodegradable Nanoparticles as Immunization Vectors Protect Against West Nile Encephalitis, J. Immunol., 185: 2989-2997 (2010).
Demento, S. et al., Biomimetic approaches to modulating the T cell immune response with nano- and micro-particles, Conf. Proc. IEEE Eng. Med. Biol. Soc., 2009: 1161-1166 (2009).
Demento, S.L. et al., Role of sustained antigen release from nanoparticle vaccines in shaping the T cell memory phenotype, Biomaterials, 33(19):4957-4964 (2012).
Dev et al., Kinetics of drug delivery to the arterial wall via polyurethane-coated removable nitinol stent: comparative study of two drugs, Catheterization and Cardiovascular Diagnosis, 34(3): 272-8 (1995).
Dev et al., Sustained local drug delivery to the arterial wall via biodegradable microspheres, Catheterization and Cardiovascular Diagnosis, 41(3): 324-32 (1997).
Dong, H. et al., Immuno-isolation of pancreatic islet allografts using pegylated nanotherapy leads to long-term normoglycemia in full MHC mismatch recipient mice, PLoS One, 7(12): e50265 (2012).
Edelman et al., Effect of controlled adventitial heparin delivery on smooth muscle cell proliferation following endothelial injury, Proc Nat. Aca. Sci, U.S.A., 87(10): 3773-7 (1990).
Edwards et al., Complement Factor H Polymorphism and Age-Related Macular Degeneration, Science, 308(5720):421-4 (2005).
Elamanchili et al., Characterization of poly(D,L-lactic-co-glycolic acid) based nanoparticulate system for enhanced delivery of antigens to dendritic cells, Vaccine, 22: 2406-2412 (2004).
Eldridge et al., Biodegradable and biocompatible poly(DL-lactide-co-glycolide) microspheres as an adjuvant for *staphylococcal* enterotoxin B toxoid which enhances the level of toxin-neutralizing antibodies, Infection and Immunity, 59(9): 2978-2986 (1991).
Eldridge et al., Biodegradable microspheres-Vaccine delivery system for oral immunization, Current Topics in Microbiology and Immunology, 146: 59-66 (1989).
Eldridge et al., Controlled vaccine release in the gut-associated lymphoid tissues. I. Orally-administered biodegradable microspheres target the Peyer's patches, J. Control. Release, 11(1-3): 205-214 (1990).
Eliaz and Szoka, Liposome-encapsulated doxorubicin targeted to CD44: a strategy to kill CD44-overexpressing tumor cells, Cancer Res, 61: 2592-2601 (2001).
Eniola et al., Artificial polymeric cells for targeted drug delivery, J Control Release, 87(1-3): 15-22 (2003).
Escribano, M.M. et al., Anaphylactic reaction cause by cherry ingestion, Allergy 51(10): 756-757 (1996).
Evora et al., Relating the phagocytosis of microparticles by alveolar macrophages to surface chemistry: the effect of 1,2-dipalmitoylphosphatidylcholine, J Control Release, 51 (23)143-52 (1998).
Fadel, T.R. et al., A carbon nanotube-polymer composite for T-cell therapy, Nat Nanotechnol., 9(8): 639-647 (2014).
Fahmy et al., Surface modification of biodegradable polyesters with fatty acid conjugates for improved drug targeting, Biomaterials, 26(28): 5727-5736 (2005).
Fahmy et al., Targeted for drug delivery, Materials Today, 8(8, Supplement 1): 18-26 (2005).
Fahmy, et al., Increased TCR avidity after T cell activation: a mechanism for sensing low-density antigen, Immunity, 14:135-43 (2001).
Fahmy, T.M. et al., A nanoscopic multivalent antigen-presenting carrier for sensitive detection and drug delivery to T cells, Nanomedicine: Nanotechnology, Biology, and Medicine, 3(1): 75-85 (2007).
Fahmy, T.M. et al., Design opportunities for actively targeted nanoparticle vaccines, Nanomedicine (Lond), 3(3): 343-355 (2008).
Fahmy, T.M. et al., Nanosystems for simultaneous imaging and drug delivery to T cells, AAPS J., 9(2): E171-180 (2007).
Faraasen et al., Ligand-specific targeting of microspheres to phagocytes by surface modification with poly(L-lysine)-grafted poly(ethylene glycol) conjugate, Pharm Res, 20(2):237-46 (2003).
Fischer, N.O. et al., Conjugation to nickel-chelating nanolipoprotein particles increases the potency and efficacy of subunit vaccines to prevent West Nile encephalitis, Bioconjugate Chemistry, 21(6): 1018-1022 (2010).
Florindo, H.F. et al., Surface modified polymeric nanoparticles for immunisation against equine strangles, International Journal of Pharmaceutics, 390(1): 25-31 (2010).
Friede et al., Need for new vaccine formulations and potential of particulate antigen and DNA delivery systems, Adv. Drug Deliv. Re., 57(3): 325-331 (2005).
Gao, W. et al., Treg versus Th17 lymphocyte lineages are cross-regulated by LIF versus IL-6, Cell Cycle, 8(9)1444-1450 (2009).
Gao, X. et al., In vivo cancer targeting and imaging with semiconductor quantum dots, Nature Biotechnology, 22(8):969-976 (2004).
Garcia-Garcia et al., Drug-eluting stents, Arch. Cardiol. Mex., 76(3): 297-319 (2006).
Gomez, S. et al., Allergen Immunotherapy With Nanoparticles Containing Lipopolysaccharide A From *Brucella ovis*, European Journal of Pharmaceutics and Biopharmaceutics, 70: 711-717 (2008).
Gomez, S. et al., Gantrez AN Nanoparticles as an Adjuvant for Oral Immunotherapy with Allergens, Vaccine, 25: 5263-5271 (2007).
Gref, R., 'Stealth' corona-core nanoparticles surface modified by polyethylene glycol (PEG): influences of the corona (PEG chain length and surface density) and of the core composition on phagocytic uptake and plasma protein adsorption, Colloids and Surfaces B: Biointerfaces, 18(3-4): 301-313 (2000).
Gref, R., Surface-engineered nanoparticles for multiple ligand coupling, Biomaterials, 24(24): 4529-4537 (2003).
Gupta et al., Adjuvants for human vaccines current status, problems, and future prospects, Vaccine, 13(14): 1263-1276 (1995).
Gupta et al., Poly(lactide-co-glycolide) microparticles for the development of single-dose controlled-release vaccines, Adv. Drug Deliv. Rev., 32(3): 225-246 (1998).
Guzman et al., Local intraluminal infusion of biodegradable polymeric nanoparticles, Circulation 94: 1441-1448 (1996).
Haines et al., Complement factor H variant increases the risk of age-related macular degeneration, Science, 308(5720):419-21 (2005).
Hallahan et al., Integrin•mediated targeting of drug delivery to irradiated tumor blood vessels, Cancer Cell, 3:63•74 (2003).
Hammer et al., Synthetic cells-self-assembling polymer membranes and bioadhesive colloids, Annu. Rev. Mater. Res., 31:387-40 (2001).
Hanes, J. et al., New advances in microsphere-based single-dose vaccines, Adv. Drug Deliv. Rev., 28(1): 97-119 (1997).
Hariharan et al., Improved graft survival after renal transplantation in the United States, 1988 to 1996, N. Eng. J. Med., 342(9):605-12 (2000).
Hattori et al., Enhanced in vitro DNA transfection efficiency by novel folate-linked nanoparticles in human prostate cancer and oral cancer, Journal of Controlled Release, 97: 173-183 (2004).

(56) References Cited

OTHER PUBLICATIONS

Hawiger, D. et al., Dendritic Cells Induce Peripheral T Cell Unresponsiveness Under Steady State Conditions In Vivo, The Journal of Experimental Medicine, 194(6):769-779 (2001).
Hawker, C.J. and Wooley, K.L., The Convergence of Synthetic Organic and Polymer Chemistries, Science, 309:1200-1205 (2005).
Heffernan, M.J. and Murthy, N., Polyketal Nanoparticles: A New pH-Sensitive Biodegradable Drug Delivery Vehicle, Bioconjugate Chemistry, 16:1340-1342 (2005).
Hong, E. et al., Configuration-dependent Presentation of Multivalent IL-15:IL-15Rα Enhances the Antigen-specific T Cell Response and Anti-tumor Immunity, J. Biol. Chem., 291(17): 8931-8950 (2016).
Hood et al., Tumor regression by targeted gene delivery to the neovasculature, Science, 296(5577):2404-2407 (2002).
Huang et al., Monoclonal antibody covalently coupled with fatty acid. A reagent for in vitro liposome targeting, J. Biol. Chem., 255(17):8015-8 (1980).
Humphrey et al., The effect of intramural delivery of polymeric nanoparticles loaded with the antiproliferative 2-aminochromone U-86983 on neointimal hyperplasia development in balloon-injured porcine coronary arteries, Adv. Drug Del. Rev., 24: 87-108 (1997).
International Search Report for PCT/US2005/023444, 3 pages dated (Sep. 26, 2007).
International Search Report for PCT/US2008/054086, 3 pages dated (Sep. 22, 2008).
International Search Report for PCT/US2013/037789, 3 pages dated (Aug. 30, 2013).
International Search Report for PCT/US2014/055625, 3 pages dated (Dec. 8, 2014).
International Search Report for PCT/US2014/32838, 4 pages dated (Sep. 4, 2014).
International Search Report for PCT/US2015/059711, 8 pages dated (May 12, 2016).
Italia et al., Disease, destination, dose and delivery aspects of ciclosporin: the state of the art, Drug Discov. Today, 11(17-18): 846-854 (2006).
Jain, R.A., The manufacturing techniques of various drug loaded biodegradable poly(lactide-co-glycolide) (PLGA) devices, Biomaterials, 21:2475-2490 (2000).
Jansen et al., Encapsulation of Guest Molecules into a Dendritic Box, Science, 266(5188): 1226-1229 ( 1994).
Jansen et al., The Dendritic Box: Shape-Selective Liberation of Encapsulated Guests, Journal of the American Chemical Society, 117:4417-4418 (1995).
Jiang et al., Biodegradable poly(lactic-co-glycolic acid) microparticles for injectable delivery of vaccine antigens, Adv. Drug Deliv. Rev., 57(3): 391-410 (2005).
Johansen et al., Revisiting PLA/PLGA microspheres: an analysis of their potential in parenteral vaccination, Eur J Pharm Biopharm, 50(1):129-46 (2000).
Keegan et al., Biodegradable Microspheres with Enhanced Capacity for Covalently Bound Surface Ligands Macromolecules, 37:9979-84 (2004).
Keegan et al., Biomimetic design in microparticulate vaccines, Biomaterials, 24(24):4435-4443 (2003).
Keegan, M.E. et al., In vitro evaluation of biodegradable microspheres with surface-bound ligands, J. Control Release, 110(3): 574-580 (2006).
Klein et al., Complement factor H polymorphism in age-related macular degeneration, Science, 308(5720):385-9 (2005).
Klimek, L. et al., Assessment of clinical efficacy of CYT003-QbG10 in patients with allergic rhinoconjunctivitis: a phase llb study, Clinical & Experimental Allergy, 41(9): 1305-1312 (2011).
Kobayashi et al., Dendrimer-based Macromolecular MRI Contrast Agents: Characteristics and Application, Mol Imaging, 2:1-10 (2003).
Kobayashi et al., Evaluation of the in vivo biodistribution of indium-111 and yttrium-88 labeled dendrimer-1B4M-DTPA and its conjugation with anti-Tac monoclonal antibody, Bioconjug Chem, 10: 103-11 (1999).
Kohn et al., Single-step immunization using a controlled release, biodegradable polymer with sustained adjuvant activity, J. Immunol. Methods, 95(1): 31-38 (1986).
Kompella et al., Subconjuctival nano- and microparticles sustain retinal delivery of budesonide, a corticosteroid capable of inhibiting VEGF expression, Invest Ophthalmol. Vis. Sci., 44: 1192-1201 (2003).
Kono et al., Abstracts of Papers of the American Chemical Society, 221: U377-U377 (2001).
Kwon et al., Enhanced antigen presentation and immunostimulation of dendritic cells using acid degradable cationic nanoparticles, J. Control Release, 105(3): 119-212 (2005).
Labhasetwar et al., Arterial uptake of biodegradable nanoparticles: effect of surface modifications, J Pharm Sci, 87:1229-1234 (1998).
Labhasetwar, et al., Nanoparticle drug delivery system for restenosis, Advanced Drug Delivery Reviews, 24:63-85 (1997).
Labowsky, M. et al., An in silico analysis of nanoparticle/cell diffusive transfer: application to nano-artificial antigen-presenting cell: T-cell interaction, Nanomedicine, 11(4): 1019-1028 (2015).
Lamprecht et al., Biodegradable nanoparticles for targeted drug delivery in treatment of inflammatory bowel disease, J Pharmacol Exp Ther, 299(2):775-81 (2001).
Langer and Folkman, Polymers for the sustained release of proteins and other macromolecules, Nature, 263(5580): 797-800 (1976).
Lathia et al., Polymeric contrast agent with targeting potential., Ultrasonics, 42(1-9):763-8 (2004).
Lavik et al., A simple synthetic route to the formation of a block copolymer of poly(lactic-co-glycolic acid) and polylysine for the fabrication of functionalized, degradable structures for biomedical applications, J Biomed Mater Res, 58(3):291-4 (2001).
Li, Z. et al., Surface Functionalization of Ordered Mesoporous Carbons—A Comparative Study, Langmuir, 21:11999-12006 (2005).
Linblad, E.B., Aluminum adjuvants—in retrospect and prospect, Vaccine, 22(27-28): 3658-3668 (2004).
Liu, Y. et al., Stability and Ostwald ripening of block copolymer stabilized nanoparticles, Abstracts of Papers of the American Chemical Society, The 230th ACS National Meeting, Washington, DC, COLL 402, 1 page (Sep. 1, 2005). URL: http://oasys2.confex.com/acs/230nm/techprogram/P862384.HTM. [Retrieved Apr. 29, 2016].
Look, M. et al., Application of nanotechnologies for improved immune response against infectious diseases in the developing world, Adv. Drug Deliv. Rev., 62(4-5): 378-393 (2010).
Look, M. et al., Nanogel-based delivery of mycophenolic acid ameliorates systemic lupus erythematosus in mice, J. Clin. Invest., 123(4): 1741-1749 (2013).
Look, M. et al., The nanomaterial-dependent modulation of dendritic cells and its potential influence on therapeutic immunosuppression in lupus, Biomaterials, 35(3): 1089-1095 (2014).
Lopes De Menezes et al., In vitro and in vivo targeting of immunoliposomal doxorubicin to human B-cell lymphoma, Cancer Res, 58:3320-3330 (1998).
Luo, D. et al., Controlled DNA delivery systems, Phar. Res., 16: 1300-1308 (1999).
Luo, et al., Poly(ethylene glycol)-Conjugated PAMAM Dendrimer for Biocompatible, High-Efficiency DNA Delivery, Macromolecules, 35:3456-3462 (2002).
Mader et al., Monitoring microviscosity and microacidity of the albumin microenvironment inside degrading microparticles from poly(lactide-co-glycolide) (PLG) or ABA-triblock polymers containing hydrophobic poly(lactide-co-glycolide) A blocks and hydrophilic poly(ethyleneoxide) B blocks, Pharm Res, 15(5):787-93 (1998).
Mainardes et al., Colloidal carriers for ophthalmic drug delivery, Curr Drug Targets, 6:363-371 (2005).
Mallajosyula, J.K. et al., Single-dose monomeric HA subunit vaccine generates full protection from influenza challenge, Human Vaccines & Immunotherapeutics, 1(3): 586-595 (2013).

(56) References Cited

OTHER PUBLICATIONS

Maloy et al., Induction of mucosal and systemic immune responses by immunization with ovalbumin entrapped in poly(lactide-co-glycolide) microparticles, Immunology, 81(4): 661-667 (1994).
Marx et al., Protection against vaginal SIV transmission with microencapsulated vaccine, Science, 260(5112): 1323-1327 (1992).
Mathiowitz, E. and Langer, R., Polyanhydride Microspheres as Drug Carriers I. Hot-Melt Microencapsulation, Journal of Controlled Release, 5:13-22 (1987).
Mathiowitz, E. et al., Novel Microcapsules for Delivery Systems, Reactive Polymers, 6:275-283 (1987).
Mathiowitz, E. et al., Polyanhydride Microspheres as Drug Carriers II. Microencapsulation by Solvent Removal, Journal of Applied Polymer Science, 35:755-774 (1988).
McHugh, M.D. et al., Paracrine co-delivery of TGF-β and IL-2 using CD4-targeted nanoparticles for induction and maintenance of regulatory T cells, Biomaterials, 59: 172-181 (2015).
McPhail, D. et al., Liposomes encapsulating polymeric chitosan based vesicles—a vesicle in vesicle system for drug delivery, International Journal of Pharmaceutics, 200(1):73-86 (2000).
Mellman, I., and Steinman, R.M., Dendritic cells: specialized and regulated antigen processing machines, Cell, 106(3): 255-258 (2001).
Mellman, I., Antigen processing and presentation by dendritic cells: cell biological mechanisms, Adv. Exp. Med. Biol., 560: 63-67 (2005).
Metcalfe, S.M. and Fahmy, T.M., Targeted nanotherapy for induction of therapeutic immune responses, Trends Mol. Med., 18(2):72-80 (2012).
Moser, C. et al., Virosomal adjuvanted antigen delivery systems, Expert Reviews in Vaccines, 2(2):189-196 (2003).
Mounzer, R. et al., Dynamic imaging of lymphatic vessels and lymph nodes using a bimodal nanoparticulate contrast agent, Lymphat Res. Biol., 5(3): 151-158 (2007).
Mu et al., A novel controlled release formulation for the anticancer drug paclitaxel (Taxol®); PLGA nanoparticles containing vitamin E TPGS, J Control Release, 86(1):33-48 (2003).
Mu et al., Vitamin E TPGS used as emulsifier in the solvent evaporation/extraction technique for fabrication of polymeric nanospheres for controlled release of paclitaxel (Taxol®), J Control Release, 80(1-3): 129-44 (2002).
Mumper et al., Genetic immunization by jet injection of targeted pDNA-coated nanoparticles, Methods, 31(3): 255-262 (2003).
Murray, C.B. et al., Synthesis and Characterization of Monodisperse Nanocrystals and Close-Packed Nanocrystal Assemblies, Annual Reviews of Material Science, 30:545-610 (2000).
Myers, E.W. and Miller, W., Optimal alignments in linear space, Comput. Appl. Biosci., 4(1): 11-17 (1988).
Müller, et al., Surface Modification of PLGA Microspheres, J Biomed Mater Res, 66A(1):55-61 (2003).
Naylor et al., Starburst Dendrimers. 5. Molecular Shape Control, Journal of the American Chemical Society, 111:2339-2341 (1989).
Nellore et al., Evaluation of biodegradable microspheres as vaccine adjuvant or hepatitis B surface antigen, J. Parenter. Sci. Technol., 46(5): 176-180 (1992).
Nelson, G.N. et al., Initial evaluation of the use of USPIO cell labeling and noninvasive MR monitoring of human tissue-engineered vascular grafts in vivo, FASEB J., 22(11): 3888-3895 (2008).
Nunn et al., Complement inhibitor of C5 activation from the soft tick *Ornithodoros moubata*, J Immunol, 174(4):2084-91 (2005).
O'Hagan et al., Long-term antibody responses in mice following subcutaneous immunization with ovalbumin entrapped in biodegradable microparticles, Vaccine, 11(9): 965-969 (1993).
O'Hagan, D.T. and Valiante, N.M., Recent Advances in the Discovery and Delivery of Vaccine Adjuvants, Nature Reviews, 2: 727-735 (2003).
O'Reilly, R.K. et al., Functionalization of Micelles and Shell Cross-linked Nanoparticles Using Click Chemistry, Chemistry Materials, 17:5976-5988 (2005).
Ochoa, J. et al., Protective immunity of biodegradable nanoparticle-based vaccine against an experimental challenge with *Salmonella enteritidis* in mice, Vaccine, 25(22): 4410-4419 (2007).
Olivier, J.C., Drug transport to brain with targeted nanoparticles, NeuroRx, 2:108-119 (2005).
Pan et al., Strategy for the treatment of acute myelogenous leukemia based on folate receptor β-targeted liposomal doxorubicin combined with receptor induction using all-trans retinoic acid, Blood, 100: 594-602 (2002).
Panyam, et al., Biodegradable nanoparticles for drug and gene delivery to cells and tissue, Adv Drug Deliv Rev, 55(3):329-47 (2003).
Park et al., Anti-HER2 immunoliposomes: enhanced efficacy attributable to targeted delivery, Clin Cancer Res, 8:1172-1181(2002).
Park et al., Integration of surface modification and 3D fabrication techniques to prepare patterned poly(L-lactide) substrate allowing regionally selective cell adhesion, J Biomater Sci Polym Ed, 9(2):89-110 (1998).
Park et al., Surface modified poly(lactide-co-glycolide) nanospheres for targeted bone imaging with enhanced labeling and delivery of radio isotope, J Biomed Mater Res, 67 A(3):751-60 (2003).
Park, J. et al., Enhancement of surface ligand display on PLGA nanoparticles with amphiphilic ligand conjugates, J. Control Release, 156(1): 109-115 (2011).
Park, J. et al., Modulation of CD4+ T lymphocyte lineage outcomes with targeted, nanoparticle-mediated cytokine delivery, Mol. Pharm., 8(1): 143-152 (2011).
Park, J. et al., PEGylated PLGA nanoparticles for the improved delivery of doxorubicin, Nanomedicine, 5(4): 410-418 (2009).
Pashine et al., Targeting the innate immune response with improved vaccine adjuvants, Nat. Med ., 11(4 Suppl): S63-S68 (2005).
Pastorino et al., Doxorubicin-loaded Fab' Fragments of Anti-disialoganglioside immunoliposomes selectively inhibit the growth and dissemination of human neuroblastoma in nude mice, Cancer Research, 63: 86-92 (2003).
Pellegrino, T. et al., On the Development of Collodial Nanoparticles towards Multifunctional Structures and their Possible Use for Biological Applications, Small, 1(1):48-63 (2005).
Pitaksuteepong et al., Uptake of antigen encapsulated in polyethylcyanoacrylate nanoparticles by D1-dendtitic cells, Pharmazie, 59(2): 134-142 (2004 ).
Pochard , P. et al., Targeting Toll-like receptors on dendritic cells modifies the T(H)2 response to peanut allergens in vitro., J Allergy Clin Immunol. Jul. 2010;126(1):92-7.e5 (2010).
Quirk et al., Cell-type-specific adhesion onto polymer surfaces from mixed cell populations, Biotech. Bioeng., 81(5):625-628 (2003).
Ragheb, R.R. et al., Induced clustered nanoconfinement of superparamagnetic iron oxide in biodegradable nanoparticles enhances transverse relaxivity for targeted theranostic, Magn. Reson. Med., 70(6): 1748-1760 (2013).
Rittchen, S., Myelin repair in vivo is increased by targeting oligodendrocyte precursor cells with nanoparticles encapsulating leukaemia inhibitory factor (LIF), Biomaterials, 56: 78-85(2015).
Saluja, S.S., Targeting human dendritic cells via DEC-205 using PLGA nanoparticles leads to enhanced cross-presentation of a melanoma-associated antigen, Int. J. Nanomedicine, 9: 5231-5246 (2014).
Samstein, R.M. et al., The use of deoxycholic acid to enhance the oral bioavailability of biodegradable nanoparticles, Biomaterials, 29(6): 703-708 (2008).
Satterfield, B.C. et al., Tentacle probe sandwich assay in porous polymer monolith improves specificity, sensitivity and kinetics, Nucleic Acids Res., 36(19): e129 (2008).
Schiffelers et al., Cancer siRNA therapy by tumor selective delivery with ligand-targeted sterically stabilized nanoparticle, Nucleic Acids Res, 32: e149 (2004).
Schneck, J.P., Monitoring antigen-specific T cells using MHC-Ig dimers, Immunol. Invest., 29:163-9 (2000).
Schöll, I. et al., Biodegradable PLGA Particles for Improved Systemic and Mucosal Treatment of Type I Allergy, Immunol. Allergy Clin. N. Am., 26(2): 349-364 (2006).

(56) References Cited

OTHER PUBLICATIONS

Sehgal K et al., Nanoparticle-mediated combinatorial targeting of multiple human dendritic cell (DC) subsets leads to enhanced T cell activation via IL-15-dependent DC crosstalk, J. Immunol., 193(5): 2297-2305 (2014).
Serebrisky, D et al., CpG oligodeoxynucleotides can reverse Th2-associated allergic airway responses and alter the B7.1/B7.2 expression in a murine model of asthma, J Immunol., 165(10):5906-5912 (2000).
Sesardic et al., European union regulatory developments for new vaccine adjuvants and delivery systems, Vaccine, 22(19): 2452-2456 (2004).
Shastri, N., Needles in haystacks: identifying specific peptide antigens for T cells, Curr. Opin. Immunol., 8(2): 271-277 (1996).
Shen et al., Enhanced and prolonged cross-presentation following endosomal escape of exogenous antigens encapsulated in biodegradable nanoparticles, Immunity, 117(1): 78-88 (2006).
Shenderova et al., The acidic microclimate in poly(lactide-co-glycolide) microspheres stabilizes camptothecins, Pharm Res, 16(2):241-248 (1999).
Shirali, A.C. et al., Nanoparticle delivery of mycophenolic acid upregulates PD-L1 on dendritic cells to prolong murine allograft survival, Am. J. Transplant, 11(12): 2582-2592 (2011).
Siefert, A.L. et al., Artificial bacterial biomimetic nanoparticles synergize pathogen-associated molecular patterns for vaccine efficacy, Biomaterials, 97: 85-96 (2016).
Siefert, A.L. et al., Immunomodulatory nanoparticles ameliorate disease in the *Leishmania* (*Viannia*) *panamensis* mouse model, Biomaterials, 108: 168-176 (2016).
Silin, D.S. and Lyubomska, V., Overcoming immune tolerance during oral vaccination against actinobacillus pleuropneumoniae, J. Vet. Med. B. Infect. Dis. Vet. Public Health, 49(4): 169-175 (2002).
Silin, D.S. et al., Oral Vaccination: Where are we?, Exp. Opin. Drug Deliv., 4(4): 323-340 (2007).
Singh et al., Advances in vaccine adjuvants for infectious diseases, Curr. HIV Res., 1(3): 309-20 (2003).
Singh et al., Controlled release microparticles as a single dose diphtheria toxoid vaccine: immunogenicity in small animal models, Vaccine, 16(4): 346-352 (1998).
Singh et al., Immunogenicity and protection in small-animal models with controlled-release tetanus toxoid microparticles as a single-dose vaccine, Infect. Immun., 65(5): 1716-1721 (1997).
Singh et al., Immunogenicity studies on diphtheria toxoid loaded biodegradable microsgheres, Int. J. Pharmaceutics, 85(1-3): R5-R8 (1992).
Singh, M. and O'Hagan, D.T., Recent advances in vaccine adjuvants, Pharm. Res., 19(6): 715-728 (2002).
Song et al., Arterial uptake of biodegradable nanoparticles for intravascular local drug delivery: results with an acute dog model, J Control Release, 54: 201-211 (1998).
Srivastava, K.D. et al., Investigation of peanut oral immunotherapy with CpG/peanut nanoparticles in a murine model of peanut allergy, J. Allergy Clin. Immunol., 138(2): 536-543e4 (2016).
Steenblock, E.R. and Fahmy, T.M., A comprehensive platform for ex vivo T-cell expansion based on biodegradable polymeric artificial antigen-presenting cells, Mol Ther., 16(4): 765-772 (2008).
Stern, E. et al., Spatiotemporal control over molecular delivery and cellular encapsulation from electropolymerized micro- and nanopatterned surfaces, Adv. Funct. Mater., 19(18): 2888-2895 (2009).
Storni et al., Immunity in response to particulate antigen delivery systems, Adv. Drug Deliv. Rev., 57(3): 333-55 (2005).
Strohbehn G et al., Imaging the delivery of brain-penetrating PLGA nanoparticles in the brain using magnetic resonance, J. Neurooncol, 121(3): 441-449 (2015).
Summerton, J.E., Endo-Porter: A Novel Reagent for Safe, Effective Delivery of Substances into Cells, Ann. N.Y. Acad. Sci., 1058: 1-14 (2005).
Supplementary Partial European Search Report for EP 13781604, 7 pages dated (Oct. 14, 2015).

Sussman, G.L. et al., The Spectrum of IgE-Mediated Responses to Latex, The Journal of the American Medical Association, 265(21):2844-2847 (1991).
Sykulev et al., High-affinity reactions between antigen-specific T-cell receptors and peptides associated with allogeneic and syngeneic major histocompatibility complex class I proteins, Proc Natl Acad Sci US A, 91: 11487-11491 (1994).
Tanahashi, K. and Mikos, A.G., Effect of hydrophilicity and agmatine modification on degradation of poly(propylene fumarate-co-ethylene glycol) hydrogels, J. Biomed. Res. A., 67(4): 1148-1154 (2003).
Tanaka et al, Structure of FK506: a novel immunosuppressant isolated from a Streptomyces, J. Am. Chem. Soc, 109: 5031-5033 (1987).
Thomasin et al., Drug microencapsulation by PLA/PLGA coacervation in the light of thermodynamics. 1. Overview and theoretical considerations, J Pharm Sci, 87(3):259-68 (1998).
Tomalia et al., Starburst dendrimers: Molecular level control of size, shape, surface chemistry, topology and flexibility of atoms to macroscopic matter, Angewandte Chemie•International Edition in English, 29:138-175 (1990).
Trindade, T. et al., Nanocrystalline Semiconductors: Synthesis, Properties, and Perspectives, Chemistry Materials, 13:3843-3858 (2001).
Vacic, A., Determination of molecular configuration by debye length modulation, J. Am. Chem. Soc.,133(35): 13886-13889 (2011).
Van Der Lubben, I.M. et al., Chitosan for mucosal vaccination, Advanced Drug Delivery Reviews, 52:139-144 (2001).
Visscher et al., Biodegradation of and tissue reaction to 50:50 poly(DI-lactide-co-glycolide) microcapsules, J Biomed Mater Vies. 19(3):349-65 ( 1985).
Wagener, K.B. and Gomez, F.J., ADMET Polymerization, Encyclopedia of Materials: Science and Technology, 48-53 (2001).
Wan et al., Characterization of surface property of poly(lactide-co-glycolide) after oxygen plasma treatment, Biomaterials. 25(19):4777-83 (2004).
Wang, et al., Preparation and characterization of poly(lactic-co-glycolic acid) microspheres for targeted delivery of a novel anti-cancer agent, taxol, Chem. Pharm. Bull. (Tokyo), 44(10)1935-40 (1996).
Wartlick et al., Highly specific HER2-mediated cellular uptake of antibody-modified nanoparticles in tumour cells, J Drug Target, 12:461-471 (2004).
Wassef et al., Liposomes as carriers for vaccines, Immunomethods, 4(3): 217-222 (1994).
Weber, A. et al., Specific interaction of IgE antibodies with a carbohydrate epitope of honey bee venom phospholipase A2, Allergy, 42(6): 464-470 (1987).
Weiss, S.J. and Halsey, J.F., A nurse with anaphylaxis to stone fruits and latex sensitivity: potential diagnostic difficulties to consider, Ann. Allergy Asthma Immunol., 77(6): 504-508 (1996).
Wikingsson, L.D. and Sjöholm, I., Polyacryl starch microparticles as adjuvant in oral immunisation inducing mucosal and systemic immune responses in mice, Vaccine, 20:3355-3363 (2002).
Written Opinion for PCT/US15/59711, 9 pages dated (May 12, 2016).
Written Opinion for PCT/US2005/023444, 5 pages dated (Sep. 26, 2007).
Written Opinion for PCT/US2008/054086, 6 pages dated (Sep. 22, 2008).
Written Opinion for PCT/US2013/037789, 11 pages dated (Aug. 30, 2013).
Written Opinion for PCT/US2014/055625, 16 pages dated (Dec. 8, 2014).
Written Opinion for PCT/US2014/32838, 15 pages dated (Sep. 4, 2014).
Yamaguchi and Anderson, In vivo biocompatibility studies of medisorb, 65/35 D,L-lactide/glycolide copolymer microspheres, J. Controlled Ref., 24(1-3):81-93 (1993).
Yang et al., Plasma-treated, collagen•anchored polylactone: Its cell affinity evaluation under shear or shear-free conditions, J. Biomed Mater Res, 67A(4): 1139-47 (2003).

(56) References Cited

OTHER PUBLICATIONS

Yoo et al., PAMAM dendrimers as delivery agents for antisense oligonucleotides, Pharm Res, 16:1799•804 (1999).
Zhao, J.W. et al., Modelling of a targeted nanotherapeutic 'stroma' to deliver the cytokine LIF or XAV939, a potent inhibitor of Wnt-β-catenin signalling, for use in human fetal dopaminergic grafts in Parkinson's disease, Dis. Model Mech., 7(10): 1193-1203 (2014).
Zheng et al., Production of microspheres with surface amino groups from blends of Poly(lactide-co-glycolide) and Poly(epsilon-CBz-L-lysine) and use for encapsulation, Biotechnology Progress, 15(4): 763-767 (1999).
Almeida et al., Solid lipid nanoparticles as a drug delivery system for peptides and proteins, Adv. Drug Delivery Rev., 59: 478-490 (2007).
Newman, et al., Uptake of poly(D,L-lactic-co-glycolic acid) microspheres by antigen-presenting cells in vivo, J. Biomed. Mater. Res., 60: 480-486 (2002).
Solbrig, et al., Polymer nanoparticles for immunotherapy from encapsulated tumor-associated antigens and whole tumor cells, Mol. Pharmaceut., 4(1): 47-57 (2007).
Bawarski, W.E. et al., Emerging nanopharmaceuticals, Nanomedicine, 4: 273-282 (2008).
Dobrovoskaia, M.A. and McNEIL, S.E., Immunological properties of engineered nanomaterials, Nature nanotechnology, 2: 469-478 (2007).

\* cited by examiner

NANOPARTICLE COMPOSITIONS

The present application claims the benefit of U.S. patent application Ser. No. 14/782,285, filed Oct. 2, 2015, which application is a National Stage Entry of Patent Cooperation Treaty application number PCT/US14/32838, filed on Apr. 3, 2014, which claims priority to U.S. Provisional patent application No. 61/808,118, filed on Apr. 3, 2013, the entire disclosure of each of which is incorporated herein by reference.

SEQUENCE LISTING

The instant application contains a Sequence Listing which has been submitted electronically in ASCII format and is hereby incorporated by reference in its entirety. Said ASCII copy, originally created on Jun. 19, 2014, is named "Sequence_Listing.txt" and is 553 bytes in size.

BACKGROUND

Many medical benefits could be realized if the immune system could be trained to respond to antigens in a desired manner, such as by developing tolerance to (e.g., for an allergic antigen or auto-antigen), or by learning to reject (e.g., for a disease-associated antigen) the antigen. The body can react to a wide variety of antigens, whether exogenous antigens (e.g., allergens, infectious agent antigens, etc) or endogenous antigens (e.g., auto-antigens, certain disease-associate antigens, etc). Diverse approaches have been applied in order to meet this challenge, including systemic drug treatments, injection of antigens, antibody therapies, etc. However, there remains a need for improved approaches.

SUMMARY

The present invention provides a novel system for modulating (including inducing, promoting or suppressing) immune responses to antigens. In particular, in some embodiments, the invention provides technologies that combine features of certain nanoparticle systems together with microbial components and/or antigen materials, either or both of which may be utilized in relatively crude form (e.g., as relatively crude extracts). Alternatively or additionally, one or more microbial component and/or antigen material may be recombinant in nature.

Among other things, the present invention provides the insight that hydrophilic and hydrophobic components of microbial systems play different roles in and/or have different effects on immune responses. In some embodiments of the present invention, such components are separated from one another and utilized together with nanoparticle entities in compositions that modulate immune responses.

The present invention also provides the insight that relatively crude microbial cellular preparations, optionally comprising primarily hydrophobic or primarily hydrophilic cellular components, are useful for combination with nanoparticle entities to modulate immune responses. The present invention specifically encompasses the recognition that combining such relatively crude microbial cellular preparations with certain nanoparticle technologies permits the development of surprisingly useful immunomodulatory nanoparticle compositions. In some embodiments, such compositions benefit from attributes of microbial cellular material that have developed through evolution. The present invention encompasses the appreciation that such evolution may have generated combinations of individual components that together impart upon the microbial cells certain desirable attributes that might be difficult to define or recreate by attempting to combine individual isolated components. Furthermore, the present invention appreciates that use of relatively crude preparations simplifies and reduces expense associated with manufacturing technologies while potentially also providing unexpected desirable attributes to inventive compositions.

In some embodiments, the present invention encompasses use of recombinant microbial components (e.g. CpG) and/or recombinant antigen materials. In some embodiments, use of recombinant nucleic acids and/or proteins may be desirable due to a lower risk of toxicity or other adverse event. In some embodiments, use of recombinant nucleic acids and/or proteins may be beneficial in that recombinant production may make it easier to produce and use large quantities of a particular nucleic acid and/or protein.

Alternatively or additionally, in some embodiments, the present invention provides nanoparticle compositions comprising polymer nanoparticles and relatively crude antigen preparations.

Still further, in some embodiments, the present invention provides nanoparticle compositions formulated for mucosal delivery.

In some embodiments, provided compositions show additional beneficial attributes such as, for example, regulated and/or tunable release of encapsulated materials from nanoparticles, optional encapsulation of antigens within nanoparticles so that they are hidden from relevant immune system components unless and until they are released, etc. Furthermore, the present invention provides facile combinations of different elements, thus facilitating, for example, targeted localization of nanoparticles and/or simultaneous modulation of responses to multiple antigens (e.g., of allergic responses to allergens, therapeutic responses to disease-associated and/or infectious antigens, and/or inappropriate responses to autoallergens.

The present invention provides, among other things, nanoparticle compositions, methods for administering provided nanoparticle compositions, and methods of forming provided nanoparticle compositions. In some embodiments, provided nanoparticle compositions include a plurality of nanoparticles, each of which is comprised of a biodegradable or biocompatible polymer arranged in a nanoparticle structure defining an internal lumen and an external surface, and a preparation of hydrophilic cellular components encapsulated within the internal lumen. In some embodiments, provided nanoparticle compositions include a plurality of nanoparticles, each of which is comprised of a biodegradable or biocompatible polymer arranged in a nanoparticle structure defining an internal lumen and an external surface and a preparation of hydrophobic cellular components associated with the external surface. In some embodiments, provided nanoparticle compositions include a plurality of nanoparticles, each of which is comprised of a biodegradable or biocompatible polymer arranged in a nanoparticle structure defining an internal lumen and an external surface, and a preparation of hydrophilic cellular components encapsulated within the internal lumen and a preparation of hydrophobic cellular components associated with the external surface. In some embodiments, the biodegradable or biocompatible polymer is poly(lactic-co-glycolic acid).

In some embodiments, the preparation of hydrophilic cellular components is or comprises a hydrophilic extract of a cellular preparation. In some embodiments, the hydrophilic extract comprises or consists of an aqueous extract of the cellular preparation. In some embodiments, the preparation of hydrophobic cellular components comprises or consists of a hydrophobic extract of a cellular preparation.

In some embodiments, provided compositions include one or more antigens. In some embodiments, the antigen is or comprises an allergic antigen. In some embodiments, wherein the antigen is or comprises an anaphylactic antigen. In some embodiments, wherein the antigen is or comprises an infectious antigen. In some embodiments, the infectious antigen is provided with one or more additional components of the infectious agent. In some embodiments, the antigen is or comprises an autoantigen. In some embodiments, the antigen is or comprises a disease-associated antigen. In some embodiments, the antigen is partly or wholly encapsulated within the lumen. In some embodiments, the antigen is partly or wholly associated with the external surface. In some embodiments, the antigen is mixed with the nanoparticles so that each is dispersed throughout the composition.

In some embodiments, the antigen or infectious agent is selected from the group consisting of a food antigen, a microbial antigen, a viral antigen, a tumor antigen, and an environmental antigen. In some embodiments, provided compositions comprise first and second antigens, the first antigen being partly or wholly encapsulated within nanoparticle lumens and the second antigen being partly or wholly associated with the external surface of nanoparticles.

In some embodiments, at least one of the hydrophilic cellular components and the hydrophobic cellular components is provided from a microbial cellular preparation. In some embodiments, at least one of the hydrophilic cellular components and the hydrophobic cellular components is provided from a tumor cell cellular preparation.

BRIEF DESCRIPTION OF THE DRAWING

The Figures described below, that together make up the Drawing, are for illustration purposes only, not for limitation.

DEFINITIONS

Figure 1:
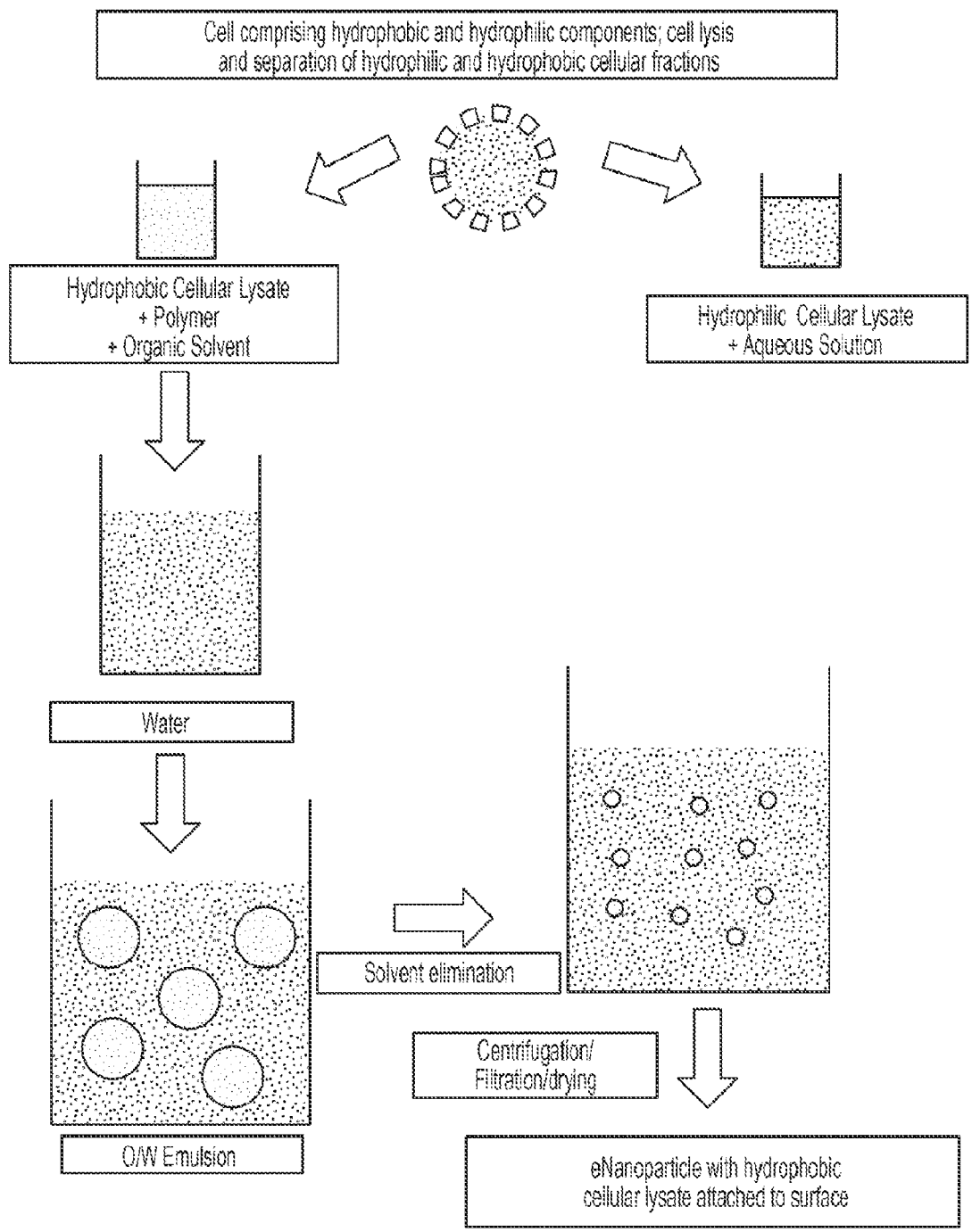
FIG. 1: depicts an exemplary flow chart according to some embodiments illustrating the production of nanoparticles with hydrophobic cellular components attached to the surface of the nanoparticle. Cells are lysed and the hydrophobic and hydrophilic cellular components separated. The hydrophobic cellular components are combined with polymer and organic solvent. The hydrophobic cellular components+polymer+organic solvent mixture is added to water (or an aqueous solution) and the solvent is then evaporated. Nanoparticles are isolated by centrifugation. The resultant nanoparticles include hydrophobic cellular components attached to the surface of the nanoparticle.
Figure 2:
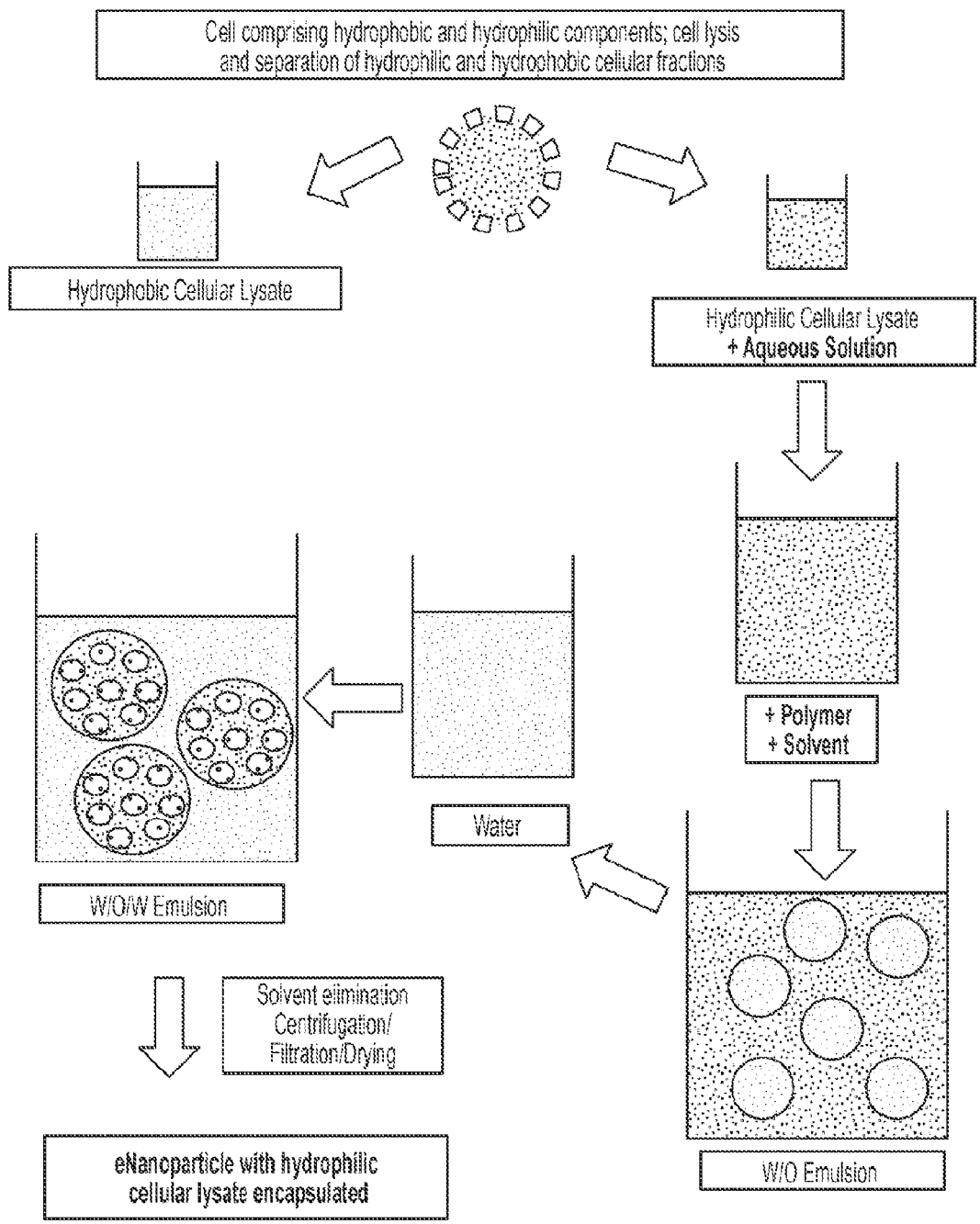
FIG. 2: depicts an exemplary flow chart according to some embodiments illustrating the production of nanoparticles with hydrophilic cellular components encapsulated within the nanoparticle. Cells are lysed and the hydrophobic and hydrophilic cellular components separated. The hydrophilic cellular components are added to an aqueous solution. Polymer and organic solvent are combined together separately. The hydrophilic cellular components in aqueous solution are added to the polymer and organic solvent solution (W/O Emulsion). The W/O emulsion is added to water (or an aqueous solution) (W/O/W Emulsion) and the solvent is then evaporated. The resultant nanoparticles are isolated by centrifugation and include encapsulated hydrophilic cellular lysate.
Figure 3:
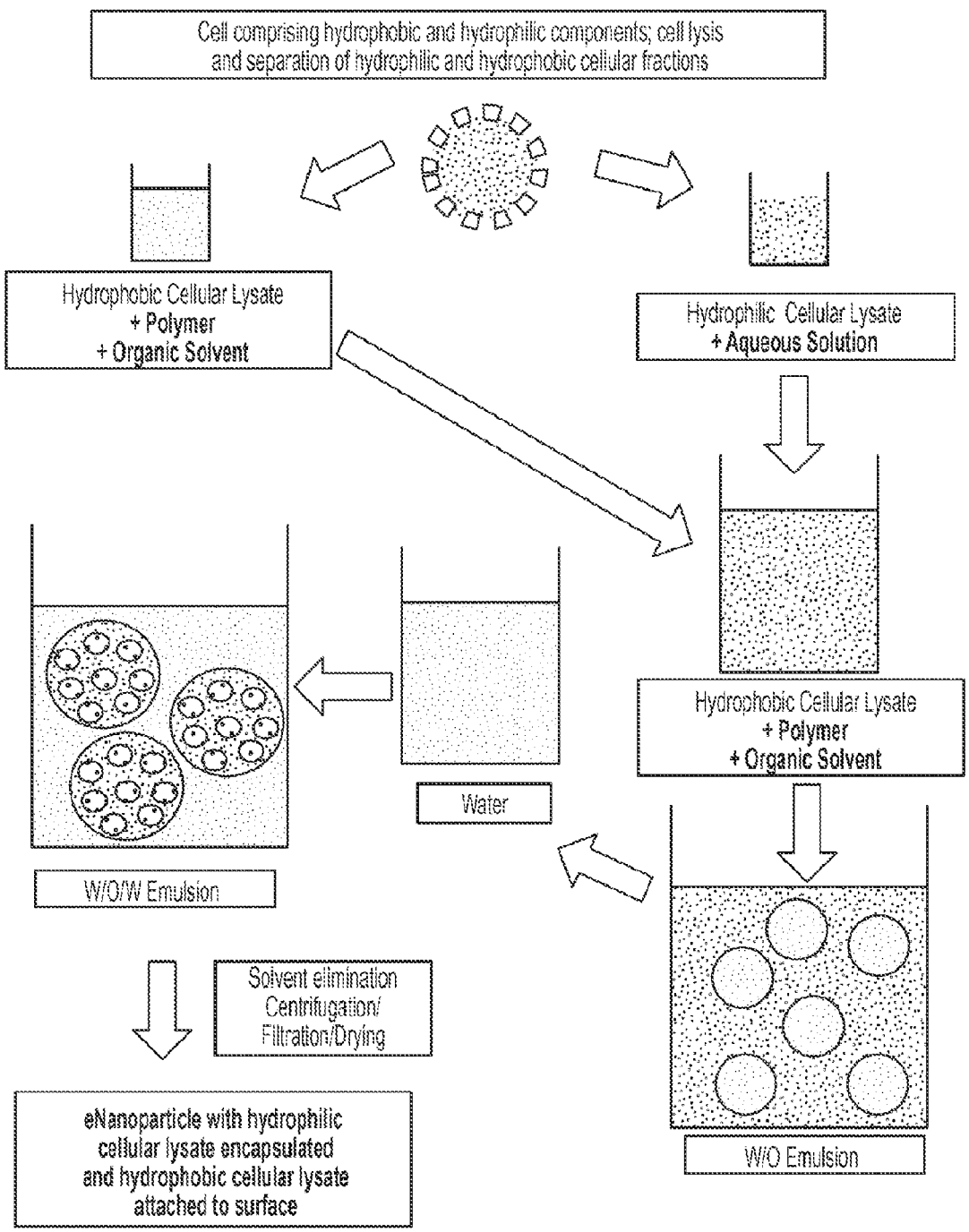
FIG. 3: depicts an exemplary flow chart according to some embodiments, illustrating the production of nanoparticles with hydrophilic cellular components encapsulated within the nanoparticle and hydrophobic cellular components attached to the surface of the nanoparticle. Cells are lysed and the hydrophobic and hydrophilic cellular components separated. The hydrophilic cellular components are added to an aqueous solution. The hydrophobic cellular components are combined with polymer and organic solvent. The hydrophilic cellular components in aqueous solution are added to the hydrophobic cellular components+polymer+organic solvent (W/O emulsion). The W/O emulsion is added to water (or an aqueous solution) (W/O/W Emulsion) and the solvent is then evaporated. The resultant nanoparticles are isolated by centrifugation and include encapsulated hydrophilic cellular lysate and hydrophobic cellular lysate attached to the surface of the nanoparticle.
Figure 4:
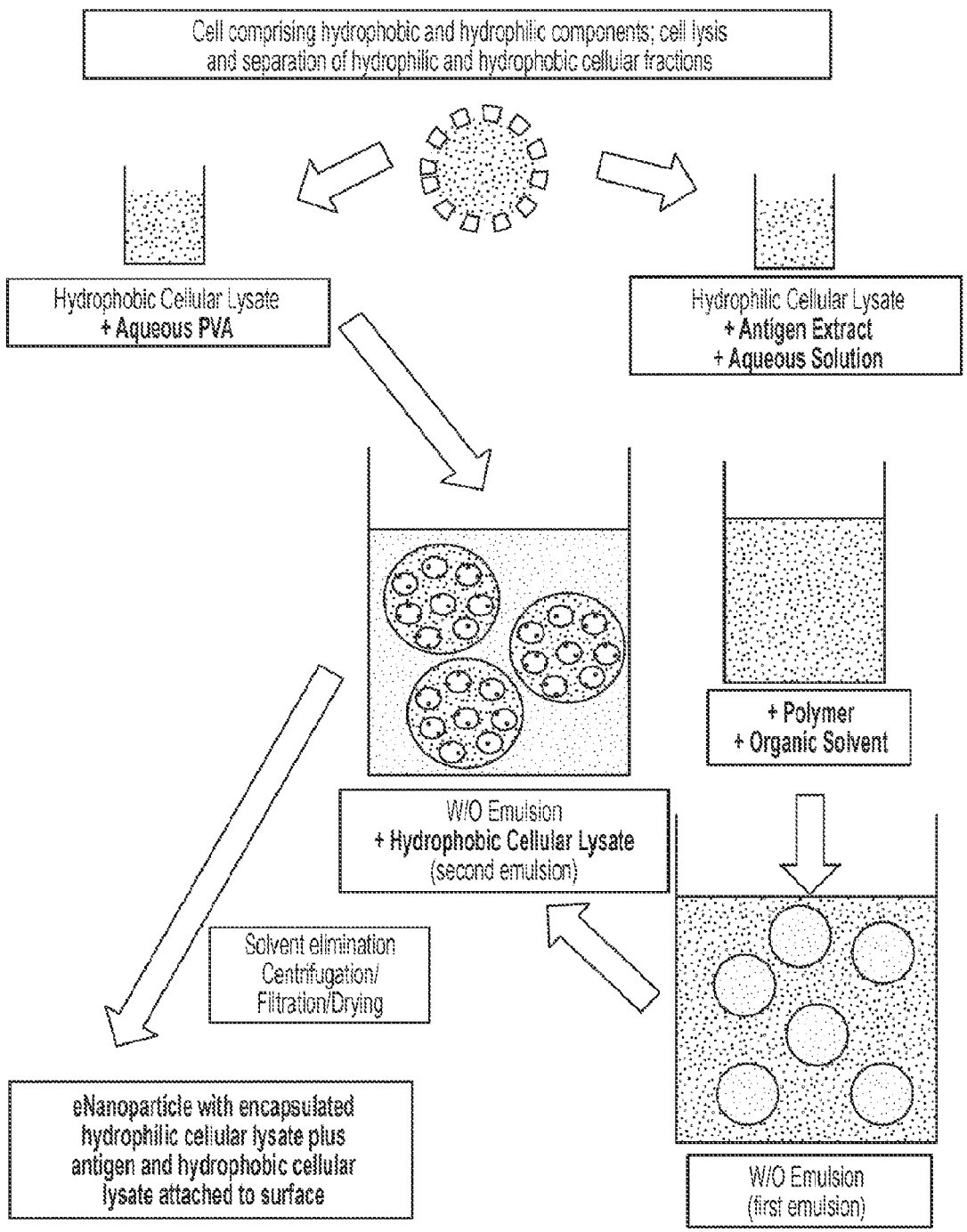
FIG. 4: depicts an exemplary flow chart according to some embodiments illustrating the production of nanoparticles with one or more antigen extracts and hydrophilic cellular components encapsulated within the nanoparticle and hydrophobic cellular components attached to the surface of the nanoparticle. Cells are lysed and the hydrophobic and hydrophilic cellular components separated. The hydrophilic cellular components are added to an aqueous solution and combined with soluble antigen extract. The hydrophobic cellular components are combined with an aqueous PVA solution. Polymer and organic solvent are combined together separately. The hydrophilic cellular components in aqueous solution are added to the polymer+organic solvent (W/O emulsion; first emulsion). The W/O emulsion is combined with the hydrophobic cellular components in aqueous PVA solution (second emulsion) and the solvent is then evaporated. The resultant nanoparticles are isolated by centrifugation and include encapsulated antigen extract, encapsulated hydrophilic cellular components, and hydrophobic cellular components attached to the surface of the nanoparticle.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Allergen: The term "allergen", as used herein, refers to those antigens that induce an allergic reaction. In some embodiments, an allergen is or comprises a polypeptide. In some embodiments, an allergen is or comprises a small molecule. In some embodiments, an allergen is selected from the group consisting of food allergens, drug allergens, environmental allergens, insect venoms, animal allergens, and latex.

Allergic reaction: The phrase "allergic reaction," as used herein, has its art-understood meaning and refers to an IgE-mediated immune response to an antigen. When an antigen induces IgE antibodies, they will bind to IgE receptors on the surface of basophils and mast cells. Subsequent exposures to the antigen trigger cross-linking of such surface-bound anti-allergen IgEs, which trigger release of histamine from stores within the cells. This histamine release triggers the allergic reaction. Typically, an allergic reaction involves one or more of the cutaneous (e.g., uticana, angiodema, pruritus), respiratory (e.g., wheezing, coughing, laryngeal edema, rhinorrhea, watery/itching eyes), gastrointestinal (e.g., vomiting, abdominal pain, diarrhea), and/or cardiovascular (e.g., if a systemic reaction occurs) systems. For the purposes of the present invention, an asthmatic reaction is considered to be a form of allergic reaction. In some embodiments, allergic reactions are mild; typical symptoms of a mild reaction include, for example, hives (especially over the neck and face) itching, nasal congestion, rashes, watery eyes, red eyes, and combinations thereof. In some embodiments, allergic reactions are severe and/or life threatening; in some embodiments, symptoms of severe allergic reactions (e.g., anaphylactic reactions) are selected from the group consisting of abdominal pain, abdominal breathing sounds (typically high-pitched), anxiety, chest discomfort or tightness, cough, diarrhea, difficulty breathing, difficulty swallowing, dizziness or light-headedness, flushing or redness of the face, nausea or vomiting, palpitations, swelling of the face, eyes or tongue, unconsciousness, wheezing, and combinations thereof. In some embodiments, allergic reactions are anaphylactic reactions.

Allergy: The term "allergy", as used herein, refers to a condition characterized by an IgE-mediated immune response to particular antigens. In some embodiments, the antigens are ones that do not elicit an IgE-mediated immune response in many or most individuals. In some embodiments, the term "allergy" is used to refer to those situations where an individual has a more dramatic IgE-mediated immune response when exposed to a particular antigen than is typically observed by members of the individual's species when comparably exposed to the same antigen. Thus, an individual who is suffering from or susceptible to "allergy" is one who experiences or is at risk of experiencing an allergic reaction when exposed to one or more allergens. In some embodiments, symptoms of allergy include, for example, presence of IgE antibodies, reactive with the allergen(s) to which the individual is allergic, optionally above a particular threshold, in blood or serum of the individual. In some embodiments, symptoms of allergy include development of a wheel/flare larger than a control wheel/flare when a preparation of the antigen is injected subcutaneously under the individual's skin. In some embodiments, an individual can be considered susceptible to allergy without having suffered an allergic reaction to the particular allergen in question. For example, if the individual has suffered an allergic reaction, and particularly if the individual has suffered an anaphylactic reaction, to a related allergen (e.g., one from the same source or one for which shared allergies are common), that individual may be considered susceptible to allergy to (and/or to an allergic or anaphylactic reaction to) the relevant allergen. Similarly, if members of an individual's family react to a particular allergen, the individual may be considered to be susceptible to allergy to (and/or to an allergic and/or anaphylactic reaction to) that allergen.

Alloantigen: The term "alloantigen", as used herein, refers to an antigen associated with allorecognition and/or graft rejection (e.g., an antigen against which a rejection immune response is directed). In general, alloantigens are agents that are present in or on tissue from one individual (e.g., a donor individual) of a particular species, but not in or on tissue from another individual (e.g., a recipient individual, for example who is genetically different from the donor individual) of the species, so that transfer of tissue from the donor individual to the recipient individual risks and/or results in a rejection immune response. In general, an antigen may be or include any chemical entity such as, for example, a small molecule, a nucleic acid, a polypeptide, a carbohydrate, a lipid, etc. In some embodiments, an alloantigen is or comprises a polypeptide. A variety of polypeptides are known in the art whose amino acid sequences can vary between and among individuals of the same species such that they might act as alloantigens.

Allorecognition: The term "allorecognition", as used herein, typically refers to an immune response mounted by the immune system of an individual (i.e., a recipient) who receives a tissue graft from another individual (i.e., a donor, who for example is genetically distinct from the recipient individual) of the same species, which immune response involves recognition of an alloantigen on the grafted tissue. Typically, allorecognition involves T cell recognition of the alloantigen. In many embodiments, T cells recognize an alloantigen peptide, for example, encoded by a polymorphic gene whose sequence differs between the donor and recipient individuals.

Amino acid: As used herein, the term "amino acid," in its broadest sense, refers to any compound and/or substance that can be incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

Anaphylactic antigen: The phrase "anaphylactic antigen", as used herein, refers to an antigen (e.g., an allergen) that is recognized to present a risk of anaphylactic reaction in allergic individuals when encountered in its natural state, under normal conditions. For example, for the purposes of the present invention, pollens and animal danders or excretions (e.g., saliva, urine) are not considered to be anaphylactic antigens. On the other hand, certain food antigens, insect antigens, drugs, and rubber (e.g., latex) antigens latex are generally considered to be anaphylactic antigens. Exemplary anaphylactic antigens include those to which reactions are so severe as to create a risk of death (e.g., nuts, seeds, and fish).

Anaphylactic reaction: The phrase "anaphylactic reaction," (e.g., "anaphylaxis") as used herein, refers to a severe, whole body allergic reaction to an allergen, characterized by pathological responses in multiple target organs, e.g., airway, skin digestive tract, and cardiovascular system. As noted above, symptoms of severe allergic reactions such as anaphylactic reactions typically develop quickly, often within minutes of exposure to the allergen, and can include, for example, abdominal pain, abdominal breathing sounds (typically high-pitched), anxiety, chest discomfort or tightness, cough, diarrhea, difficulty breathing, difficulty swallowing, dizziness or light-headedness, flushing or redness of the face, nausea or vomiting, palpitations, swelling of the face, eyes or tongue, unconsciousness, wheezing, and combinations thereof. Particular signs of anaphylaxis may include, for example, abnormal heart rhythm (arrhythmia), fluid in the lungs (pulmonary edema), hives, low blood pressure, mental confusion, rapid pulse, skin that is blue from lack of oxygen or pale (e.g., from shock), swelling (angioedema) in the throat that may be severe enough to block the airway, swelling of the eyes and/or face, weakness, wheezing. The most severe anaphylactic reactions can result in loss of consciousness and/or death.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antigen: The term "antigen", as used herein, refers to an agent that elicits an immune response; and/or (ii) an agent that binds to a T cell receptor (e.g., when presented by an MHC molecule) or to an antibody (e.g., produced by a B cell). In some embodiments, an antigen elicits a humoral response (e.g., including production of antigen-specific antibodies); in some embodiments, an elicits a cellular response (e.g., involving T-cells whose receptors specifically interact with the antigen). In general, and antigen may be or include any chemical entity such as, for example, a small molecule, a nucleic acid, a polypeptide, a carbohydrate, a lipid, etc. In some embodiments, an antigen is or comprises a polypeptide. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen.

Antigen presenting cell: The phrase "antigen presenting cell" or "APC," as used herein, has its art understood meaning referring to cells which process and present antigens to T-cells. Exemplary antigen cells include dendritic cells, macrophages and certain activated epithelial cells.

Approximately: As used herein, the term "approximately" and "about" is intended to encompass normal statistical variation as would be understood by those of ordinary skill in the art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are "associated" with one another if they interact, directly or indirectly, so that they are and remain in physical proximity with one another.

Autoantigen: As used herein, the term "autoantigen" is used to refer to antigens produced by an individual that are recognized by the immune system of that individual. In some embodiments, an autoantigen is one whose recognition by the individual's immune system is associated with an autoimmune disease, disorder or condition. In general, an autoantigen may be or include any chemical entity such as, for example, a small molecule, a nucleic acid, a polypeptide, a carbohydrate, a lipid, etc. In some embodiments, an autoantigen is or comprises a polypeptide. Those of skill in the art are familiar with a variety of agents, including polypeptides, that can act as autoantigens, and particular that are recognized in immune reactions associated with autoimmunity diseases, disorders and/or conditions.

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Biodegradable: As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Biologically active: As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

Cellular lysate: As used herein, the term "cellular lysate" or "cell lysate" refers to a fluid containing contents of one or more disrupted cells (i.e., cells whose membrane has been disrupted). In some embodiments, a cellular lysate includes both hydrophilic and hydrophobic cellular components. In some embodiments, a cellular lysate is a lysate of one or more cells selected from the group consisting of plant cells, microbial (e.g., bacterial or fungal) cells, animal cells (e.g., mammalian cells), human cells, and combinations thereof. In some embodiments, a cellular lysate is a lysate of one or more abnormal cells, such as cancer cells. In some embodiments, a cellular lysate is a crude lysate in that little or no purification is performed after disruption of the cells, which generates a "primary" lysate. In some embodiments, one or more isolation or purification steps is performed on the primary lysate. However, the term "lysate" refers to a preparation that includes multiple cellular components and not to pure preparations of any individual component.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Combination therapy: As used herein, the term "combination therapy" refers to those situations in which a subject is simultaneously exposed to two or more therapeutic agents. In some embodiments, such agents are administered simultaneously; in some embodiments, such agents are administered sequentially; in some embodiments, such agents are administered in overlapping regimens.

Corresponding to: As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Derivative: As used herein, the term "derivative" refers to a structural analogue substance that is produced or formed from another substance of similar structure in one or more steps. In some embodiments, a derivative refers to a second chemical substance related structurally to a first chemical substance and theoretically derivable from the first chemical substance. Examples of cellulose derivatives include, but are not limited to, cellulose esters (such as organic and inorganic esters), cellulose ethers (such as alkyl, hydroxyalkyl and carboxyalkyl ethers), sodium carboxymethyl cellulose and cellulose acetate. Examples of cellulose organic esters include, but are not limited to cellulose acetate, cellulose triacetate, cellulose propionate, cellose acetate propionate and cellulose acetate butyrate. Examples of cellulose inorganic esters include, but are not limited to, cellulose nitrate and cellulose sulfate. Examples of cellulose alkyl ethers include, but are not limited to, methylcellulose, ethylcellulose and ethyl methyl cellulose. Examples of cellulose hydroxyalkyl ethers include, but are not limited to, hydroxyethyl cellulose, hydroxypropyl cellulose, hydroxyethyl methyl cellulose, hydroxypropyl methyl cellulose and ethyl hydroxyethyl cellulose. Examples of a cellulose carboxyalkyl ethers include, but are not limited to carboxymethyl cellulose.

Dosage form: As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is correlated with a desired or beneficial outcome when administered across a relevant population (i.e., is a therapeutic dosing regimen).

Encapsulated: The term "encapsulated" is used herein to refer to substances that are completely surrounded by another material.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, the term "functional" is used to refer to a form or fragment of an entity that exhibits a particular property and/or activity.

Graft rejection: The term "graft rejection" as used herein, refers to rejection of tissue transplanted from a donor individual to a recipient individual. In some embodiments, graft rejection refers to an allograft rejection, wherein the donor individual and recipient individual are of the same species. Typically, allograft rejection occurs when the donor tissue carries an alloantigen against which the recipient immune system mounts a rejection response. In some embodiments, graft rejection refers to a xenograft rejection, wherein the donor and recipient are of different species. Typically, xenograft rejection occurs when the donor species tissue carries a xenoantigen against which the recipient species immune system mounts a rejection response.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| --- | --- | --- | --- | --- | --- |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

-continued

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Human: In some embodiments, a human is an embryo, a fetus, an infant, a child, a teenager, an adult, or a senior citizen.

Hydrophilic: As used herein, the term "hydrophilic" and/or "polar" refers to a tendency to mix with, or dissolve easily in, water.

Hydrophobic: As used herein, the term "hydrophobic" and/or "non-polar", refers to a tendency to repel, not combine with, or an inability to dissolve easily in, water.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

Infection: As used herein, the term "infection" refers to the invasion of a host organism's body by a disease-causing organism that multiplies in the host. Symptoms of an infection may result from action of toxins produced by the disease-causing organism and/or be reaction of host tissues to the organisms and/or to toxins they produce.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients.

Nanoemulsion: An emulsion is traditionally defined in the art "as a system . . . consisting of a liquid dispersed with or without an emulsifier in an immiscible liquid usually in droplets of larger than colloidal size" Medline Plus Online Medical Dictionary, Merriam Webster (2005). The term "nanoemulsion," as used herein, refers to an emulsion in which at least some of the droplets (or particles) have diameters in the nanometer size range. As will be understood by those of ordinary skill in the art, a nanoemulsion is characterized by droplets or particles one thousand fold smaller than microemulsion droplets or particles.

Nanoparticle: As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer.

Nanoparticle composition: As used herein, the term "nanoparticle composition" refers to a composition that contains at least one nanoparticle and at least one additional agent or ingredient. In some embodiments, a nanoparticle composition contains a substantially uniform collection of nanoparticles as described herein.

Nanoparticle membrane: As used herein, the term "nanoparticle membrane" refers to the boundary or interface between a nanoparticle outer surface and a surrounding environment. In some embodiments, the nanoparticle membrane is a polymer membrane having an outer surface and bounding lumen.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Patient: As used herein, the term "patient" or "subject" refers to a human or any non-human animal (e.g., mouse, rat, rabbit, dog, cat, cattle, swine, sheep, horse or primate) to whom therapy is administered. In many embodiments, a patient is a human being. In some embodiments, a patient is a human presenting to a medical provider for diagnosis or treatment of a disease, disorder or condition. In some embodiments, a patient displays one or more symptoms or characteristics of a disease, disorder or condition. In some embodiments, a patient does not display any symptom or characteristic of a disease, disorder, or condition. In some embodiments, a patient is someone with one or more features characteristic of susceptibility to or risk of a disease, disorder, or condition.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Polypeptide: The term "polypeptide", as used herein, generally has its art-recognized meaning of a polymer of at least three amino acids. In some embodiments, the term is used to refer to specific functional classes of polypeptides, such as, for example, autoantigen polypeptides, nicotinic acetylcholine receptor polypeptides, alloantigen polypeptides, etc. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Refractory: As used herein, the term "refractory" refers to any subject that does not respond with an expected clinical efficacy following the administration of provided compositions as normally observed by practicing medical personnel.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Stable: The term "stable," when applied to compositions herein, means that the compositions maintain one or more aspects of their physical structure (e.g., size range and/or distribution of particles) over a period of time. In some embodiments, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time under specified conditions. In some embodiments, a stable provided composition is one for which a biologically relevant activity is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. For example, if a population of nanoparticles is subjected to prolonged storage, temperature changes, and/or pH changes, and a majority of the nanoparticles in the composition maintain a diameter within a stated range, the nanoparticle composition is stable. In some embodiments, a stable composition is stable at ambient conditions. In some embodiments, a stable composition is stable under biologic conditions (i.e. 37° C. in phosphate buffered saline).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from allergy, etc.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic agent: As used herein, the phrase "therapeutic agent" refers to any agent that has a therapeutic effect and/or elicits a desired biological and/or pharmacological effect, when administered to a subject. In some embodiments, an agent is considered to be a therapeutic agent if its administration to a relevant population is statistically correlated with a desired or beneficial therapeutic outcome in the population, whether or not a particular subject to whom the agent is administered experiences the desired or beneficial therapeutic outcome.

Therapeutically effective amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition (e.g., allergy). In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

Therapeutic regimen: A "therapeutic regimen", as that term is used herein, refers to a dosing regimen whose administration across a relevant population is correlated with a desired or beneficial therapeutic outcome.

Treatment: As used herein, the term "treatment" (also "treat" or "treating") refers to any administration of a substance that partially or completely alleviates, ameliorates, relives, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Uniform: The term "uniform," when used herein in reference to a nanoparticle composition, refers to a nanoparticle composition in which individual nanoparticles have diameters within a specified range. For example, in some embodiments, a uniform nanoparticle composition is one in which the difference between the minimum diameter and maximum diameter does not exceed about 300 nm. In some embodiments, a uniform nanoparticle composition contains nanoparticles with diameters within the range of about 100 nm to about 300 nm. In some embodiments, a uniform nanoparticle composition contains nanoparticles with an average particle size that is under about 500 nm. In some embodiments, a uniform nanoparticle composition contains nanoparticles with an average particle size that is within a range of about 100 nm to about 500 nm. In some embodiments, a uniform nanoparticle composition is one in which a majority of the particles within the composition have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

DETAILED DESCRIPTION OF CERTAIN EMBODIMENTS

The present invention is based, in part, on the surprising insight that desirable immunomodulatory compositions can be prepared by combining features of certain nanoparticles together with cellular components of microbial cells. The present invention provides the particular insight that such immunomodulatory compositions can be prepared with preparations comprising either hydrophilic or hydrophobic microbial cellular components, or both. In some particular embodiments, the present invention provides the insight that desirable immunomodulatory compositions can be prepared by encapsulating hydrophilic microbial cellular components within nanoparticles and/or associating hydrophobic microbial cellular components with the external surface of the nanoparticles.

Nanoparticles

Nanoparticles useful in accordance with the present invention include those in which the nanoparticles are comprised of at least one polymer assembled into a micelle that bounds an interior lumen and has an external surface. In some embodiments, nanoparticles are comprised of at least one polymer that is a homopolymer, a diblock polymer, a triblock polymer, a multiblock copolymer, a linear polymer, a dendritic polymer, a branched polymer, a random block, etc., or combinations thereof. In some embodiments, nanoparticles are comprised of a blend and/or mixture of polymers.

In some embodiments, nanoparticles are comprised of one or more biocompatible polymers and/or one or more biodegradable polymers. In some embodiments, nanoparticles are comprised of one or more synthetic polymers, or derivatives thereof. In some embodiments, nanoparticles are comprised of one or more natural polymers, or derivatives thereof. In some embodiments, nanoparticles are comprised of combinations of synthetic and natural polymers, or derivatives thereof.

In some embodiments, nanoparticles are comprised of one or more polymers selected from the group consisting of poly(hydroxy acids) such as poly(lactic acid), poly(glycolic acid), poly(lactic acid-co-glycolic acid), poly(lactic-co-glycolic acid), and derivatives of poly(lactic-co-glycolic acid), PEGylated poly(lactic-co-glycolic acid), poly(lactide), poly (glycolide), poly(lactide-co-glycolide), poly(anhydrides), PEGylated poly(anhydrides), poly (ortho esters), derivatives of poly(ortho esters), PEGylated poly(ortho esters), poly (caprolactones), derivatives of poly(caprolactone), PEGylated poly(caprolactones), polyamines (e.g. spermine, spermidine, polylysine, and derivatives thereof), PEGylated polylysine, polyamides, polycarbonates, poly(propylene fumarates), polyamides, polyphosphazenes, polyamino acids, polyethers, polyacetals, polylactides, polyhydroxyalkanoates, polyglycolides, polyketals, polyesteramides, poly (dioxanones), polyhydroxybutyrates, polyhydroxyvalyrates, polycarbonates, polyorthocarbonates, poly(vinyl pyrrolidone), polycyanoacrylates, polyalkylene oxalates, polyalkylene succinates, poly(malic acid), poly(methyl vinyl ether), poly(ethylene imine), poly(acrylic acid), poly(maleic anhydride), poly(ethylene imine), derivatives of poly(ethylene imine), PEGylated poly(ethylene imine), poly(acrylic acid), derivatives of poly(acrylic acid), PEGylated poly(acrylic acid), poly(urethane), PEGylated poly(urethane), derivatives of poly(urethane), poly(lactide), poly(glycolide), poly (hydroxy acids), polyesters, poly(arylates), polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone) and/or derivatives thereof.

In some embodiments, nanoparticles are comprised of one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly (methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and/or combinations thereof.

In some embodiments, nanoparticles are comprised of one or more natural polymers. Exemplary natural polymers include, but are not limited to, proteins (such as albumin, collagen, gelatin), prolamines (for example, zein), polysaccharides (such as alginate), cellulose derivatives (such as hydroxypropyl cellulose, sodium carboxymethyl cellulose, ethyl cellulose and cellulose acetate), polyhydroxyalkanoates (for example, polyhydroxybutyrate), and/or combinations thereof. In some embodiments, a natural polymer may comprise or consist of chitosan.

In some embodiments, nanoparticles are comprised of one or more polymers such as poly(lactide-co-glycolide) copolymerized with polyethylene glycol (PEG). Without wishing to be bound by any particular theory, it is proposed that arrangement of a nanoparticle so that PEG is exposed on the external surface, may increase stability of the nanoparticle in blood, perhaps at least in part due to the hydrophilicity of PEG.

In some particular embodiments, nanoparticles are comprised of PLGA.

In some particular embodiments, nanoparticles utilized in accordance with the present invention are as described in one or more of U.S. Pat. No. 7,534,448, U.S. Pat. No. 7,534,449, U.S. Pat. No. 7,550,154, US20090239789A1, US20090269397A1, US20100104503A1, US20100151436A1, US20100284965A1, WO2006080951, WO2008115641, WO2008109347, WO2009094273, WO2012167261 and WO2013003157.

In general, a nanoparticle is or comprises a particle having a diameter (e.g., average diameter) of less than 1000 nanometers (nm). In some embodiments, provided nanoparticle compositions comprise a population of nanoparticles. In some embodiments, a population of nanoparticles comprises nanoparticles of a uniform size. In some embodiments, a population of nanoparticles comprises nanoparticles of different sizes; in some embodiments showing a particular size distribution. In many embodiments, provided nanoparticle compositions comprise nanoparticles having sizes (e.g., average sizes) within a range defined by a lower limit and an upper limit. In some embodiments, the lower limit is 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, or more. In some embodiments, the upper limit is 1000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm or less. In some embodiments, provided nanoparticle compositions comprise nanoparticles having sizes (e.g., average sizes) similar to the size of bacterial cells. For example, in some embodiments, provided nanoparticle compositions comprise nanoparticles having sizes (e.g., average sizes) ranging between 100 nm and 2000 nm, between 100 nm and 1000 nm, between 100 nm and about 500 nm, between 100 nm and about 300 nm, or between 100 nm and about 200 nm.

In some embodiments, provided nanoparticle compositions are substantially free of particles larger than about 2000 nm, about 1000 nm, about 900 nm, about 800 nm, about 700 nm, about 600 nm, about 500 nm, about 400 nm, or about 300 nm. In some embodiments, provided nanoparticle compositions comprise no more than about 50%, about 25%, about 10%, about 5%, or about 1% of particles larger than about 2000 nm, about 1000 nm, about 900 nm, about 800 nm, about 700 nm, about 600 nm, about 500 nm, about 400 nm, or about 300 nm.

Nanoparticles—Exemplary Methods of Making

In another aspect, the present invention provides methods of producing nanoparticles. In some embodiments, for example, embodiments wherein the nanoparticles include one or more of hydrophilic cellular component(s) and hydrophobic cellular component(s), provided methods of making nanoparticles may include one or more of separating, associating, forming, emulsions, hot melt microencapsulation, solvent removal, spray-drying, and/or ionic gelation steps, and combinations thereof.

Forming

In some embodiments, provided nanoparticles may be formed using any available method in the art. In some embodiments, provided nanoparticles and/or nanoparticle compositions may be prepared by nanoprecipitation, flow focusing using fluidic channels, spray drying, single and double emulsion solvent evaporation, solvent extraction, phase separation, hot melt microencapsulation, milling, microemulsion procedures, microfabrication, nanofabrication, sacrificial layers, simple and complex coacervation, and other methods well known to those of ordinary skill in the art. In some embodiments, provided nanoparticle compositions are prepared by aqueous and organic solvent syntheses (see for example, Pellegrino et al., 2005, Small, 1:48; Murray et al., 2000, Ann. Rev. Mat. Sci., 30:545; and Trindade et al., 2001, Chem. Mat., 13:3843). In some embodiments, provided nanoparticle compositions are prepared by nanoprecipitation or spray drying. Conditions used in preparing particles may be altered to yield particles of a desired size or property (e.g., hydrophobicity, hydrophilicity, external morphology, "stickiness," shape, etc.). In general, methods of preparing nanoparticles and/or conditions used (e.g., solvent, temperature, concentration, air flow rate, etc.) may depend on identity of functional elements (e.g., cellular lysate components) associated with the particles and/or the composition of the polymer matrix.

In some embodiments, additional methods for making nanoparticles for delivery of encapsulated agents are described in the literature (see for example, Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755).

Methods of Making—with Antigen

In some embodiments, provided methods further include a step of associating an antigen with a nanoparticle. Suitable antigens and/or antigenic extracts may include those described herein. In some embodiments, the antigen is an infectious agent antigen. In some embodiments, the infectious agent antigen is provided with one or more additional components of the infectious agent. In some embodiments, the antigen is part of a raw or crude antigenic or allergenic extract (e.g. dust mite extract or raw nut extract).

In some embodiments, provided methods further include a step wherein an antigen is associated with either or both of the hydrophilic and/or hydrophobic cellular components so that some or all of the antigen(s) is/are encapsulated within the internal lumen. In some embodiments, one or more antigens are associated with the hydrophilic cellular components so that some or all of the antigen(s) is/are encapsulated within the internal lumen. In some embodiments, one or more antigen(s) are associated with the hydrophobic cellular components so that some or all of the antigen(s) is/are encapsulated within the internal lumen.

As a more detailed example of some embodiments only, the use of certain methods, such as double emulsion, hot melt encapsulation, solvent removal, spray-drying, and ionic gelation methods for forming nanoparticles are provided. Exemplary methods for forming nanoparticles may be found in Demento et al., "TLR9-Targeted Biodegradable Nanoparticles as Immunization Vectors Protect Against West Nile Encephalitis", 2010, J. Immunol. 185:2989-2997; see also Demento et al., "Inflammasome-activating nanoparticles as modular systems for optimizing vaccine efficacy", 2009, Vaccine 27(23): 3013-3021.

Emulsions

In some embodiments, the polymer is dissolved in a volatile organic solvent, such as methylene chloride. The payload (either soluble or dispersed as fine particles) is added to the solution, and the mixture is suspended in an aqueous solution that contains a surface active agent such as poly(vinyl alcohol). The resulting emulsion is stirred until most of the organic solvent evaporates, leaving solid nanoparticles. The resulting nanoparticles are washed with water and dried overnight in a lyophilizer. Freeze dried nanoparticles may then be stored at −20° C. for later use.

In some embodiments, a water-in-oil-in-water (W/O/W) emulsion method may be used for preparation of the nanoparticles. In some embodiments, the nanoparticles include one or more hydrophilic cellular components. For example, in a first emulsion (W/O), aqueous cellular components in phosphate-buffered saline (PBS) are added to a vortexing PLGA solution dissolved in methylene chloride. The first emulsion of polymer and aqueous cellular lysate are then added drop-wise to PVA in a second emulsion (W/O/W). After each emulsion, samples are sonicated for 30 seconds on ice. The second emulsion is then rapidly added to 0.3% PVA. This external phase is then vigorously stirred for 3 hours at constant room temperature to evaporate the methylene chloride, leaving solid nanoparticles. Particles are collected by centrifugation. The resulting nanoparticles are washed with deionized water, flash-frozen, lyophilized, and stored at −20° C. for later use.

In some embodiments, the nanoparticles include one or more hydrophobic cellular components. The hydrophobic cellular component(s) are first combined with a second emulsion. The first emulsion of polymer (with or without aqueous cellular lysate and/or antigen) is then added drop-wise to the second emulsion (W/O/W).

In some embodiments, the nanoparticles further include one or more encapsulated antigens (for example, allergen extracts such as dust mite or peanut). In a first emulsion (W/O), concentrated antigen in phosphate-buffered saline (PBS) is added to a vortexing PLGA solution dissolved in methylene chloride. In some embodiments an aqueous cellular lysate is combined with the first emulsion. Polymer and encapsulant are then added drop-wise to a second emulsion (W/O/W). In some embodiments, the second emulsion has been combined with one or more hydrophobic cellular components. After each emulsion, samples are sonicated for 30 seconds on ice. The second emulsion is then rapidly added to 0.3% PVA. This external phase is then vigorously stirred for 3 hours at constant room temperature to evaporate the methylene chloride, leaving solid nanoparticles. Particles are collected by centrifugation. The resulting nanoparticles are washed with deionized water, flash-frozen, lyophilized, and stored at −20° C. for later use.

Hot Melt Microencapsulation

In this method, the polymer is first melted and then mixed with the solid particles. The mixture is suspended in a non-miscible solvent (like silicon oil), and, with continuous stirring, heated to a temperature, for example, 5° C., above the melting point of the polymer. Once the emulsion is stabilized, it is cooled until the polymer particles solidify. The resulting nanoparticles are washed by decantation with petroleum ether to give a free-flowing powder. Nanoparticles with sizes between 0.5 to 1000 microns may be obtained with this method. The external surfaces of nanoparticles prepared with this technique are usually smooth and dense. This procedure is used to prepare nanoparticles made of polyesters and polyanhydrides. In some embodiments, such a method may use polymers with molecular weights between 1,000-50,000.

Solvent Removal

This technique is primarily designed for polyanhydrides according to known methods. In some embodiments, a payload to be encapsulated (for example, allergen extracts such as dust mite or peanut) is dispersed or dissolved in a solution of the selected polymer in a volatile organic solvent like methylene chloride. This mixture is suspended by stirring in an organic oil (such as silicon oil) to form an emulsion. Unlike solvent evaporation, this method may be used to make nanoparticles from polymers with high melting points and different molecular weights. The external morphology of nanoparticles produced with this technique is highly dependent on the type of polymer used.

Spray-Drying

In some embodiments using this method, the polymer is dissolved in organic solvent. A known amount of the payload (for example, allergen extracts such as dust mite or peanut) is suspended (insoluble extract) or co-dissolved (soluble extract) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm.

Ionic Gelation

In some embodiments, such as those including nanoparticles made of gel-type polymers, such as alginate, traditional ionic gelation techniques may be used. Typically, the polymer(s) are first dissolved in an aqueous solution, mixed with barium sulfate or some bioactive agent, and then extruded through a nanodroplet forming device, which in some instances employs a flow of nitrogen gas to break off the droplet. A slowly stirred (approximately 100-170 RPM) ionic hardening bath is positioned below the extruding device to catch the forming nanodroplets. The nanoparticles are left to incubate in the bath for twenty to thirty minutes in order to allow sufficient time for gelation to occur. Nanoparticle size is controlled by using various size extruders or varying either the nitrogen gas or polymer solution flow rates. Chitosan nanoparticles can be prepared by dissolving the polymer in acidic solution and crosslinking it with tripolyphosphate. Carboxymethyl cellulose (CMC) nanoparticles can be prepared by dissolving the polymer in acid solution and precipitating the nanoparticle with lead ions. In the case of negatively charged polymers (e.g., alginate, CMC), positively charged ligands (e.g., polylysine, polyethyleneimine) of different molecular weights can be ionically attached.

Microbial Cellular Components

As described herein, the present invention encompasses the recognition that certain advantages are achieved when hydrophilic and hydrophilic components of microbial cellular preparations, such as lysates that are separated from one another so that a hydrophilic cellular component preparation and/or a hydrophobic cellular component preparation is/are generated and one or both of such preparations is/are combined with nanoparticles to create nanoparticle compositions of the present invention.

In some embodiments, one or more of a hydrophilic cellular component preparation and a hydrophobic cellular component preparation may be provided from a microbial cellular lysate. In such embodiments, a hydrophilic cellular component may be referred to as a microbial hydrophilic cellular component and a hydrophobic cellular component may be referred to as a microbial hydrophobic cellular component. Without wishing to be bound by any particular theory, some embodiments of the present invention including one or more of a microbial hydrophilic cellular component and/or a microbial hydrophobic cellular component may permit development and/or production of useful immunomodulatory nanoparticle compositions at least in part because they utilize various evolved attributes of microbial cells relating to their ability to modulate or evade human or animal immune reactions. The present invention also captures the insight that combining such evolved attributes with various features of certain nanoparticle systems such as, for example, ability to sequester antigens and/or cellular hydrophilic components from immune system elements (e.g., by encapsulation within a lumen of a nanoparticle), tunable degradation rates and/or locations, and/or modular association with targeting, adjuvant, or other surface entities, permits development and/or production of particularly useful immunomodulatory compositions.

The present invention recognizes the source of a problem with various prior art approaches to providing immunomodulatory compositions. Specifically, the present invention encompasses the recognition that use of pure components, and in particular pure adjuvant components, loses certain advantages, including certain immunological effects, achieved by collections of components, and particularly by collections that mimic or contain absolute and/or relative amounts as are found in such microbial cells. In some embodiments, the present invention encompasses the recognition that use of isolated individual microbial components (e.g., particular CpG and/or LPS molecules) may fail to induce as broad or effective an immune response as could be achieved with an extract that includes multiple components and in some embodiments presents a plurality of components in relative amounts that approximate what is found in nature.

In some embodiments, the present invention provides microbial extracts—e.g., hydrophilic or hydrophobic extracts of microbial cells for use in or which nanoparticle compositions. In some embodiments, such microbial extracts may contain a collection of microbial components that share a chemical feature, so that they associate with other included components and not with excluded components during production of the extract. In some embodiments, extracts may contain at least some cellular components at relative levels comparable to those at which they are present in the cells. Those skilled in the art will be aware of a variety of techniques available to determine presence and/or level of particular components, and to compare such determined level(s) with those observed in intact cells. Moreover, those of ordinary skill in the art will readily appreciate reasonable and expected experimental variation and therefore will be able to determine whether components are present in absolute or relative levels or concentrations in an extract that are reasonably comparable to those at which they are present in cells.

In general, microbial extracts are prepared from microbial cell preparations. Microbial cell preparations are prepared by culturing microbial cells for a period of time and under conditions sufficient to achieve cell growth to a desirable level (e.g., optical density, concentration, colony size, total protein, total DNA, and colony forming units). In some embodiments, microbial cell preparations contain intact cells, and optionally are substantially free of lysed cells. In some embodiments, microbial cell preparations contain lysed cells, and optionally are substantially free of intact cells.

In some embodiments, the present invention provides hydrophilic microbial extracts, for example extracts prepared by contacting a microbial cell preparation with a hydrophilic solvent so that hydrophilic cellular components partition into solution in the hydrophilic solvent. The hydrophilic solvent can then be separated from non-solubilized components which may, for example, be precipitated, solubilized in a hydrophobic solvent (optionally not miscible with the hydrophilic solvent), or otherwise separable from the hydrophilic solvent. In some embodiments, hydrophilic cellular components that partition into a hydrophilic solvent include, for example, components that are miscible and/or soluble in such solvent.

Separating

Any of a variety of separation methods may be used to separate hydrophilic cellular components from hydrophobic cellular components. Exemplary suitable methods include solvent extraction, detergent extraction, and phase separation.

Exemplary hydrophilic components that may be found in certain embodiments of hydrophilic cellular extracts include, but are not limited to, cytosol components; carbohydrates including sugars; amphipathic molecules (e.g., glycolipids and/or lipoproteins); salts; soluble proteins (i.e., polar proteins); nucleic acids (e.g., DNA and/or RNA); and/or combinations thereof. In some embodiments, a hydrophilic cellular extract includes sheared DNA or RNA. In some embodiments, a hydrophilic cellular extract includes lipopolysaccharides (LPS). In some embodiments, a hydrophilic cellular extract includes one or more CpGs. In some embodiments, a hydrophilic cellular extract is substantially free of membrane lipids or membrane proteins.

In some embodiments, the present invention provides hydrophobic microbial extracts, for example extracts prepared by contacting a microbial cell preparation with a hydrophobic solvent so that hydrophobic cellular components partition into solution in the hydrophobic solvent. The hydrophobic solvent can then be separated from non-solubilized components which may, for example, be precipitated, solubilized in a hydrophilic solvent (optionally not miscible with the hydrophobic solvent), or otherwise separable from the hydrophobic solvent. In some embodiments, hydrophobic cellular components that partition into a hydrophobic solvent include that are miscible and/or soluble in the solvent; in some embodiments, such hydrophobic cellular components include components that are substantially immiscible and/or insoluble in water and/or other aqueous solvents.

Exemplary components that may be found in some embodiments of hydrophobic cellular extracts include, but are not limited to, cell membrane components; certain carbohydrates including certain glycoproteins and/or glycolipids; certain proteins including certain glycoproteins, transmembrane proteins, lipid anchored proteins (i.e., non-polar proteins); lipids including phospholipids, glycolipids, and cholesterols; and/or combinations thereof. In some embodiments, a hydrophobic cellular extract includes lipopolysaccharides (LPS). In some embodiments, a hydrophobic cellular extract is substantially free of components found exclusively in the cytoplasm (e.g., hydrophilic proteins, DNA, and RNA).

In some embodiments, a hydrophilic extract is substantially free of hydrophobic components; in some embodiments, a hydrophobic extract is substantially free of hydrophilic components. However, as will be appreciated by those skilled in the art, separation of cellular components by extract preparation is often not complete. That is, in some embodiments, at least some cellular components may partition substantially equally into hydrophilic and hydrophobic extracts; other components may partition favorably but not exclusively into one or the other of a hydrophilic and a hydrophobic extract. To give but a few examples, in some embodiments, amphiphilic entities such as for example certain membrane spanning proteins, glycolipids and/or lipoproteins, LPS, etc., and combinations thereof.

Microbial extracts for use in accordance with the present invention can be prepared from extracts of any microbial cells, or combinations thereof. In some embodiments, microbial extracts are prepared from bacterial, fungal, archael, and/or protest cells, or combinations thereof.

In some embodiments, microbial extracts can be prepared from bacterial cells including, but not limited to *Actinomyces, Aeromonas, Anabaena, Arthrobacter, Bacillus, Bacteroides, Bdellovibrio, Bordetella, Borrelia, Campylobacter, Caulobacter, Chlamydia, Chlorobium, Chromafium, Citrobacter, Clostridium, Corynebacterium, Cytophaga, Deinococcus, Enterobacter, Escherichia, Francisella, Halobacterium, Heliobacter, Haemophilus, Hemophilus* influenza type B (HIB), *Hyphomicrobium, Klebsiella, Lactococcus, Legionella, Leptspirosis, Listeria, Meningococcus* A, B and C *Methanobacterium, Micrococcus, Morganella, Myobacterium, Mycoplasma, Myxococcus, Neisseria, Nitrobacter, Oscillatoria, Peptococcus, Phodospirillum, Plesiomonas, Prochloron, Proteus, Providencia, Pseudomonas, Rickettsia, Salmonella, Serratia, Shigella, Spirillum, Spirochaeta, Sporolactobacillu, Staphylococcus, Streptococcus, Streptomyces, Sulfolobus, Thermoplasma, Thiobacillus*, and *Treponema, Vibrio, Yersinia*, and combinations thereof. In some embodiments, microbial extracts can be prepared from *E coli* cells.

In some embodiments, microbial extracts can be prepared from yeast cells such as, for example, *Brettanomyces anomalus, Brettanomyces bruxellensis, Brettanomyces claussenii, Brettanomyces custersianus, Brettanomyces lambicus, Brettanomyces naardenensis, Brettanomyces nanus, Canida albicans, Candida blankii, Candida slooffi, Dekkera intermedia, Leucosporidium frigidum, Rhodotorula rubra, Saccharomyces cerevisiae, Saccharomyces pastorianus, Saccharomyces telluris, Schizosaccharomyces pombe, Sporidiobolus johnsonii, Sporidiobolus longiusculus, Sporidiobolus metaroseus, Sporidiobolus pararoseus, Sporidiobolus ruineniae, Sporidiobolus salmonicolor, Sporidiobolus veronae, Trichosporon beigelii, Trichosporon cutaneum*, and combinations thereof. In some embodiments, microbial extracts can be prepared from *S. cerevisiae* cells.

In some embodiments, microbial extracts can be prepared from one or more microbial cell types that are pathogenic in the organism to which inventive compositions are to be administered. In some embodiments, microbial extracts can be prepared from one or more microbial cell types that naturally colonize subjects to which inventive compositions are to be administered. In some embodiments, microbial extracts can be prepared from microbial cell types that are present in foods consumed by organisms to which inventive compositions are to be administered.

Without wishing to be held to a particular theory, some embodiments may be beneficial and/or desirable in their ability to recreate natural environmental exposure to one or more substances. For example, in some embodiments, the presence of a mix of naturally occurring microbial extract components may replicate an environmental exposure to one or more toxins, infectious agents, antigens and/or allergens.

Antigens

In some embodiments, provided nanoparticles and/or nanoparticle compositions further include an antigen. Antigens can be any of a variety of antigens including peptides, proteins, polysaccharides, saccharides, lipids, glycolipids, nucleic acids, or combinations thereof. The antigen can be derived from any source, including, but not limited to, a virus, bacterium, parasite, plant, protozoan, fungus, tissue or transformed cell such as a cancer or leukemic cell and can be a whole cell or immunogenic component thereof, e.g., cell wall components or molecular components thereof. In some embodiments, crude extracts including one or more antigens may be used.

In some embodiments, an antigen is an infectious agent antigen. In some embodiments, an infectious agent antigen is provided with one or more additional components of an infectious agent. In some embodiments, an antigen or infectious agent is selected from the group consisting of an allergen, an infectious antigen, a disease-associated antigen (e.g. a tumor-associated antigen), an autoantigen, or combinations thereof. In some embodiments, some or all of the antigen is encapsulated within the internal lumen of the nanoparticle.

In some embodiments, suitable antigens are known in the art and are available from commercial government and scientific sources. In some embodiments, antigens are provided from whole inactivated or attenuated organisms. In some embodiments, antigens may be provided from infectious organisms, such as viruses, parasites and bacteria. In some embodiments, antigens may be provided from tumor cells. In some embodiments, the antigens may be purified or partially purified polypeptides derived from tumors or viral or bacterial sources. Exemplary criteria for identifying and selecting effective antigenic peptides (e.g., minimal peptide sequences capable of eliciting an immune response) may be found in the art. For example, Apostolopoulos, et al. (*Curr. Opin. Mol. Ther.*, 2:29-36 (2000)), discusses the strategy for identifying minimal antigenic peptide sequences based on an understanding of the three dimensional structure of an antigen-presenting molecule and its interaction with both an antigenic peptide and T-cell receptor. Shastri, (*Curr. Opin. Immunol.*, 8:271-7 (1996)), discloses how to distinguish rare peptides that serve to activate T cells from the thousands peptides normally bound to MHC molecules. The antigens may be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

In some embodiments, antigens may be provided as single antigens or may be provided in combination. In some embodiments, antigens may also be provided as complex mixtures of polypeptides or nucleic acids.

In some embodiments, antigens are provided as crude extract (e.g. whole peanut extract). In some embodiments, provided nanoparticles and/or nanoparticle compositions may include one or more crude antigenic extracts. In some embodiments, crude extract can be a useful and inexpensive alternative to using individual antigens in provided nanoparticle compositions.

In some embodiments, provided nanoparticles and/or nanoparticle compositions may include one or more viral antigens. Generally, a virus consists of either two or three parts: 1) genetic material, which may be DNA or RNA, depending on the virus, 2) a protein coat that surrounds and protects the genetic material, and, in some viruses, 3) a lipid envelope that surrounds the protein coat. In some embodiments, a viral antigen may be provided from any component of a virus. In some embodiments, a viral antigen may be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carla virus, Caulimovirus, Circoviridae, Closterovirus, Comoviridae, Coronavtridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenza virus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D 1 NS 1, Dengue D 1 NS2, and Dengue D1NS3. In some embodiments, a viral antigen may comprise or consist of fragments of one or more viruses, such as fragments from an influenza virus, for example. In some embodiments, viral fragments are provided from one or more of 1) viral genetic material 2) a portion of a viral protein coat, and/or 3) a portion of a viral lipid envelope. In some embodiments, viral fragments may be provided from two or more of 1) viral genetic material 2) a portion of a viral protein coat, and/or 3) a portion of a viral lipid envelope.

Exemplary viral antigens include, but are not limited to, those found in the following viral strains such as an adenovirus, borrelia, chagas, coxsackieviruses, cytomegalovirus, dengue, Epstein-Barr (EBV), encephalitis (e.g. equine encephalitis and Japanese encephalitis), hantavirus, hepatitis A (HAV), hepatits B (HBV), hepatitis C (HCV), delta hepatitis D (HDV), hepatitis E (HEV), hepatitis G virus (HGV), herpes simplex virus (HSV)(i.e. HSV1 and HSV2), human immunodeficiency virus (HIV), human T-lymphotrophic virus (HTLV), influenza, lymphocytic choriomeningitis (LCMV), malaria, measles, *mycoplasma*, papillomavirus (e.g. human papillomavirus, HPV), parainfluenza, parvovirus, rhinovirus, Rift Valley fever, rotavirus, rubella, SARS, *toxoplasma*, treponema, varicella-zoster (VZV), west nile virus (WNV), yellow fever, and combinations thereof.

In some embodiments, provided nanoparticles and/or nanoparticle compositions may include one or more bacterial antigens. Bacterial antigens may originate from any bacteria including, but not limited to *Actinomyces, Aeromonas, Anabaena, Arthrobacter, Bacillus, Bacteroides, Bdellovibrio, Bordetella, Borrelia, Campylobacter, Caulobacter, Chlamydia, Chlorobium, Chromatium, Citrobacter, Clostridium, Corynebacterium, Cytophaga, Deinococcus, Enterobacter, Escherichia, Francisella, Haemophilus, Halobacterium, Heliobacter, Hemophilus* influenza type B (HIB), *Hyphomicrobium, Klebsiella, Lactococcus, Legion-* ella, *Leptspirosis, Listeria, Meningococcus* A, B and C, *Methanobacterium, Micrococcus, Morganella, Mycoplasma, Myobacterium, Myxococcus, Neisseria, Nitrobacter, Oscillatoria, Peptococcus, Phodospirillum, Plesiomonas, Prochloron, Proteus, Providencia, Pseudomonas, Rickettsia, Salmonella, Serratia, Shigella, Spirillum, Spirochaeta, Sporolactobacillu, Staphylococcus, Streptococcus, Streptomyces, Sulfolobus, Thermoplasma, Thiobacillus, Treponema, Vibrio, Yersinia*, and combinations thereof.

In some embodiments, provided nanoparticles and/or nanoparticle compositions may include one or more parasite antigens. Parasite antigens can be obtained from parasites such as, but not limited to, an antigen derived from *Candida albicans, Candida tropicalis, Chlamydia trachomatis, Chlamydial psittaci, Cryptococcus neoformans, Entamoeba histolytica, Histoplasma capsulatum, Mycoplasma pneumoniae, Nocardia asteroides, Plasmodium falciparum, Rickettsia ricketsii, Rickettsia typhi, Schistosoma mansoni, Toxoplasma gondii, Trichomonas vaginalis* and *Trypanosoma brucei*. These include Sporozoan antigens, Plasmodian antigens, such as all or part of a Circumsporozoite protein, a Sporozoite surface protein, a liver stage antigen, an apical membrane associated protein, or a Merozoite surface protein.

In some embodiments, provided nanoparticles and/or nanoparticle compositions may include one or more environmental antigens. Exemplary environmental antigens include, but are not limited to, those derived from naturally occurring allergens such as pollen allergens (tree-, weed-, and grass pollen allergens), insect allergens (inhalant, saliva and venom allergens), animal hair and/or dander allergens.

In some embodiments, an antigen may be an allergen found in certain foods, venom, drugs or rubber that are capable of eliciting allergic responses, and in particular anaphylactic allergic responses in an individual. Exemplary allergens that may induce anaphylaxis, include several protein allergens found in food (peanut, milk, egg, wheat), insect venom (i.e. bees, reptiles), drugs, and latex. In some embodiments, an environmental antigen may be one or more venoms. Stings from organisms that inject venoms, such as insect stings are known to cause anaphylaxis in individuals with allergies to the venom. In general, insect venom includes venom from Hymenoptera such as bees, hornets, wasps, yellow jackets, velvet ants, and fire ants. For example, venom from honey bees of the genus *Apis* can cause anaphylaxis in stung victims who are allergic (Weber et al. *Allergy* 42:464-470). The venom from honey bees contains numerous compounds which have been extensively studied and characterized (see for a reference, Banks and Shipolini. *Chemistry and Pharmacology of Honey-bee Venom*. Chapter 7 of *Venoms of the Hymenoptera*. Ed. T. Piek. Academic Press. London. 1986). The two main components of bee venom are phospholipase A2 and melittin and may be used in some embodiments for treating and preventing allergies to bee venom. Non-limiting examples of protein allergens found in food include proteins found in nuts (e.g., peanut, walnut, almond, pecan, cashew, hazelnut, pistachio, pine nut, brazil nut), seafood (e.g. shrimp, crab, lobster, clams), fruit (e.g. plums, peaches, nectarines; *Ann Allergy Asthma Immunol* 7(6):504-8 (1996); cherries, *Allergy* 51(10):756-7 (1996)), seeds (sesame, poppy, mustard), and soy and dairy products (e.g., egg, milk).

In some embodiments, protein antigens found in pollen-related food allergies may be used (e.g. birch pollen related to apple allergies). Important pollen allergens from trees, grasses and herbs originate from the taxonomic orders of Fagales, Oleales, Pinales and platanaceae including i.a., birch (*Betula*), alder (*Alnus*), hazel (*Corylus*), hornbeam (*Carpinus*) and olive (*Olea*), cedar (*Cryptoineriaand Juniperus*), Plane tree (*Platanus*), the order of Poales including i.e. grasses of the genera *Lolium, Phleum, Poa, Cynodon, Dactylis, Holcus, Phalaris, Secale*, and *Sorghum*, the orders of Asterales and Urticales including i.e. herbs of the genera *Ambrosia, Artemisia*, and *Parietaria*.

In some embodiments, an antigen may be one or more allergens from house dust mites of the genus *Dermatophagoides* and *Euroglyphus*, storage mite e.g *Lepidoglyphys, Glycyphagus* and *Tyrophagus*, cockroaches, midges and fleas e.g. *Blatella, Periplaneta, Chironomus* and *Ctenocephalides*, mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

In some embodiments, it may be desirable to work in systems in which a single compound (e.g., a single protein) is responsible for an observed allergy. In some embodiments, an antigen may comprise more complex allergens and/or crude allergenic extracts. Therefore, collections of more than one antigen may be used so that immune responses to multiple antigens may be modulated with a single embodiment.

In an effort to better exemplify some embodiments, an exemplary list of antigens and/or antigenic extracts (such as one or more allergens and/or allergenic extracts) that may be used in some embodiments include, but are not limited to, *Acarus siro* (mite) fatty acid-binding protein (Aca s 13); *Actinidia chinensis* (kiwi) cysteine protease (Act c 1); *Aedes aegyptii* (mosquito) antigen (Aed a 2); *Aedes aegyptii* (mosquito) antigen (Aed a 2); *Aedes aegyptii* (mosquito) apyrase (Aed a 1); *Aedes aegyptii* (mosquito) apyrase (Aed a 1); *Alnus glutinosa* (alder) antigen (Aln g 1); *Alternaria alternata* (fungus) acid, ribosomal protein P1 (Alt a 12); *Alternaria alternata* (fungus) aldehyde dehydrogenase (Alt a 10); *Alternaria alternata* (fungus) antigen (Alt a 1); *Alternaria alternata* (fungus) antigen (Alt a 2); *Alternaria alternata* (fungus) enloase (Alt a 11); *Alternaria alternata* (fungus) heat shock protein (Alt a 3); *Alternaria alternata* (fungus) ribosomal protein (Alt a 6); *Alternaria alternata* (fungus) YCP4 protein (Alt a 7); *Ambrosia artemisiifolia* (short ragweed) antigen E (Amb a 1); *Ambrosia artemisiifolia* (short ragweed) antigen K (Amb a 2); *Ambrosia artemisiifolia* (short ragweed) Ra3 antigen (Amb a 3); *Ambrosia artemisiifolia* (short ragweed) Ra5 antigen (Amb a 5); *Ambrosia artemisiifolia* (short ragweed) Ra6 antigen (Amb a 6); *Ambrosia artemisiifolia* (short ragweed) Ra7 antigen (Amb a 7); *Ambrosia trifida* (giant ragweed) Ra5G antigen (Amb t 5); *Anisakis simplex* (nematode) antigen (Ani s 1); *Anisakis simplex* (nematode) paramyosin (Ani s 2); *Apis mellifera* (honey bee) antigen (Api m 6); *Apis mellifera* (honey bee) hyaluronidase (Api m 2); *Apis mellifera* (honey bee) melittin (Api m 4); *Apis mellifera* (honey bee) phospholipase A2 (Api m 1); *Apium graveolens* (celery) antigen (Api g 5); *Apium graveolens* (celery) Bet v 1 homologue (Api g 1); *Apium graveolens* (celery) profilin (Api g 4); *Arachis hypogaea* (peanut) (conglutin Ar a h 2); *Arachis hypogaea* (peanut) (profilin Ar a h 5); *Arachis hypogaea* (peanut) conglutin homologue (Ar a h 6); *Arachis hypogaea* (peanut) conglutin homologue (Ar a h 7); *Arachis hypogaea* (peanut) glycinin (Ar a h 3); *Arachis hypogaea* (peanut) glycinin (Ar a h 4); *Arachis hypogaea* (peanut) vicilin (Ar a h 1); *Artemisia vulgaris* (mugwort) antigen (Art v 1); *Artemisia vulgaris* (mugwort) antigen (Art v 2); *Ascaris suum* (worm) antigen (Asc s 1); *Aspergillus flavus* (fungus) alkaline serine proteinase (Asp fl 13); *Aspergillus Fumigatus* (fungus) alkaline serine proteinase (Asp f 13); *Aspergillus Fumigatus* (fungus) antigen (Asp f 1); *Aspergillus Fumigatus* (fungus) antigen (Asp f 15); *Aspergillus Fumigatus* (fungus) antigen (Asp f 16); *Aspergillus Fumigatus* (fungus) antigen (Asp f 17); *Aspergillus Fumigatus* (fungus) antigen (Asp f 2); *Aspergillus Fumigatus* (fungus) antigen (Asp f 4); *Aspergillus Fumigatus* (fungus) antigen (Asp f 7); *Aspergillus Fumigatus* (fungus) antigen (Asp f 9); *Aspergillus Fumigatus* (fungus) aspartis protease (Asp f 10); *Aspergillus Fumigatus* (fungus) heat shock protein P70 (Asp f 12); *Aspergillus Fumigatus* (fungus) metalloprotease (Asp f 5); *Aspergillus Fumigatus* (fungus) Mn superoxide dismutase (Asp f 6); *Aspergillus Fumigatus* (fungus) peptidyl-prolyl isomerase (Asp f 11); *Aspergillus Fumigatus* (fungus) peroxisomal protein (Asp f 3); *Aspergillus Fumigatus* (fungus) ribosomal protein P2 (Asp f 8); *Aspergillus Fumigatus* (fungus) vacuolar serine (Asp f 18); *Aspergillus niger* (fungus) antigen (Asp n 18); *Aspergillus niger* (fungus) beta-xylosidase (Asp n 14); *Aspergillus niger* (fungus) vacuolar serine proteinase; *Aspergillus oryzae* (fungus) alkaline serine proteinase (Asp o 13); *Aspergillus oryzae* (fungus) TAKA-amylase A (Asp o 2); *Bertholletia excelsa* (Brazil nut) 2S albumin (Ber e 1); *Betula verrucosa* (birch) antigen (Bet v 1); *Betula verrucosa* (birch) antigen (Bet v 3); *Betula verrucosa* (birch) antigen (Bet v 4); *Betula verrucosa* (birch) cyclophilin (Bet v 7); *Betula verrucosa* (birch) isoflavone reductase homologue (Bet v 5); *Betula verrucosa* (birch) profilin (Bet v 2); *Blattella germanica* (German cockroach) aspartic protease (Bla g 2); *Blattella germanica* (German cockroach) Bd90k (Bla g 1); *Blattella germanica* (German cockroach) calycin (Bla g 4); *Blattella germanica* (German cockroach) glutathione transferase (Bla g 5); *Blattella germanica* (German cockroach) troponin C (Bla g 6); *Blomia tropicalis* (mite) antigen (Blo t 5); *Blomia tropicalis* (mite) Bt11a antigen (Blo t 12); *Blomia tropicalis* (mite) Bt6 fatty acid-binding protein (Blo t); *Bombus pennsylvanicus* (bumble bee) phospholipase (Bom p 1); *Bombus pennsylvanicus* (bumble bee) protease (Bom p 4); *Bos domesticus* (cow) Ag3, lipocalin (Bos d 2); *Bos domesticus* (cow) alpha-lactalbumin (Bos d 4); *Bos domesticus* (cow) beta-lactalbumin (Bos d 5); *Bos domesticus* (cow) casein (Bos d 8); *Bos domesticus* (cow) immunoglobulin (Bos d 7); *Bos domesticus* (cow) serum albumin (Bos d 6); *Brassica juncea* (oriental mustard) 2S albumin (Bra j 1); *Brassica rapa* (turnip) prohevein-like protein (Bar r 2); *Candida albicans* (fungus) antigen (Cand a 1); *Candida boidinii* (fungus) antigen (Cand b 2); *Canis familiaris* (dog) albumin (Can f?); *Canis familiaris* (dog) antigen (Can f 1); *Canis familiaris* (dog) antigen (Can f 2); *Carpinus betulus* (hornbeam) antigen (Car b 1); *Castanea sativa* (chestnut) Bet v 1 homologue (Cas s 1); *Castanea sativa* (chestnut) chitinase (Cas s 5); *Chironomus thummi thummi* (midge) component I (Chi t 2.0101); *Chironomus thummi thummi* (midge) component IA (Chi t 2.0102); *Chironomus thummi thummi* (midge) component II-beta (Chi t 3); *Chironomus thummi thummi* (midge) component III (Chi t 1.01); *Chironomus thummi thummi* (midge) component IIIA (Chi t 4); *Chironomus thummi thummi* (midge) component IV (Chi t 1.02); *Chironomus thummi thummi* (midge) component IX (Chi t 6.02); *Chironomus thummi thummi* (midge) component VI (Chi t 5); *Chironomus thummi thummi* (midge) component VIIA (Chi t 6.01); *Chironomus thummi thummi* (midge) component VIIB (Chi t 7); *Chironomus thummi thummi* (midge) component VIII (Chi t 8); *Chironomus thummi thummi* (midge) component X (Chi t 9); *Chironomus thummi thummi* (midge) hemoglobin (Chi t 1-9); *Cladosporium herbarum* (fungus) acid, ribosomal protein P1 (Cla h 12); *Cladosporium herbarum* (fungus) aldehyde dehydrogenase (Cla h 3); *Cladosporium herbarum* (fungus) antigen (Cla h 1); *Cladosporium herbarum* (fungus) antigen (Cla h 2); *Cladosporium herbarum* (fungus) enolase (Cla h 6); *Cladosporium herbarum* (fungus) ribosomal protein); *Cladosporium herbarum* (fungus) YCP4 protein (Cla h 5); *Coprinus comatus* (shaggy cap) antigen (Cop c 1); *Coprinus comatus* (shaggy cap) antigen (Cop c 2); *Coprinus comatus* (shaggy cap) antigen (Cop c 3); *Coprinus comatus* (shaggy cap) antigen (Cop c 5); *Coprinus comatus* (shaggy cap) antigen (Cop c 7); *Corylus avellana* (hazel) antigen (Cor a 1); *Corylus avellana* (hazelnut) Bet v 1 homologue (Cor a 1.0401); *Cryptomeria japonica* (sugi) antigen (Cry j 1); *Cryptomeria japonica* (sugi) antigen (Cry j 2); *Ctenocephalides felis felis* (cat flea) antigen (Cte f 1); *Cynodon dactylon* (Bermuda grass) antigen (Cyn d 1); *Cynodon dactylon* (Bermuda grass) antigen (Cyn d 7); *Cynodon dactylon* (Bermuda grass) profilin (Cyn d 12); *Dactylis glomerata* (orchard grass) AgDg1 antigen (Dac g 1); *Dactylis glomerata* (orchard grass) antigen (Dac g 2); *Dactylis glomerata* (orchard grass) antigen (Dac g 3); *Dactylis glomerata* (orchard grass) antigen (Dac g 5); *Dermatophagoides farinae* (mite) antigen (Der f 1); *Dermatophagoides farinae* (mite) antigen (Der f 2); *Dermatophagoides farinae* (mite) antigen (Der f 3); *Dermatophagoides farinae* (mite) Mag 3, apolipophorin (Der f 14); *Dermatophagoides farinae* (mite) paramyosin (Der f 11); *Dermatophagoides farinae* (mite) tropomyosin (Der f 10); *Dermatophagoides microceras* (mite) antigen (Der m 1); *Dermatophagoides pteronyssinus* (mite) amylase (Der p 4); *Dermatophagoides pteronyssinus* (mite) antigen (Der p 2); *Dermatophagoides pteronyssinus* (mite) antigen (Der p 5); *Dermatophagoides pteronyssinus* (mite) antigen (Der p 7); *Dermatophagoides pteronyssinus* (mite) antigen P1 (Der p 1); *Dermatophagoides pteronyssinus* (mite) apolipophorin like p (Der p 14); *Dermatophagoides pteronyssinus* (mite) chymotrypsin (Der p 6); *Dermatophagoides pteronyssinus* (mite) collagenolytic serine prot. (Der p 9); *Dermatophagoides pteronyssinus* (mite) glutathione transferase (Der p 8); *Dermatophagoides pteronyssinus* (mite) tropomyosin (Der p 10); *Dermatophagoides pteronyssinus* (mite) trypsin (Der p 3); *Dolichovespula arenaria* (yellow hornet) antigen 5 (Dol a 5); *Dolichovespula maculata* (white face hornet) antigen 5 (Dol m 5); *Dolichovespula maculata* (white face hornet) phospholipase (Dol m 1); *Dolichovespula maculate* (white face hornet) hyaluronidase (Dol m 2); *Equus caballus* (horse) lipocalin (Equ c 1); *Equus caballus* (horse) lipocalin (Equ c 2); *Euroglyphus maynei* (mite) apolipophorin (Eur m 14); *Felis domesticus* (cat) cat-1 antigen (Fel d 1); *Fraxinus excelsior* (ash) antigen (Fra e 1); *Gadus callarias* (cod) allergen M (Gad c 1); *Gallus domesticus* (chicken) conalbumin; A22 (Gal d 3); *Gallus domesticus* (chicken) lysozyme (Gal d 4); *Gallus domesticus* (chicken) ovalbumin (Gal d 2); *Gallus domesticus* (chicken) ovomucoid (Gal d 1); *Gallus domesticus* (chicken) serum albumin (Gal d 5); *Glycine max* (soybean) antigen (Gly m 2); *Glycine max* (soybean) HPS (Gly m 1.0101); *Glycine max* (soybean) HPS (Gly m 1.0102); *Glycine max* (soybean) profilin (Gly m 3); *Haliotis Midae* (abalone) antigen (Hal m 1); *Helianthus annuus* (sunflower) antigen (Hel a 1); *Helianthus annuus* (sunflower) profilin (Hel a 2); *Hevea brasiliensis* (rubber) 1,3-glucanase (Hey b 2); *Hevea brasiliensis* (rubber) antigen (Hey b 3); *Hevea brasiliensis* (rubber) antigen (Hey b 5); *Hevea brasiliensis* (rubber) component of microhelix protein complex (Hey b 4); *Hevea brasiliensis* (rubber) C-terminal fragment antigen (Hey b 6.03); *Hevea brasiliensis* (rubber) elongation factor (Hey b 1); *Hevea brasiliensis* (rubber) enolase (Hey b 9); *Hevea brasiliensis* (rubber) hevein (Hey b 6.02); *Hevea brasiliensis* (rubber) hevein precursor (Hey b 6.01); *Hevea brasiliensis* (rubber) Mn-superoxide dismut (Hey b 10); *Hevea brasiliensis* (rubber) patatin homologue (Hey b 7); *Hevea brasiliensis* (rubber) profilin (Hey b 8); *Holcus lanatus* (velvet grass) antigen (Hol l 1); *Homo sapiens* (human autoallergen) antigen (Hom s 1); *Homo sapiens* (human autoallergen) antigen (Hom s 2); *Homo sapiens* (human autoallergen) antigen (Hom s 3); *Homo sapiens* (human autoallergen) antigen (Hom s 4); *Homo sapiens* (human autoallergen) antigen (Hom s 5); *Hordeum vulgare* (barley) BMAI-1 (Hor v 1); *Juglans regia* (English walnut) 2S albumin (Jug r 1); *Juglans regia* (English walnut) vicilin (Jug r 2); *Juniperus ashei* (mountain cedar) antigen (Jun a 1); *Juniperus ashei* (mountain cedar) antigen (Jun a 3); *Juniperus oxycedrus* (prickly juniper) calmodulin-like antigen (Jun o 2); *Juniperus sabinoides* (mountain cedar) antigen (Jun s 1); *Juniperus virginiana* (eastern red cedar) antigen (Jun v 1); *Lepidoglyphus destructor* (storage mite) antigen (Lep d 2.0101); *Lepidoglyphus destructor* (storage mite) antigen (Lep d 2.0102); *Ligustrum vulgare* (privet) antigen (Lig v 1); *Lolium perenne* (rye grass) antigen (Lol p Ib); *Lolium perenne* (rye grass) group I antigen (Lol p 1); *Lolium perenne* (rye grass) group II antigen (Lol p 2); *Lolium perenne* (rye grass) group III antigen (Lol p 3); *Lolium perenne* (rye grass) group IX antigen (Lol p 5); *Lolium perenne* (rye grass) trypsin (Lol p 11); *Malassezia furfur* (fungus) antigen (Mal f 1); *Malassezia furfur* (fungus) antigen (Mal f 4); *Malassezia furfur* (fungus) antigen (Mal f 5); *Malassezia furfur* (fungus) cyclophilin homologue (Mal f 6); *Malassezia furfur* (fungus) MF1 peroxisomal membrane protein (Mal f 2); *Malassezia furfur* (fungus) MF2 peroxisomal membrane protein (Mal f 3); *Malus domestica* (apple) Bet v 1 homologue (Mal d 1); *Malus domestica* (apple) lipid transfer protein (Mal d 3); *Mercurialis annua* (annual mercury) profilin (Mer a 1); *Metapenaeus ensis* (shrimp) tropomyosin (Met e 1); *Mus musculus* (mouse) MUP antigen (Mus m 1); *Myrmecia pilosula* (Australian jumper ant) antigen (Myr p 1); *Myrmecia pilosula* (Australian jumper ant) antigen (Myr p 2); *Olea europea* (olive) antigen (Ole e 1); *Olea europea* (olive) antigen (Ole e 3); *Olea europea* (olive) antigen (Ole e 4); *Olea europea* (olive) antigen (Ole e 6); *Olea europea* (olive) profilin (Ole e 2); *Olea europea* (olive) superoxide dismutase (Ole e 5); *Oryza sativa* (rice) antigen (Ory s 1); *Penaeus aztecus* (shrimp) tropomyosin (Pen a 1); *Penaeus indicus* (shrimp) tropomyosin (Pen i 1); *Penicillium brevicompactum* (fungus) alkaline serine proteinase (Pen b 13); *Penicillium citrinum* (fungus) alkaline serine proteinase (Pen c 13); *Penicillium citrinum* (fungus) heat shock protein P70 (Pen c 1); *Penicillium citrinum* (fungus) peroxisomal membrane protein (Pen c 3); *Penicillium notatum* (fungus) alkaline serine proteinase (Pen n 13); *Penicillium notatum* (fungus) N-acetyl glucosaminidase (Pen n 1); *Penicillium notatum* (fungus) vacuolar serine proteinase (Pen n 18); *Penicillium oxalicum* (fungus) vacuolar serine proteinase (Pen o 18); *Periplaneta americana* (American cockroach) Cr-PI (Per a 3); *Periplaneta americana* (American cockroach) Cr-PII (Per a 1); *Periplaneta americana* (American cockroach) tropomyosin (Per a 7); *Persea americana* (avocado) endochitinase (Pers a 1); *Phalaris aquatica* (canary grass) antigen (Pha a 1); *Phleum pratense* (timothy grass) antigen (Phl p 1); *Phleum pratense* (timothy grass) antigen (Phl p 2); *Phleum pratense* (timothy grass) antigen (Phl p 4); *Phleum pratense* (timothy grass) antigen (Phl p 6); *Phleum pratense* (timothy grass) antigen Ag 25 (Phl p 5); *Phleum pratense* (timothy grass) polygalacturonase (Phl p 13); *Phleum pratense* (timothy grass) profilin (Phl p 12); *Poa pratensis* (Kentucky blue grass) antigen (Poa p 5); *Poa pratensis* (Kentucky blue grass) group I antigen (Poa p 1); *Polistes annularies* (wasp) antigen 5 (Pol a 5); *Polistes annularies* (wasp) hyaluronidase (Pol a 2); *Polistes annularies* (wasp) phospholipase A1 (Pol a 1); *Polistes dominulus* (Mediterranean paper wasp) antigen (Pol d 1); *Polistes dominulus* (Mediterranean paper wasp) antigen (Pol d 5); *Polistes dominulus* (Mediterranean paper wasp) serine protease (Pol d 4); *Polistes exclamans* (wasp) antigen 5 (Pol e 5); *Polistes exclamans* (wasp) phospholipase A1 (Pol e 1); *Polistes fuscatus* (wasp) antigen 5 (Pol f 5); *Polistes metricus* (wasp) antigen 5 (Pol m 5); *Prunus armeniaca* (apricot) Bet v 1 homologue (Pru ar 1); *Prunus armeniaca* (apricot) lipid transfer protein (Pru ar 3); *Prunus avium* (sweet cherry) Bet v 1 homologue (Pru av 1); *Prunus avium* (sweet cherry) profilin (Pru av 4); *Prunus avium* (sweet cherry) thaumatin homologue (Pru av 2); *Prunus persica* (peach) lipid transfer protein (Pru p 3); *Psilocybe cubensis* (fungus) antigen (Psi c 1); *Psilocybe cubensis* (fungus) cyclophilin (Psi c 2); *Pyrus communis* (pear) Bet v 1 homologue (Pyr c 1); *Pyrus communis* (pear) isoflavone reductase homologue (Pyr c 5); *Pyrus communis* (pear) profilin (Pyr c 4); *Quercus alba* (white oak) antigen (Que a 1); *Rattus norvegius* (rat) antigen (Rat n 1); *Ricinus communis* (castor bean) 2S albumin (Ric c 1); *Salmo salar* (Atlantic salmon) parvalbumin (Sal s 1); *Sinapis alba* (yellow mustard) 2S albumin (Sin a 1); *Solanum tuberosum* (potato) patatin (Sol t 1); *Solenopsis geminata* (tropical fire ant) antigen (Sol g 2); *Solenopsis geminata* (tropical fire ant) antigen (Sol g 4); *Solenopsis invicta* (fire ant) antigen (Sol i 2); *Solenopsis invicta* (fire ant) antigen (Sol i 3); *Solenopsis invicta* (fire ant) antigen (Sol i 4); *Solenopsis saevissima* (Brazilian fire ant) antigen (Sol s 2); *Sorghum halepense* (Johnson grass) antigen (Sor h 1); *Syringa vulgaris* (lilac) antigen (Syr v 1); *Todarodes pacificus* (squid) tropomyosin (Tod p 1); *Trichophyton rubrum* (fungus) antigen (Tri r 2); *Trichophyton rubrum* (fungus) serine protease (Tri r 4); *Trichophyton tonsurans* (fungus) antigen (Tri t 1); *Trichophyton tonsurans* (fungus) serine protease (Tri t 4); *Vespa crabo* (European hornet) antigen 5 (Vesp c 5.0101); *Vespa crabo* (European hornet) antigen 5 (Vesp c 5.0102); *Vespa crabo* (European hornet) phospholipase (Vesp c 1); *Vespa mandarina* (giant Asian hornet) antigen (Vesp m 1.01); *Vespa mandarina* (giant Asian hornet) antigen (Vesp m 1.02); *Vespa mandarina* (giant Asian hornet) antigen (Vesp m 5); *Vespula flavopilosa* (yellowjacket) antigen 5 (Ves f 5); *Vespula germanica* (yellowjacket) antigen 5 (Ves g 5); *Vespula maculifrons* (yellowjacket) antigen 5 (Ves m 5); *Vespula maculifrons* (yellowjacket) hyaluronidase (Ves m 2); *Vespula maculifrons* (yellowjacket) phospholipase A1 (Ves m 1); *Vespula pennsylvanica* (yellowjacket) (antigen 5Ves p 5); *Vespula squamosa* (yellowjacket) antigen 5 (Ves s 5); *Vespula vidua* (wasp) antigen (Ves vi 5); *Vespula vulgaris* (yellowjacket) antigen 5 (Ves v 5); *Vespula vulgaris* (yellowjacket) hyaluronidase (Ves v 2); *Vespula vulgaris* (yellowjacket) phospholipase A1 (Ves v 1); *Zea mays* (maize, corn) lipid transfer protein (Zea m 14); and/or combinations thereof.

In some embodiments, provided nanoparticles and/or nanoparticle compositions may include cancer/tumor antigens. In some embodiments, antigens can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAAO205, Mart2, Mum-1, 2, and 3, neo-PAP, myosin class I, OS-9, pmlRARa fusion protein, PTPRK, K-ras, N-ras, Triosephosphate isomeras, Bage-1, Gage 3,4,5,6,7, GnTV, Hcrv-K-mcl, Lage-1, MagcAl, 2,3, 4,6,10,12, Mage-C2, NA-88, NY-Eso-1/Lage-2, SP17, SSX-2, and TRP2-Int2, MelanA (MART-I), gplOO (Pmell7), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-25 23H1, PSA, TAG-72-4, CA 19-9, CA 72-4, CAM 17.1, NuMa, K-ras, pCatenin, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA15-3 (CA 27.29\BCAA), CA 195, CA 242, CA-50, CAM43, CD68\KP1, C0-029, FGF-5, G250, Ga733 (EpCAM), HTgp-175, M344, MA-50, MG7-30 Ag, MOV18, NB\70K, NY-C0-1, RCAS1, SDCCAG16, TA-90 (Mac-2 binding protein\cyclophilin C-associated protein), TAAL6, TAG72, TLP, and TPS.

In some embodiments, provided nanoparticles and/or nanoparticle compositions may include one or more allergens listed in Table 1. Exemplary crude extracts include, but are not limited to, to extracts derived from the Allergen Source listed in Table 1.

TABLE 1

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| *WEED POLLENS* | | | | | |
| *Asterales* | | | | | |
| *Ambrosia artemisiifolia* (short ragweed) | Amb a 1; antigen E | | | P27759 | 1702434 |
| | | | | P27760 | 1809687 |
| | | | | P27761 | 1809687 |
| | | | | P28744 | 1809687 |
| | Amb a 2; Amb a II; antigen K; AgK | | | P27762 | 1809687 |
| | Amb a 3; Amb a III; Ra3 | | | P00304 | 7459340 |
| | Amb a 5; Allergen Amb a V; Ra5 | | | P02878 | 1390654 |
| | Amb a 6; Amb a VI; Allergen Ra6 | | | O04004 | 6863927 |
| | Amb a 8 | | | AAB51146 | 9714407 |
| | Major allergen | | | Q64LH1 | 15237444 |
| | | | | AAA32670 | 1809687 |
| *Ambrosia trifida* (giant ragweed) | Amb t 5; Ra5G | 4.4 | C | P10414 | 1711499 |
| | | | | | 3862954 |
| | | | | | 1606135 |
| *Artemisia vulgaris* (mugwort) | Art v 1 | 27-29 | C | Q84ZX5 | 12475905 |
| | | | | | 14510717 |
| | Art v 2 | 35 | P | Q7M1G9 | 1703533 |
| | | | | | 2233755 |
| | Art v 3 | | | P0C088 | 10998016 |
| *Helianthus annuus* (sunflower) | Hel a 1 | 34 | — | | 7920032 |
| | Hel a 2; profilin | 15.7 | C | O81982 | 9798651 |
| | | | | CAA75506 | 9798651 |
| | | | | Y15210 | 9798651 |
| *Mercurialis annua* | Mer a 1; profilin | 14-15 | C | O49894 | 9525453 |
| | | | | Y13271 | n/a |
| *GRASS POLLENS* | | | | | |
| *Poales* | | | | | |
| *Cynodon dactylon* (Bermuda grass) | Cyn d 1 | 32 | C | O04701 | 8757211 |
| | | | | AAB50734 | 8757211 |
| | Cyn d 7 | | C | P94092 | 9037188 |
| | | | | | 9363908 |
| | | | | X91256 | 9037188 |
| | Cyn d 12; profilin | 14 | C | O04725 | 9420135 |
| | Profilin | | | Y08390 | 9420135 |
| | Profilin 1 | | | CAA69670 | 9420135 |
| | Profilin 2 | | | CAA69669 | 9420135 |
| | Cyn d 15 | | | AAP80171 | n/a |
| *Dactylis glomerata* (orchard grass) | Dac g 2 | | | Q41183 | 1526648 |
| | Dac g II | | | 2103117A | 8116860 |
| | Dac g 3 | | | P93124 | 8811075 |
| | Dac g 4 | | | P82946 | 8977507 |
| *Holcus lanatus* (velvet grass) | Hol l 1 | | C | P43216 | 9215246 |
| | | | | | 8768803 |
| *Lolium perenne* (rye grass) | Lol p 1 | | | P14946 | 1697854 |
| | | | | | 2001733 |
| | | | | | 3718469 |
| | Lol p 2-A | | | P14947 | 2472390 |
| | Lol p 3; Lol p III | | | P14948 | 2605214 |
| | Lol p 4 | | | CAH92637 | 16198308 |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| | Lol p 5a | | | Q40240 | 1671715 |
| | Lol p 5b | | | Q40237 | 8262382 |
| | Lol p 11 | | | Q7M1X5 | 7751518 |
| *Phalaris aquatica* (canary grass) | Pha a 1 | | C | Q41260 | 8564724 7687099 |
| | Pha a 5 | | | P56166 | 8564724 |
| *Phleum pratense* (timothy grass) | Phl pI | | | CAA81613 | 7751520 |
| | Phl p 4 | | | CAD54670 | 16198308 |
| | Phl p6 | | | CAA76556 | n/a |
| | Phl p11 | | | AAN32987 | 12220472 |
| *Phleum pratense* (timothy grass) | Phl p 1 | 27 | C | X78813 | |
| | Phl p 2 | | C | 41, X75925 | |
| | Phl p 4 | | P | 41A | |
| | Phl p 5; Ag25 | 32 | C | 42 | |
| | Phl p 6 | | C | 43, Z27082 | |
| | Phl p 12; profilin | | C | 44, X77583 | |
| | Phl p 13; polygalacturonase | 55-60 | C | AJ238848 | |
| *Poa pratensis* (Kentucky blue grass) | Poa p 1; group I | 33 | P | 46 | |
| | Poa p 5 | 31/34 | C | 34, 47 | |
| *Sorghum halepense* (Johnson grass) | Sor h 1 | | C | 48 | |
| TREE POLLENS Fagales | | | | | |
| *Alnus glutinosa* (alder) | Aln g 1 | 17 | C | S50892 | |
| *Betula verrucosa* (birch) | Bet v 1 | 17 | C | see list of isoallergens | |
| | Bet v 2; profilin | 15 | C | M65179 | |
| | Bet v 3 | 8 | C | X79267 | |
| | Bet v 4 | | C | X87153/S54819 | |
| | Bet v 5; isoflavone reductase homologue | 33.5 | C | AF135127 | |
| | Bet v 7; cyclophilin | 18 | C | P P81531 | |
| *Carpinus betulus* (hornbeam) | Car b 1 | 17 | C | 51 | |
| *Castanea sativa* (chestnut) | Cas s 1; Bet v 1 homologue Cas s5; chitinase | 22 | P | 52 | |
| *Corylus avelana* (hazel) | Cor a 1 | 17 | C | 53 | |
| *Quercus alba* (white oak) | Que a 1 | 17 | P | 54 | |
| *Cryptomeria japonica* (sugi) | Cry j 1 | 41-45 | C | 55, 56 | |
| | Cry j 2 | | C | 57, D29772 | |
| *Juniperus ashei* (mountain cedar) | Jun a 1 | 43 | P | P81294 | |
| | Jun a 3 | 30 | P | P81295 | |
| *Juniperus oxycedrus* (prickly juniper) | Jun o 2; calmodulin-like | 29 | C | AF031471 | |
| *Juniperus sabinoides* (mountain cedar) | Jun s 1 | 50 | P | 58 | |
| *Juniperus virginiana* (eastern red cedar) | Jun v 1 | 43 | P | P81825 | |
| Oleales | | | | | |
| *Fraxinus excelsior* (ash) | Fra e 1 | 20 | P | 58A | |
| *Ligustrum vulgare* (privet) | Lig v 1 | 20 | P | 58A | |
| *Olea europea* (olive) | Ole e 1; | 16 | C | 59, 60 | |
| | Ole e 2; profilin | 15-18 | C | 60A | |
| | Ole e 3; | 9.2 | | 60B | |
| | Ole e 4; | 32 | P | P80741 | |
| | Ole e 5; superoxide dismutase | 16 | P | P80740 | |
| | Ole e 6; | 10 | C | U86342 | |
| *Syringa vulgaris* (lilac) | Syr v 1 | 20 | P | 58A | |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| MITES | | | | | |
| *Acarus siro* (mite) | Aca s 13; fatty acid-bind.prot. | 14* | C | AJ006774 | |
| *Blomia tropicalis* (mite) | Blo t 5; | | C | U59102 | |
| | Blo t 12; Bt11a | | C | U27479 | |
| | Blo t 13; Bt6 fatty acid-binding prot | | C | U58106 | |
| *Dermatophagoides pteronyssinus* (mite) | Der p 1; antigen P1 | 25 | C | 61 | |
| | Der p 2; | 14 | C | 62 | |
| | Der p 3; trypsin | 28/30 | C | 63 | |
| | Der p 4; amylase | 60 | C | 64 | |
| | Der p 5; | 14 | P | 65 | |
| | Der p 6; chymotrypsin | 25 | C | 66 | |
| | Der p 7; | 22-28 | C | 67 | |
| | Der p 8; glutathione transferase | | P | 67A | |
| | Der p 9; collagenolytic serine prot. | | C | 67B | |
| | Der p 10; tropomyosin | 36 | C | Y14906 | |
| | Der p 14; apolipophorin like p | | | Epton p.c. | |
| *Dermatophagoides microceras* (mite) | Der m 1; | 25 | P | 68 | |
| *Dermatophagoides farinae* (mite) | Der f 1; | 25 | C | 69 | |
| | Der f 2; | 14 | C | 70, 71 | |
| | Der f 3; | 30 | C | 63 | |
| | Der f 10; tropomyosin | 98 | C | 72 | |
| | Der f 11; paramyosin | | C | 72a | |
| | Der f 14; Mag3, apolipophorin | | C | D17686 | |
| *Euroglyphus maynei* (mite) | Eur m 14; apolipophorin | 177 | C | AF149827 | |
| *Lepidoglyphus destructor* (storage mite) | Lep d 2.0101; | 15 | C | 73, 74, 75 | |
| | Lep d 2.0102; | 15 | C | 75 | |
| ANIMALS | | | | | |
| *Bos domesticus* (domestic cattle) (see also foods) | Bos d 2; Ag3, lipocalin | 20 | C | 76, L42867 | |
| | Bos d 4; alpha-lactalbumin | 14.2 | C | M18780 | |
| | Bos d 5; beta-lactoglobulin | 18.3 | C | X14712 | |
| | Bos d 6; serum albumin | 67 | C | M73993 | |
| | Bos d 7; immunoglobulin | 160 | | 77 | |
| | Bos d 8; caseins | 20-30 | | 77 | |
| *Canis familiaris* (*Canis domesticus*) (dog) | Can f 1; | 25 | C | 78, 79 | |
| | Can f 2; | 27 | C | 78, 79 | |
| | Can f?; albumin | | C | S72946 | |
| *Equus caballus* (domestic horse) | Equ c 1; lipocalin | 25 | C | U70823 | |
| | Equ c 2; lipocali | 18.5 | P | 79A, 79B | |
| *Felis domesticus* (cat saliva) | Fel d 1; cat-1 | 38 | C | 15 | |
| *Mus musculus* (mouse urine) | Mus m 1; MUP | 19 | C | 80, 81 | |
| *Rattus norvegius* (rat urine) | Rat n 1 | 17 | C | 82, 83 | |
| FUNGI Ascomycota Dothidiales | | | | | |
| *Alternaria alternata* | Alt a 1; | 28 | C | U82633 | |
| | Alt a 2; | 25 | C | U87807, U87808 | |
| | Alt a 3; heat shock protein | 70 | C | X78222, | |
| | Alt a 6; ribosomal protein | 11 | C | U87806 | |
| | Alt a 7; YCP4 protein | 22 | C | X78225 | |
| | Alt a 10; aldehyde dehydrogenase | 53 | C | X78227, P42041 | |
| | Alt a 11; enolase | 45 | C | U82437 | |
| | Alt a 12; acid.ribosomal prot P1 | 11 | C | X84216 | |
| *Cladosporium herbarum* | Cla h 1; | 13 | | 83a, 83b | |
| | Cla h 2; | 23 | | 83a, 83b | |
| | Cla h 3; aldehyde dehydrogenase | 53 | C | X78228 | |
| | Cla h 4; ribosomal protein | 11 | C | X78223 | |
| | Cla h 5; YCP4 protein | 22 | C | X78224 | |
| | Cla h 6; enolase | 46 | C | X78226 | |
| | Cla h 12; acid.ribosomal prot P1 | 11 | C | X85180 | |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| | Eurotiales | | | | |
| | Asp fl 13; alkaline serine proteinase | 34 | | 84 | |
| *Aspergillus Fumigatus* | Asp f 1; | 18 | C | 83781, S39330 | |
| | Asp f 2; | 37 | C | U56938 | |
| | Asp f 3; peroxisomal protein | 19 | C | U20722 | |
| | Asp f 4; | 30 | C | AJ001732 | |
| | Asp f 5; metalloprotease | 42 | C | Z30424 | |
| | Asp f 6; Mn superoxide dismutase | 26.5 | C | U53561 | |
| | Asp f 7; | 12 | C | AJ223315 | |
| | Asp f 8; ribosomal protein P2 | 11 | C | AJ224333 | |
| | Asp f 9; | 34 | C | AJ223327 | |
| | Asp f 10; aspartic protease | 34 | | X85092 | |
| | Asp f 11; peptidyl-prolyl isom | 24 | C | 84a | |
| | Asp f 12; heat shock prot. P70 | 65 | | U92465 | |
| | Asp f 13; alkaline serine proteinase | 34 | C | 84b | |
| | Asp f 15; | 16 | C | AJ002026 | |
| | Asp f 16; | 43 | C | g3643813 | |
| | Asp f 17; | 34 | | AJ224865 | |
| | Asp f 18; vacuolar serine | 90 | P | 84c | |
| | Asp f?; | 55 | P | 85 | |
| | Asp f?; | | | 86 | |
| *Aspergillus niger* | Asp n 14; beta-xylosidase | 105 | C | AF108944 | |
| | Asp n 18; vacuolar serine proteinase | 34 | C | 84b | |
| | Asp n ?; | 85 | C | Z84377 | |
| *Aspergillus oryzae* | Asp o 2; TAKA-amylase A | 53 | C | D00434, M33218 | |
| | Asp o 13; alkaline serine proteinase | 34 | C | X17561 | |
| *Penicillium brevicompactum* | Pen b 13; alkaline serine Proteinase | 33 | | 86a | |
| *Penicillium citrinum* | Pen c 1; heat shock protein P70 | 70 | C | U64207 | |
| | Pen c 3; peroxisomal membrane protein | | | 86b | |
| | Pen c 13; alkaline serine proteinase | 33 | | 86a | |
| *Penicillium notatum* | Pen n 1; N-acetyl glucosaminidase | 68 | | 87 | |
| | Pen n 13; alkaline serine proteinase | 34 | | 89 | |
| | Pen n 18; vacuolar serine proteinase | 32 | | 89 | |
| *Penicillium oxalicum* | Pen o 18; vacuolar serine proteinase | 34 | | 89 | |
| | Onygenales | | | | |
| *Trichophyton rubrum* | Tri r 2; | | C | 90 | |
| | Tri r 4; serine protease | | C | 90 | |
| *Trichophyton tonsurans* | Tri t 1; | 30 | P | 91 | |
| | Tri t 4; serine protease | 83 | C | 90 | |
| | Saccharomycetales | | | | |
| *Candida albicans* | Cand a 1 | 40 | C | 88 | |
| *Candida boidinii* | Cand b 2 | 20 | C | J04984, J04985 | |
| | Basidiomycota Basidiolelastomycetes | | | | |
| *Malassezia furfur* | Mal f 1; | | | 91a | |
| | Mal f 2; MF1 peroxisomal membrane protein | 21 | C | AB011804 | |
| | Mal f 3; MF2 peroxisomal membrane protein | 20 | C | AB011805 | |
| | Mal f 4, | 35 | C | Takesako, p.c. | |
| | Mal f 5; | 18* | C | AJ011955 | |
| | Mal f 6; cyclophilin homologue | 17* | C | AJ011956 | |
| | Basidiomycetes | | | | |
| *Psilocybe cubensis* | Psi c 1; | 16 | | 91b | |
| | Psi c 2; cyclophilin | | | | |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| *Coprinus comatus* (shaggy cap) | Cop c 1; Cop c 2; Cop c 3; Cop c 5; Cop c 7; | 11 | C | AJ132235 Brander, p.c. Brander, p.c. Brander, p.c. | |
| INSECTS | | | | | |
| *Aedes aegyptii* (mosquito) | Aed a 1; apyrase Aed a 2; | 68 37 | C C | L12389 M33157 | |
| *Apis mellifera* (honey bee) | Api m 1; phospholipase A2 | 16 | C | 92 | |
| | Api m 2; hyaluronidase | 44 | C | 93 | |
| | Api m 4; melittin | 3 | C | 94 | |
| | Api m 6; | 7-8 | P | Kettner, p.c. | |
| *Bombus pennsylvanicus* (bumble bee) | Bom p 1; phospholipase Bom p 4; protease | 16 | P P | 95 95 | |
| *Blattella germanica* (German cockroach) | Bla g 1; Bd90k Bla g 2; aspartic protease Bla g 4; calycin Bla g 5; glutathione transf. Bla g 6; troponin C | 36 21 22 27 | C C C C C | 96 97 98 98 | |
| *Periplaneta americana* (American cockroach) | Per a 1; Cr-PII Per a 3; Cr-PI Per a 7; tropomyosin | 72-78 37 | C C C | 98A Y14854 | |
| *Chironomus thummi thummi* (midges) | Chi t 1-9; hemoglobin Chi t 1.01; component III Chi t 1.02; component IV Chi t 2.0101; component I Chi t 2.0102; component IA Chi t 3; component II-beta Chi t 4; component IIIA Chi t 5; component VI Chi t 6.01; component VIIA Chi t 6.02; component IX Chi t 7; component VIIB Chi t 8; component VIII Chi t 9; component X | 16 16 16 16 16 16 16 16 16 16 16 16 16 | C C C C C C C C C C C C C | 99 P02229 P02230 P02221 P02221 P02222 P02231 P02224 P02226 P02223 P02225 P02227 P02228 | |
| *Dolichovespula maculata* (white face hornet) | Dol m 1; phospholipase A1 Dol m 2; hyaluronidase Dol m 5; antigen 5 | 35 44 23 | C C C | 100 101 102, 103 | |
| *Dolichovespula arenaria* (yellow hornet) | Dol a 5; antigen 5 | 23 | C | 104 | |
| *Polistes annularies* (wasp) | Pol a 1; phospholipase A1 Pol a 2; hyaluronidase Pol a 5; antigen 5 | 35 44 23 | P P C | 105 105 104 | |
| *Polistes dominulus* (Mediterranean paper wasp) | Pol d 1; Pol d 4; serine protease Pol d 5; | 32-34 | C | DR Hoffman DR Hoffman P81656 | |
| *Polistes exclamans* (wasp) | Pol e 1; phospholipase A1 Pol e 5; antigen 5 | 34 23 | P C | 107 104 | |
| *Polistes fuscatus* (wasp) | Pol f 5; antigen 5 | 23 | C | 106 | |
| *Polistes metricus* (wasp) | Pol m 5; antigen 5 | 23 | P | 106 | |
| *Vespa crabo* (European hornet) | Vesp c 1; phospholipase Vesp c 5.0101; antigen 5 Vesp c 5.0102; antigen 5 | 34 23 23 | P C C | 107 106 106 | |
| *Vespa mandarina* (giant asian hornet) | Vesp m 1.01; Vesp m 1.02; Vesp m 5; | | | DR Hoffman DR Hoffman P81657 | |
| *Vespula flavopilosa* (yellowjacket) | Ves f 5; antigen 5 | 23 | C | 106 | |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| *Vespula germanica* (yellowjacket) | Ves g 5; antigen 5 | 23 | C | 106 | |
| *Vespula maculifrons* (yellowjacket) | Ves m 1; phospholipase A1 | 33.5 | C | 108 | |
| | Ves m 2; hyaluronidase | 44 | P | 109 | |
| | Ves m 5; antigen 5 | 23 | 23 | 104 | |
| *Vespula pennsylvanica* (yellowjacket) | Ves p 5; antigen 5 | 23 | C | 106 | |
| *Vespula squamosa* (yellowjacket) | Ves s 5; antigen 5 | 23 | C | 106 | |
| *Vespula vidua* (wasp) | Ves vi 5; | 23 | C | 106 | |
| *Vespula vulgaris* (yellowjacket) | Ves v 1; phopholipase A1 | 35 | C | 105A | |
| | Ves v 2; hyaluronidase | 44 | P | 105A | |
| | Ves v 5; antigen 5 | 23 | C | 104 | |
| *Myrmecia pilosula* (Australian jumper ant) | Myr p 1, | | C | X70256 | |
| | Myr p 2; | | C | S81785 | |
| *Solenopsis geminata* (tropical fire ant) | Sol g 2; | | | DR Hoffman | |
| | Sol g 4 | | | DR Hoffman | |
| *Solenopsis invicta* (fire ant) | Sol i 2; | 13 | C | 110, 111 | |
| | Sol i 3; | 24 | C | 110 | |
| | Sol i 4; | 13 | C | 110 | |
| *Solenopsis saevissima* (brazilian fire ant) | Sol s 2; | | | DR Hoffman | |

FOODS

| *Gadus callarias* (cod) | Gad c 1; allergen M | 12 | C | 112, 113 | |
| *Salmo salar* (Atlantic salmon) | Sal s 1; parvalbumin | 12 | C | X97824, X97825 | |
| *Bos domesticus* (domestic cattle) | Bos d 4; alpha-lactalbumin | 14.2 | C | M18780 | |
| | Bos d 5; beta-lactoglobulin | 18.3 | C | X14712 | |
| | Bos d 6; serum albumin | 67 | C | M73993 | |
| | Bos d 7; immunoglobulin | 160 | | 77 | |
| | Bos d 8; caseins | 20-30 | | 77 | |
| *Gallus domesticus* (chicken) | Gal d 1; ovomucoid | 28 | C | 114, 115 | |
| | Gal d 2; ovalbumin | 44 | C | 114, 115 | |
| | Gal d 3; conalbumin (Ag22) | 78 | C | 114, 115 | |
| | Gal d 4; lysozyme | 14 | C | 114, 115 | |
| | Gal d 5; serum albumin | 69 | C | X60688 | |
| *Metapenaeus ensis* (shrimp) | Met e 1; tropomyosin | | C | U08008 | |
| *Penaeus aztecus* (shrimp) | Pen a 1; tropomyosin | 36 | P | 116 | |
| *Penaeus indicus* (shrimp) | Pen i 1; tropomyosin | 34 | C | 117 | |
| *Todarodes pacificus* (squid) | Tod p 1; tropomyosin | 38 | P | 117A | |
| *Haliotis Midae* (abalone) | Hal m 1 | 49 | — | 117B | |
| *Apium graveolens* (celery) | Api g 1; Bet v 1 homologue | 16* | C | Z48967 AF129423 | |
| | Api g 4; profilin | 55/58 | P | P81943 | |
| | Api g 5; | | | | |
| *Brassica juncea* (oriental mustard) | Bra j 1; 2S albumin | 14 | C | 118 | |
| *Brassica rapa* (turnip) | Bra r 2; prohevein-like protein | 25 | ? | P81729 | |
| *Hordeum vulgare* (barley) | Hor v 1; BMAI-1 | 15 | C | 119 | |
| *Zea mays* (maize, corn) | Zea m 14; lipid transfer prot. | 9 | P | P19656 | |
| *Corylus avellana* (hazelnut) | Cor a 1.0401; Bet v 1 homologue | 17 | C | AF136945 | |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| *Malus domestica* (apple) | Mal d 1; Bet v 1 homologue | | C | X83672 | |
| | Mal d 3; lipid transfer protein | 9 | C | Pastorello | |
| *Pyrus communis* (pear) | Pyr c 1; Bet v 1 homologue | 18 | C | AF05730 | |
| | Pyr c 4; profilin | 14 | C | AF129424 | |
| | Pyr c 5; isoflavone reductase homologue | 33.5 | C | AF071477 | |
| *Oryza sativa* (rice) | Ory s 1; | | C | U31771 | |
| *Persea americana* (avocado) | Pers a 1; endochitinase | 32 | C | Z78202 | |
| *Prunus armeniaca* (apricot) | Pru ar 1; Bet v 1 homologue | | C | U93165 | |
| | Pru ar 3; lipid transfer protein | 9 | P | | |
| *Prunus avium* (sweet cherry) | Pru av 1; Bet v 1 homologue | | C | U66076 | |
| | Pru av 2; thaumatin homologue | 15 | C | U32440 | |
| | Pru av 4; profilin | | C | AF129425 | |
| *Prunus persica* (peach) | Pru p 3; lipid transfer protein | 10 | P | P81402 | |
| *Sinapis alba* (yellow mustard) | Sin a 1; 2S albumin | 14 | C | 120 | |
| *Glycine max* (soybean) | Gly m 1.0101; HPS | 7.5 | P | 121 | |
| | Gly m 1.0102; HPS | 7 | P | 121 | |
| | Gly m 2 | 8 | P | A57106 | |
| | Gly m 3; profilin | 14 | C | AJ223982 | |
| *Arachis hypogaea* (peanut) | Ara h 1; vicilin | 63.5 | C | L34402 | |
| | Ara h 2; conglutin | 17 | C | L77197 | |
| | Ara h 3; glycinin | 14 | C | AF093541 | |
| | Ara h 4; glycinin | 37 | C | AF086821 | |
| | Ara h 5; profilin | 15 | C | AF059616 | |
| | Ara h 6; conglutin homolog | 15 | C | AF092846 | |
| | Ara h 7; conglutin homolog | 15 | C | AF091737 | |
| *Actinidia chinensis* (kiwi) | Act c 1; cysteine protease | 30 | P | P00785 | |
| *Solanum tuberosum* (potato) | Sol t 1; patatin | 43 | P | P15476 | |
| *Bertholletia excelsa* (Brazil nut) | Ber e 1; 2S albumin | 9 | C | P04403, M17146 | |
| *Juglans regia* (English walnut) | Jug r 1; 2S albumin | 44 | C | U66866 | |
| | Jug r 2; vicilin | | C | AF066055 | |
| *Ricinus communis* (Castor bean) | Ric c 1; 2S albumin | | C | P01089 | |
| OTHERS | | | | | |
| *Anisakis simplex* (nematode) | Ani s 1 | 24 | P | A59069 | |
| | Ani s 2; paramyosin | 97 | C | AF173004 | |
| *Ascaris suum* (worm) | Asc s 1; | 10 | P | 122 | |
| *Aedes aegyptii* (mosquito) | Aed a 1; apyrase | 68 | C | L12389 | |
| | Aed a 2; | 37 | C | M33157 | |
| *Hevea brasiliensis* (rubber) | Hev b 1; elongation factor | 58 | P | 123, 124 | |
| | Hev b 2; (1,3-glucanase | 58 | P | 123, 124 | |
| | Hev b 2; (1,3-glucanase | 34/36 | C | 125 | |
| | Hev b 3 | 24 | P | 126, 127 | |
| | Hev b 4; component of microhelix protein complex | 100/110/115 | P | 128 | |
| | Hev b 5 | 16 | C | U42640 | |
| | Hev b 6.01 hevein precursor | 20 | C | M36986/p02877 | |
| | Hev b 6.02 hevein | 5 | C | M36986/p02877 | |
| | Hev b 6.03 C-terminal fragment | 14 | C | M36986/p02877 | |
| | Hev b 7; patatin homologue | 46 | C | U80598 | |

TABLE 1-continued

Exemplary Antigens

| ALLERGEN SOURCE | SYSTEMATIC AND ORIGINAL NAMES | MW KDA | SEQ | ACCESSION NO. | PMID (CITATION) |
|---|---|---|---|---|---|
| | Hev b 8; profilin | 14 | C | Y15042 | |
| | Hev b 9; enolase | 51 | C | AJ132580/AJ132581 | |
| | Hev b 10; Mn-superoxide dismut | 26 | C | AJ249148 | |
| *Ctenocephalides felis felis* (cat flea) | Cte f 1; | — | — | — | |
| | Cte f 2; M1b | 27 | C | AF231352 | |
| *Homo sapiens* (human autoallergens) | Hom s 1; | 73* | C | Y14314 | |
| | Hom s 2; | 10.3* | C | X80909 | |
| | Hom s 3; | 20.1* | C | X89985 | |
| | Hom s 4; | 36* | C | Y17711 | |
| | Hom s 5; | 42.6* | C | P02538 | |

In some embodiments, cancer antigens are provided in crude form such as a cellular lysate or cellular fraction. Exemplary cellular lysates and/or cellular lysate fractions include, but are not limited to, cancer cells from acute lymphoblastic leukemia (ALL); adrenocortical carcinoma; AIDS-related cancers including AIDS-related lymphoma; anal cancer; appendix cancer; astrocytomas; basal cell carcinoma; bile duct cancer; bladder cancer; bone cancer (e.g., osteosarcoma and malignant fibrous histiocytoma); brainstem glioma; brain cancer; brain tumors; breast cancer; bronchial adenomas/carcinoids; Burkitt lymphoma; carcinoid tumors (e.g., childhood and gastrointestinal tumors); carcinoma (including carcinoma of unknown primary (CUP) whose origin or developmental lineage is unknown but that possess specific molecular, cellular, and histological characteristics of epithelial cells); central nervous system lymphoma; cerebellar astrocytoma; malignant glioma; cervical cancer; childhood cancers; chronic lymphocytic leukemia; chronic myelogenous leukemia; chronic myeloproliferative disorders; colon Cancer; cutaneous T-cell lymphoma; desmoplastic small round cell tumor; endometrial cancer; ependymoma; esophageal cancer; Ewing's sarcoma in the Ewing family of tumors; extracranial germ cell tumor; extragonadal germ cell tumor; ovarian germ cell tumor; extrahepatic bile duct cancer; eye cancer; intraocular melanoma; retinoblastoma; gallbladder cancer; gastric cancer; gastrointestinal carcinoid tumor; gastrointestinal stromal tumor (GIST); gestational trophoblastic tumor; gastric carcinoid; hairy cell leukemia; head and neck cancer; heart cancer; hepatocellular (liver) cancer; Hodgkin lymphoma; hypopharyngeal cancer; hypothalamic and visual pathway glioma; intraocular Melanoma; Islet Cell Carcinoma (Endocrine Pancreas); kaposi sarcoma; soft tissue sarcoma; uterine sarcoma; kidney cancer (renal cell carcinoma); laryngeal cancer; leukemias (including acute lymphoblastic or acute lymphocytic leukemia, acute myeloid or acute myelogenous leukemia, chronic lymphocytic or chronic lymphocytic leukemia, chronic myelogenous or chronic myeloid leukemia); Lip and Oral Cavity Cancer; liposarcoma; liver cancer; lung cancer (including non-small cell and small cell); lymphomas (e.g., AIDS-related, Burkitt, cutaneous T-Cell, Hodgkin, non-Hodgkin, Primary Central Nervous System); macroglobulinemia; medulloblastoma; melanoma; Merkel Cell Carcinoma; mesothelioma (e.g., adult malignant mesothelioma, childhood mesothelioma); metastatic squamous neck cancer; mouth cancer; Multiple Endocrine Neoplasia Syndrome; Multiple Myeloma; Mycosis Fungoides; Myelodysplastic Syndromes; Myelodysplastic/Myeloproliferative Diseases; Myelogenous Leukemia; Myeloid Leukemia; (e.g. Adult Acute; nasal cavity and paranasal sinus cancer; nasopharyngeal carcinoma; neuroblastoma; oral cancer; oropharyngeal cancer; ovarian cancer; ovarian epithelial cancer (Surface epithelial-stromal tumor); ovarian germ cell tumor; ovarian low malignant potential tumor; pancreatic cancer; paranasal sinus and nasal cavity cancer; parathyroid cancer; penile cancer; pharyngeal cancer; pheochromocytoma; pineal astrocytoma; pineal germinoma; pineoblastoma and supratentorial primitive neuroectodermal tumors; pituitary adenoma; pleuropulmonary blastoma; prostate cancer; rectal cancer; renal pelvis and ureter and transitional cell cancer; rhabdomyosarcoma; Sézary syndrome; skin cancer (including melanoma and nonmelanoma); skin carcinoma; small intestine cancer; squamous cell carcinoma; stomach cancer; testicular cancer; throat cancer; thymoma and thymic carcinoma; thyroid cancer; urethral cancer; endometrial uterine cancer; vaginal cancer; vulvar cancer; and/or combinations thereof.

In some embodiments, provided nanoparticles include one or more alloantigens. As described herein, an alloantigen refers to an antigen associated with allorecognition and/or graft rejection (e.g., an antigen against which a rejection immune response is directed). Alloantigens are generally polypeptides expressed by an individual that are genetically different from another individual of the same species. The term "alloantigen polypeptide" refers to a polypeptide whose amino acid sequence includes at least one characteristic sequence of an alloantigen. A wide variety of alloantigen sequences are known in the art.

In some embodiments, an alloantigen for use in accordance with the present invention is a major histocompatibility complex (MHC) polypeptide. In some embodiments, an alloantigen for use in accordance with the present invention is a Class I MHC polypeptide. In some embodiments, an alloantigen for use in accordance with the present invention is a Class II MHC polypeptide. In some embodiments, an alloantigen for use in accordance with the present invention contains part of or all of an extracellular domain of an MHC polypeptide. In some embodiments, an alloantigen for use in accordance with the present invention is a minor histocompatibility complex polypeptide. In some embodiments, an alloantigen for use in accordance with the present invention is a costimulatory entity (e.g., CD28, CD80, and CD86, among others). In some embodiments, an alloantigen for use in accordance with the present invention is a non-MHC protein produced by or present in graft tissue and not produced by or present in a host. One of ordinary skill in the art will recognize that alloantigens described herein are exemplary. Any polypeptide that is associated with an allorecognition and/or graft rejection can be classified as an alloantigen.

It will be appreciated that alloantigen polypeptides may have a complete sequence, or alternatively may be polypeptides that represent functional fragments (i.e., fragments retaining at least one activity and/or one characteristic sequence or portion) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another alloantigen polypeptide of the same class, is encompassed within the relevant term "alloantigen polypeptide" as used herein.

In some embodiments, it may be desirable to include nanoparticles encapsulating more than one polypeptide, such as an autoantigen and/or alloantigen polypeptide. In some embodiments, a nanoparticle may encapsulate more than one polypeptide. In some embodiments, a mixture of nanoparticles that each encapsulate one or more polypeptides may be used in accordance with the present invention. To give but one example, at least three different autoantigen polypeptides, Pancreatic β-cell antigens, insulin and glutamic acid decarboxylase (GAD) are thought to contribute to Insulin-Dependent Diabetes Mellitus (e.g., Type I diabetes abbreviated IDDM). To give another non-limiting example, several different alloantigen polypeptides are thought to contribute to graft rejection, including major histocompatibility complex polypeptides, minor histocompatibility polypeptides, and costimulatory entities. Inventive compositions may include a mixture of nanoparticles that encapsulate more than one or all of the autoantigen or alloantigen polypeptides. Also, it may be desirable to include autoantigen polypeptides that are associated with a variety of different kinds autoimmune disorders so that multiple autoimmune disorders are treated simultaneously.

Other Agents

In some embodiments, the provided nanoparticles and/or nanoparticle compositions may include one or more other agents (e.g. adjuvants). Without wishing to be held to a particular theory, it is possible that some embodiments may mimic one or more characteristics or features of microbial (e.g., bacterial) cells. In some embodiments, adjuvants may be provided from one or more bacterial sources, including bacterial cellular lysates and/or cellular lysate fractions. In some embodiments, bacterial cellular lysate fractions are or comprise entities known as pathogen-associated molecular patterns ("PAMPs"). In some embodiments, one or more of a hydrophobic bacterial cellular lysate fraction and/or hydrophilic bacterial cellular lysate fraction include one or more PAMPs as a hydrophilic cellular component and/or hydrophobic cellular component.

In some embodiments, PAMPs are entities associated with bacterial cells that are recognized by cells of the innate immune system. In some embodiments, PAMPs are recognized by Toll-like receptors (TLRs) and other pattern recognition receptors (PRRs) in both plants and animals. In some embodiments, PAMPs are recognized by C-type lectin receptors (CLRs). In some embodiments, a CLR is a type I or type II CLR. In some embodiments, PAMPs are or comprise entities associated with the outer surface of a bacterial cell, including, but not limited to, membrane-associated proteins and/or peptides, receptors embedded in bacterial membranes, etc. Exemplary PAMPs include, but are not limited to, bacterial lipopolysaccharide (LPS), bacterial flagellin, lipoteichoic acid from gram positive bacteria, peptidoglycan, double-stranded RNAs (dsRNAs), unmethylated CpG motifs, any of the TLR ligands presented in Table 2, characteristic portions thereof, and/or combinations thereof.

TABLE 2

Exemplary TLRs and TLR Ligands

| TLR | TLR Ligand(s) |
| --- | --- |
| TLR1 | Multiple triacyl lipopeptides (e.g., from bacteria and mycobacteria), such as lipopeptide Pam3Cys-SK4 ("Pam") |
| TLR2 | Multiple glycolipids, lipopeptides and lipoproteins, such as lipopeptide Pam3Cys-SK4 ("Pam") |
|  | Lipoteichoic acid |
|  | Peptidoglycan |
|  | HSP70 |
|  | Zymosan |
|  | Heat shock proteins, such as Hsp60 |
| TLR3 | Double-stranded RNA |
|  | Single-stranded RNA |
|  | Poly(I:C) |
| TLR4 | lipopolysaccharide (LPS) |
|  | Monophosphoryl lipid A (MPL) |
|  | Several heat shock proteins |
|  | Fibrinogen |
|  | Heparin sulfate fragments |
|  | Hyaluronic acid fragments |
| TLR5 | Flagellin |
| TLR6 | Multiple diacyl lipopeptides |
|  | Lipoteichoic acid (LTA) |
|  | Zymosan |
| TLR7 | Imidazoquinolines (e.g., imiquimod and resiquimod) |
|  | Single-stranded RNA, such as GU-rich single-stranded RNA |
|  | Loxoribine (a guanosine analog) |
|  | Bropirime |
| TLR8 | Imidazoquinolines (e.g., imiquimod and resiquimod) |
|  | GU-rich single-stranded RNA |
|  | Small synthetic compounds |
|  | Single-stranded RNA |
| TLR9 | Unmethylated CpG DNA |
|  | Hemazoin crystals |
|  | Double-stranded DNA |
| TLR10 |  |
| TRL11 | *Toxoplasma gondii* profilin |
|  | Uropathogenic-bacteria-derived protein |

In some embodiments, the one or more other agents is or comprises one or more adjuvants. In some embodiments, an adjuvant is a mucosal adjuvant (i.e. an adjuvant capable of eliciting or enhancing an immune response to a mucosally administered antigen). Exemplary mucosal antigens include, but are not limited to, TLR4 ligands (e.g. LPS, MPL), cytokines (e.g. IL-1α), c48/80, R848, Pam3CSK4, CpG (ODN1826), lethal factor (LF), and cholera toxin. It will be recognized by those of skill in the art that particular mucosal adjuvants may induce different immune responses. The skilled artisan will understand and be aware of technologies that may be used to select particular adjuvant(s) for use in a particular product or products and such variation is specifically contemplated as within the scope of the present invention.

One of skill in the art will recognize that multiple antigenic molecules may be delivered by nanoparticles simultaneously and/or sequentially in accordance with methods of the present invention. Without limitation, different antigenic molecules for one antigenic protein may be delivered. Different antigenic molecules from different antigenic proteins may also be delivered. Further, multiple antigenic polypeptides and proteins may be delivered in accordance with the present invention. It is also recognized that single or multiple antigenic polypeptides and single or multiple cytokines may be delivered to individuals by nanoparticles in accordance with the present invention. For example, but without limitation, allergenic antigens of the present invention and immunomodulatory molecules such as interleukins may be delivered by nanoparticles using methods in accordance with the present invention.

The present invention encompasses the recognition that a particular subject may benefit from being exposed to a combination of antigens, such as multiple allergens. In some embodiments, it may be desirable to provide a nanoparticle composition comprising multiple antigens relevant to a specific subject, and/or to a population of subjects. For example, in some embodiments, a particular provided composition will contain a combination of allergens to address some or all of a particular subject's allergies and/or a combination of allergens to address some or all allergies commonly present within a population. For example, if a particular subject is allergic to peanuts and to dust mites, a nanoparticle composition may be designed and manufactured to address both allergies. Alternatively or additionally, in some embodiments it may be desirable to prepare nanoparticle compositions including antigens from a plurality of allergens (i) to which members of a particular community are commonly exposed (e.g., by virtue of geographic location); (ii) to which subjects are exposed by a common route (e.g., inhalation, injestion, contact, etc); (iii) to which incidence of allergy within a relevant population (e.g., a geographic population, an age population, an ethnic population, etc) is above a designated threshold; (iv) to which subjects allergic to one allergen also tend of have allergy to, for example, subjects allergic to tree nuts tend to also be allergic to pecans, walnuts, and pistachios, subjects with allergy to crustaceans (e.g., lobster, crab, shrimp, or crayfish) or mollusks (e.g., clams, mussels, oysters, or scallops) tend to have allergy to various types, not just a single crustacean or mollusk.

In some embodiments, a particular provided composition may contain a combination of antigens other than allergens. For example, in some embodiments, a particular provided composition may contain a combination of antigens associated with a particular disease, disorder or condition (e.g., with a particular cancer, a particular infectious disease, a particular graft v host or host v graft syndrome, etc).

Those of skill in the art will recognize a wide variety of potential applications utilizing combinations of antigens; each of these is contemplated as within the scope of the present invention.

According to various embodiments, provided compositions comprising an antigen or other protein agent may comprise the antigen or other protein agent in any of a variety of forms. Exemplary forms include, without limitation, RNA, DNA, protein, and combinations thereof. In some embodiments, the antigen or protein agent may be provided as a portion of a cell, tissue or extract thereof.

Nanoparticle Compositions

The present invention provides a variety of new and/or improved nanoparticle compositions. The present invention encompasses the recognition that the many advantages of certain known nanoparticle compositions (such as, for example, those described in one or more of U.S. Pat. No. 7,534,448, U.S. Pat. No. 7,534,449, U.S. Pat. No. 7,550,154, US20090239789A1, US20090269397A1, US20100104503A1, US20100151436A1, US20100284965A1, WO2006080951, WO2008115641, WO2008109347, WO2009094273, WO2012167261, and WO2013003157, each of which is incorporated herein by reference) can beneficially be exploited and improved through use with one or more microbial cellular extracts and/or one or more crude antigen preparations. According to the present invention, in some embodiments, combination of nanoparticles with microbial cellular extracts comprising multiple microbial cellular components (optionally together with one or more antigens and/or one or more other agents) provides improved nanoparticles that embody certain immunologically relevant features of microbial cells.

The present invention further encompasses the recognition that known nanoparticle compositions (such as, for example, those described in one or more of U.S. Pat. No. 7,534,448, U.S. Pat. No. 7,534,449, U.S. Pat. No. 7,550,154, US20090239789A1, US20090269397A1, US20100104503A1, US20100151436A1, US20100284965A1, WO2006080951, WO2008115641, WO2008109347, WO2009094273, WO2012167261, and WO2013003157, each of which is incorporated herein by reference) can beneficially be exploited for the treatment and/or prevention of allergies. In some embodiments, the present invention provides nanoparticle compositions comprising nanoparticles together with one or more allergens. In certain such embodiments, the present invention provides nanoparticle compositions comprising nanoparticles together with one or more relatively crude allergen preparations.

The present invention further encompasses the recognition that known nanoparticle compositions (such as, for example, those described in one or more of U.S. Pat. No. 7,534,448, U.S. Pat. No. 7,534,449, U.S. Pat. No. 7,550,154, US20090239789A1, US20090269397A1, US20100104503A1, US20100151436A1, US20100284965A1, WO2006080951, WO2008115641, WO2008109347, WO2009094273, WO2012167261, and WO2013003157, each of which is incorporated herein by reference), can desirably be exploited and/or improved in a variety of contexts through combination with one or more antigen preparations and/or one or more microbial cellular extracts and/or one or more other agents as described herein.

In certain embodiments, provided nanoparticle compositions comprise nanoparticles combined with one or more cellular extracts, one or more antigen preparations, and/or one or more other agents so that certain combined elements are entrapped within lumens of the nanoparticles. In some embodiments, provided nanoparticle compositions comprise nanoparticles combined with one or more cellular extracts, one or more antigen preparations, and/or one or more other agents so that certain combined elements are associated with the external surface of nanoparticles. In some embodiments, provided nanoparticle compositions comprise nanoparticles combined with one or more cellular extracts, one or more antigen preparations, and/or one or more other agents so that certain combined elements are present both in and on nanoparticles. In some embodiments, provided nanoparticle compositions comprise nanoparticles combined with one or more cellular extracts, one or more antigen preparations, and/or one or more other agents so that certain combined elements are mixed with, but not specifically associated with any site on or in, nanoparticles.

In certain particular embodiments, the present invention provides nanoparticle compositions in which components of a hydrophilic cellular extract are localized within nanoparticle lumens; in some such embodiments, all components of a hydrophilic cellular extract are preferentially localized within nanoparticle lumens; in some such embodiments, all components of a hydrophilic cellular extract are substantially exclusively localized within nanoparticle lumens.

In certain particular embodiments, the present invention provides nanoparticle compositions in which components of a hydrophobic cellular extract are localized on the external surface of nanoparticle; in some such embodiments, all components of a hydrophobic cellular extract are preferentially localized on the nanoparticle external surface; in some such embodiments, all components of a hydrophobic cellular extract are substantially exclusively localized on the external surface.

In certain particular embodiments, the present invention provides nanoparticle compositions in which components of a hydrophilic cellular extract are localized (e.g., preferentially or substantially exclusively) within nanoparticle lumens; and components of a hydrophobic cellular extract are localized (e.g., preferentially or substantially exclusively) on the external surface of nanoparticles.

In some embodiments, it may be desirable that all or substantially all of one or more microbial components, one or more antigen preparations, and/or one or more other agents are entrapped within lumens of nanoparticles in provided compositions, for example, when administering an anaphalactic allergen to a sensitive individual. In some embodiments, it may be desirable for one or more microbial components, antigen preparations, and/or other agents to be located both within the lumens of the nanoparticles as well as on the external surface of the nanoparticles.

Associating

Any of a variety of methods of associating one or more cellular preparations, cellular extracts, one or more antigen preparations, and/or one or more other agents with a biodegradable and/or biocompatible polymer may be used according to various embodiments. Exemplary methods of associating include, but are not limited to: mixing, blending or combining under pressure substantially equal to atmospheric pressure, mixing, blending or combining under pressures elevated above atmospheric pressure, mixing, blending or combining under pressure less than atmospheric pressure (e.g. vacuum).

In some embodiments, one or more extracts, preparations and/or agents is associated covalently with a nanoparticle surface. In some embodiments, one or more extracts, preparations and/or agents is associated non-covalently with a nanoparticle surface. In some embodiments, non-covalent association involves incorporation of one or more components into the nanoparticle membrane. In some embodiments, non-covalent association involves specific binding with the nanoparticle membrane or an element incorporated therein. In some specific embodiments, one or more particular components of an extract, preparation, or agent may be coupled with a ligand that specifically binds with a target in the nanoparticle membrane. In some embodiments, a ligand-target combination utilized in such an embodiment may be, for example, biotin-avidin, antibody-antigen, GST-glutathione, mannose binding protein-mannose, Protein A-IgG, and/or S-tag.

In some embodiments, provided nanoparticle compositions may include a plurality of sets of nanoparticles that share one or more structural and/or functional characteristics. For example, in some embodiments, provided nanoparticle compositions may comprise a plurality of sets of nanoparticles, each of which includes a targeting agent that localizes members of the set to a particular target site (see U.S. Pat. Nos. 7,534,448, and 7,534,449, hereby incorporated in their entirety, for exemplary targeting agents and methods of incorporating targeting agents in nanoparticles). Alternatively or additionally, in some embodiments, provided nanoparticle compositions may comprise a plurality of sets each of which is designed to have and/or is characterized by a different half-life (e.g., in a relevant tissue or organ of interest), different components (e.g. in the lumen or associated with external surface, different populations of antigens, etc).

Pharmaceutical Compositions

In some embodiments, the present invention provides pharmaceutical compositions comprising a provided nanoparticle composition together with one or more pharmaceutically acceptable excipients.

In some embodiments, provided pharmaceutical compositions may be prepared by any appropriate method, for example as known or hereafter developed in the art of pharmacology. In general, such preparatory methods include the step of bringing a provided nanoparticle composition into association with one or more pharmaceutically acceptable excipients, and then, if necessary and/or desirable, shaping and/or packaging the product into an appropriate form for administration, for example as or in a single- or multi-dose unit.

In some embodiments, compositions may be prepared, packaged, and/or sold in bulk, as a single unit dose, and/or as a plurality of single unit doses. As used herein, a "unit dose" is a discrete amount of the pharmaceutical composition comprising a predetermined amount of the provided nanoparticle composition. The amount of the provided nanoparticle composition is generally equal to the dosage of the provided nanoparticle which would be administered to a subject and/or a convenient fraction of such a dosage such as, for example, one-half or one-third of such a dosage.

In many embodiments, provided pharmaceutical compositions are specifically formulated for mucosal delivery (e.g., oral, nasal, rectal or subligual delivery).

In some embodiments, appropriate excipients for use in provided pharmaceutical compositions may, for example, include one or more pharmaceutically acceptable solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. Alternatively or additionally, pharmaceutically acceptable excipients such as cocoa butter and/or suppository waxes, coloring agents, coating agents, sweetening, flavoring, and/or perfuming agents can be utilized. Remington's *The Science and Practice of Pharmacy*, 21$^{st}$ Edition, A. R. Gennaro (Lippincott, Williams & Wilkins, Baltimore, Md., 2005; incorporated herein by reference) discloses various excipients used in formulating pharmaceutical compositions and known techniques for the preparation thereof.

In some embodiments, an appropriate excipient is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

In some embodiments, liquid dosage forms (e.g., for oral and/or parenteral administration) include, but are not limited to, emulsions, microemulsions, solutions, suspensions, syrups, and/or elixirs. In addition to provided nanoparticle compositions, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

In some embodiments, injectable preparations, for example, sterile aqueous or oleaginous suspensions, may be formulated according to known methods using suitable dispersing agents, wetting agents, and/or suspending agents. Sterile liquid preparations may be, for example, solutions, suspensions, and/or emulsions in nontoxic parenterally acceptable diluents and/or solvents, for example, as a solution in 1,3-butanediol. Among the acceptable vehicles and solvents that may be employed, for example, are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of liquid formulations.

Liquid formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, one or more strategies may be utilized prolong and/or delay the effect of a provided nanoparticle composition after delivery.

In some embodiments, provided pharmaceutical compositions may be formulated as suppositories, for example for rectal or vaginal delivery. In some embodiments, suppository formulations can be prepared by mixing utilizing suitable non-irritating excipients such as cocoa butter, polyethylene glycol or a suppository wax which are solid at ambient temperature but liquid at body temperature and therefore melt in the body (e.g., in the rectum or vaginal cavity) and release the provided nanoparticle composition.

In some embodiments, solid dosage forms (e.g., for oral administration) include capsules, tablets, pills, powders, and/or granules. In such solid dosage forms, the provided nanoparticle composition may be mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

In some embodiments, solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

Exemplary enteric coatings include, but are not limited to, one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); HP55; polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac, and combinations thereof.

In some embodiments, solid dosage forms may optionally comprise opacifying agents and can be of a composition that they release the provided nanoparticle composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In some embodiments, the present invention provides compositions for topical and/or transdermal delivery, e.g., as a cream, liniment, ointment, oil, foam, spray, lotion, liquid, powder, thickening lotion, or gel. Particular exemplary such formulations may be prepared, for example, as products such as skin softeners, nutritional lotion type emulsions, cleansing lotions, cleansing creams, skin milks, emollient lotions, massage creams, emollient creams, make-up bases, lipsticks, facial packs or facial gels, cleaner formulations such as shampoos, rinses, body cleansers, hair-tonics, or soaps, or dermatological compositions such as lotions, ointments, gels, creams, liniments, patches, deodorants, or sprays.

In some embodiments, an adjuvant is provided in the same formulation with provided nanoparticle composition(s) so that adjuvant and provided nanoparticle composition are delivered substantially simultaneously to the individual. In some embodiments, an adjuvant is provided in a separate formulation. Separate adjuvant may be administered prior to, simultaneously with, or subsequent to provided nanoparticle composition administration.

In some embodiments, provided compositions are stable for extended periods of time, such as 1 week, 2 weeks, 1 month, 2 months, 6 months, 1 year, 2 years, 3 years, or more. In some embodiments, provided compositions are easily transportable and may even be sent via traditional courier or other package delivery service. Accordingly, some embodiments may be useful in situations of disease outbreak, such as epidemics, or attacks with biological agents (e.g. anthrax, smallpox, viral hemorrhagic fevers, plague, and others) at least in part due to their ability to be stored for long periods of time and transported quickly, easily, and safely. Such attributes may allow for rapid distribution of provided compositions to those in need.

In some embodiments, it may be advantageous to release encapsulated agent, for example, an antigen, at various locations along a subject's gastrointestinal (GI) tract. In some embodiments, it may be advantageous to release encapsulated agent, for example, an antigen, in a subject's mouth as well as one or more locations along the subject's GI tract. Accordingly, in some embodiments, a plurality of provided compositions (e.g. two or more) may be administered to a single subject to facilitate release of encapsulated agent at multiple locations. In some embodiments, each of the plurality of compositions has a different release profile, such as provided by various enteric coatings, for example. In some embodiments, each of the plurality of compositions has a similar release profile. In some embodiments, the plurality of compositions comprises one or more antigens. In some embodiments, each of the plurality of administered compositions comprises a different antigen. In some embodiments, each of the plurality of compositions comprises the same antigen.

In some embodiments, one or more agents may be included that can affect rate and/or extent of release of agent (e.g., an antigen) from nanoparticles. In some embodiments, such an agent would affect rate and/or extent of release by leakage or otherwise undesired release (e.g., at a site other than a target site and/or at a time other than a desired time). Without wishing to be bound by any particular theory, in some embodiments, such agents may coat or block release sites on nanoparticle surfaces. In some embodiments, such agents may be or comprise tannic acid.

Routes of Administration

In some embodiments, provided nanoparticle compositions may be formulated for any appropriate route of delivery. In some embodiments, provided nanoparticles and/or nanoparticle compositions may be formulated for any route of delivery, including, but not limited to, bronchial instillation, and/or inhalation; buccal, enteral, interdermal, intraarterial (IA), intradermal, intragastric (IG), intramedullary, intramuscular (IM), intranasal, intraperitoneal (IP), intrathecal, intratracheal instillation (by), intravenous (IV), intraventricular, mucosal, nasal spray, and/or aerosol, oral (PO), as an oral spray, rectal (PR), subcutaneous (SQ), sublingual; topical and/or transdermal (e.g., by lotions, creams, liniments, ointments, powders, gels, drops, etc.), transdermal, vaginal, vitreal, and/or through a portal vein catheter; and/or combinations thereof. In some embodiments, the present invention provides methods of administration of provided nanoparticle compositions via mucosal administration. In some embodiments, the present invention provides methods of administration of provided nanoparticle compositions via oral administration. In some embodiments, the present invention provides methods of administration of provided nanoparticle compositions via sublingual administration.

Methods of Treatment

The present invention provides, among other things, methods of administering to a subject in need thereof a nanoparticle composition including a plurality of nanoparticles, each of which is comprised of a biodegradable or biocompatible polymer arranged in a nanoparticle structure defining an internal lumen and external surface, and at least one of a preparation of hydrophilic cellular components encapsulated within the internal lumen and/or at least one preparation of hydrophobic cellular components associated with the external surface of the nanoparticle.

In some embodiments, the present invention provides methods of treating various diseases, disorders and/or conditions. In some embodiments, provided compositions may be administered to a subject for treatment and/or prevention of allergy, infection, cancer, and combinations thereof. Exemplary suitable compositions include those described herein.

Allergy

The present invention provides, among other things, methods and compositions for the treatment and/or prevention of allergy. In some embodiments, provided nanoparticle compositions are useful as vaccines to prevent and/or delay the onset of an allergic reaction. In some embodiments, provided nanoparticle compositions are useful as vaccines to lessen the severity and/or duration of a future allergic reaction. In some embodiments, provided nanoparticle compositions are useful as therapeutics to alleviate and/or arrest an allergic reaction in progress. In some embodiments, the subject in need thereof is suffering from an allergic condition as herein described, including, but not limited to allergic rhinitis, asthma, atopic eczema, anaphylaxis, insect venom, drug allergies, food allergies, and/or combinations thereof.

In some embodiments, provided nanoparticle compositions may be used for treatment and/or prevention of allergies associated with anaphylactic allergens, e.g., food allergens, insect allergens, and rubber allergens (e.g., from latex).

In some embodiments, provided nanoparticle compositions may be used for treatment and/or prevention of allergies associated with food. Food allergies are mediated through the interaction of IgE to specific proteins contained within the food. Examples of common food allergens include proteins from nuts (e.g., from peanut, walnut, almond, pecan, cashew, hazelnut, pistachio, pine nut, brazil nut), dairy products (e.g., from egg, milk), seeds (e.g., from sesame, poppy, mustard), soybean, wheat, and fish (e.g., shrimp, crab, lobster, clams, mussels, oysters, scallops, crayfish).

In some embodiments, provided nanoparticle compositions may be used for treatment and/or prevention of allergies associated with insect allergens. Examples of common insect allergens include, but are not limited to, proteins from insects such as fleas, ticks, ants, cockroaches, and bees.

In some embodiments, allergens elicit a reaction when ingested, inhaled, and/or injected. Allergens can also elicit a reaction based solely on contact with the skin. Latex is a well-known example. Latex products are manufactured from a milky fluid derived from the rubber tree (*Hevea brasiliensis*) and other processing chemicals. A number of the proteins in latex can cause a range of allergic reactions. Many products contain latex, such as medical supplies and personal protective equipment. Two types of reactions can occur in persons sensitive to latex: local allergic dermatitis and immediate systemic hypersensitivity (or anaphylaxis).

In some embodiments, provided nanoparticle compositions may be used for treatment and/or prevention of allergies associated with local allergic dermatitis. Local allergic dermatitis may develop within a short time after exposure to latex and generally includes symptoms of urticaria or hives. The reaction is thought to be allergic and triggered by direct contact, not inhalation (Sussman et al., 1991, *JAMA*, 265: 2844; incorporated herein by reference). Symptoms of immediate systemic hypersensitivity vary from skin and respiratory problems (e.g., urticaria, hives, rhinoconjunctivitis, swelling of lips, eyelids, and throat, wheezing, and coughing) to anaphylaxis which may progress to hypotension and shock. Such a reaction may be triggered by inhalation or skin exposure to the allergen.

In some embodiments, provided nanoparticle compositions may function to suppress and/or decrease a subject's $T_H2$-type responses and/or enhance and/or increase a subject's $T_H1$-type responses. In some embodiments, provided nanoparticle compositions may function to enhance and/or increase a subject's $T_H2$-type responses and/or suppress and/or decrease a subject's $T_H1$-type responses. In some embodiments, a subject's $T_H2$-type responses are enhanced through targeting of a cell surface receptor for CpG oligonucleotides (e.g. DEC205).

In some embodiments, provided nanoparticle compositions effectively treat and/or prevent all of a subject's allergies falling into a particular class of allergy. In some embodiments, exemplary "classes" of allergies include, but are not limited to, anaphylactic allergies and non-anaphylactic allergies. In some embodiments, exemplary "classes" of allergies include, but are not limited to food allergies, insect allergies, pet dander allergies, pollen allergies, grass allergies, rubber allergies, and so forth. Thus, in some embodiments, provided nanoparticle compositions may be useful for treating all of a subject's food allergies. In some embodiments, exemplary "classes" of allergies include, but are not limited to, particular individual foods which contain multiple allergens. For example, there are at least eleven known peanut allergen proteins. Thus, in some embodiments, a "class" of allergies is "peanut" allergy, and provided nanoparticle compositions may be useful for treating all of a subject's allergies associated with all seven different peanut allergen proteins.

In some embodiments, provided nanoparticle compositions may be useful for treating and/or preventing a single allergy, even though no allergy-specific antigen is included. In some embodiments, provided nanoparticle compositions may be useful for treating and/or preventing multiple different allergies. In some embodiments, provided nanoparticle compositions may be useful for treating and/or preventing substantially all of a subject's allergies. For example, subjects suffering from and/or susceptible to allergy are frequently allergic to more than one allergen, e.g., at least 1, at least 2, at least 3, at least 4, at least 5, at least 6, at least 7, at least 8, at least 9, at least 10, at least 15, at least 20, at least 25, or more different allergens. Thus, in some embodiments, an provided nanoparticle composition may be used for treating and/or preventing at least 1, at least 2, at least 3, at least 4, at least 5, at least 6, at least 7, at least 8, at least 9, at least 10, at least 15, at least 20, at least 25, or more different allergies in a single patient. In some embodiments, an provided nanoparticle composition is administered to a subject suffering from and/or susceptible to multiple different allergies, e.g., at least 1, at least 2, at least 3, at least 4, at least 5, at least 6, at least 7, at least 8, at least 9, at least 10, at least 15, at least 20, at least 25, or more different allergies, such that the subject's symptoms are reduced and/or improved. In some embodiments, an provided nanoparticle composition is administered to a subject suffering from and/or susceptible to multiple different allergies, e.g., at least 1, at least 2, at least 3, at least 4, at least 5, at least 6, at least 7, at least 8, at least 9, at least 10, at least 15, at least 20, at least 25, or more different allergies, such that onset of the subject's symptoms is delayed.

In some embodiments, provided compositions maybe used as oral vaccines to treat allergy. One of the major benefits of oral vaccines is the ability to generate both mucosal and systemic immunity. While oral vaccines have been developed previously, but they have been almost entirely directed to prevention of infectious disease, and have met with widely varying levels of success. For example, oral vaccines have been developed for anthrax, cholera, gastoenteritis, infant diarrhea, malaria, measles, and tuberculosis, among others (see Aziz et al., Oral Vaccines: New Needs, New Possibilities, 2007, BioEssays 29.6: 591-604; see also Silin et al., Oral Vaccination: Where are we?, Exp. Opin. Drug Deliv., 2007, 4(4):323-340, both of which are hereby incorporated by reference in their entirety). Part of the reason for such unpredictable results is the complex nature of the gut mucosa. Briefly, the base of the mucosa in the gut is lined by gut- or mucosa-associated lymphoid tissue, with underlying lamina propria that is rich in intra-epithelial lymphocytes (sometimes referred to as diffuse lymphoid tissue). The majority of T-cells in the gut mucosa are either $\alpha\beta$ or $\gamma\delta$ types. Both CD4 and CD8 cells are found in the gut mucosa, which also carries B cells, monocytes/macrophages, dendrocytes and other immune cells. In fact, the gut is known to house ~90% of the total number of immunocompetent cells in the human body, with circulating lymphocytes only comprising ~2% of the total lymphocytes (see Silin et al.). Furthermore, the gut is known to accommodate ~80% of all immunoglobin or Ig-producing cells and releases 2 to 3 times more secretory IgA that the total output of circulating IgG (see Silin et al.). Accordingly, any therapy that is exposed to the gut environment has the potential to engender a wide variety of responses and be affected by any of several immune or other cells.

In order to have an effective oral vaccine to treat allergy, effective presentation of one or more antigens to an antigen presenting cell (APC) is required. While M-cells and Peyer's patches are popular targets of oral therapies, additional targets include, but are not limited to, enterocytes, mesenteric lymph nodes, and intestinal epithelial cells. Each APC may be targeted by various embodiments. Oral immunization is known to generate significant quantities of secretory IgA (sIgA), which is known to play a major role in mucosal defense against pathogens. However, the value of sIgA is questionable when one considers non-mucosal pathogens or conditions. Various embodiments recognize this and do not trigger large amounts of sIgA release, instead substantially generating a Th2 response.

Major known barriers to providing effective oral vaccines include proteolytic degradation of antigens in the gut, tuning of proper release profile in the intestine, and problems delivering enough antigen in a reasonable sized dose. Additionally, the development of oral tolerance to an antigen is thought to be a major point of concern in developing oral vaccines in general. Oral tolerance is a phenomenon where oral antigen exposure can lead to immune tolerance and a suppression of the systemic immune response to subsequent challenges. The development of oral tolerance is not an automatic feature of oral antigen exposure, but rather depends on several factors including, but not limited to, age of subject, MHC restriction, delivery site, nature, size and dose of antigen, degree of antigenic uptake, and processing and frequency of administration of antigen. Oral tolerance is thought to be mediated by several immunological mechanisms including: induction of regulatory T-cells (suppressors) that downregulate specific cytokines including IL-4, IL-10, and TGF-$\beta$, functional of clonal deletion of effector cells, and antibody-mediated suppression (see Silin et al.).

In some embodiments, provided compositions are able to present antigen to APCs without inducing oral tolerance. Without wishing to be held to a particular theory, it is possible certain embodiments are able to present larger quantities of antigen to the immune system than traditionally known methods of oral immunization. It is suspected that oral tolerance may manifest, at least in part, due to very small amounts of antigen being presented to APCs (see Silin et al., Overcoming immune tolerance during oral vaccination against *actinobacillus pleuropneumoniae,* 2002, J Vet. Med. 49:169-175). In some embodiments, provided compositions present antigens to APCs in such a manner as to promote immune tolerance. Without wishing to be held to a particular theory, it may be advantageous to promote immune tolerance in some clinical circumstances, such as in cases of anaphalaxis, autoimmune disease, or certain infectious diseases including, but not limited to, dengue fever and RSV.

Infection

In some embodiments, the subject in need thereof is suffering from an infection caused by, but not limited to viruses, prions, bacteria, viroids, macroparasites, fungi, and/or combinations thereof. In some embodiments, the subject is suffering from a primary infection. In some embodiments, the subject is suffering from a secondary infection. In some embodiments, the subject is suffering from an active symptomatic infection. In some embodiments, the subject is suffering from an active asymptomatic infection (i.e., infection is active, but does not produce noticeable symptoms; e.g. silent or subclinical infection). In some embodiments, the subject is suffering from a latent infection (i.e., inactive or dormant infection).

Exemplary infections that may be treated by some embodiments include, but are not limited to actinomycosis, African sleeping sickness, AIDS, anthrax, hemorrhagic fevers, bacterial pneumonia, candidiasis, cellulitis, Chagas disease, chickpox, cholera, *C. difficile* infection, Creutzfeldt-Jakob disease, dengue fever, diphtheria, ebola, *enterococcus* infection, food poisoning, gangrene, gonorrhea, streptococcal infections, hepatitis A-E, herpes, hookworm, mononucleosis, leishmaniasis, leprosy, lyme disease, malaria, measles, meningitis, mumps, conjunctivitis, pertussis, rabies, respiratory syncytial virus, rhinovirus, rubella, SARS, scabies, sepsis, shingles, syphilis, tetanus, trichinellosis, tuberculosis, tularemia, viral pneumonia, west nile fever, and yellow fever.

Without wishing to be held to a particular theory, it is contemplated that some embodiments may maintain antibacterial immune surveillance in an otherwise immune compromised subject. For example, a subject suffering from a viral or other immune compromising condition may normally exhibit reduced bacterial resistance, however, with administration of provided compositions may reduce or eliminate the degree of reduced bacterial resistance exhibited by the subject. In some embodiments, provided compositions are administered at regular intervals in order to maintain anti-bacterial immune surveillance. In some embodiments, In some embodiments, provided compositions are administered to a subject suffering from or susceptible to a non-bacterial immune challenge. In some embodiments, provided compositions are administered to a subject that has recently suffered from a non-bacterial immune challenge.

Cancer

In some embodiments, the subject in need thereof is suffering from a cancer including, but not limited to acute lymphoblastic leukemia (ALL); adrenocortical carcinoma; AIDS-related cancers including AIDS-related lymphoma; anal cancer; appendix cancer; astrocytomas; basal cell carcinoma; bile duct cancer; bladder cancer; bone cancer (e.g., osteosarcoma and malignant fibrous histiocytoma); brainstem glioma; brain cancer; brain tumors; breast cancer; bronchial adenomas/carcinoids; Burkitt lymphoma; carcinoid tumors (e.g., childhood and gastrointestinal tumors); carcinoma (including carcinoma of unknown primary (CUP) whose origin or developmental lineage is unknown but that possess specific molecular, cellular, and histological characteristics of epithelial cells); central nervous system lymphoma; cerebellar astrocytoma; malignant glioma; cervical cancer; childhood cancers; chronic lymphocytic leukemia; chronic myelogenous leukemia; chronic myeloproliferative disorders; colon Cancer; cutaneous T-cell lymphoma; desmoplastic small round cell tumor; endometrial cancer; ependymoma; esophageal cancer; Ewing's sarcoma in the Ewing family of tumors; extracranial germ cell tumor; extragonadal germ cell tumor; ovarian germ cell tumor; extrahepatic bile duct cancer; eye cancer; intraocular melanoma; retinoblastoma; gallbladder cancer; gastric cancer; gastrointestinal carcinoid tumor; gastrointestinal stromal tumor (GIST); gestational trophoblastic tumor; gastric carcinoid; hairy cell leukemia; head and neck cancer; heart cancer; hepatocellular (liver) cancer; Hodgkin lymphoma; hypopharyngeal cancer; hypothalamic and visual pathway glioma; intraocular Melanoma; Islet Cell Carcinoma (Endocrine Pancreas); kaposi sarcoma; soft tissue sarcoma; uterine sarcoma; kidney cancer (renal cell carcinoma); laryngeal cancer; leukemias (including acute lymphoblastic or acute lymphocytic leukemia, acute myeloid or acute myelogenous leukemia, chronic lymphocytic or chronic lymphocytic leukemia, chronic myelogenous or chronic myeloid leukemia); Lip and Oral Cavity Cancer; liposarcoma; liver cancer; lung cancer (including non-small cell and small cell); lymphomas (e.g., AIDS-related, Burkitt, cutaneous T-Cell, Hodgkin, non-Hodgkin, Primary Central Nervous System); macroglobulinemia; medulloblastoma; melanoma; Merkel Cell Carcinoma; mesothelioma (e.g., adult malignant mesothelioma, childhood mesothelioma); metastatic squamous neck cancer; mouth cancer; Multiple Endocrine Neoplasia Syndrome; Multiple Myeloma; Mycosis Fungoides; Myelodysplastic Syndromes; Myelodysplastic/Myeloproliferative Diseases; Myelogenous Leukemia; Myeloid Leukemia; (e.g. Adult Acute; nasal cavity and paranasal sinus cancer; nasopharyngeal carcinoma; neuroblastoma; oral cancer; oropharyngeal cancer; ovarian cancer; ovarian epithelial cancer (Surface epithelial-stromal tumor); ovarian germ cell tumor; ovarian low malignant potential tumor; pancreatic cancer; paranasal sinus and nasal cavity cancer; parathyroid cancer; penile cancer; pharyngeal cancer; pheochromocytoma; pineal astrocytoma; pineal germinoma; pineoblastoma and supratentorial primitive neuroectodermal tumors; pituitary adenoma; pleuropulmonary blastoma; prostate cancer; rectal cancer; renal pelvis and ureter and transitional cell cancer; rhabdomyosarcoma; Sézary syndrome; skin cancer (including melanoma and nonmelanoma); skin carcinoma; small intestine cancer; squamous cell carcinoma; stomach cancer; testicular cancer; throat cancer; thymoma and thymic carcinoma; thyroid cancer; urethral cancer; endometrial uterine cancer; vaginal cancer; vulvar cancer; and/or combinations thereof.

Dosing

In some embodiments, provided pharmaceutical compositions are administered according to a dosing regimen sufficient to achieve a desired immunological reaction. For example, in some embodiments, a dosing regimen is sufficient to achieve a desired immunological reaction if its administration to a relevant patient population shows a statistically significant correlation with achievement of the desired immunological reaction.

In some embodiments, the desired immunological reaction is a reduction in the degree and/or prevalence of symptoms of allergy of at least about 20%, about 25%; about 30%; about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In some embodiments, a provided pharmaceutical composition is administered according to a dosing regimen sufficient to achieve a reduction in the degree and/or prevalence of symptoms of allergy of a specified percentage of a population of patients to which the composition is administered. In some embodiments, the specified percentage of population of patients to which the composition was administered is at least about 5%, about 10%, about 15%, about 20%, about 25%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

To give but a few illustrative examples, in some embodiments, administration of at least one provided pharmaceutical composition according to a dosing regimen is sufficient to achieve a reduction in the degree and/or prevalence of allergy of at least about 20% in at least about 50% of the population of patients to which the composition was administered. In some embodiments, administration of at least one provided pharmaceutical composition according to a dosing regimen is sufficient to achieve a reduction in the degree and/or prevalence of allergy of at least about 30% in at least about 50% of the population of patients to which the composition was administered.

In some embodiments, at least one provided pharmaceutical composition is administered according to a dosing regimen sufficient to achieve a delay in the onset of symptoms of allergy. In some embodiments, at least one provided pharmaceutical composition is administered according to a dosing regimen sufficient to prevent the onset of one or more symptoms of allergy.

In some embodiments, a provided dosing regimen comprises or consists of a single dose. In some embodiments, a provided dosing regimen comprises or consists of multiple doses, separated from one another by intervals of time that may or may not vary. In some embodiments, a provided dosing regimen comprises or consists of dosing once every 20 years, once every 10 years, once every 5 years, once every 4 years, once every 3 years, once every 2 years, once per year, twice per year, 3 times per year, 4 times per year, 5 times per year, 6 times per year, 7 times per year, 8 times per year, 9 times per year, 10 times per year, 11 times per year, once per month, twice per month, three times per month, once per week, twice per week, three times per week, 4 times per week, 5 times per week, 6 times per week, daily, twice daily, 3 times daily, 4 times daily, 5 times daily, 6 times daily, 7 times daily, 8 times daily, 9 times daily, 10 times daily, 11 times daily, 12 times daily, or hourly.

In some embodiments, a provided dosing regimen comprises or consists of an initial dose with one or more booster doses. In some embodiments, one or more booster doses are administered 1 day, 2 days, 3 days, 4 days, 5 days, 6 days, 1 week, 2 weeks, 1 month, 2 months, 6 months, 1 year, 2 years, 5 years, 10 years, or longer than 10 years after the initial dose. In some embodiments, an initial dose comprises a series of doses administered over a period of time. For example, in some embodiments, an initial dose comprises a series of 1, 2, 3, 4, 5, 6, 7, 8, 9, 10, 11, 12, 13, 14, 15, 16, 17, 18, 19, 20, 21, 22, 23, 24, or more doses administered at regular intervals, e.g., intervals that are close in time to one another, such as 5 minute intervals, 10 minute intervals, 15 minute intervals, 20 minute intervals, 25 minute intervals, 30 minute intervals, 45 minute intervals, hourly intervals, every 2 hours, etc.

In some embodiments, an initial dose and booster doses contain the same amount of provided nanoparticle and/or nanoparticle composition. In some embodiments, an initial dose and booster doses contain different amounts of provided nanoparticle composition. In certain embodiments, provided nanoparticle compositions at dosage levels sufficient to deliver from about 0.001 mg/kg to about 100 mg/kg, from about 0.01 mg/kg to about 50 mg/kg, preferably from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day. In some embodiments, provided nanoparticle compositions are formulated into a unit dose. In some embodiments, a unit dosage is about 10 mg, about 25 mg, about 50 mg, about 100 mg, about 250 mg, about 500 mg, about 1 g, about 5 g, about 10 g, about 25 g, about 50 g, about 100 g, or more than about 100 g. In some embodiments, the amount of provided nanoparticle composition present in a particular unit dose depends on the subject to which the composition is to be administered. To give but a few examples, in some embodiments, a unit dose appropriate for a mouse is smaller than a unit dose that is appropriate for a rat, which is smaller than a unit dose that is appropriate for a dog, is smaller than a unit dose that is appropriate for a human.

In some embodiments, a provided dosing regimen comprises or consists of administration of multiple doses over the course of the subject's entire lifespan. In some embodiments, a provided dosing regimen comprises administration of multiple doses over the course of several years (e.g., 2, 3, 4, 5, 6, 7, 8, 9, 10, 15, 20, 25, 30, 35, 40, 45, 50, 60, 70, 80, 90, or 100 years). In some embodiments, a provided dosing regimen comprises or consists of multiple doses over the course of 1, 2, 3, 4, 5, 6, 7, 8, 9, 10, 11, or 12 months.

In some embodiments, when provided compositions are used in the treatment of allergy, prior to the first dose, a subject's baseline allergic response is determined by one or more of a variety of methods, including, but not limited to, (1) performing a prick skin test (PST) of one or more of the subject's 1, 2, 3, 4, 5, 6, 7, 8, 9, 10, 11, 12, 13, 14, 15, 16, 17, 18, 19, 20, or more than 20 allergens, and measuring the wheal and flare response to the PST; (2) measuring blood serum IgE levels; (3) noting the subject's own description of her typical symptoms (e.g., nature, severity, and/or duration of symptoms) upon exposure to one or more of her 1, 2, 3, 4, 5, 6, 7, 8, 9, 10, 11, 12, 13, 14, 15, 16, 17, 18, 19, 20, or more than 20 allergens; (4) exposing the subject to a certain dose of one or more of her 1, 2, 3, 4, 5, 6, 7, 8, 9, 10, 11, 12, 13, 14, 15, 16, 17, 18, 19, 20, or more than 20 allergens (e.g., if only a small or nonexistent risk of anaphylaxis); (5) measuring expression (e.g., levels, spatial distribution, temporal distribution, etc.), of one or more molecular markers, including, but not limited to, T-cell markers CD4+ and/or CD8+; (6) performing a basophil histamine release assay; and/or combinations thereof. In some embodiments, a subject's allergic response is monitored using any combination of methods, e.g. methods (1)-(6) described above, throughout the course of the treatment regimen and/or after the treatment regimen is completed, e.g., at regular intervals. In some embodiments, allergic response is monitored daily, weekly, bi-weekly, monthly, 6 times per year, 4 times per year, 3 times per year, 2 times per year, once per year, every 2 years, every 5 years, and/or every 10 years, etc.

In some embodiments, a subject is challenged with a single allergen and/or multiple allergens, e.g., a subset of the subject's allergens (e.g., allergens to which the subject is known to be allergic) and/or all of the subject's allergens (e.g., allergens to which the subject is known to be allergic). In some embodiments, allergy challenge is performed after 1 week, 2 weeks, 1 month, 2 months, 6 months, and 1 year after initiation of treatment.

In some embodiments, provided compositions may be administered via any medically acceptable route. For example, in some embodiments, a provided composition may be administered via intravenous administration; intradermal administration; transdermal administration; oral administration; subcutaneous administration; transmucosal administration; and/or combinations thereof. In some embodiments, exemplary routes of transmucosal administration include, but are not limited to buccal administration; nasal administration; bronchial administration; vaginal administration; rectal administration; sublingual administration; and/or combinations thereof.

Combination Therapy

In some embodiments, provided pharmaceutical compositions are administered to a subject in combination with one or more other therapeutic agents or modalities, for example, useful in the treatment of one or more diseases, disorders, or conditions treated by the relevant provided pharmaceutical composition, so the subject is simultaneously exposed to both. In some embodiments, a provided nanoparticle composition is utilized in a pharmaceutical formulation that is separate from and distinct from the pharmaceutical formulation containing the other therapeutic agent. In some embodiments, a provided nanoparticle composition is admixed with the composition comprising the other therapeutic agent. In other words, in some embodiments, a provided nanoparticle composition is produced individually, and the provided nanoparticle composition is simply mixed with another composition comprising another therapeutic agent.

The particular combination of therapies (substances and/or procedures) to employ in a combination regimen will take into account compatibility of the desired substances and/or procedures and the desired therapeutic effect to be achieved. In some embodiments, provided nanoparticle compositions can be administered concurrently with, prior to, or subsequent to, one or more other therapeutic agents (e.g., desired known allergy therapeutics).

It will be appreciated that the therapies employed may achieve a desired effect for the same disorder (for example, a provided nanoparticle composition useful for treating allergy may be administered concurrently with a known allergy therapeutic that is also useful for treating allergy), or they may achieve different effects (for example, a provided nanoparticle composition that is useful for treating allergy may be administered concurrently with a therapeutic agent that is useful for alleviating adverse side effects, for instance, inflammation, nausea, etc.). In some embodiments, provided nanoparticle compositions in accordance with the invention are administered with a second therapeutic agent that is approved by the U.S. Food and Drug Administration (FDA).

As used herein, the terms "in combination with" and "in conjunction with" mean that the provided nanoparticle compositions can be administered concurrently with, prior to, or subsequent to, one or more other desired therapeutics. In general, each substance will be administered at a dose and/or on a time schedule determined for that agent.

For example, in some embodiments, provided pharmaceutical compositions for the treatment of allergy may, in some embodiments, be administered in combination with, for example, one or more antihistamines (i.e., histamine antagonist), corticosteroids including glucocorticoids; epinephrine (adrenaline); theophylline (dimethylxanthine); cromolyn sodium; anti-leukotrienes; anti-cholinergics; decongestants; mast cell stabilizers; immunotherapy (progressively larger doses of a specific allergen); monoclonal anti-IgE antibodies (e.g., omalizumab); and/or combinations thereof.

Exemplary antihistamines include, but are not limited to Azelastine; Brompheniramine; Buclizine; Bromodiphenhydramine; Carbinoxamine; Cetirizine; Cyclizine; Chlorpheniramine; Chlorodiphenhydramine; Clemastine; Cyproheptadine; Desloratadine; Dexbrompheniramine; Deschlorpheniramine; Dexchlorpheniramine; Dimetindene; Diphenhydramine (Benadryl); Doxylamine; Ebastine; Embramine; Fexofenadine; Levocetirizine; Loratadine; Olopatadine (Patanol); Phenindamine (Nolahist and Thephorin); Pheniramine (Avil); Phenyltoloxamine; Promethazine; Pyrilamine; Rupatadine; Tripelennamine; Triprolidine; and/or combinations thereof.

Exemplary corticosteroids and glucocorticoids include, but are not limited to Beclometasone dipropionate and Beclomethasone (Clenil, Qvar, Beconase AQ, Alanase, Vancenase); Budesonide (Rhinocort, Rhinosol, Pulmicort, Budicort, Symbicort, Noex); Ciclesonide (Alvesco, Omnaris, Omniair); Flunisolide (Aerobid); Fluticasone (Veramyst); Fluticasone (Flonase); Mometasone and Mometasone furoate (Nasonex); Triamcinolone (Nasacort AQ); Prednisone; Methylprednisolone (Depo-Medrol); Triamcinolone (Kenalog); and/or combinations thereof.

Exemplary forms of cromolyn sodium include, but are not limited to, Rynacrom; Nasalcrom; Prevalin; Intal; Optocrom; Optrex; Gastrocrom; Intercron; and/or combinations thereof.

Exemplary anti-leukotrienes and leukotriene inhibitors (or modifiers) include, but are not limited to Montelukast (Singulair, Montelo-10, and Monteflo); Zafirlukast (Accolate, Accoleit, Vanticon); Pranlukast; Zileuton (Zyflo, Zyflo CR); and/or combinations thereof.

Exemplary anti-cholinergics include, but are not limited to, Ipratropium bromide (Atrovent®, Apovent, Ipraxa, Aervoent); Combivent (Ipratropium bromide and Albuterol); Benztropine (Cogentin); Oxitropium (Oxivent); Tiotropium (Spiriva); Glycopyrrolate (Robinul); Oxybutinin (Ditropan, Driptane, Lyrinel XL); Tolterodine (Detrol, Detrusitol); Chlorphenamine (Chlor-Trimeton); Diphenhydramine (Benadryl, Sominex, Advil PM, etc.); Dimenhydrinate (Dramamine); Bupropion (Zyban, Wellbuterin); Hexamethonium; Tubo curarine; Dextromethorphan; Mecamylamine; Doxacurium; and/or combinations thereof.

Exemplary decongestants include, but are not limited to, Ephedrine; Levo-methamphetamine; Naphazoline; Oxymetazoline; Phenylephrine; Phenylpropanolamine; Propylhexedrine; Synephrine; Tetrahydrozoline; and/or combinations thereof.

Exemplary mast cell stabilizers include, but are not limited to, Cromoglicic acid; Ketotifen and Ketotifen fumarate (Zaditor, Zaditen, Alaway, Zyrtec Itchy-Eye Drops, Claritin Eye); Methyl xanthines; and/or combinations thereof.

In some embodiments, exemplary known allergy therapeutics that can be administered in combination with provided nanoparticle compositions in accordance with the invention include, but are not limited to, any of the therapeutics described in U.S. Pat. Nos. 5,558,869, 5,973,121, 6,835,824, 6,486,311, and/or 7,485,708, and/or in US Patent Publication Numbers 2003/0035810, 2003/0202980, 2004/0208894, 2004/0234548, 2007/0213507, 2010/0166802, and/or 2011/0027298, all of which are incorporated herein by reference.

As an additional example, in some embodiments, provided pharmaceutical compositions for the treatment of infectious disease may be administered in combination with, for example, an antibiotic such as an antibacterial agent, an antiviral agent, and/or an antifungal agent. In some embodiments, provided pharmaceutical compositions may be administered in combination with a vaccine.

Exemplary antibacterial agents include, but are not limited to sulfanilamide; folic acid analogs; beta-lactams such as penicillins, cephalosporins, and carbapenems; aminoglycosides such as streptomycin, kanamycin, neomycin, and gentamycin; tetracyclines such as chlortetracycline, oxytetracycline, and doxycycline; macrolides; lincosamides; streptogramins; fluoroquinolones, rifampin, mupirocin, cycloserine, aminocyclitols, glycopeptides, oxazolidinones, and derivatives/analogs and/or combinations thereof.

Exemplary antiviral agents include, but are not limited to Abacavir, Aciclovir, Acyclovir, Adefovir, Amantadine, Amprenavir, Ampligen, Arbidol, Atazanavir, Atripla, Boceprevirertet, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fomivirsen, Fosamprenavir, Foscarnet, Fosfonet, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir, Peginterferon alfa-2a, Penciclovir, Peramivir, Pleconaril, Podophyllotoxin, Raltegravir, Reverse transcriptase inhibitors, Ribavirin, Rimantadine, Ritonavir, Pyramidine, Saquinavir, Stavudine, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and derivatives/analogs and/or combinations thereof.

Exemplary antifungal agents include, but are not limited to polyene agents such as amphotericin, candicidin, filipin, hamycin, natamycin, nystatin, and rimocidin; imidazole, triazole and thiazolc agents such as bifonazolc, butoconazolc, clotrimazole, econazole, fenticonazole, isoconazole, ketoconazole, miconazole, omoconazole, oxiconazole, sertaconazole, sulconazole, tioconazole, alboconazole, fluconazole, isavuconazole, posaconazole, ravuconazole, terconazole, voriconazole, and abafungin; allylamines such as amorolfin, butenafine, naftafine, and terbinafine; and echinocandins such as anidulafungin, caspofungin, and micafungin and derivatives/analogs and/or combinations thereof.

As an additional example, in some embodiments, provided pharmaceutical compositions for the treatment of cancer may be administered in combination with, for example, alkylating agents, antimetabolite agents, and/or other anticancer medications.

Exemplary alkylating agents include, but are not limited to polyfunctional alkylating agents such as cyclophosphamide (Cytoxan), mechlorethamine, melphan (Alkeran), chlorambucil (Leukeran), thiopeta (Thioplex), and busulfan (Mylean); procarbazine, dacarbazine, altretamine, cisplatin, and derivatives/analogs and/or combinations thereof.

Exemplary antimetabolite agents include, but are not limited to methotrexate; purine antagonists such as mercaptopurine (6-MP), thioguanine (6-TG), fludarabine phosphate, cladribine, and pentostatin; pyrimidine antagonists such as fluorouracil, cytarabine, and azacitidine; plant alkaloids such as vinblastine (Velban), vincristine (Oncovin), etoposide (VP-16), teniposide (Vimon), topotecan (Hycamtin), irinotecan (Camptosar), paclitaxel (Taxol), and docetaxel (Taxotere) and derivatives/analogs and/or combinations thereof.

Exemplary other anticancer agents include, but are not limited to amsacrine; hydroxyurea (Hydrea); asparaginase (El-spar); mitoxantrone (Novantrone); mitotane; retinoic acid, bone marrow growth factors, amifostine, and derivatives/analogs and/or combinations thereof.

Kits

The present invention provides kits comprising vaccine and/or therapeutic compositions including provided nanoparticles. In some embodiments, a kit may comprise (i) at least one provided nanoparticle composition; and (ii) at least one pharmaceutically acceptable excipient; and, optionally, (iii) instructions for use.

In some embodiments, kits include multiple (e.g., 1, 2, 3, 4, 5, 6, 7, 8, 9, 10, 11, 12, 13, 14, 15, 16, 17, 18, 19, 20, or more) doses of provided nanoparticle compositions. In some embodiments, kits include multiple (e.g., 1, 2, 3, 4, 5, 6, 7, 8, 9, 10, 11, 12, 13, 14, 15, 16, 17, 18, 19, 20, or more) populations of provided nanoparticles having different functional elements (e.g., microbial mimic entities). In some embodiments, multiple populations of provided nanoparticles are packaged separately from one another in provided kits. In some embodiments, provided kits may include provided compositions and one or more other therapeutic agents intended for administration with the provided compositions.

In some embodiments, the present invention provides pharmaceutical packs or kits including provided nanoparticle compositions to be used in treatment methods according to the present invention. In some embodiments, pharmaceutical packs or kits include preparations or pharmaceutical compositions containing provided nanoparticle compositions in one or more containers filled with optionally one or more additional ingredients of pharmaceutical compositions in accordance with the invention. In some embodiments, the pharmaceutical pack or kit includes an additional approved therapeutic agent for use in combination therapies, as described herein. Optionally associated with such container(s) can be a notice in the form prescribed by a governmental agency regulating the manufacture, use or sale of pharmaceutical products, which notice reflects approval by the agency of manufacture, use, or sale for human administration.

In some embodiments, kits are provided that include provided nanoparticle compositions and instructions for use. Pharmaceutical doses or instructions therefor may be provided in a kit for administration to an individual suffering from and/or susceptible to allergy.

EXEMPLIFICATION

Example 1: Preparation of Aqueous E. coli Extract

The present Example describes preparation of an aqueous extract of microbial cells, here *E. coli*, containing hydrophilic components of the cells, for use in accordance with the present invention.

The present Example describes preparation of an aqueous *E. coli* extract (i.e., an aqueous extract of an *E. coli* cell culture; "AEE") using standard available procedures. The production strain may be a common and non-pathogenic strain of *E. coli*. A master and working cell bank of the production strain may be established prior to clinical manufacture.

Cells are harvested from high cell density fermentation and then the media is exchanged for phosphate buffered saline (PBS) containing 5 mM ethylene diamine tetraacetic acid (EDTA) as a protease inhibitor. Cells suspended in the PBS-EDTA are homogenized (using a French press, for example) and then clarified to remove cellular debris. The clarified extract is treated to inactivate residual enzymes, for example using mild heat treatment. The resultant extract is clarified again, if necessary, and stored frozen prior to use in the nanoparticle manufacturing process. In addition to bacterial proteins and DNA, it is expected the AEE will also contain LPS. In some embodiments, one or more components of the AEE will be processed in some manner to facilitate nanoencapsulation, for example, shearing DNA to break up large stretches into smaller pieces more suitable for nanoencapsulation.

Exemplary specifications for the AEE are presented in Table 3. Given that both protein and LPS give banding patterns in sodium dodecyl sulfate-polyacrylamide gel electrophoresis (SDS-PAGE) analysis, it is anticipated that an SDS-PAGE profile will be too complex to provide meaningful comparisons between batches. Keto-deoxyoctulosonic acid (KDO) is a carbohydrate exclusively found in bacterial LPS and will be used as a surrogate assay for LPS content of the extract.

TABLE 3

Specification for Aqueous *E. Coli* Extract

| Test | Method | Acceptance Criteria |
| --- | --- | --- |
| Appearance | Visual | Clear, colorless to pale yellow solution |
| Total protein | BCA | 1.0-5.0 mg/mL |
| Total DNA | PicoGreen or $A_{270}/A_{280}$ ratio | 14-18 mg/mL |
| Total LPS activity | LAL | 72,000,000 EU/mL |
| KDO content | Colorimetric | 0.3-0.9 mg/mL |
| Microbial limits | USP<61> | |
| Total aerobic microbial count | | NMT $10^3$ CFU/mL |
| Total yeasts and molds count | | NMT $10^2$ CFU/mL |
| *E. coli* | | Absent |

BCA = bicinchoninic acid;
CFU = colony forming units;
DNA = deoxyribonucleic acid;
KDO = keto-deoxyoctulosonic acid;
LAL = limulus amebocyte lysate;
LPS = lipopolysaccharide;
NMT = not more than;
TBD = to be determined;
USP = United Stated Pharmacopeia

Example 2: Manufacture of Hydrophobic E. coli Extract

The present Example describes preparation of an organic extract of microbial cells, containing hydrophobic components of the cells, for use in accordance with the present invention.

The present example describes preparation of a hydrophobic (organic) *E. coli* extract (i.e., an organic extract of an *E. coli* cell culture, "OEE") manufactured using standard available procedures. The same production strain used to manufacture the AEE may be used for the OEE. As with the AEE, the production strain may be a common and non-pathogenic strain of *E. coli*. A master and working cell bank of the production strain may be established prior to clinical manufacture.

Briefly, an extract is prepared using the well-known phenol-chloroform-petroleum ether process, with the exception that hexane is used in lieu of petroleum ether, as petroleum ether is a pharmaceutically unacceptable solvent. Dried bacterial cells are suspended in the phenol-chloroform-hexane (PCH) mixture for about 30 minutes. The slurry is then centrifuged to remove the remaining cells. The remaining cells are then treated with PCH twice more. The combined organic extracts is evaporated to remove the volatile organic solvents. Water is added drop-wise to the phenol concentrate to precipitate the LPS and lipids. The precipitated OEE is then washed with 95% phenol followed by acetone, suspended in water, lyophilized, and stored frozen prior to use in the nanoparticle manufacturing process. It is expected that the OEE will be comprised mainly of bacterial LPS and lipids.

Exemplary specifications for the OEE are presented in Table 4. It is anticipated that substantially no proteins or nucleic acids will be extracted into the OEE.

TABLE 4

Specification for Organic *E. Coli* Extract

| Test | Method | Acceptance Criteria |
| --- | --- | --- |
| Appearance | Visual | White to pale yellow powder |
| Lipid chromatographic fingerprint | LC/MS | Consistent with reference fingerprint |
| Total LPS activity | LAL | 250,000 EU/mg |
| KDO content | Colorimetric | 0.01-0.03 mg/mg |
| Microbial limits | USP<61> | |
| Total aerobic microbial count | | NMT $10^3$ CFU/mL |
| Total yeasts and molds count | | NMT $10^2$ CFU/mL |
| *E. coli* | | Absent |

CFU = colony forming unit;
KDO = keto-deoxyoctulosonic acid;
LAL = limulus amebocyte lysate;
LC/MS = liquid chromatography/mass spectrometry;
LPS = lipopolysaccharide;
NMT = not more than;
TBD = to be determined;
USP = United Stated Pharmacopeia

Example 3: Production of Nanoparticle Compositions Containing Encapsulated E. coli Hydrophilic Components and Surface-Associated E. coli Hydrophobic Components This Example describes an exemplary preparation of E-nanoparticles (i.e., nanoparticles containing hydrophilic and/or hydrophobic *E. coli* extract preparations) using a double emulsion (water-oil-water) process. Briefly, AEE at a protein concentration of c.a. 60 mg/mL is used to reconstitute allergen extracts (dust mite or peanut, for example) also at a concentration of 60 mg/mL. Higher or lower concentrations of both the AEE and/or the allergen extract may be used. The AEE-allergen extract solution is homogenized with a dichloromethane solution of PLGA (c.a. 35.7 mg/mL) with an aqueous to organic ratio of 0.20 mL:28 mL. This mixture is designated as the first emulsion and comprises or consists essentially of nanodroplets of the AEE (including, in this Example, antigen, DNA, and LPS) in the OEE.

In some embodiments, for example where it is desirable to increase the level of surface-associated hydrophobic components (such as LPS), OEE, such as that described above in Example 2, is dissolved in 5% aqueous PVA at a concentration of c.a. 2.2 mg/mL total LPS. Higher or lower concentrations of OEE in PVA solution may be used. Half of the first emulsion (14 mL) is added to the OEE-PVP solution (14 mL) and homogenized. This mixture is designated as the second emulsion, and includes several structural similarities to the first emulsion, described above (i.e. nanodroplets of the AEE in the OEE).

The first or, if generated, the second emulsion (28 mL) is added to 935 mL of 0.33% aqueous PVA and stirred for c.a. 4 hours to allow the dichloromethane to evaporate. The nanoparticle suspension is concentrated and the nanoparticles are isolated by centrifugation. After removal of the supernatant, the nanoparticles are washed 2 to 3 times with water, resuspended in water, and isolated by freeze drying. In this example, DNA, LPS and antigen are distributed throughout the nanoparticles, and LPS and lipids are coated on the surface. The nanoparticles in this Example are approximately 450 nm+/−150 nm in diameter.

Example 4: In Vivo Desensitization Study of Orally Administered CpG-Coated, PLGA-Encapsulated Peanut Extract Nanoparticles The present Example describes an exemplary study assessing the in vivo desensitization efficacy of an orally administered nanoparticle composition comprising relatively crude antigen (specifically, a peanut extract) in PLGA nanoparticles coated with CpG and furthermore evaluating the safety of said nanoparticles by assessing anaphylactic potential in peanut-sensitized animals.

Among other things, the present Example describes administration of an exemplary nanoparticle composition that, when orally administered to peanut-sensitized mice, resulted in desensitization to subsequent oral peanut challenges relative to vehicle control mice.

Materials and Methods

CpG-Coated, PLGA-Encapsulated Peanut Extract Nanoparticles

Among other things, the present Example describes nanoparticles which contain encapsulated allergenic extract of peanuts, *Arachis hypogaea*. Briefly, commercially available roasted peanuts in shells (White Rose Brand, N.J.) were de-shelled, homogenized in phosphate buffered saline (PBS, pH 7.4), and subjected to acetone extraction. The final concentration of peanut protein in PBS was determined to be 13.2 mg/mL by bicinchoninic acid (BCA) assay.

Prior to nanoparticle manufacture, the 13.2 mg protein/mL peanut extract solution was concentrated using an Amicon Ultra-4 Centrifugal Filter Unit with Ultracel-3 Membrane (3 kDa cutoff; Millipore, catalog no. UFC8-003). The final protein concentration was determined to be 27.3 mg/mL via BCA assay.

CpG-coated, PLGA-encapsulated peanut extract nanoparticles were manufactured using a double-emulsion method. To minimize endotoxin in the final product, all glassware was baked at 250° C. for 2 hours and plastic instruments were decontaminated in Pyro-Clean (AlerChek, Inc., catalog no. I30103) for 30 minutes and subsequently washed in UltraPure water (Millipore, catalog no. H20CC1006).

A total of 0.7 mL of concentrated peanut extract in PBS (19 mg peanut protein) was added drop-wise to 14 mL of 25 mg/mL PLGA in methylene chloride (Thermo Fisher Scientific, catalog no. D65100) divided over four tubes. The PLGA used for NP-401 manufacture was a 50:50 poly(DL-lactide-co-glycolide) with an ester end group and an inherent viscosity of 0.95-1.2 dL/g (Durect, product no. B6010-4). The resulting suspensions were briefly vortexed and then sonicated for 30 seconds in 10 second intervals, icing for 30 seconds between sonications, using a Tekmar Sonic Distributor fitted with a CV26 sonicator (38% amplitude).

For the second emulsion, the first emulsions were pooled and added drop-wise to 14 mL of 1.25% poly vinyl alcohol (w/v) (PVA, Sigma Aldrich, catalog no. P8136), 1% sodium deoxycholate (w/v), 1.25 mg/mL avidin-palmitate divided over four tubes. The resulting suspensions were briefly vortexed and then sonicated for 30 seconds on ice using a Tekmar Sonic Distributor fitted with a CV26 sonicator (38% amplitude).

The avidin-palmitate used in the nanoparticle manufacture was prepared by incubating 5 mg/ml avidin (EMD Millipore, catalog no. 189725) in 2% sodium deoxycholate (Sigma-Aldrich, catalog no. D6750) with a 15-fold molar excess of palmitic acid N-hydroxy-succinimide ester (Sigma-Aldrich, catalog no. P1162) for 3 hours at 37° C. Excess palmitic acid was removed by dialysis in a 2% sodium deoxycholate bath over 24 hours at 37° C.

The second emulsion was pooled and immediately added to 350 mL of room temperature (RT) 0.3% PVA (w/v) in one beaker. The methylene chloride was evaporated by stirring with a stir bar for 3 hours at RT. The nanoparticles were collected by centrifugation at 18,500 g for 15 minutes at 4° C. The pellet was resuspended in 10 mL UltraPure water, centrifuged at 18,500 g for 15 minutes at 4° C., and the supernatant decanted. This washing step was repeated a total of 3 times. The nanoparticles were then flash-frozen, lyophilized, and stored at −20° C.

The nanoparticles were labeled with CpG-biotin immediately prior to use. CpG oligodeoxynucleotide 1826 (5'-TCC ATG ACG TTC CTG ACG TT-3' SEQ ID NO:1) with a phosphorotioate backbone was synthesized and conjugated to biotin (5' end). For labeling, PLGA-encapsulated peanut extract nanoparticles and CpG-biotin were suspended in sterile PBS, pH (7.4) at 7.34 mg nanoparticles/mL and 3.67 μg/mL (0.5 μg/mg nanoparticle), respectively, vortexed, and then incubated for 15 minutes at RT. The labeled material was used immediately for study without further processing.

Characterization of CpG-Coated, PLGA-Encapsulated Peanut Extract Nanoparticles

Particle size was measured by a liquid phase Stokes diffusion particle-tracking system (NanoSight; Wiltshire, U.K.). CpG-coated, PLGA-encapsulated peanut extract nanoparticles (hereinafter interchangeable referred to as "CpG-coated, PLGA-encapsulated peanut extract nanoparticles" and/or "Agent") had an average particle size diameter of 214±39 nm.

Total protein was measured by dissolving the nanoparticles in 0.2 N NaOH at RT overnight and assaying with a micro BCA protein assay (Pierce, catalog no. 23235). The following two protein standards were used: peanut extract in PBS, 0.2N NaOH and bovine serum albumin (BSA; provided in BCA kit) in PBS, 0.2N NaOH. Control nanoparticles, including PLGA nanoparticles encapsulating peanut extract without avidin, empty avidin-palmitate nanoparticles, and empty nanoparticles without avidin, were dissolved in the same buffer and used to correct for assay background signals from avidin and PLGA. CpG-coated, PLGA-encapsulated peanut extract nanoparticles were loaded with 54.53 µg protein/mg nanoparticle.

Total avidin was measured by the micro BCA assay on intact nanoparticles to quantify surface protein. CpG-coated, PLGA-encapsulated peanut extract nanoparticles had 25.28±0.31 µg avidin/mg nanoparticle. Under the CpG-biotin labeling conditions used for this study (described above), all of the CpG-biotin added is anticipated to be attached to the nanoparticles with no free CpG in solution. Thus, the CpG-coated, PLGA-encapsulated peanut extract nanoparticles are anticipated to be coated with 0.5 µg/mg CpG-biotin/mg nanoparticle.

Dosage Preparation and Analyses

The final CpG-coated, PLGA-encapsulated peanut extract nanoparticles were formulated fresh the day of each dose administration. Briefly, the PLGA-encapsulated peanut extract nanoparticles and CpG-biotin were suspended in sterile PBS, pH 7.4, and then incubated for 15 minutes at RT to allow for labeling (described above). The CpG-biotin labeled PLGA-encapsulated peanut extract nanoparticles were held at RT until dosing was complete and was used within 30 minutes of preparation. No dose formulation analyses were performed for this study.

Study Design and Experimental Procedure (A-H)

The mice used in this study were female C3H/HeJ obtained from The Jackson Laboratory, Bar Harbor, Me. Mice were 6 weeks old, approximately 15 grams at the start of sensitization, and housed 4-6/cage (JAG 75 cage, Allentown Caging Equipment, Allentown, N.J.). Food and water were provided ad libitum. The mice were acclimated for 6 days prior to use on study. The study design is summarized in Table 5, and described in detail below.

Briefly, all mice (including those in Group 3) were fasted for 2 hours. After 2 hours of fasting, each of the mice to be sensitized (Groups 1-2) were orally gavaged with 0.5 ml of a PBS solution containing 10 mg freshly ground whole peanut (i.e. peanut and skin, with no shell), 20 µg cholera toxin, 16.5 µl of alcohol, and 1.5% sodium bicarbonate (w/v). This was repeated for 3 consecutive days. Following the initial sensitization (Study Week 0), the same process was repeated weekly for an additional 5 weeks (Study Weeks 1-5); however, the sensitizations were administered only once per week (rather than 3 consecutive days per week as in Study Week 0). One week and three weeks later (i.e., Study Weeks 6 and 8, respectively), the mice were sensitized as above (i.e., once per week), except that the amount of freshly ground whole peanut was increased to 50 mg per mouse.

B. Desensitization (Weeks 11, 12, 13, and 14)

Eighteen days after the last sensitization boost (Study Week 11), all but the naïve mice (Group 3) began a desensitization treatment regimen. The mice were administered either 0 (vehicle; Group 1) or 3.67 mg CpG-coated, PLGA-encapsulated peanut extract nanoparticles (Group 2)/mouse by oral gavage once a week for four consecutive weeks. The 3.67 mg/mouse nanoparticle dose corresponds to 200 µg peanut protein and 1.835 µg CpG-biotin. The dose volume for each desensitization treatment was 0.5 mL/mouse. All mice (including those in Group 3) were fasted for 2 hours prior to desensitization treatments.

C. Oral Food Challenge (Weeks 14, 18, 22, 26, and 30)

At Study Weeks 14 (5 days after last desensitization treatment), 18, 22, 26, and 30, the mice subjected to desensitization treatments (Groups 1 and 2) were challenged orally with freshly ground whole dry-roasted peanut. The naive mice (Group 3) were challenged at Week 30 only. Briefly, all mice (including those in Group 3) were fasted overnight. The next morning, each of the mice in Groups 1-2 were orally gavaged with 0.5 ml of a PBS solution containing 100 mg freshly ground whole peanut, 10 µg cholera

TABLE 5

Summary of Study Design

| | | | Desensitization Treatment (Week 11[d], 12, 13, 14) | | | | | No. Mice Challenged with Whole Peanut | | | | |
|---|---|---|---|---|---|---|---|---|---|---|---|---|
| Group No. | No. Mice/ Group | Sensitization Treatment[a]? | Test Material | Dose Concentration (mg/mL) | Dose Volume (ml/mouse) | Daily Dose (mg/mouse) | Dosage Regimen | Route | Wk 14[e] | Wk 18 | Wk 22 | Wk 26 | Wk 30 |
| 1 | 8 | Yes | Vehicle Control | 0 | 0.5 | 0 | 1/week × 4 weeks | Oral | 8 | 8 | 8 | 8 | 8 |
| 2 | 12 | Yes | NP-401 | 7.34[c] | 0.5 | 3.67[d] | 1/week × 4 weeks | Oral | 12 | 12 | 12 | 12 | 12 |
| 3 | 10 | No (naïve) | — | — | — | — | — | — | 0 | 0 | 0 | 0 | 10 |

1.835 µg/mouse, respectively
[e]Five days after last desensitization dose
[a]At study week 0, 1, 2, 3, 4, 5, 6, and 8.
[b]Eighteen days after last sensitization dose.
[c]Dose concentration of nanoparticles. The corresponding concentrations of peanut protein and CpG-biotin are 400 and 3.67 µg/ml, respectively.
[d]Dose of nanoparticles. The corresponding dose of peanut protein and CpG-biotin are 200 and 1.835 µg/mouse, respectively.
[e]Five days after last desensitization dose.

A. Sensitization (Weeks 0, 1, 2, 3, 4, 5, 6, and 8)

Three groups (Groups 1-3) of 6-week-old female C3H/HeJ mice, weighing approximately 15 g each, were used for this study. Group 1 had 8 mice, Group 2 had 12 mice, and Group 3 had 10 mice. Groups 1 and 2 were sensitized with peanut plus cholera toxin over a period of 8 weeks, while Group 3 (naïve control) received no sensitization treatments.

toxin, 8.25 µl of alcohol, and 1.5% sodium bicarbonate (w/v). Thirty minutes later, the mice were orally gavaged with an additional 0.5 ml of the above solution (i.e., for a total of 200 mg of ground whole peanut per mouse).

Twenty-four hours after each oral food challenge (OFC), the mice in Groups 1-2 were orally gavaged with 0.5 ml of a PBS solution containing 10 mg freshly ground whole peanut, 20 µg cholera toxin, 16.5 µl of alcohol, and 1.5% sodium bicarbonate (w/v). This was done to maintain reactivity of the mice for the long duration of the study.

D. Anaphylactic Symptom Scores

Mice were observed for symptoms of anaphylaxis for a period of 1 hour after each desensitization treatment (Weeks 11, 12, 13, and 14) and for a period of 30 minutes after each OFC (Weeks 14, 18, 22, 26, and 30). The following scoring system was used for evaluating anaphylactic symptoms: 0 for no symptoms; 1 for scratching and rubbing around the nose and head; 2 for puffiness around the eyes and snout, diarrhea, pilar erecti, reduced activity, and/or decreased activity with increased respiratory rate; 3 for wheezing, labored respiration, and cyanosis around the mouth and the tail; 4 for no activity after gentle prodding or tremor and convulsion; 5 for death.

E. Body Temperature

Thirty minutes after administration of each OFC (Weeks 14, 18, 22, 26, and 30), the mice were evaluated for body temperature using a rectal thermometer. The Group 3 mice that were not challenged at Weeks 14, 18, 22, and 26 had their temperatures recorded at the same time point as the Group 1 and 2 animals.

F. Plasma Histamine Levels

Plasma histamine levels were measured after administration of each OFC (Weeks 14, 18, 22, 26, and 30). Briefly, 30 minutes after administration of the OFC, blood was collected, plasma was isolated, and the plasma stored at −80° C. until assayed. The level of plasma histamine was measured using a commercially available histamine enzyme linked immunosorbent assay (ELISA) kit (Immunotech, Marseille, France), with the concentration of histamine calculated by comparison with the standard curve provided.

G. Serum Peanut-Specific IgE and IgG2a Levels

Serum levels of peanut-specific IgE and IgG2a were measured one day prior to the first desensitization at Week 11, and one day prior to each OFC (Weeks 14, 18, 22, 26, and 30). At the above specified time points, blood was collected, serum isolated, and the serum stored at −80° C. until assayed.

Peanut-specific IgE was measured as follows: Ninety-six-well Immulon 4HB (Thermo Scientific, Milford, Mass.) plates were coated with crude peanut extract (500 µg/ml defatted peanut preparation) or rat anti-mouse IgE (2 µg/ml, BD Biosciences, San Diego, Calif.). After an overnight incubation at 4° C., the plates were washed three times, and then blocked for 3 hours at 37° C. with 2% BSA (Sigma, St. Louis, Mo.) in PBS. The plates were washed three times, and then a 1:50 dilution of the test serum sample was added to the crude peanut extract-coated wells, and ten serial dilutions (1:2, starting at 1,000 ng/mL) of purified mouse IgE (BD Biosciences, San Diego, Calif.) were added to the rat anti-mouse IgE-coated wells to generate a reference curve. All dilutions were made with 2% BSA in PBS. Following an overnight incubation, the plates were washed three times, and then biotinylated rat anti-mouse IgE (1 µg/ml, BD Biosciences, San Diego, Calif.) was added for 1 hour at RT. The plates were washed 6 times, and then incubated for 15 minutes with a 1:4,000 dilution of streptavidin-horseradish peroxidase (1 mg/ml, Sigma, St. Louis, Mo.). The plates were washed six times, and then developed with ABTS® peroxidase substrate (KPL, Gaithersburg, Md.) for 30 minutes. Absorbance was measured at 405 nm by a microplate reader.

Peanut-specific IgG2a were measured as follows: Ninety-six-well Immulon 4HB plates were coated with crude peanut extract (2 µg/ml) or dinitrophenyl (DNP, 2 µg/ml, Sigma, St. Louis, Mo.). After an overnight incubation at 4° C., the plates were washed three times, and then blocked for 3 hours at 37° C. with 1% human serum albumin (Sigma, St. Louis, Mo.) in PBS with 0.5% Tween-20 (Sigma, St. Louis, Mo.). The plates were washed three times, and then dilutions of the test serum sample (1:1,000 for IgG2a method) were added to the crude peanut extract-coated wells, and ten serial dilutions (1:3, starting at 2,000 ng/mL) of mouse anti-DNP IgG2a (Accurate, N.Y.) were added to the DNP-coated wells to generate a reference curve. All dilutions were made in 1% human serum albumin in PBS with 0.5% Tween-20. Following an overnight incubation, the plates were washed three times, and then biotinylated rat IgG2a (0.25 µg/ml, BD Biosciences, San Diego, Calif.) was added for 1 hour at RT. The plates were washed 6 times, and then incubated for 15 minutes with a 1:4,000 dilution of streptavidin-horseradish peroxidase (1 mg/ml, Sigma, St. Louis, Mo.). The plates were washed six times, and then developed with ABTS® peroxidase substrate for 30 minutes. Absorbance was measured at 405 nm by a microplate reader.

H. Spleen Cell Cytokine Levels

Thirty to forty minutes after the fifth OFC, all mice were sacrificed, their spleens removed, spleen cells isolated, and the resulting spleen cell cultures assayed for cytokines (IL-4, IL-5, IL-10, IL-13, IFN-γ, and TGF-β) in the presence or absence of crude peanut extract. Individual cultures were set up for each animal. The spleen cells were suspended in RPMI 1640 (Mediatech, Herndon, Va.) supplemented with 10% fetal bovine serum (Invitrogen, Carlsbad, Calif.) and 1% penicillin/streptomycin (MP Biomedicals, Solon, Ohio) and plated in 24-well plates in the presence or absence of crude peanut extract. Seventy-two hours later, the culture supernatants were collected and the level of cytokines assayed by commercially available ELISA kits. OptEIA ELISA Kits (BD Biosciences, San Diego, Calif.) were used for all cytokines, except TGF-β and IL-13, which were measured using duo-set kits from R&D systems (Minneapolis, Minn.).

Results

I. Serum Peanut-Specific IgE Levels

Figure 5:
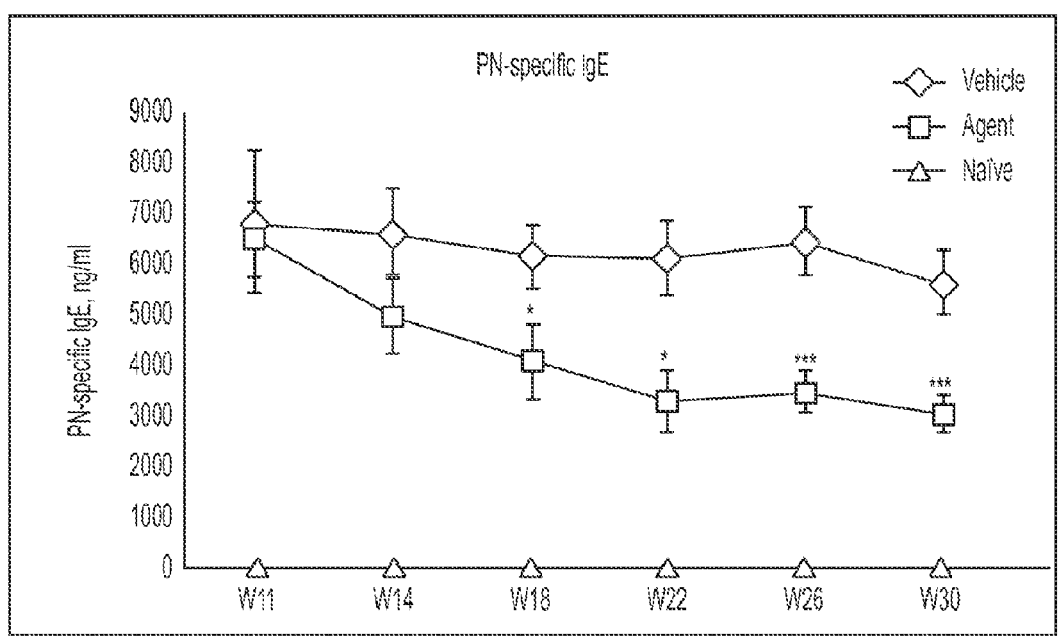
FIG. 5: depicts an exemplary result illustrating the mean±standard error of the mean (SEM) serum concentrations of peanut-specific IgE one day prior to initiation of desensitization treatment at Week 11 (pre-therapy) and one day prior to each oral food challenge (OFC) at Weeks 14, 18, 22, 26, and 30. "Agent" depicts mice treated with CpG-coated, PLGA-encapsulated peanut extract nanoparticles; "vehicle" depicts mice treated with control; "naïve" depicts mice receiving no treatments of any type.

Exemplary mean±standard error of the mean (SEM) serum concentrations of peanut-specific IgE one day prior to the first desensitization at Week 11 (pre-therapy) and one day prior to the OFC at Weeks 14, 18, 22, 26, and 30 are shown in FIG. 5. Mice receiving no treatments of any type (naïve control) had undetectable peanut-specific IgE levels throughout the study. Both groups of mice subjected to sensitization treatments showed presence of peanut-specific IgE levels at Weeks 11 through 30. No statistical difference in mean peanut-specific IgE was observed between vehicle and Agent treated groups at Week 11 (one day prior to desensitization; vehicle control: 6,844±1,411 ng/mL, Agent: 6,525±729 ng/mL).

Four days after the completion of the desensitization treatments (Week 14, one day prior to the first OFC), Agent treated mice showed a trend of decreased levels of peanut-specific IgE (4,980±732 ng/mL) when compared to mice administered vehicle (6,662±861 ng/mL, P<0.07). During the remainder of the study, mean peanut-specific IgE levels in Agent treated mice were significantly lower than those observed for vehicle treated mice (P<0.05-0.001).

2. Peanut-Specific IgG2a Levels

Figure 6:
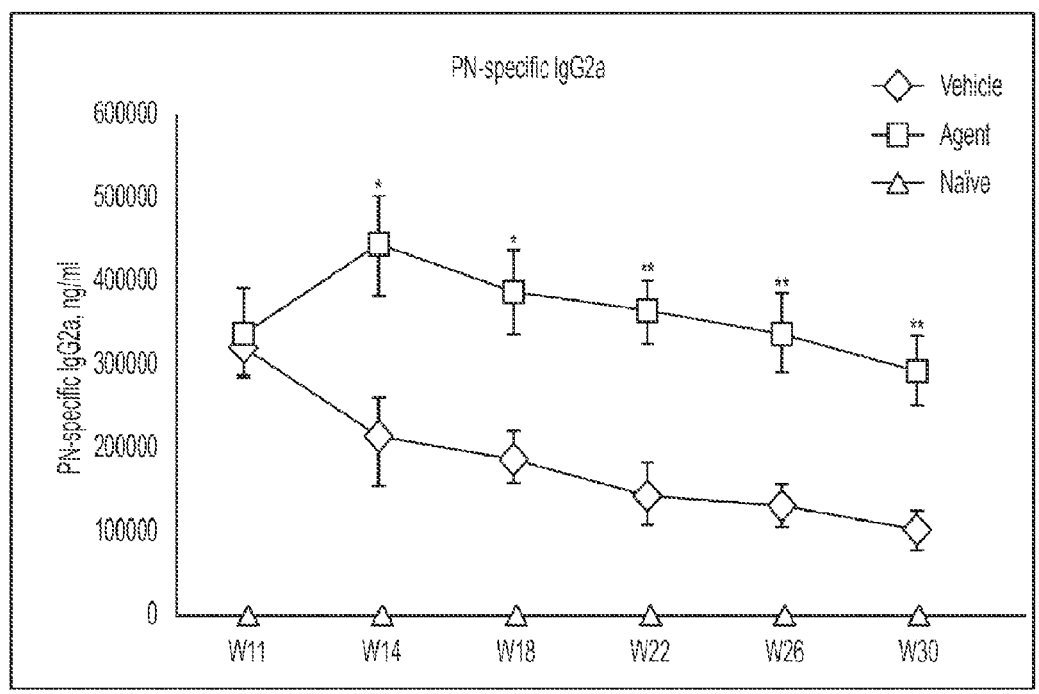
FIG. 6: depicts an exemplary result illustrating the mean±SEM serum concentrations of peanut-specific IgG2a one day prior to the sensitizations at Week 11 (pre-therapy) and one day prior to the OFC at Weeks 14, 18, 22, 26, and 30. "Agent" depicts mice treated with CpG-coated, PLGA-encapsulated peanut extract nanoparticles; "vehicle" depicts mice treated with control; "naïve" depicts mice receiving no treatments of any type.

Exemplary mean±SEM serum concentrations of peanut-specific IgG2a one day prior to the sensitizations at Week 11 (pre-therapy) and one day prior to the OFC at Weeks 14, 18, 22, 26, and 30 are shown in FIG. 6. Mice receiving no treatments of any type (naïve control) had undetectable peanut-specific IgG2a levels throughout the study. Both groups of mice subjected to sensitization treatments showed presence of peanut-specific IgG2a levels at Weeks 11 through 30. No statistical difference in mean peanut-specific IgG2a was observed between vehicle and Agent treated groups at Week 11 (one day prior to desensitization; vehicle control: 318,286±32,586 ng/mL, Agent: 339,592±51,494 ng/mL).

Four days after the completion of the desensitization treatments (Week 14, one day prior to the first OFC), the Agent treated mice showed an increase in the level of mean peanut-specific IgG2a (444,426±60,288 ng/mL) while the mice administered vehicle showed a decrease in the level of mean peanut-specific IgG2a (207,741±53,494 ng/mL, P<0.05). After Week 14, the mean peanut-specific IgG2a levels decreased for both the vehicle and AGENT treated mice; however, at all time points subsequent to Week 11, the mean levels of peanut-specific IgG2a in the Agent treated mice remained significantly higher than those observed in the vehicle treatment group (P<0.05-0.01).

3. Anaphylactic Symptom Scores During Desensitization Period

Mice treated with vehicle control or 3.67 mg/mouse Agent (200 µg peanut protein and 1.835 µg CpG-biotin) showed no signs of anaphylaxis during the 1-hour observation period following each desensitization treatment. All mice had anaphylactic symptom scores of 0 (0=no symptoms).

4. Anaphylactic Symptom Scores Following OFCs

Figure 7:
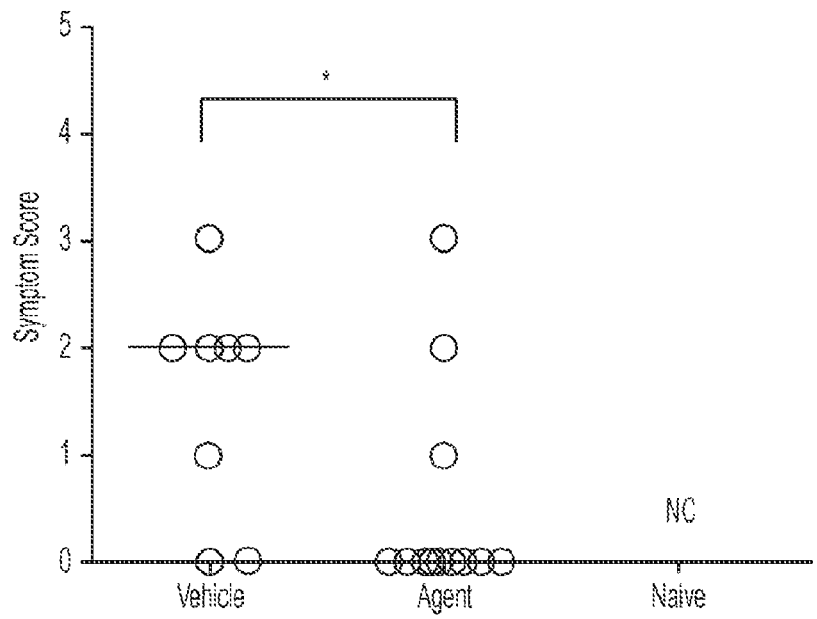
FIG. 7: depicts an exemplary result illustrating individual and median anaphylactic symptom scores following OFC at Weeks 14 and 18 (*=P<0.05; NC=not challenged). "Agent" depicts mice treated with CpG-coated, PLGA-encapsulated peanut extract nanoparticles (200 µg peanut protein and 1.835 µg CpG-biotin); "vehicle" depicts mice treated with control; "naïve" depicts mice receiving no treatments of any type.
Figure 7:
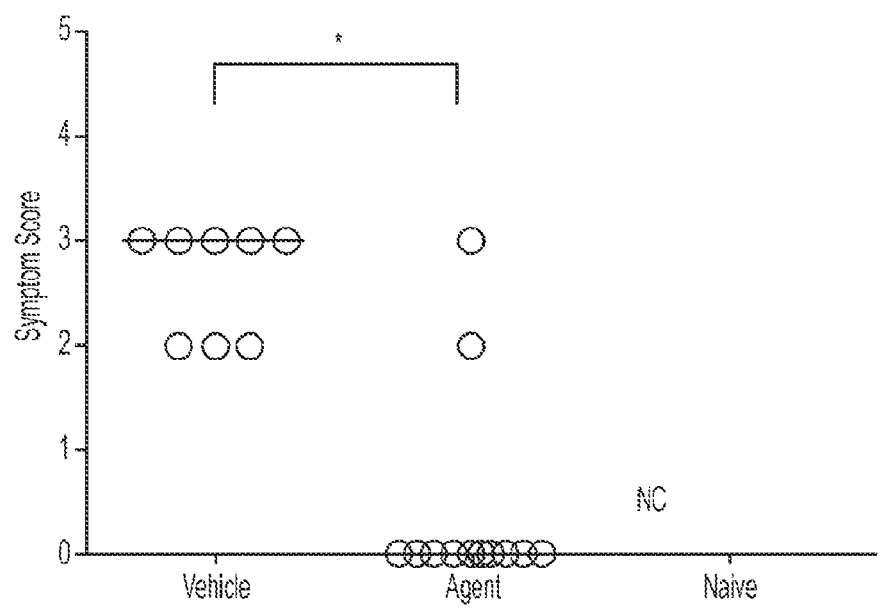
Figure 8:
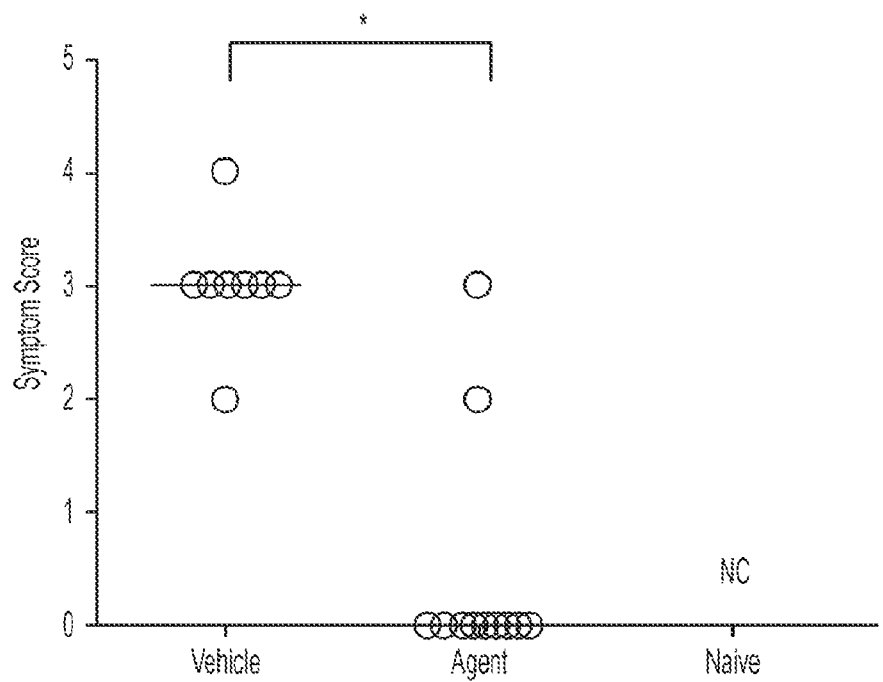
FIG. 8: depicts an exemplary result illustrating individual and median anaphylactic symptom scores following OFC at Weeks 22 and 26 (*=P<0.05; NC=not challenged). "Agent" depicts mice treated with CpG-coated, PLGA-encapsulated peanut extract nanoparticles (200 µg peanut protein and 1.835 μg CpG-biotin); "vehicle" depicts mice treated with control; "naïve" depicts mice receiving no treatments of any type.
Figure 8:
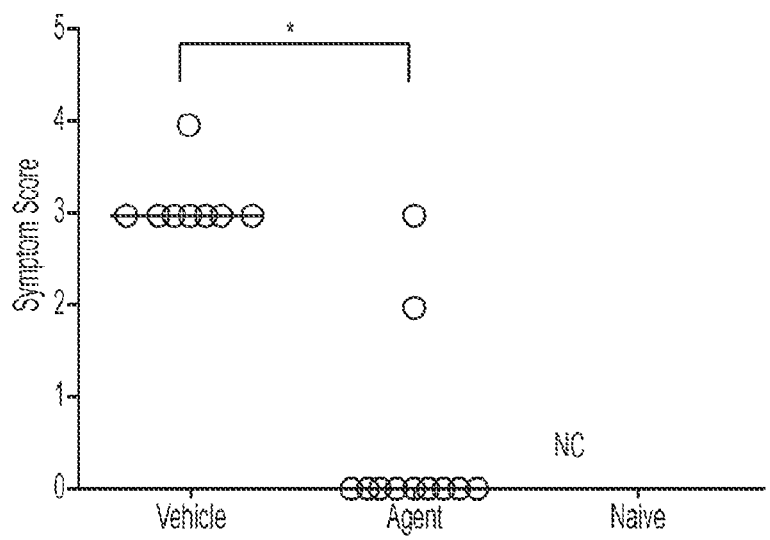
Figure 9:
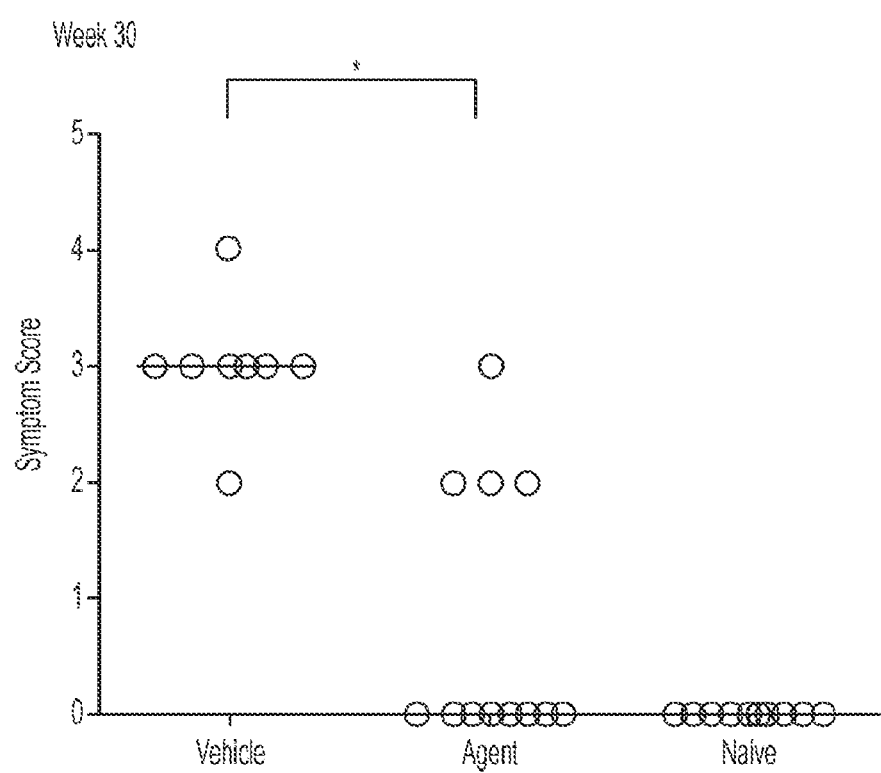
FIG. 9: depicts an exemplary result illustrating individual and median anaphylactic symptom scores following OFC at Weeks 30 (*=P<0.05). "Agent" depicts mice treated with CpG-coated, PLGA-encapsulated peanut extract nanoparticles (200 μg peanut protein and 1.835 CpG-biotin); "vehicle" depicts mice treated with control; "naïve" depicts mice receiving no treatments of any type.

Exemplary individual and median anaphylactic symptom scores following the OFC at Weeks 14 and 18, 22 and 26, and 30 are shown in FIGS. 7, 8, and 9, respectively. Mice receiving no sensitization/treatments of any type (i.e., naïve control) showed no anaphylactic symptoms (i.e., all mice had an anaphylactic symptom score of 0) following the OFC at Week 30. The naïve control mice were not challenged at Weeks 14, 18, 22, and 26.

Sensitized mice administered vehicle control showed signs of anaphylaxis following the OFC at Week 14. Specifically, 1 mouse scored a 3 (wheezing, labored respiration, and cyanosis around the mouth and tail), 4 mice scored a 2 (puffiness around eyes and snout, diarrhea, pilar erecti, reduced activity, and/or decreased activity with increased respiratory rate), and 1 mouse scored a 1 (scratching and rubbing around the nose and head). Two mice showed no symptoms (score of 0). The anaphylactic symptoms in these mice worsened with subsequent challenges up through Week 26, with 1 mouse scoring a 4 (no activity after gentle prodding or tremor and convulsion) and the remaining 7 mice scoring a 3. At Week 30, 1 mouse that had scored a 3 at Week 26 had reduced symptoms (score of 2).

Oral administration of 3.67 mg/mouse Agent (200 µg peanut protein and 1.835 µg CpG-biotin) once a week for four consecutive weeks in peanut-sensitized mice resulted in a statistically significant decrease in the anaphylactic symptom scores at all five OFCs (P<0.05). Nine of the 12 mice (75%) were completely protected from anaphylactic symptoms (score of 0) after the first challenge, with the remaining three having symptom scores of 1, 2, and 3, respectively. By the second challenge, the mouse that had scored a 1 at the first challenge scored a 0, bringing the total number of completely protected to 10 (83%). This remained the same through the fourth challenge (i.e., 3 months after desensitization treatment was stopped). Four months after desensitization treatment was stopped, 2 of the 10 mice that were completely protected at Week 26 had increased symptoms (score of 2).

5. Body Temperatures Following OFCs

Figure 10:
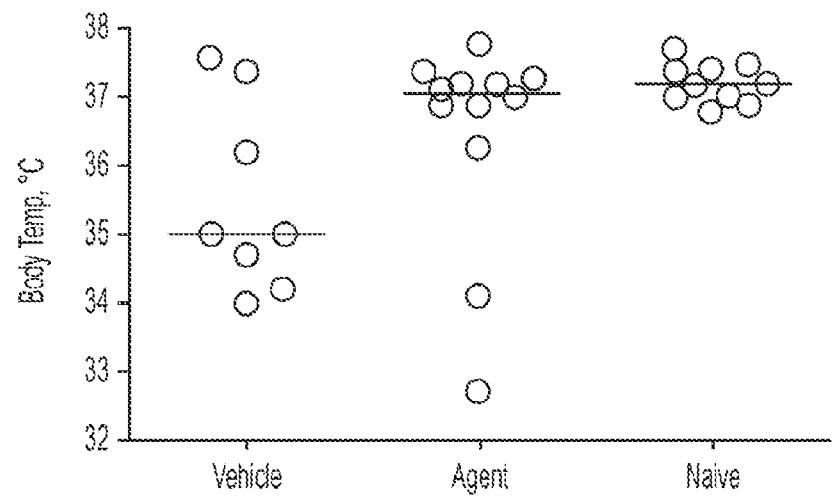
FIG. 10: depicts an exemplary result illustrating individual and mean body temperatures following OFCs at Weeks 14 and 18 (*=P<0.05). "Agent" depicts mice treated with CpG-coated, PLGA-encapsulated peanut extract nanoparticles (200 μg peanut protein and 1.835 μg CpG-biotin); "vehicle" depicts mice treated with control; "naïve" depicts mice receiving no treatments of any type.
Figure 10:
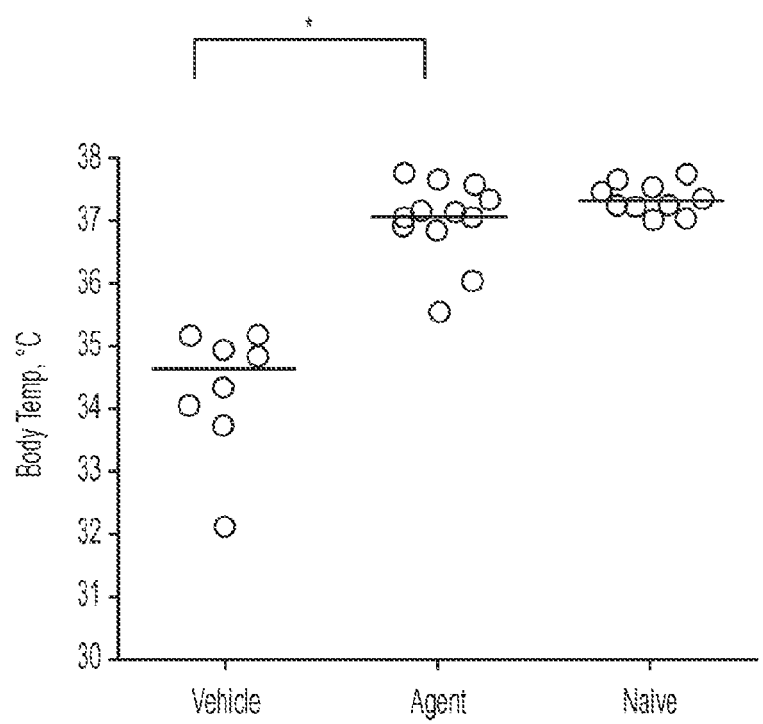
Figure 11:
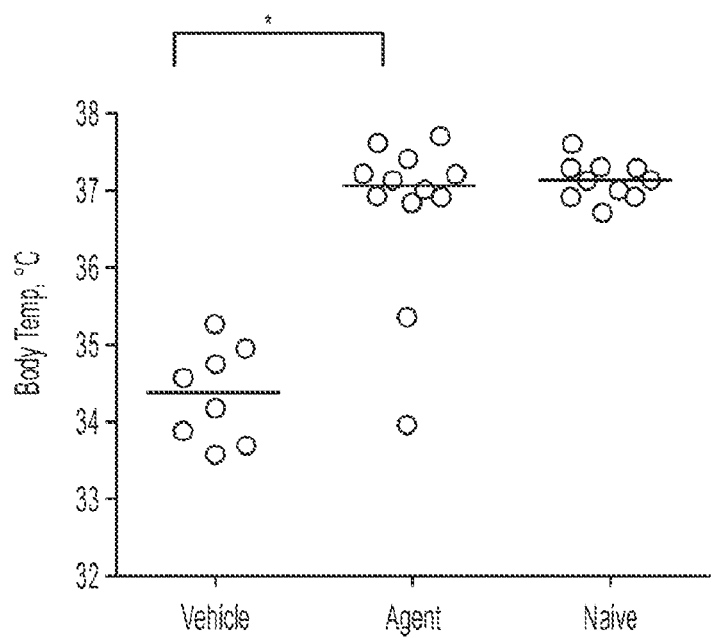
FIG. 11: depicts an exemplary result illustrating individual and mean body temperatures following OFCs at Weeks 22 and 26 (*=P<0.05). "Agent" depicts mice treated with CpG-coated, PLGA-encapsulated peanut extract nanoparticles (200 μg peanut protein and 1.835 μg CpG-biotin); "vehicle" depicts mice treated with control; "naïve" depicts mice receiving no treatments of any type.
Figure 11:
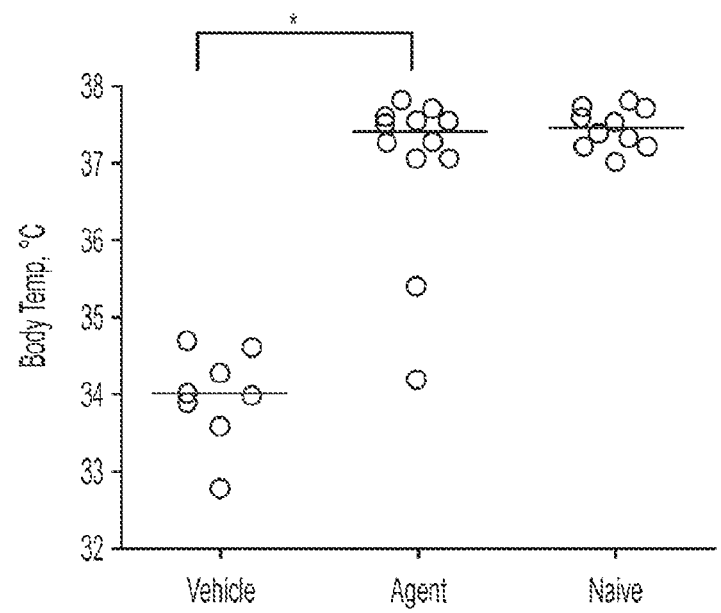
Figure 12:
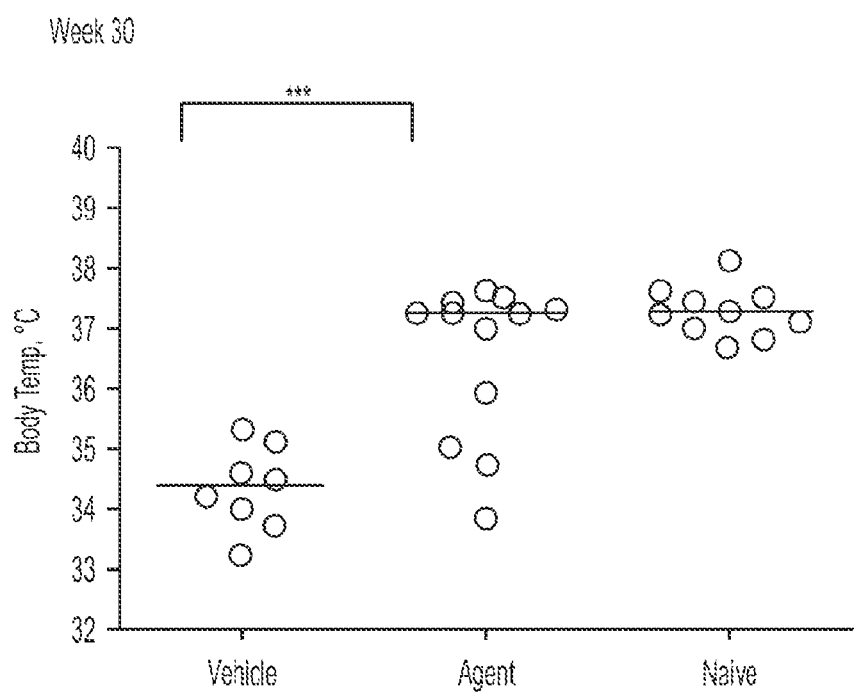
FIG. 12: depicts an exemplary result illustrating individual and mean body temperatures following OFC at Week 30 (*=P<0.05). "Agent" depicts mice treated with CpG-coated, PLGA-encapsulated peanut extract nanoparticles (200 μg peanut protein and 1.835 μg CpG-biotin); "vehicle" depicts mice treated with control; "naïve" depicts mice receiving no treatments of any type.

Exemplary individual and mean body temperatures following OFCs at Weeks 14 and 18, 22 and 26, and 30 are shown in FIGS. 10, 11, and 12, respectively. The Group 3 mice that were not challenged at Weeks 14, 18, 22, and 26 had their temperatures recorded at the same time point as the Group 1 and 2 animals. Following each OFC, the vehicle control group had mean body temperatures that were consistently lower than that of the naïve control mice. Oral administration of 3.67 mg/mouse Agent (200 µg peanut protein and 1.835 µg CpG-biotin) once a week for four consecutive weeks in peanut-sensitized mice resulted in an increase in the mean body temperatures relative to vehicle control animals at all five OFCs. The increase was statistically significant at all but the first challenge (P<0.05 at $2^{nd}$, $3^{th}$ and $4^{th}$ challenge and P<0.001 at the $5^{th}$ challenge).

6. Plasma Histamine Levels Following OFCs

Figure 13:
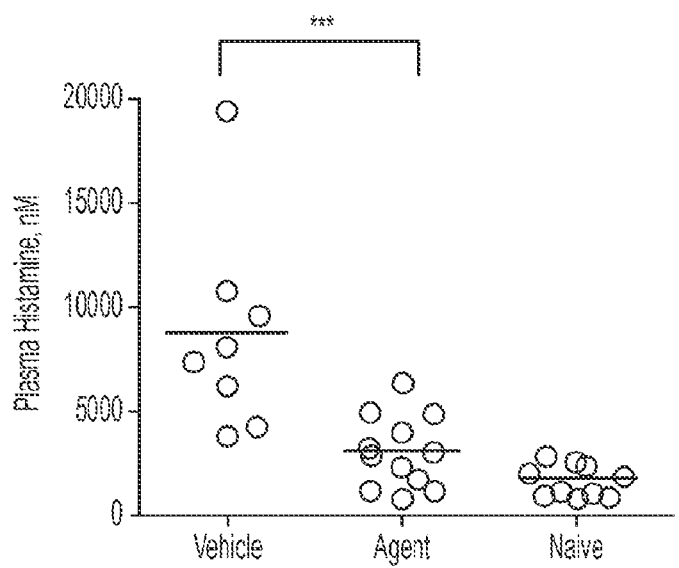
FIG. 13: depicts an exemplary result illustrating individual and mean plasma histamine levels following OFCs at Weeks 14 and 18 (***=P<0.001). "Agent" depicts mice treated with CpG-coated, PLGA-encapsulated peanut extract nanoparticles (200 μg peanut protein and 1.835 μg CpG-biotin); "vehicle" depicts mice treated with control; "naïve" depicts mice receiving no treatments of any type.
Figure 13:
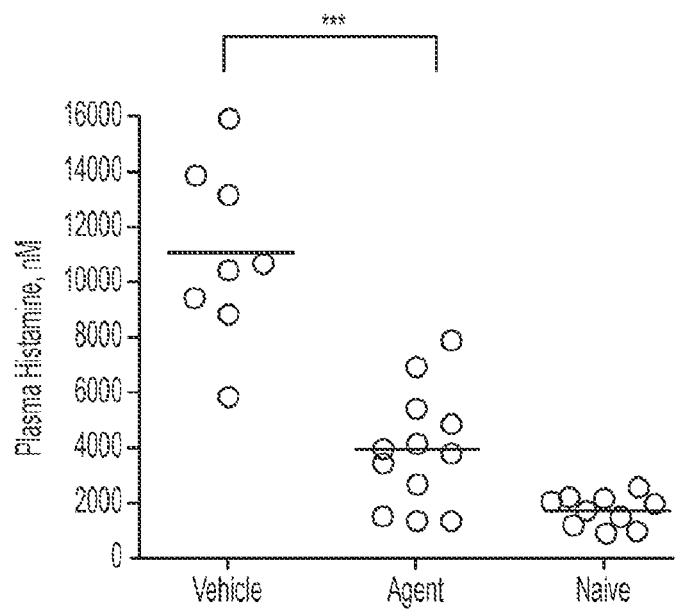
Figure 14:
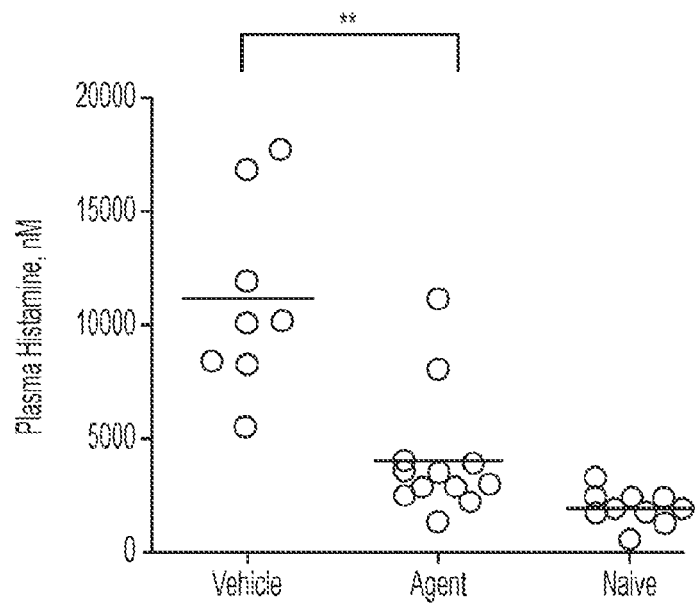
FIG. 14: depicts an exemplary result illustrating individual and mean plasma histamine levels following OFCs at Weeks 22 and 26 (*=P<0.05; **P<0.01). "Agent" depicts mice treated with CpG-coated, PLGA-encapsulated peanut extract nanoparticles (200 μg peanut protein and 1.835 μg CpG-biotin); "vehicle" depicts mice treated with control; "naïve" depicts mice receiving no treatments of any type.
Figure 14:
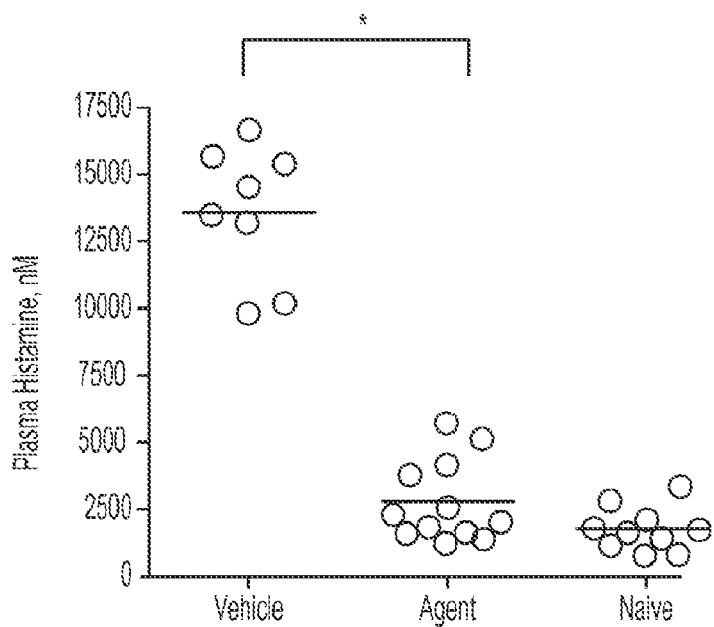
Figure 15:
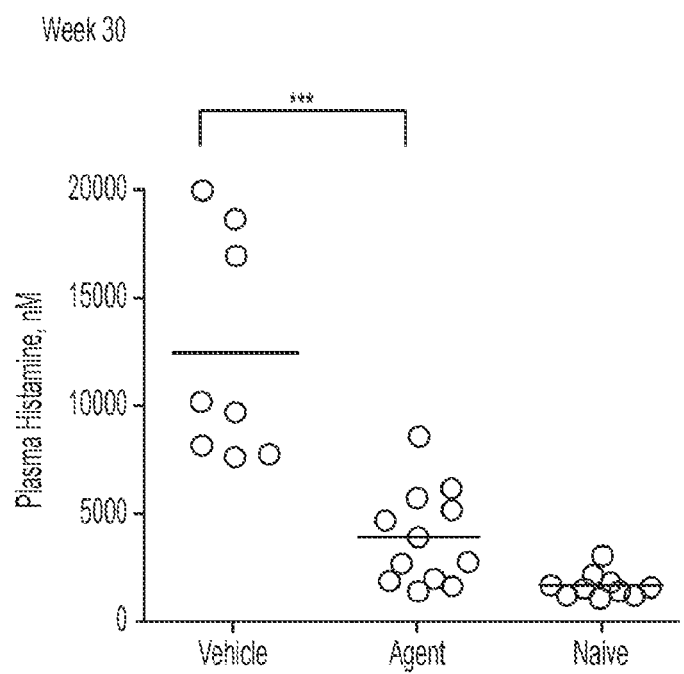
FIG. 15: depicts an exemplary result illustrating individual and mean plasma histamine levels following OFC at Week 30 (*=P<0.05). "Agent" depicts mice treated with CpG-coated, PLGA-encapsulated peanut extract nanoparticles (200 μg peanut protein and 1.835 μg CpG-biotin); "vehicle" depicts mice treated with control; "naïve" depicts mice receiving no treatments of any type.

Exemplary individual and mean plasma histamine levels following OFCs at Weeks 14 and 18, 22 and 26, and 30 are shown in FIGS. 13, 14, and 15, respectively. The Group 3 mice that were not challenged at Weeks 14, 18, 22, and 26 had their plasma histamine measured at the same time point as the Group 1 and 2 animals. The mean plasma histamine levels 30 minutes after each OFC were higher in the vehicle control group relative to the naïve control group. Oral administration of 3.67 mg/mouse Agent (200 µg peanut protein and 1.835 µg CpG-biotin) once a week for four consecutive weeks in peanut-sensitized mice resulted in a statistically significant decrease in the mean plasma histamine levels relative to vehicle control animals at all five OFCs (P<0.05-0.001).

Figure 16:
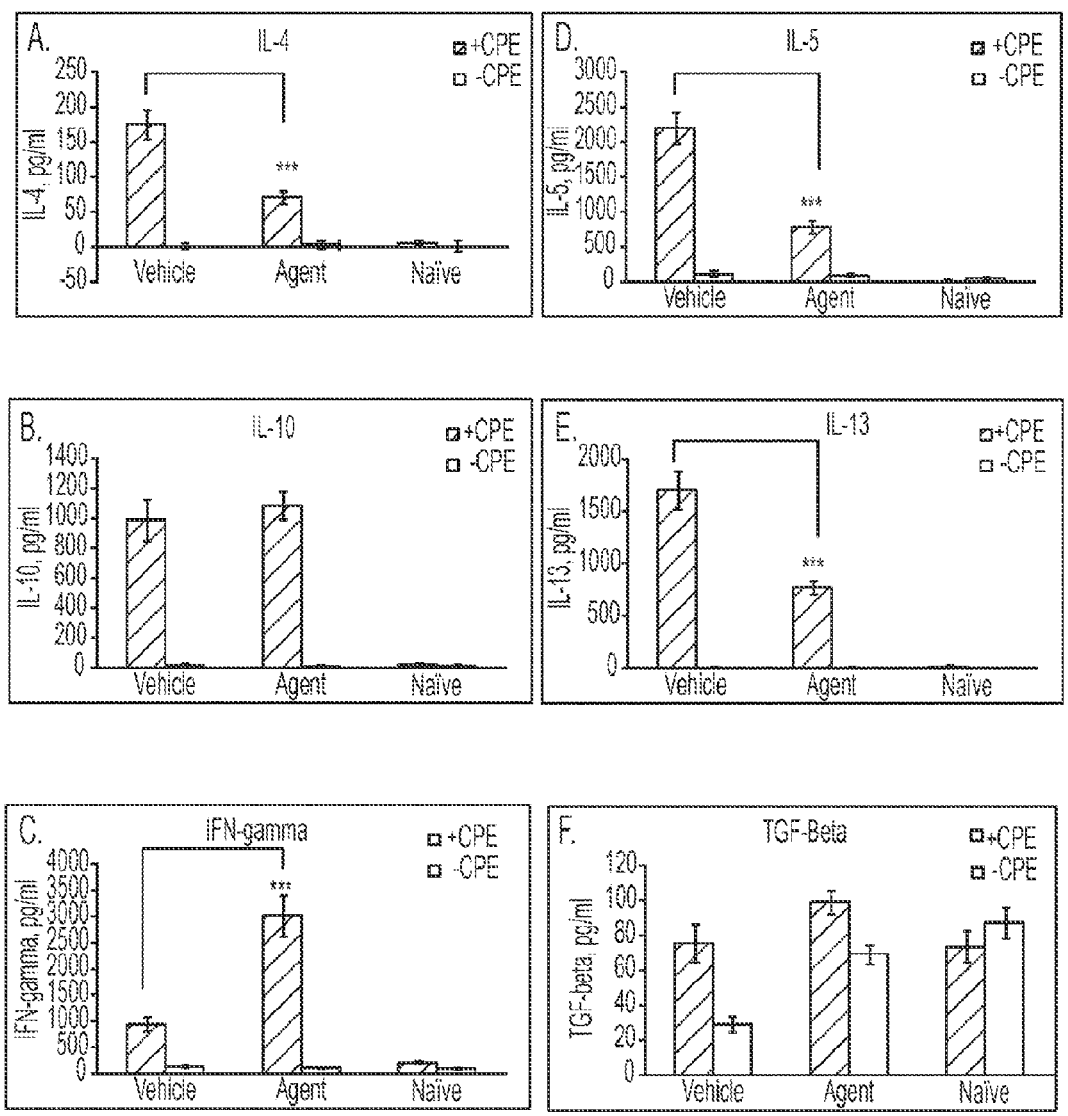
FIG. 16: depicts an exemplary result illustrating mean±SEM cytokine levels in post-OFC (Week 30) spleen cell cultures incubated with crude peanut extract (***=P<0.001 Vehicle vs. Agent). "Agent" depicts mice treated with CpG-coated, PLGA-encapsulated peanut extract; "vehicle" depicts mice treated with control; "naïve" depicts mice receiving no treatments of any type. Panel A depicts an exemplary result illustrating mean±SEM interleukin-4 (IL-4) levels. Panel B depicts an exemplary result illustrating mean±SEM interleukin-10 (IL-10) levels. Panel C depicts an exemplary result illustrating mean±SEM interferon (IFN)-gamma levels. Panel D depicts an exemplary result illustrating mean±SEM interleukin-5 (IL-5) levels. Panel E depicts an exemplary result illustrating mean±SEM interleukin-13 (IL-13) levels. Panel F depicts an exemplary result illustrating mean±SEM transforming growth factor (TGF)-Beta levels.
Figure 17:
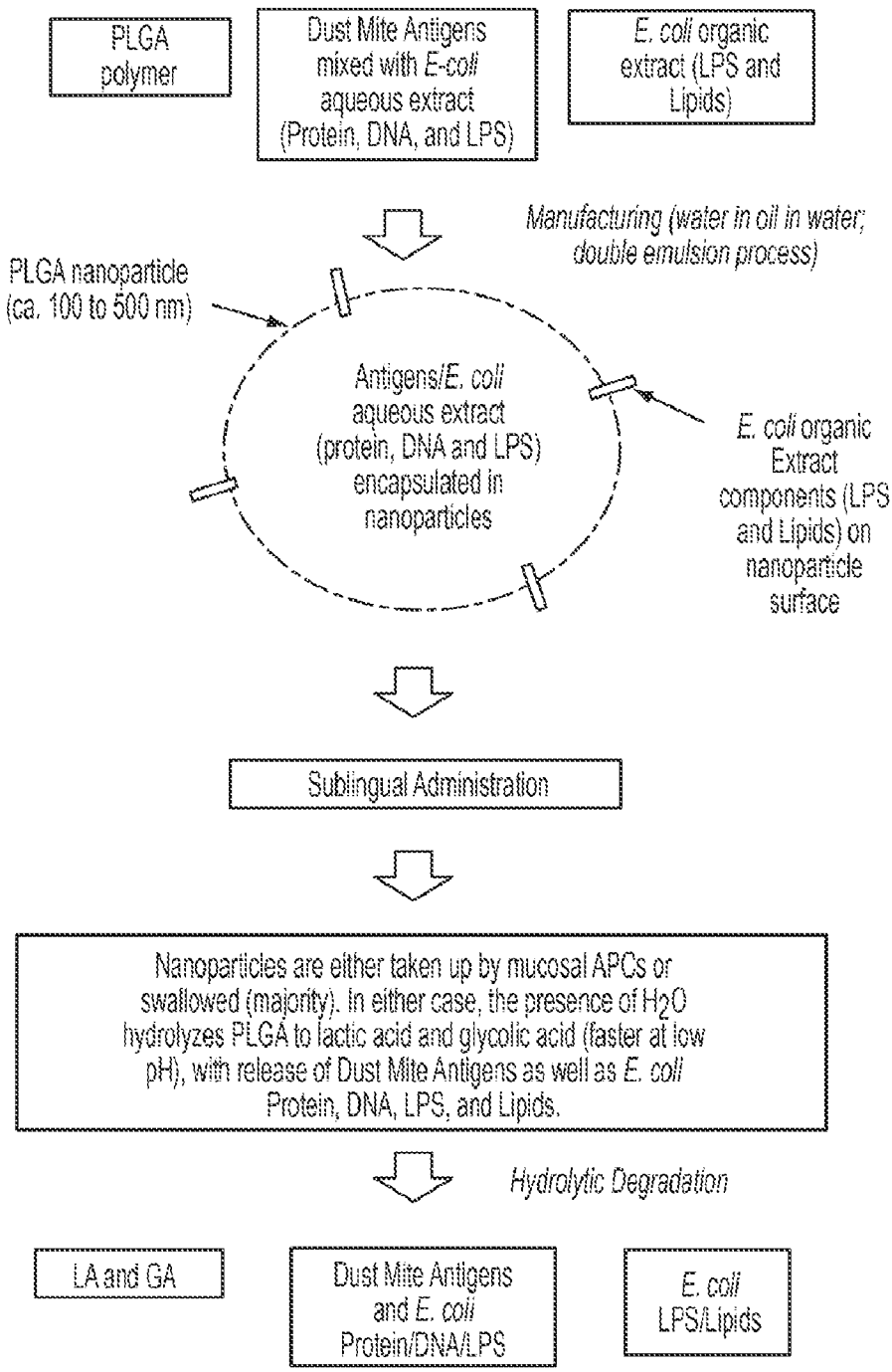
FIG. 17: depicts an exemplary schematic, according to some embodiments, of the manufacture, administration, and hydrolytic degradation of organic *E. coli* extract-coated poly(lactic-co-glycolic acid)-(PLGA-) nanoparticles encapsulating *D. farinae* and/or *D. pteronyssinus* dust mite extract and aqueous *E. coli* extract.
Figure 18:
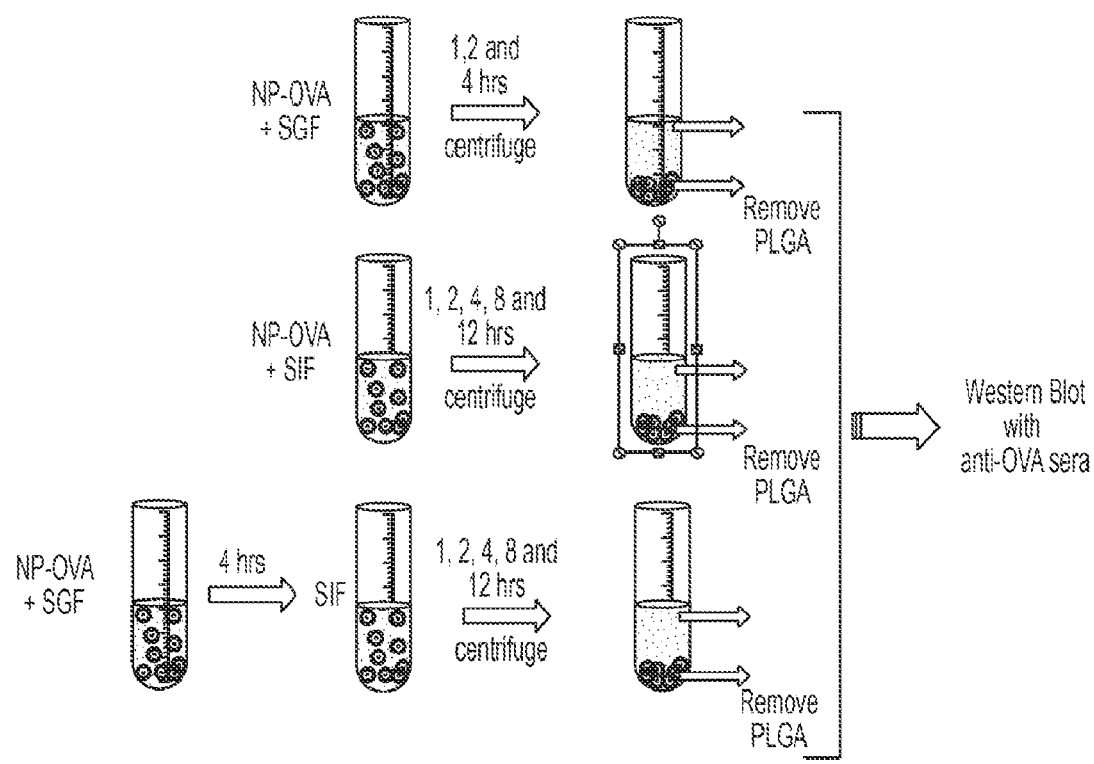
FIG. 18: shows an exemplary flow diagram of a protocol to test the affects of simulated gastric digestion in simulated gastric fluid (SGF) and/or simulated intestinal digestion in simulated intestinal fluid (SIF) on provided nanoparticles.

7. Cytokine Levels in Post-OFC (Week 30) Spleen Cell Cultures Incubated with Crude Peanut Extract Exemplary mean±SEM cytokine levels in post-OFC (Week 30) spleen cell cultures incubated with crude peanut extract are shown in FIG. 16. FIG. 16A depicts an exemplary result illustrating mean±SEM IL-4 cytokine levels. FIG. 16B depicts an exemplary result illustrating mean±SEM IL-10 cytokine levels. FIG. 16C depicts an exemplary result illustrating mean±SEM IFN-gamma cytokine levels. FIG. 16D depicts an exemplary result illustrating mean±SEM IL-5 cytokine levels. FIG. 16E depicts an exemplary result illustrating mean±SEM IL-13 cytokine levels. FIG. 16F depicts an exemplary result illustrating mean±SEM TGF-β cytokine levels.

The mean spleen cell production of IL-4, IL-5, IL-10, IL-13, IFN-γ, and TGF-β in the presence of crude peanut extract was higher in the vehicle control group relative to the naïve control group. Oral administration of 3.67 mg/mouse Agent (200 µg peanut protein and 1.835 µg CpG-biotin) once a week for four consecutive weeks in peanut-sensitized mice resulted in statistically significant decreases in mean spleen cell production of IL-4 (p<0.001), IL-5 (p<0.001), and IL-13 (p<0.001) relative to vehicle control, and in statistically significant increases in mean spleen cell production of IFN-γ (p<0.001) relative to vehicle control. No significant differences were observed between vehicle and Agent treated groups for IL-10 and TGF-β.

Conclusion

Peanut-sensitized mice orally administered 3.67 mg/mouse Agent (200 µg peanut protein and 1.835 µg CpG-biotin; i.e. CpG-coated, PLGA-encapsulated peanut extract nanoparticles) once a week for four consecutive weeks showed no symptoms of anaphylaxis during the desensitization period, indicating that CpG-coated, PLGA-encapsulated peanut extract nanoparticles lack anaphylactic potential in peanut-sensitized mice.

Further, oral administration of 3.67 mg/mouse Agent once a week for four consecutive weeks in peanut-sensitized mice resulted in desensitization to subsequent oral peanut challenges relative to vehicle control mice. This was evidenced by lower median anaphylactic symptom scores, higher mean body temperature (essentially similar to naïve mice), lower mean plasma histamine levels, a decrease in the mean serum peanut-specific IgE levels, an increase in the mean serum peanut-specific IgG2a levels, a decrease in the mean spleen cell production of IL-4, IL-5 and IL-13, and an increase in the mean spleen cell production of IFN-γ compared to vehicle-treated mice. The desensitization was still evident at four months after treatment with Agent was stopped, suggesting that tolerance may have been achieved in some animals.

Example 5: Preparation of *Arachis hypogaea* (Peanut) Allergen Extracts

The present Example describes preparation of a *Arachis hypogaea* (Peanut) Allergen Extract (i.e. crude peanut extract) for use in accordance with the present invention.

The present Example describes preparation of a Peanut Allergen Extract, containing Ara h 1, Ara h 2 and Ara h3 antigens, among others, for use in accordance with the present invention.

The present Example also describes preparation of recombinant modified peanut proteins (mAra h 1, mAra h 2, and mAra h 3, where m stands for modified), for use in accordance with the present invention.

*Arachis hypogaea* (Peanut) Allergen Extract (i.e. crude peanut extract) may be prepared as follows. Commercially available roasted peanuts in shells (White Rose Brand, N.J.) are de-shelled, homogenized in phosphate buffered saline (PBS, pH) 7.4), and subjected to acetone extraction. The final concentration of peanut protein in PBS is determined by bicinchoninic acid (BCA) assay. Peanut allergen extract may then be combined with aqueous *E. coli* extract (AEE) and prepared substantially as described in Example 3, for example.

Recombinant peanut proteins were prepared as follows. The three recombinant modified peanut proteins (mAra h 1, mAra h 2, and mAra h 3) were separately expressed in *E. coli* strain BLR(DE3), and the *E. coli* were subsequently killed using heat and phenol. The expressed proteins remained encapsulated within the dead *E. coli*., which resulted in three whole-cell suspensions referred to as EMP-1, EMP-2, and EMP-3 (i.e., encapsulated mAra h 1, mAra h 2, and mAra h 3, respectively). Each whole-cell suspension was then to used prepare aqueous *E. coli* extract (AEE)), as described in Example 1, which included the expressed recombinant peanut protein in the aqueous phase, for fabrication of a nanoparticle composition substantially as described in Example 3.

Example 6: In Vitro Cytokine Studies of Nanoparticle Compositions in Peripheral Blood Mononuclear Cells (PBMCs) of Allergic Patients The present Example describes exemplary in vitro stimulation of patient peripheral blood mononuclear cells (PBMCs) for evaluating the immunogenicity of provided nanoparticle compositions (i.e., nanoparticles containing hydrophilic and/or hydrophobic *E. coli* extract preparations) for use in accordance with the present invention.

The present Example describes exemplary in vitro stimulation of patient peripheral blood mononuclear cells (PBMCs) for evaluating the immunogenicity of provided nanoparticle compositions that comprise one or more antigens, including crude allergenic extract (such as *Arachis hypogaea, Dermatophagoides farina* or *Dermatophagoides pteronyssinus*), for use in accordance with the present invention.

The present example describes exemplary in vitro cytokine studies to evaluate the immunogenicity of organic *Escherichi coli* extract ("OEE") coated polylactide co-glycolide-("PLGA-") encapsulated *Dermatophagoides* (D.) *farinae* and *D. pteronyssinus* dust mite extract and aqueous *E. coli* extract (AEE) nanoparticles (hereinafter referred to as the "Agent").

In some embodiments, the studies described herein, including stimulation of allergic patient PBMCs, may be used for assessing immunological characteristics or effects of certain embodiments of the present invention.

In some embodiments, provided compositions may modulate immununological function in a subject. In some embodiments, such modulation may comprise desensitization. In some embodiments, such modulation does not comprise densitization. In some embodiments, immunological characteristics or effects include an altered allergen-specific Th2-dominated phenotype of dust mite allergic patient toward a Th1/Th0-like phenotype.

The objective of this in vitro study is to assess the ability of the Agent to alter the allergen-specific Th2-dominated phenotype of dust mite allergic patient peripheral blood mononuclear cells (PBMCs) toward a Th1/Th0-like phenotype. This model system includes polyclonal T cells and B cell antigen presenting cells (APCs) in a single culture.

The Agent in this Example comprises standardized allergenic extracts of two common house dust mites, *D. farinae* and *D. pteronyssinus*, mixed 1:1 by allergy unit. The dust mite extracts are the same as those found in the commercially available standardized dust mite extracts approved by FDA for use in subcutaneous immunotherapy (SCIT). The dust mite extracts are encapsulated within PLGA nanoparticles wherein the dust mite extract and bacterial protein, deoxyribonucleic acid (DNA), and lipopolysaccharide (LPS) of the AEE is encapsulated on the inside of the nanoparticles and the bacterial LPS and lipids of the OEE is coated on the outside of the nanoparticles.

Without wishing to be held to a particular theory, a pharmacological rationale for the encapsulation of the dust mite extract in provided nanoparticle compositions is to facilitate uptake by APCs in the sublingual mucosa and activation of the innate immune system, and thus to potentially improve the efficacy of sublingual immunotherapy (SLIT) with the extracts alone. Specifically, the Agent is designed to maximize the incorporation of the known toll-like receptor (TLR) agonists, bacterial LPS and CpG DNA motifs, as well as any potential unidentified agonists that may be present in the bacterial cells, thereby enhancing the potential efficacy of the Agent drug product.

This study will assess in vitro IFN-γ, IL-10, IL-5, and IL-4 levels in dust mite allergic patient PBMCs following treatment with the Agent compared against dust mite extract encapsulated within nanoparticles that lack *E. coli* components (Agent minus adjuvant), semi-synthetic bacterial cells without dust mite extract (Agent minus dust mite extract), and empty nanoparticles (Agent minus adjuvant and dust mite extract).

The general method of this Example (summarized below) is substantially based on the method published by Bohle et al. (Bohle et al., *J. Immunology,* 2004; 172:6642-6648) for a birch pollen allergy study. The method can be modified as necessary to improve the study design. In particular, one of skill in the art will recognize that certain parameters, including, but not limited to, the number of cells per well, the duration of culture, the culture conditions, and the dose of agent and stimulant may need to be optimized for a particular antigen and patient population.

Peripheral blood is collected from 10 dust mite allergic patients via venipuncture into heparinized syringes. All patients must have a history of perennial allergic rhinitis for a minimum of one year prior to blood collection and a demonstrated sensitivity to *D. farinae* or *D. pteronyssinus* by a positive prick skin test (PST) at the time of blood collection. A PST is defined as a mean wheal diameter 3 mm greater than that elicited by the negative control (saline) at 15-20 minutes. Patients must not have received allergen immunotherapy or immunomodulatory therapy within 6 and 3 months prior to blood collection, respectively. Patients must not have clinical history of significant symptomatic perennial allergic rhinitis and/or asthma due to another allergen (i.e., other than dust mites) to which the subject is regularly exposed.

PBMCs are isolated from the peripheral blood of dust mite allergic patients by Ficoll-Hypaque density gradient centrifugation (Pharmacia). The whole blood should be processed to PBMCs as soon after collection as possible, ideally within 8-12 hours. The PBMCs are typically not be frozen prior to assay.

The PBMCs are cultured in 96-well plates (Nunclone; Nunc) in serum-free Ultra Culture Medium (BioWhittaker, Walkersville, Md.) supplemented with 2 mM L-glutamine, $2 \times 10^{-5}$ M 2-mercaptoethanol, and study drug/control. Triplicate wells at $1 \times 10^6/200$ µl and triplicate wells at $2 \times 10^5/200$ µL will be set up for each of the following study drug/controls for each dust mite allergic patient's PBMCs:
1. Low dose Agent [dose will be expressed as the final concentration of nanoparticles (mg/ml) in culture media];
2. Mid dose Agent;
3. High dose Agent;
4. Agent minus adjuvant (same dose as #3);
5. Agent minus dust mite extract (same dose as #3);
6. Agent minus adjuvant and dust mite extract (same dose as #3);
7. Media only control.

As described above, triplicate wells are set up at $1 \times 10^6/200$ µl and are used to follow the Th1-related cytokines After 48 hours of culture with study drug/controls, the supernatants is collected and analyzed for IFN-γ and IL-10 content using an enzyme-linked immunosorbent assay (ELISA) with endogen matched Ab pairs (Endogen, Woburn, Mass.) according to the manufacturer's instructions.

Additionally, triplicate wells are set up at $2 \times 10^5/200$ µL and are used to follow each of the Th2-related cytokines After 6 days of culture with study drug/controls, the cells are washed, counted, and restimulated at $1 \times 10^6/200$ µl with phorbol myristate acetate (PMA, 10 ng/ml) plus ionomycin (1 µM) for 24 hours. After 24 hours of restimulation, the supernatants are collected and analyzed for IL-5 and IL-4 content using an ELISA with endogen matched Ab pairs (Endogen, Woburn, Mass.).

Example 7: A Phase 1, Randomized, Double-Blind, Placebo-Controlled Safety, Pharmacodynamic, and Preliminary Efficacy Study of Dust Mite Allergy Vaccine Administered Sublingually in Adult Subjects with Perennial Allergic Rhinitis and Sensitive to *Dermatophagoides farinae* or *Dermatophagoides pteronyssinus*

This present Example describes an exemplary phase 1, single-center, randomized, double-blind, placebo-controlled, safety, pharmacodynamic, and preliminary efficacy study of provided nanoparticle compositions (in this Example, nanoparticles containing hydrophilic and/or hydrophobic *E. coli* extract preparations), in adult subjects with perennial allergic rhinitis (with or without asthma) and sensitive to *D. farinae* or *D. pteronyssinus*, for use in accordance with the present invention.

In some embodiments, provided nanoparticle compositions are organic *Escherichia coli* extract ("OEE") coated poly(lactic-co-glycolic acid)-("PLGA-") encapsulated *Dermatophagoides* (D) *farinae* and *D. pteronyssinus* dust mite extract and aqueous *E. coli* extract (AEE) nanoparticles (hereinafter referred to as the "Agent" and/or "Dust Mite Allergy Vaccine").

The present Example describes an exemplary clinical trial design for evaluating the pharmacodynamics and preliminary efficacy of provided nanoparticle compositions (in this Example, nanoparticles containing hydrophilic and/or hydrophobic *E. coli* extract preparations) for use in accordance with the present invention.

The present Example describes an exemplary protocol synopsis for evaluating the pharmacodynamics and preliminary efficacy of sublingual administration of certain provided nanoparticle compositions containing *Dermatophagoides farinae* or *Dermatophagoides pteronyssinus* extracts (i.e. antigens) and bacterial components for use in accordance with the present invention.

Chemical Name and Structure

The drug substances in the Dust Mite Allergy Vaccine of this Example are standardized allergenic extracts of two common house dust mites, *D. farinae* and *D. pteronyssinus*, mixed 1:1 by allergy unit (AU). As such, there is no conventional chemical name or structure for the Dust Mite Allergy Vaccine drug substances.

The dust mite extracts in the Dust Mite Allergy Vaccine will be the same as those found in the commercially available standardized dust mite extracts approved by the Food and Drug Administration (FDA) for use in subcutaneous immunotherapy (SCIT) [Standardized Mite Extract (*Dermatophagoides farinae*) and Standardized Mite Extract (*Derinatophagoides pteronyssinus*), Greer, Lenoir, N.C.].

The dust mite extracts will be encapsulated within PLGA nanoparticles manufactured using a double-emulsion process. In the first emulsion, the dust mite extracts and an AEE that contains bacterial deoxyribonucleic acid (DNA) will be mixed with PLGA in organic solvent. The resulting emulsion will be microfluidized or homogenized to generate nanoparticles with the dust mite extracts and AEE encapsulated within the particles. OEE, containing mainly bacterial lipids and LPS, in a 5% polyvinyl alcohol solution will then be added and the resulting second emulsion microfluidized/homogenized to coat the nanoparticles generated during the first emulsion.

The final PLGA nanoparticles are thus designed to mimic bacteria so as to facilitate uptake by antigen presenting cells (APCs) in the GI tract and enhance activation of the innate immune system, and thus potentially improve the efficacy of conventional SLIT with naked dust mite extract alone. The Dust Mite Allergy Vaccine bulk nanoparticles will include the addition of the AEE and the second emulsion will use the OEE rather than LPS alone. Stated another way, these PLGA nanoparticles are designed to be "semi-synthetic bacterial cells" in which the dust mite extracts and bacterial protein, DNA, and LPS of the AEE will be encapsulated on the inside of the nanoparticles, and the bacterial LPS and lipids of the OEE will be coated on the outside of the nanoparticles. Placebo will be generated the same way, only with no dust mite extract present.

Proposed Indication

The Dust Mite Allergy Vaccine is being developed for SLIT for the treatment of perennial allergic rhinitis in patients with a demonstrated sensitivity to *D. farinae* or *D. pteronyssinus* as determined by positive prick skin test (PST).

Dosage Form, Route of Administration, and Dosing Regimen

The final dosage form of the Dust Mite Allergy Vaccine will be a solid oral dosage form suitable for sublingual administration. Formulation development approaches may include a dry blend of the nanoparticles with a water-soluble excipient such as lactose monohydrate packaged in plastic straws or a direct-compression, rapidly-dissolving tablet. Dosing will take the form of a dose escalation up to a maximum dose of 1,400 AU. All subjects will be administered Dust Mite Allergy Vaccine once per week for six weeks. During this period, the dose will be increased weekly, starting in three fold increments up to a maximum dose of 1,400 AU and then decreasing to a 1.5-fold increment. Protocol-specified dose modifications will be required if allergic symptoms are observed or doses missed. After the initial six weeks of dose escalation, patients who tolerate the Dust Mite Allergy Vaccine will then receive additional doses qd for five months (maintenance dosing period). The dose during the maintenance dosing period will be the maximum tolerated dose (MTD) established during the subject's dose escalation phase.

The route of administration of the Dust Mite Allergy Vaccine is sublingual for use as sublingual immunotherapy (SLIT).

The proposed dosing regimen to be used for the Dust Mite Allergy Vaccine for the treatment of perennial allergic rhinitis in patients sensitive to *D. farinae* or *D. pteronyssinus* is based on previous clinical trials of oral immunotherapy (OIT) and SLIT. The dosage regimens for OIT and SLIT for perennial allergic rhinitis are commonly once daily (qd) for chronic use according to an extended dosing period.

Additional Information and Possible Mechanisms

The Dust Mite Allergy Vaccine of this Example is designed to act as an "allergy vaccine" to induce tolerance to dust mites when used as SLIT for the treatment of perennial allergic rhinitis in patients sensitive to *D. farinae* or *D. pteronyssinus*. The dust mite allergens to be used in the Agent are the same allergens found in the commercially available standardized dust mite extracts approved by FDA for use in SCIT [Standardized Mite Extract (*Dermatophagoides farinae*) and Standardized Mite Extract (*Dermatophagoides pteronyssinus*), Greer, Lenoir, N.C.]. One difference between the extracts in the Greer products and the Agent is that the Greer products are formulated as a liquid in glycerin and the Agent will use lyophilized extracts for incorporation into PLGA nanoparticles that include bacterial components intended to facilitate APC recognition and uptake of the particles and enhance a Th1/Th0-like immune response associated with desensitization and eventual tolerance to dust mite allergens.

Traditional allergen-injection vaccines have been used for control of allergic disease for many years. Standardized extracts of *D. farinae* and *D. pteronyssinus*, both individually and mixed, are commercially available for SCIT of dust mite allergy. SCIT is reported to be capable of modifying the natural history of disease (i.e., the onset of asthma in rhinitis patients) and result in long-lasting effects after discontinuation. However, due to concerns about adverse reactions elicited by allergen injections and the inconvenience of regular subcutaneous injections at a clinician's office for over a period of 3 to 5 years, the widespread adoption of SCIT has been limited. Sublingual administration as used for SLIT appears to be a more viable alternative route of administration of allergen extracts.

The Dust Mite Allergy Vaccine product is designed to encapsulate the dust mite extracts and bacterial DNA within PLGA nanoparticles coated with bacterial LPS and lipids on the surface (refer to schematic in FIG. 17). The pharmacological rationale is as follows.

A dust mite allergy vaccine should protect against exposure to the main dust mite proteins responsible for allergic reactions in order for efficacy to be achieved. *D. farinae* and *D. pteronyssinus* are the most common house dust mite species, and numerous allergens have been identified for each. Hence, the Agent includes standardized extracts from both species as antigens.

Delivery of the dust mite antigens encapsulated in PLGA nanoparticles mimicking bacterial cells may enhance the activation of the innate immune system, and thus to potentially improve the efficacy of SLIT with dust mite extracts alone. Specifically, bacterial LPS and CpG DNA motifs, as well as any potential unidentified bacterial moieties on the interior of the nanoparticle may enhance the potential efficacy of the Agent to produce the desired Th1/Th0-like immune response associated with desensitization and eventual tolerance to dust mite allergens.

In addition, encapsulation of the dust mite antigens within PLGA nanoparticles mimicking bacterial cells may facilitate uptake by APCs in the sublingual mucosa, and thus to potentially improve the efficacy of SLIT using the dust mite extracts alone. Specifically, the Agent is designed to maximize the recognition and internalization by APCs of the encapsulated dust mite proteins by both surface display on the nanoparticle exterior and incorporation within the nanoparticle of the known toll-like receptor (TLR) agonists.

Further, encapsulation of the dust mite antigens within an intact delivery system (i.e., PLGA nanoparticles) may reduce the potential for allergic reactions upon administration of the proteins by hiding the proteins from mast cells. Hence, the dust mite proteins in the Agent are encapsulated within PLGA nanoparticles mimicking bacterial cells.

As exemplified in FIG. 17, there are no covalent bonds between the components of the Agent in this Example. In the presence of water, the nanoparticles will continuously erode by hydrolysis and the encapsulated dust mite extract proteins and bacterial protein, DNA, and LPS, as well as the coating of bacterial LPS and lipids will be continuously released. Hydrolysis of the PLGA polymer results in lactic acid (LA) and glycoic acid (GA) monomers, which are harmless. The rate of PLGA hydrolysis is dependent upon the ratio of LA to GA, and PLGA polymer used for the Agent will be selected so that it releases the encapsulated dust mite extract proteins within 48 to 72 hours based on an in vitro drug release assay.

After sublingual administration, the nanoparticles that are not taken up and processed by APCs will be swallowed. In either case, the presence of $H_2O$ hydrolyzes PLGA to LA and GA (faster at low pH), with release of the dust mite extracts (i.e., antigens) and bacterial components. After release, the extract proteins and bacterial components will be digested in the same way as dust mite proteins or bacterial components would be when consumed in daily life or in food.

Clinical Trial Design and Methodology The Clinical Trial Design is a phase 1, single-center, randomized, double-blind, placebo-controlled safety, pharmacodynamic, and preliminary efficacy study of the Agent in adult subjects with perennial allergic rhinitis (with or without asthma) and sensitive to *D. farinae* or *D. pteronyssinus*.

Twelve subjects will be randomized 1:2 to receive placebo or the Agent. The placebo and active cohorts will include both subjects sensitive to *D. farinae* and *D. pteronyssinus* and subjects sensitive to only one of the two species, so as to allow for monitoring of neo-sensitization.

All subjects will be administered a sublingual dose of study drug (placebo or active) once per week for six weeks. During this period, the dose will be increased weekly, starting with 3-fold increments culminating in a dose of 1,400 AU, and then progressively decreasing to a 1.5-fold increment. If no dose limiting toxicities [DLTs; defined as any adverse event (AE) of a severity greater than moderate and assigned at least a possible relationship to study drug] occur, the subject will then take the maximum tolerated dose once daily (qd) for six months.

A. Screening Visit:

Within 14 days prior to the first dose of study drug (Day 1), each subject will be provided with written information (informed consent form) describing the study and will have any questions answered. Subjects that consent in writing to participate in the study will undergo eligibility assessments, including complete medical history, comprehensive physical examination, height, weight, vital signs (blood pressure, pulse rate, respiration rate, and oral body temperature), 12-lead electrocardiogram (ECG), spirometry [forced expiratory volume in 1 second (FEV1), forced vital capacity (FVC), and peak expiratory flow (PEF)], complete blood count (CBC) with differential, serum chemistry, urinalysis, urine human chorionic gonadotropin (HCG) pregnancy test for women of childbearing potential (WCBP), blood collection for *D. farinae*- or *D. pteronyssinus*-specific IgE and IgG4 levels, blood collection for *D. farinae*- or *D. pteronyssinus*-stimulated PBMC T-lymphocyte phenotype, prick skin tests (PSTs) and endpoint skin test titrations to standardized *D. farinae* and *D. pteronyssinus* extracts, and record of medications taken within 30 days prior to the screening visit.

B. Study Day 1:

Subjects that meet all eligibility requirements at screening will be randomized 1:2 to receive placebo or the Agent and will return to the clinic on the morning of Day 1 for the following baseline procedures: medical history update, targeted physical examination, weight, vital signs, PEF, CBC with differential, serum chemistry, urinalysis, urine HCG pregnancy test for WCBP, and record of medications taken since screening visit.

Subjects that continue to meet eligibility requirements after the baseline assessments will be given a single sublingual dose of study drug (placebo or active). Administration of the study drug will take place in a clinic with experience in treating severe allergic reactions. Specifically, a crash cart will be available in the facility and there will be medical personnel and a physician present to treat anaphylaxis.

AE monitoring will begin immediately following administration of study drug and will continue throughout the study. Subjects will remain in the clinic under observation for 4 hours post-dose. Vital signs will be monitored at 5, 10, 15, and 30 minutes post-dose.

Subjects will be given a diary to record any AEs or medications used between visits, and will be given forms to assess the severity of rhinoconjunctivitis symptoms (visual analog scale) and the use of rescue medications on a daily basis throughout the trial. Subjects will be given a 24-hour emergency telephone number to call in the event of an adverse reaction.

C. Study Day 2:

Subjects will return to the clinic on the mornings of Days 2 and 7 for the following procedures: targeted physical examination, vital signs, PEF, urine HCG pregnancy test for WCBP, review of the AE and concomitant medication diary, and review of the daily forms assessing the severity of rhinoconjunctivitis symptoms and rescue medication use.

D. Weekly Visits During Dose Escalation:

Subjects will return to the clinic once a week during the dose escalation period for evaluations, as well as administration of study drug. The following procedures will be performed on the morning of Days 8, 15, 22, 29, and 36: targeted physical examination, vital signs, PEF, urine HCG pregnancy test for WCBP, review of the AE and concomitant medication diary, and review of the daily forms assessing the severity of rhinoconjunctivitis symptoms and rescue medication use. Pending no safety concerns, the subjects will be given a single sublingual dose of study drug (placebo or active). Subjects will remain in the clinic under observation for 4 hours post-dose. Vital signs will be monitored at 5, 10, 15, and 30 minutes post-dose.

E. Monthly Visits During Maintenance Therapy:

Subjects will return to the clinic one week after completion of the dose escalation phase (morning of Day 43) and then monthly thereafter for 5 months during the maintenance dosing period for the following procedures: targeted physical examination, vital signs, PEF, CBC with differential, serum chemistry, urinalysis, urine HCG pregnancy test for WCBP, review of the AE and concomitant medications diary, and review of the daily forms assessing the severity of rhinoconjunctivitis symptoms and rescue medication use.

At the first, third, and fifth monthly visit (i.e., after 2.5, 4.5, and 6.5 months of study drug treatment), the following additional procedures will be performed: blood collection for *D. farinae*- or *D. pteronyssinus*-specific IgE and IgG4 levels, blood collection for *D. farinae*- or *D. pteronyssinus*-stimulated PBMC T-lymphocyte phenotype, endpoint titration PSTs to standardized *D. farinae* and *D. pteronyssinus* extracts, and endpoint titration PST to non-dust mite extract (selected at Screening). Further, at the fifth monthly visit (after 6.5 months of study drug treatment), allergen bronchoprovocation to standardized *D. farinae* or *D. pteronyssinus* extracts will be performed.

Pending no safety concerns following the monthly assessments, the subjects will be provided with sufficient study drug for four weeks of dosing and a dairy to record the details of study drug administration at home. The subjects will be instructed to take qd at home and to return to the clinic for monthly evaluations. At each visit, the study drug diary will be reviewed and the study drug containers and any unused study drug will be collected to monitor compliance. No study drug will be given after the fifth monthly visit (i.e., after 6.5 months of treatment).

F. Final Study Visit

All subjects will return four weeks after their last dose of study drug for their final study visit. The following procedures will be performed at the final visit: complete physical examination, weight, vital signs, PEF, CBC with differential, serum chemistry, urinalysis, urine HCG pregnancy test for WCBP, blood collection for *D. farinae*- or *D. pteronyssinus*-specific IgE and IgG4 levels, blood collection for *D. farinae*- or *D. pteronyssinus*-stimulated PBMC T-lymphocyte phenotype, endpoint titration PST to standardized *D. farinae* and *D. pteronyssinus* extracts, endpoint titration PST to non-dust mite extract (selected at Screening), review of the AE and concomitant medication diary, and review of the daily forms assessing the severity of rhinoconjunctivitis symptoms and rescue medication use.

Diagnosis and Main Criteria for Inclusion:

Subjects 18 to 50 years of age with a history of perennial allergic rhinitis for a minimum of one year prior to Screening, and a demonstrated sensitivity to *D. farinae* or *D. pteronyssinus* by a positive PST at Screening [mean wheal diameter 3 mm greater than that elicited by the negative control (saline) at 15-20 minutes].

Subjects may or may not have asthma. For subjects with asthma, the subject must be diagnosed with either intermittent or mild persistent asthma, as defined by National Heart Lung and Blood Institute (NHLBI) guidelines, for a minimum of one year prior to Screening. For all subjects, FEV1 must be greater than 80% predicted and FEV1/FVC must be normal at Screening Both males and WCBP agree to use adequate contraceptive methods while on study (from Screening through final study visit);

Adequate contraceptive methods include those with a low failure rate, i.e., less than 1% per year, when used consistently and correctly, such as complete abstinence from sexual intercourse, and some double barrier methods (condom with spermicide) in conjunction with use by the partner of an IUD, diaphragm with spermicide, oral contraceptives, birth control patch or vaginal ring, oral, or injectable or implanted contraceptives.

Subjects meeting any of the following criteria will be excluded from the trial: history of severe anaphylactic event requiring mechanical ventilation or use of intravenous vasopressor drugs (i.e., subject underwent cardio-respiratory arrest); life-threatening asthma exacerbation requiring intubation or mechanical ventilation or resulting in a hypoxic seizure within two years of Screening; asthma requiring oral steroid use within 6 months prior to Screening; clinical history of significant symptomatic perennial allergic rhinitis and/or asthma due to another allergen (i.e., other than dust mites) to which the subject is regularly exposed; clinical history of significant symptomatic seasonal allergic rhinitis and/or asthma to which the subject will be exposed during the study; unstable angina, significant arrhythmia, uncontrolled hypertension, chronic sinusitis, or other chronic or immunologic diseases that, in the opinion of the Investigator, may interfere with the study or pose additional risk to the subject; evidence of clinically significant neurologic, cardiac, pulmonary, hepatic, or renal disease by history, physical examination, and/or laboratory studies; viral upper respiratory infection within 30 days of Screening; acute infection requiring antibiotics within 30 days of Screening; use of allergen immunotherapy within 180 days prior to Screening; use of omalizumab or immunomodulatory therapy (not including corticosteroids) within 90 days prior to Screening; use of intravenous antihistamines or corticosteroids within 30 days of Screening; use of another investigational drug within 30 days of Screening; use of tricyclic antidepressants or beta-adrenergic blocker drugs within 14 days of Screening; use of monoamine oxidate (MAO) inhibitors or any medications known to interfere with the treatment of anaphylaxis within 14 days of Screening; use of any prescription medication (other than the rescue medications referenced above under Methodology) within 14 days of Screening; use of any over-the-counter, non-prescription preparations (including vitamins, minerals, and phytotherapeutic/herbal/plant-derived preparations; excluding rescue medications referenced above under Methodology) within 14 days of Screening; inability to temporarily discontinue antihistamines (five half-lives of the antihistamine) prior to skin testing; pregnancy or breast-feeding (if female); use of any tobacco-containing or nicotine-containing products (including cigarette, pipe, cigar, chewing tobacco, nicotine patch, or nicotine gum) within 6 months prior to Screening; behavioral, cognitive, or psychiatric disease that in the opinion of the Investigator affects the ability of the subject to understand and cooperate with the study protocol; history of drug or alcohol abuse, that in the opinion of the Investigator, would interfere with the study; known allergy to inactive ingredients of study drug; and cannot perform spirometry.

Product, Dose and Mode of Administration:

The final dosage form of the Agent will be a solid oral dosage form suitable for sublingual administration. Formulation development approaches will include a dry blend of the nanoparticles with a water-soluble excipient such as lactose monohydrate packaged in plastic straws or a direct-compression, rapidly-dissolving tablet. As described above, the study in this Example includes dose escalation, with a maximum dose of 1,400 AU.

The placebo will be AEE-encapsulated, OEE-coated PLGA nanoparticles that do not contain encapsulated dust mite extract (antigen). The placebo will be visually indistinguishable from the active solid oral dosage form.

All subjects will be administered study drug (placebo or Agent) sublingually once a week for 6 weeks (dose escalation). During this period, the dose will be increased weekly, starting with 3-fold increments and progressively decreasing to a 1.5-fold increment. Protocol-specified dose modifications will be required if allergic symptoms are observed or doses are missed.

After the initial 6 weeks (dose escalation), subjects who tolerate study drug (placebo or ENDM-500) will then take study drug qd for five months (maintenance dosing period). The dose during the maintenance therapy phase will be the MTD established during the subject's dose escalation phase. Protocol-specified dose modifications will be required if allergic symptoms are observed or doses are missed.

The study drug will be administered under the tongue. Subjects will be instructed to hold the contents under the tongue for 2 minutes and not to eat or drink for 15 minutes after the dose. Each dose of study drug will be taken in the morning prior to eating breakfast (i.e., on an empty stomach). The Day 1 dose will be administered in the clinic, and all remaining doses will be self-administered at home.

The study drug will be administered in the clinic during the dose escalation phase (first 6 weeks of dosing). All remaining doses (maintenance dosing period) will be self administered at home.

Example 8: A Phase 1, Randomized, Double-Blind, Placebo-Controlled Safety, Pharmacodynamic, and Preliminary Efficacy Study of Peanut Allergy Vaccine Administered Sublingually in Adult Subjects As a further example of how provided compositions and methods may be used to treat allergy, this Example outlines a study providing an embodiment containing a peanut allergen to assess safety and preliminary efficacy in adult subjects.

This present Example, similarly to Example 7 above, describes an exemplary phase 1, single-center, randomized, double-blind, placebo-controlled, safety, pharmacodynamic, and preliminary efficacy study of provided nanoparticle compositions (in this Example, nanoparticles containing hydrophilic and/or hydrophobic E. coli extract preparations), in adult subjects. In this Example, rather than suffering from perennial allergic rhinitis (with or without asthma) and being sensitive to *D. farinae* or *D. pteronyssinus*, the subjects in this Example suffer from peanut allergy.

In some embodiments, provided nanoparticle compositions are organic *Escherichia coli* extract ("OEE") coated poly(lactic-co-glycolic acid)-("PLGA-") encapsulated *Arachis hypogaea* peanut extract and aqueous *E. coli* extract (AEE) nanoparticles (hereinafter referred to as the "Agent" and/or "Peanut Allergy Vaccine").

The present Example describes an exemplary clinical trial design for evaluating the pharmacodynamics and preliminary efficacy of provided nanoparticle compositions (in this Example, nanoparticles containing hydrophilic and/or hydrophobic *E. coli* extract preparations) for use in accordance with the present invention.

Chemical Name and Structure

The drug substance in the Peanut Allergy Vaccine of this Example is an allergenic extract of the common peanut (*Arachis hypogaea*). As such, there is no conventional chemical name or structure for the Peanut Allergy Vaccine drug substance.

The peanut extract in the Peanut Allergy Vaccine will be the same as those found in the commercially available peanut extract approved by the Food and Drug Administration (FDA) for diagnostic use [Peanut (*Arachis hypogaea*) Extract, Greer, Lenoir, N.C.].

The peanut extract will be encapsulated within PLGA nanoparticles manufactured using a double-emulsion process. In the first emulsion, the peanut extract and an AEE that contains bacterial deoxyribonucleic acid (DNA) will be mixed with PLGA in organic solvent. The resulting emulsion will be microfluidized or homogenized to generate nanoparticles with the peanut extract and AEE encapsulated within the particles. OEE, containing mainly bacterial lipids and LPS, in a 5% polyvinyl alcohol solution will then be added and the resulting second emulsion microfluidized/homogenized to coat the nanoparticles generated during the first emulsion.

The final PLGA nanoparticles are thus designed to mimic bacteria so as to facilitate uptake by antigen presenting cells (APCs) in the GI tract and enhance activation of the innate immune system, and thus potentially improve the efficacy of conventional SLIT with naked peanut extract alone. The Peanut Allergy Vaccine bulk nanoparticles will include the addition of the AEE and the second emulsion will use the OEE rather than LPS alone. Stated another way, these PLGA nanoparticles are designed to be "semi-synthetic bacterial cells" in which the peanut extracts and bacterial DNA of the AEE will be encapsulated on the inside of the nanoparticles, and the bacterial LPS and lipids of the OEE will be coated on the outside of the nanoparticles. Placebo will be generated the same way, only with no peanut extract present.

Dosage Form, Route of Administration, and Dosing Regimen

The final dosage form of the Peanut Allergy Vaccine will be a solid oral dosage form suitable for sublingual administration. Formulation development approaches may include a dry blend of the nanoparticles with a water-soluble excipient such as lactose monohydrate packaged in plastic straws or a direct-compression, rapidly-dissolving tablet. Dosing will take the form of a dose escalation up to a maximum dose of 2,000 micrograms of peanut protein. All subjects will be administered Peanut Allergy Vaccine once per week for 18 weeks. During this period, the dose will be increased biweekly, up to a maximum dose of 2,000 micrograms of peanut protein. Protocol-specified dose modifications will be required if allergic symptoms are observed or doses missed. After the initial 18 weeks of dose escalation, patients who tolerate the Peanut Allergy Vaccine will then receive additional doses qd for 12 weeks (maintenance dosing period). The dose during the maintenance dosing period will be the maximum tolerated dose (MTD) established during the subject's dose escalation phase.

The route of administration of the Peanut Allergy Vaccine is sublingual for use as sublingual immunotherapy (SLIT).

The proposed dosing regimen to be used for the Peanut Allergy Vaccine for the treatment of peanut allergy is based on previous clinical trials of oral immunotherapy (OIT) and SLIT. The dosage regimens for OIT and SLIT for peanut allergy are commonly once daily (qd) for chronic use according to an extended dosing period.

Clinical Trial Design and Methodology

This study of this Example is a phase 1, single-center, open-label, single-arm, dose escalation study to evaluate the safety, tolerability, and preliminary efficacy of a Peanut Allergy Vaccine in 12 adult subjects with peanut allergy. All subjects will be administered Peanut Allergy Vaccine sublingually qd for 18 weeks (dose escalation).

The dose of Peanut Allergy Vaccine will be increased approximately 2-fold every two weeks during the 18-week dose escalation. Protocol-specified dose modifications will be required if allergic symptoms are observed or doses are missed.

After the initial 18 weeks (dose escalation), subjects who tolerate the Peanut Allergy Vaccine will be given the option to receive an additional 12-week course (maintenance therapy; qd at fixed dose). The dose during the maintenance therapy phase will be the maximum tolerated dose established during the subject's dose escalation phase.

A. Screening Visit

Within 14 days prior to the first dose of study drug (Day 1), each subject will be provided with written information (informed consent form) describing the study and will have any questions answered. Subjects that consent in writing to participate in the study will undergo eligibility assessments, including complete medical history, comprehensive physical examination, height, weight, vital signs (blood pressure, pulse rate, respiration rate, and oral body temperature), 12-lead electrocardiogram (ECG), spirometry [forced expiratory volume in 1 second (FEV1), forced vital capacity (FVC), and peak expiratory flow (PEF)], complete blood count (CBC) with differential, serum chemistry, urinalysis, urine human chorionic gonadotropin (HCG) pregnancy test for women of childbearing potential (WCBP), blood collection for peanut-specific IgE and IgG4 levels, PST to a panel of antigens, including peanut, endpoint titration PST to peanut extract, DBPCFC to peanut.

B. Study Day 1

Subjects that meet all eligibility requirements at Screening will return to the clinic on the morning of Day 1 for the following baseline procedures: medical history update, targeted physical examination, weight, vital signs, PEF, CBC with differential, serum chemistry, urinalysis, urine pregnancy test for WCBP, and record of medications taken since screening visit.

Subjects that continue to meet eligibility requirements after the baseline assessments will be given a single sublingual dose of study drug. Administration of the study drug will take place in a General Clinical Research Center (GCRC) or comparable monitored clinical site with experience in treating severe allergic reactions. Specifically, a crash cart will be available in the facility and there will be medical personnel and a physician present to treat anaphylaxis.

Monitoring for treatment emergent adverse events (AEs) will begin immediately following administration of study drug and will continue throughout the study. Subjects will remain in the clinic under observation for 4 hours post-dose. Vital signs will be monitored at 0.25, 0.5, 1, and 2 hours post-dose. Subjects will be given a diary to record any AEs or concomitant medications used between visits.

C. Study Day 2

Subjects will return to the clinic on the morning of Day 2 for the following procedures: targeted physical examination, vital signs, PEF, and review of the AE and concomitant medication diary. Subjects that tolerate the first dose of study drug will be given their second dose of study drug and will remain in the clinic under observation for 4 hours post-dose. Vital signs will be monitored at 0.25, 0.5, 1, and 2 hours post-dose.

Pending no safety issues, the subjects will be provided with sufficient study drug to complete the first week of dosing at home, and a dairy to record the details of study drug administration. The subjects will be instructed on how to sublingually administer the study drug, and will be instructed to take the study drug qd at approximately the same time each day. All subjects will be provided with EpiPens and instructed on their use in the event of a severe allergic reaction between study visits. Subjects will be given a 24-hour emergency telephone number and instructed to call the investigational site immediately should an AE occur between visits.

D. Weekly Visits During close Escalation

Subjects will return to the clinic once a week during the dose escalation period for evaluations, as well as administration of study drug (first dose of each week) and supply of additional study drug to take at home. The following procedures will be performed at each weekly visit prior to administering the study drug: targeted physical examination, vital signs, PEF, review of the AE and concomitant medication diary, and review of the study drug administration diary and returned study drug containers and any unused study drug (for monitoring of compliance).

Following administration of the study drug, subjects will remain in the clinic under observation for 4 hours post-dose. Vital signs will be monitored at 0.25, 0.5, 1, and 2 hours post-dose. Pending no safety issues, the subjects will be provided with sufficient study drug to complete another week of dosing at home. A phone interview will be conducted the next day to assess for any AEs.

E. Visits at Completion of 18-Week Dose Escalation

Subjects will return to the clinic the day following their last dose of the dose escalation period and the following procedures will be performed: targeted physical examination, vital signs, PEF, CBC with differential, serum chemistry, urinalysis, urine pregnancy test for WCBP, review of the AE and concomitant medication diary, review of the study drug administration diary and returned study drug containers and any unused study drug (for monitoring of compliance), blood collection for peanut-specific IgE and IgG4 levels, and endpoint titration PST to peanut and non-peanut extract (selected at Screening) The subjects will return 6 days later for a DBPCFC to peanut.

F. Visits During Optional 12-Week Maintenance Therapy

Subjects who tolerate the Peanut Allergy Vaccine will be given the option to receive a 12-week course of Peanut Allergy Vaccine maintenance therapy. Following completion of the 18-week dose escalation evaluations (including the DBPCFC to peanut), these subjects will be provided with sufficient study drug for 2 weeks of dosing and a dairy to record the details of study drug administration at home. The subjects will be instructed to take the study drug qd at approximately the same time each day, and to return to the clinic in two weeks.

At each biweekly visit during the optional maintenance therapy, the subjects will undergo the following procedures: targeted physical examination, vital signs, PEF, review of the AE and concomitant medications diary, review of study drug diary, and review of the study drug administration diary and returned study drug containers and any unused Peanut Allergy Vaccine (for monitoring of compliance). Pending no safety issues, the subjects will be provided with sufficient study drug to complete another two weeks of dosing at home.

Subjects will return to the clinic the day following their last dose of the maintenance therapy period and the following procedures will be performed: targeted physical examination, vital signs, PEF, CBC with differential, serum chemistry, urinalysis, urine pregnancy test for WCBP, review of the AE and concomitant medication diary, review of the study drug administration diary and returned study drug containers and any unused study drug (for monitoring of compliance), blood collection for peanut-specific IgE and IgG4 levels, and endpoint titration PST to peanut and non-peanut extract (selected at Screening) The subjects will return 6 days later for a DBPCFC to peanut.

Subjects who do not tolerate the Peanut Allergy Vaccine during the 18-week dose escalation or who do not opt to participate in the additional 12-week course of Peanut Allergy Vaccine maintenance therapy will return to the clinic four weeks after their last dose of study drug for their final clinic visit.

G. Final Study Visit

All subjects will return to the clinic 4 weeks after their last dose of study drug for the final study visit. The following procedures will be performed: review of the AE and concomitant medication diary, complete physical examination, weight, PEF, vital signs, CBC with differential, serum chemistry, urinalysis, urine pregnancy test for WCBP, blood collection for peanut-specific IgE and IgG4 levels, and endpoint titration PST to peanut and non-peanut extract (selected at Screening)

If a subject is withdrawn from the study early, all evaluations described for the final study visit will be performed if feasible. Any subject with a possible study drug-related AE at the final study visit will be followed until resolution or stabilization of the event.

All peanut allergic subjects may continue their usual medications, including those taken for asthma, allergic rhinitis, and atopic dermatitis, during the study (except for those listed as exclusion criteria). Subjects must be able to temporarily discontinue antihistamines (5 half-lives of the antihistamine) prior to skin testing and prior to DBPCFC. Regular topical steroids use is permitted at the time of skin testing. If a burst of oral steroids is administered during the course of the trial to treat an allergic reaction, the DBPCFC will not be administered until at least two weeks after completion of the oral steroid treatment.

The study will be discontinued if there is any death related to the Peanut Allergy Vaccine dosing. If more than one severe anaphylactic reaction (cyanosis or Sp02<92% at any stage, hypotension, confusion, collapse, loss of consciousness, or incontinence) related to the Peanut Allergy Vaccine dosing occurs, study enrollment and further dosing of subjects already enrolled in the trial will be stopped until a Data Safety Monitoring Board (DSMB) convenes and determines that it is safe to proceed.

Diagnosis and Main Criteria for Inclusion:

Subjects 18 to 50 years of age with a convincing history of peanut allergy and meeting the three main inclusion criteria of: 1) a positive PST to peanut at screening [mean wheal diameter 3 mm greater than that elicited by the negative control (saline) at 15-20 minutes], 2) serum peanut-specific IgE level greater than or equal to 0.35 $kU_A/L$ (UniCAP) at screening, and 3) positive DBPCFC to peanut at a cumulative dose of less than 1 g of peanut protein at screening will be admitted to the study, absent the subject meeting one or more of the exclusion criteria.

Figure 19:
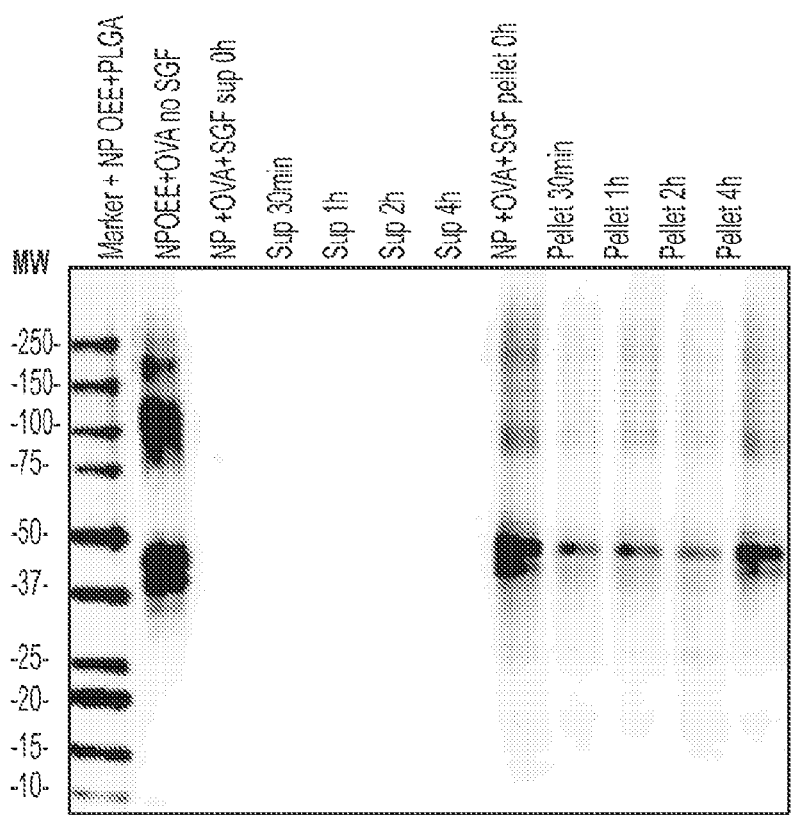
FIG. 19: shows an exemplary Western Blot of provided organic *E coli* extract (OEE)-coated nanoparticles encapsulating *E coli* DNA and OVA (also referred to as "OEE/DNA+OVA") digested in SGF for up to four hours.
Figure 20:
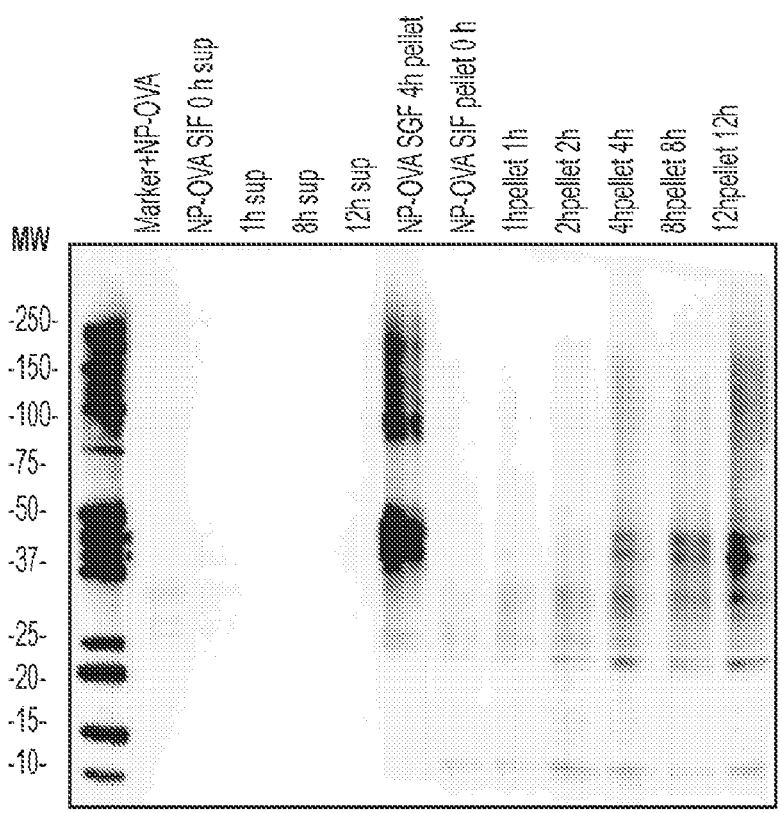
FIG. 20: shows an exemplary Western Blot of provided OEE/DNA+OVA nanoparticles digested in SIF for up to 12 hours.
Figure 21:
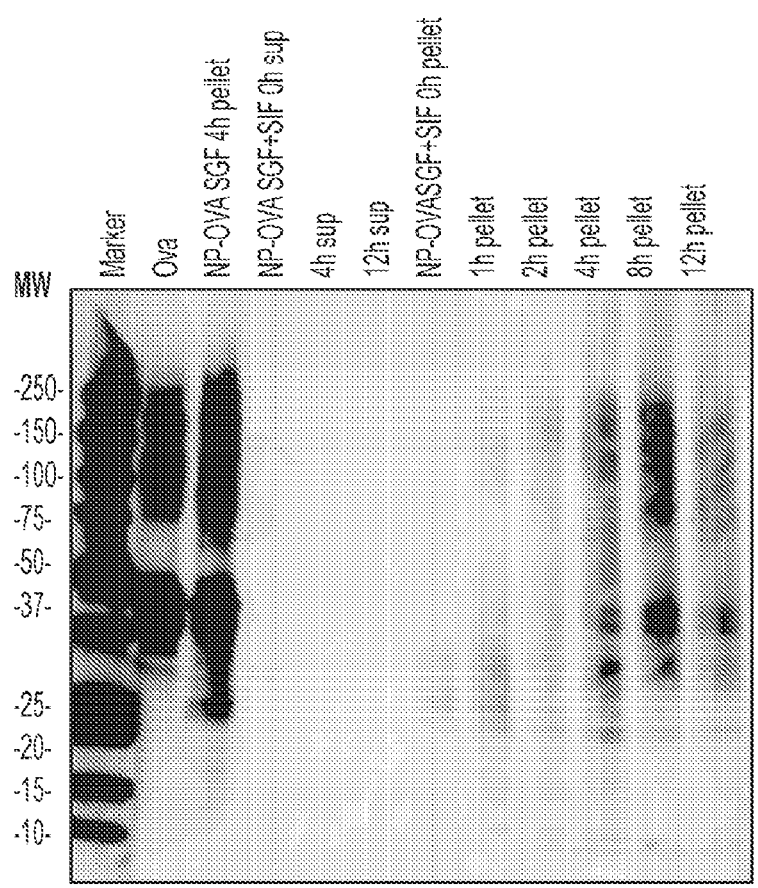
FIG. 21: shows exemplary Western Blot of provided OEE/DNA+OVA nanoparticles digested in SGF for four hours followed by digestion in SIF for up to 12 hours.

A subject meeting any of the exclusion criteria will be excluded form the study. The exclusion criteria include history of severe anaphylactic event requiring mechanical ventilation or use of intravenous vasopressor drugs (i.e., subject underwent cardio-respiratory arrest); more than mild persistent asthma per NHLBI classification, forced expiratory volume in one second (FEV1)<80% predicted at screening, poor control or persistent activation of atopic dermatitis, any hospitalization in the past year for asthma or any emergency room visit in the past 6 months for asthma, eosinophilic gastroenteritis, use of oral or IV corticosteroids within 30 days of screening, inability to discontinue antihistamines for skin testing and DBPCFC, use of omalizumab or other non-traditional forms of allergen immunotherapy or immunomodulatory therapy (not including corticosteroids) or biologic therapy within one year of screening, use of any other allergen immunotherapy within one year of screening, use of immunosuppressive drugs within 30 days of screening, use of b-blockers (oral), angiotensin-converting enzyme (ACE) inhibitors, angiotensin-receptor blockers (ARBs), or calcium channel blockers, evidence of clinically significant immunosuppressive, neurologic, cardiac, pulmonary, hepatic, rheumatologic, autoimmune, or renal disease by history, physical examination, and/or laboratory studies including urinanalysis, pregnancy or breast-feeding (if female); behavioral, cognitive, or psychiatric disease that in the opinion of the Investigator affects the ability of the subject to understand and cooperate with the study protocol, known allergy to inactive ingredients of study drug, known allergy to oat flour (placebo for DBP-CFC), and/or participation in another investigational vaccine or drug trial within 30 days of screening Example 9: Production of Nanoparticle Compositions Containing Encapsulated Fragments of One or More Influenza Viral Particles This Example describes an exemplary preparation of nanoparticles containing fragments of one or more influenza virus particles using a double emulsion (water-oil-water) process. In some embodiments, packaging of "flu fragments" may be desirable to treat or prevent development of influenza infections, such as via oral immunization. Briefly, AEE at a protein concentration of c.a. 60 mg/mL is used to reconstitute a crude antigen extract containing fragments of one or more influenza virus particles, also at a concentration of 60 mg/mL. Higher or lower concentrations of both the AEE and/or the crude extract may be used. The AEE-crude extract solution is homogenized with a dichloromethane solution of PLGA (c.a. 35.7 mg/mL) with an aqueous to organic ratio of 0.20 mL:28 mL. This mixture is designated as the first emulsion.

In some embodiments, for example where it is desirable to increase the level of surface-associated hydrophobic components (such as LPS), OEE, such as that described above in Example 2, is dissolved in 5% aqueous PVA at a concentration of c.a. 2.2 mg/mL total LPS. Higher or lower concentrations of OEE in PVA solution may be used. Half of the first emulsion (14 mL) is added to the OEE-PVP solution (14 mL) and homogenized. This mixture is designated as the second emulsion.

The first or, if generated, the second emulsion (28 mL) is added to 935 mL of 0.33% aqueous PVA and stirred for c.a. 4 hours to allow the dichloromethane to evaporate. The nanoparticle suspension is concentrated and the nanoparticles are isolated by centrifugation. After removal of the supernatant, the nanoparticles are washed 2 to 3 times with water, resuspended in water, and isolated by freeze drying.

Example 10: Simulated Digestion of Nanoparticle Compositions

In some embodiments, as discussed elsewhere herein, provided nanoparticle compositions may be administered via any medically appropriate route, for example, via oral administration. This Example confirms that provided nanoparticle compositions are stable after exposure to up to four hours to simulated gastric fluid and/or exposure of up to 12 hours to simulated intestinal fluid and that no significant leakage of antigen (here, OVA) is detected after simulated digestion.

In this Example, organic *E coil* extract (OEE)-coated nanoparticles encapsulating *E coli* DNA and OVA (also referred to as "OEE/DNA+OVA") were exposed to simulated gastric fluid (SGF) for up to four hours and/or simulated intestinal fluid (SIF) for up to 12 hours. After exposure, provided nanoparticles were centrifuged to separate disrupted nanoparticle membrane and any intact nanoparticles from the supernatant, which contained material that may have "leaked" from partially digested nanoparticles. A western blot was then run on each sample using anti-OVA sera. A flow diagram of the procedure is shown in FIG. 18.

FIG. 19 shows a western blot of provided nanoparticles digested in SGF for up to four hours, with the supernatant ("sup") and pellet being analyzed separately. In addition, intact OEE/DNA+OVA nanoparticles (undigested) were used as a positive control. As shown in FIG. 19, no OVA was detected in the supernatant of test samples, while significant amounts of OVA remained in the pelleted nanoparticles. This result indicates that provided nanoparticles are stable in SGF for up to four hours.

FIG. 20 shows a western blot of provided nanoparticles digested in SIF for up to twelve hours, with the supernatant ("sup") and pellet being analyzed separately. In addition, intact OEE/DNA+OVA nanoparticles (undigested) were used as a positive control. As shown in FIG. 20, no OVA was detected in the supernatant of test samples, while significant amounts of OVA remained in the pelleted nanoparticles. This result indicates that provided nanoparticles are stable in SIF for up to twelve hours.

FIG. 21 shows a western blot of provided nanoparticles digested in SGF for four hours followed by digestion in SIF for up to twelve hours, with the supernatant ("sup") and pellet being analyzed separately. In addition, intact OEE/DNA+OVA nanoparticles (undigested) were used as a positive control and a partially digested (SGF only) OEE/DNA+OVA sample was also used as a control. As shown in FIG. 21, no OVA was detected in the supernatant of test samples, while significant amounts of OVA remained in the pelleted nanoparticles. This result indicates that provided nanoparticles are stable in SGF for four hours followed by treatment with SIF for twelve hours. Unlike FIGS. 19 and 20, FIG. 21 also contains an OVA control lane. The lack of detectable levels of OVA in the supernatant of tested conditions indicates that provided nanoparticles are able to survive simulated digestive processes in a condition sufficient to prevent the escape of OVA.

This Example confirms that, in some embodiments, provided nanoparticles are able to survive in simulated gastric and/or intestinal conditions for biologically relevant periods of time. This data also confirms that oral administration of provided nanoparticles is appropriate according to various embodiments.

Example 11: In Vitro Stimulation of CD8+ or CD4+ T Cell Activity

In this Example, the ability of provided nanoparticles to stimulate CD8+ and/or CD4+ activity was confirmed. Provided nanoparticles were created as described in Table 6 below:

TABLE 6

Experimental Group Designations

| Description | Nomenclature | Experimental Value |
|---|---|---|
| empty nanoparticle | —/— | negative control |
| LPS on surface, empty inside | LPS/— | effect of particulate adjuvant with no antigen |
| nothing on surface, CpG inside | —/CpG | effect of particulate adjuvant with no antigen |
| nothing on surface, OVA inside | —/OVA | effect of particulate antigen with no adjuvant |
| CpG on surface, OVA inside | CpG/OVA | compare CpG to DNA |
| LPS on surface, OVA inside | LPS/OVA | compare LPS against OEE (part vs. whole) |
| nothing on surface, CpG inside | —/OVA + CpG | compare CpG against DNA (part vs. whole) |
| OEE on surface, DNA and OVA inside | OEE/DNA + OVA | compare artificial bacteria to E. coli |
| nothing on surface, DNA and OVA inside | —/DNA + OVA | determine if DNA alone is sufficient |
| OEE on surface, OVA inside | OEE/OVA | determine if OEE alone is sufficient |
| nothing on surface, DNA inside | —/DNA | effect of particulate adjuvant with no antigen |
| OEE on surface, nothing inside | OEE/— | effect of particulate adjuvant with no antigen |
| heat-inactivated *E. coli* | Ecoli | vehicle control of whole bacteria |
| heat-inactivated *E. coli* expressing OVA | Ecoli/OVA | positive control: antigen-expressing bacteria |

In this Example, bone marrow-derived dendritic cells (BMDCs) from C57/B16 mice were incubated with one of the provided nanoparticles or controls listed in Table 6 for 24 hours. Subsequently, exposed Dendritic cells (DCs) were co-incubated with OVA-specific CD8+ T cells for 3 days and the proliferation of CD8+ T Cells as well as the production of IL-2 and IFNγ were measured.

Figure 22:
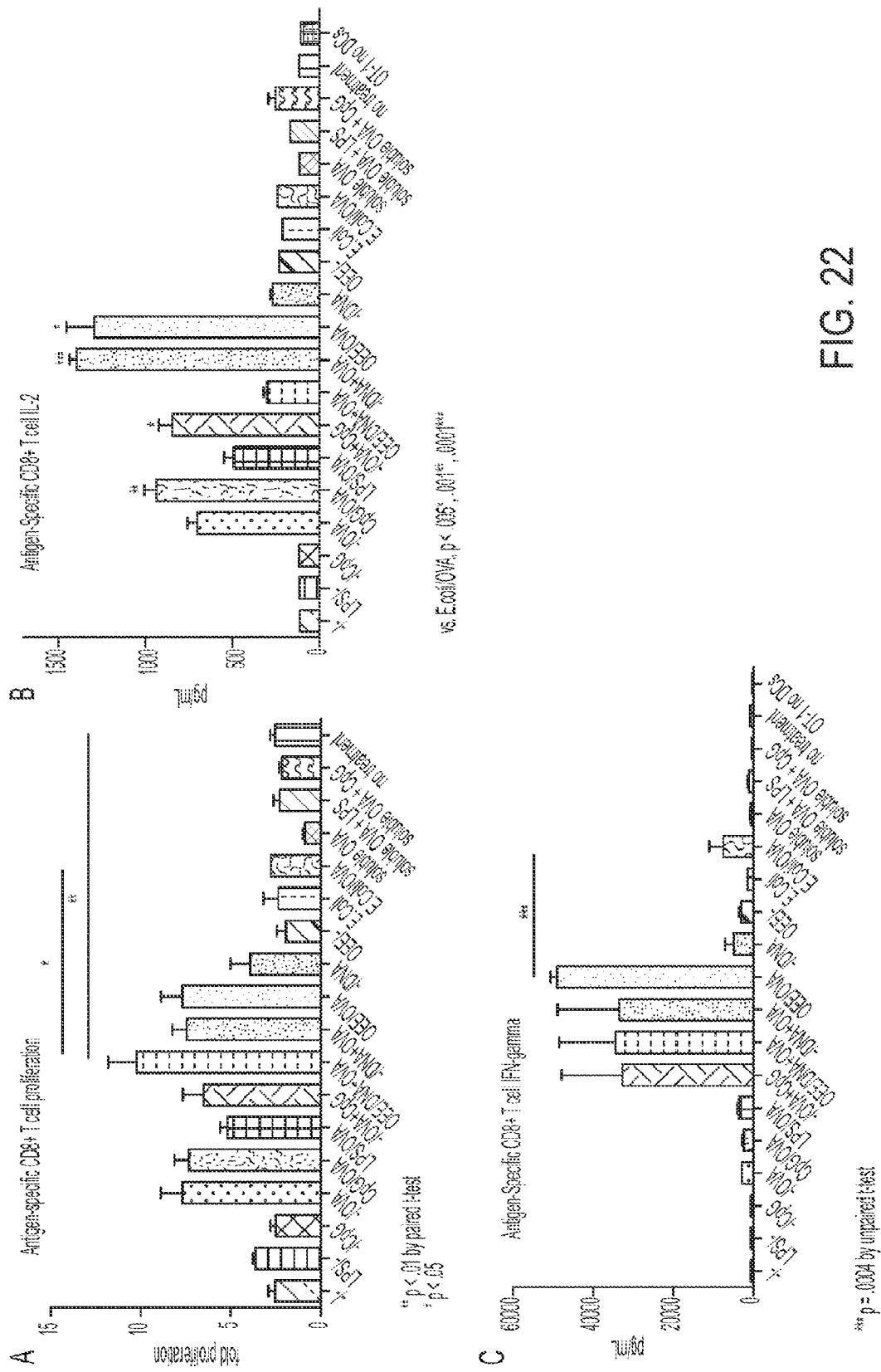
FIG. 22: shows exemplary graphs of: A) antigen-specific CD8+ T cell proliferation after incubation with one or more antigens or provided nanoparticle or nanoparticle compositions; B) antigen-specific IL-2 production by CD8+ T cells after incubation with one or more antigens or provided nanoparticle or nanoparticle compositions; and C) antigen-specific production of IFNγ production by CD8+ T cells after incubation with one or more antigens or provided nanoparticle or nanoparticle compositions.

FIG. 22A shows the fold proliferation in OVA-specific CD8+ T cells after exposure to DCs treated with a provided nanoparticle or control for 24 hours. As shown in FIG. 22A, the OEE/DNA+OVA treatment resulted in the highest amount of proliferation in antigen-specific CD8+ T cells, which was significantly greater than any other treatment or control group. Treatment with uncoated DNA+OVA nanoparticles, OEE-coated empty nanoparticles, uncoated nanoparticles encapsulating OVA, or CpG-coated nanoparticles containing OVA also showed increased proliferation, though to a lesser degree than the OEE/DNA+OVA group.

FIG. 22B shows the amount of IL-2 produced by antigen-specific CD8+ T cells treated as described above. Interestingly, DCs exposed to uncoated nanoparticles containing *E coli* DNA and OVA, and OEE-coated nanoparticles containing only OVA resulted in the highest amount of IL-2 production while exposure to OEE-coated nanoparticles containing both *E coli* DNA and OVA showed relatively little IL-2 response.

Figure 23:
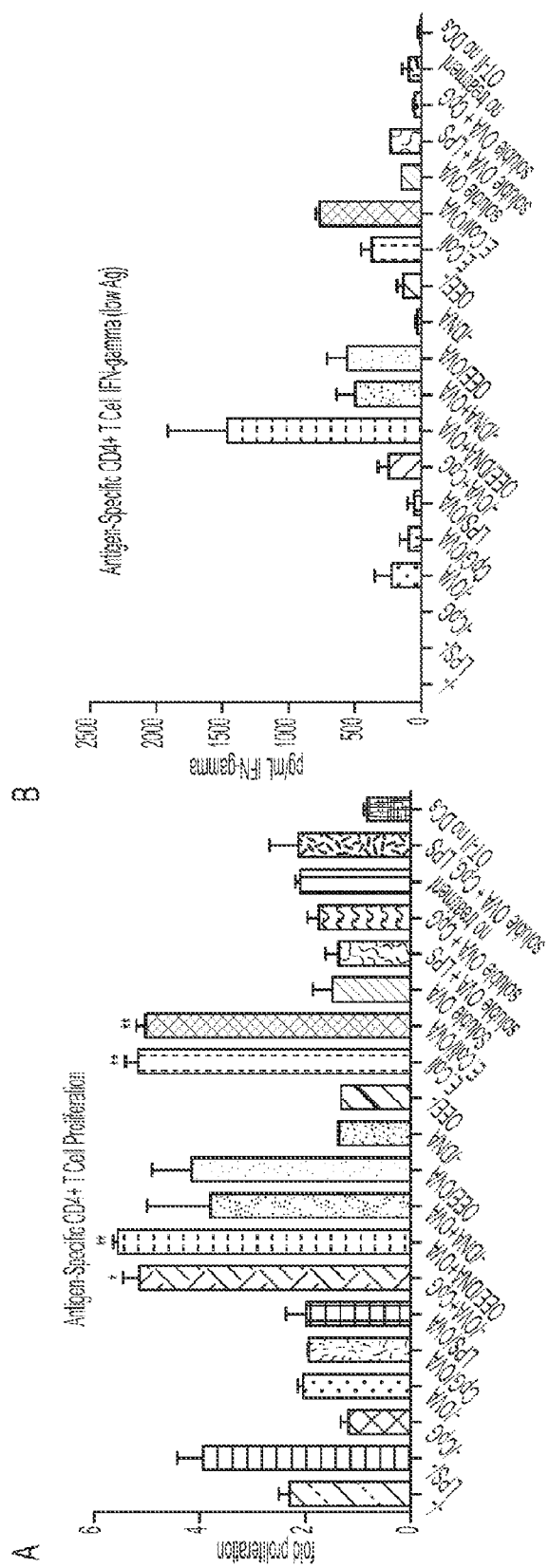
FIG. 23: shows exemplary graphs of: A) antigen-specific CD4+ T cell proliferation after incubation with one or more antigens or provided nanoparticle or nanoparticle compositions; and B) antigen-specific IFNγ production by CD4+ T cells after incubation with one or more antigens or provided nanoparticle or nanoparticle compositions.

FIG. 23C shows the amount of IFNγ produced by antigen-specific CD8+ T cells treated as described above. As shown in FIG. 23C, DCs treated with OEE-coated nanoparticles containing OVA had the highest levels of IFNγ production, while DCs treated with one of: uncoated nanoparticles containing OVA and CpGs, OEE-coated nanoparticles containing *E coli* DNA and OVA, or uncoated nanoparticles containing *E coli* DNA and OVA also showed increased levels of IFNγ production.

Though the production of IL-2 resulting from administration of provided nanoparticles was less than that resulting from *E coli* administration, administration of provided nanoparticles resulted in higher proliferation of CD8+ T cells, indicating that provided nanoparticles, in some embodiments, are be capable of MHC class I antigen presentation.

An analysis of T cell proliferation and IFNγ production was also conducted using the same design as the above studies, only examining CD4+ T cells rather than CD8+ T cells. FIG. 23A shows the CD4+ T-cell proliferation results, where OEE-coated nanoparticles containing either *E coli* DNA and OVA or just OVA alone resulted in significantly enhanced CD4+ T cell proliferation. In addition, treatment with uncoated nanoparticles containing either OVA alone or OVA+*E coli* DNA also triggered significantly increased CD4+ T cell proliferation. In each case, the level of increased proliferation observed was similar to those observed in the groups exposed only to dead *E coli* or to dead *E coli* containing OVA.

FIG. 23B shows the IFNγ production of CD4+ T cells after treatments as described above. In this case, OEE-coated nanoparticles containing *E coli* DNA and OVA elicited the strongest increase in production by more than two-fold.

Example 12: Organic *E Coli* Extract (OEE) in Eliciting Cytokine Production from Dendritic Cells and CD4+ T Cells As is shown in the various Examples herein, the immune response in a subject may differ based upon the specific embodiment or embodiments administered. In order to partially characterize the importance of coating nanoparticles with OEE, the cytokine production of Dendritic Cells and CD4+ T Cells were assayed after administration of OEE/DNA+OVA nanoparticles or uncoated nanoparticles containing *E coli* DNA and OVA, as compared to one of two control groups: uncoated nanoparticles containing OVA (negative control), or dead *E Coli* containing OVA (positive control).

Figure 24:
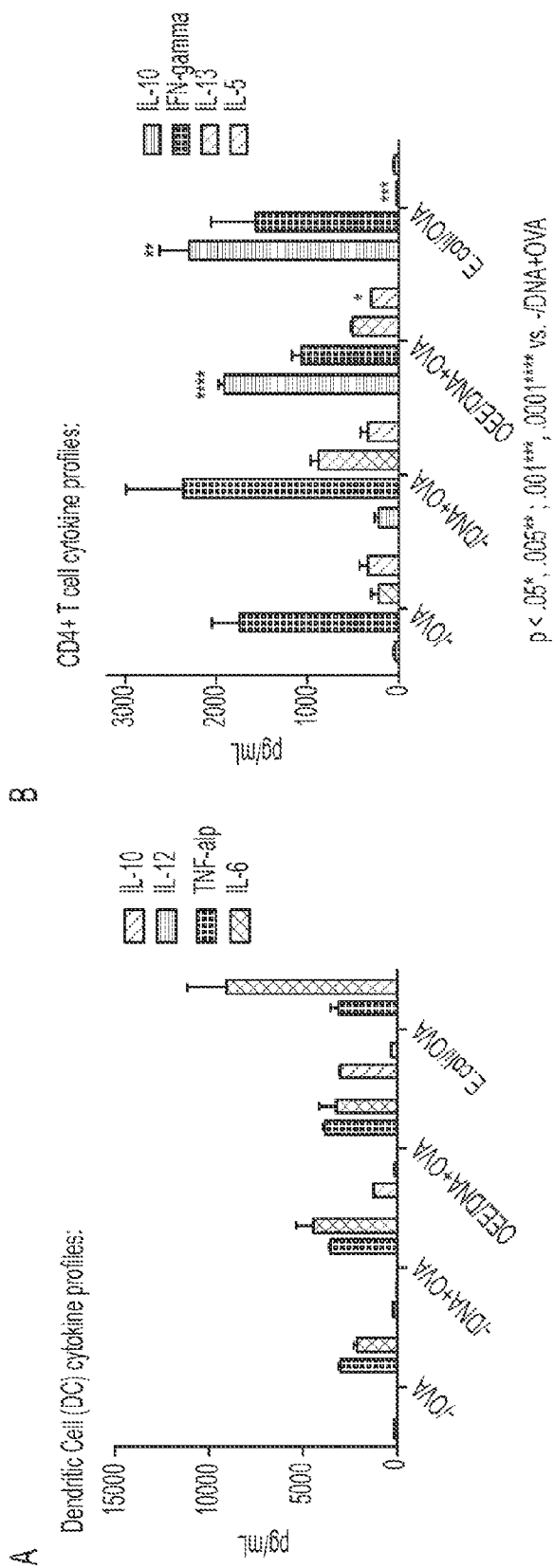
FIG. 24: shows exemplary graphs of: A) IL-10, IL-12, IL-6, and TNFα cytokine production by dendritic cells after incubation with ovalbumin (OVA), nanoparticles containing *E coli* DNA and OVA, nanoparticles coated with an organic extract of an *E. coli* cell culture (OEE) and containing *E. coli* DNA and OVA, or dead *E. coli* containing OVA; and B) IL-10, IL-13, IL-5, and IFNγ cytokine production by CD4+ T cells after incubation with ovalbumin (OVA), nanoparticles containing *E. coli* DNA and OVA, nanoparticles coated with OEE and containing *E coli* DNA and OVA, or dead *E. coli* containing OVA.
Figure 25:
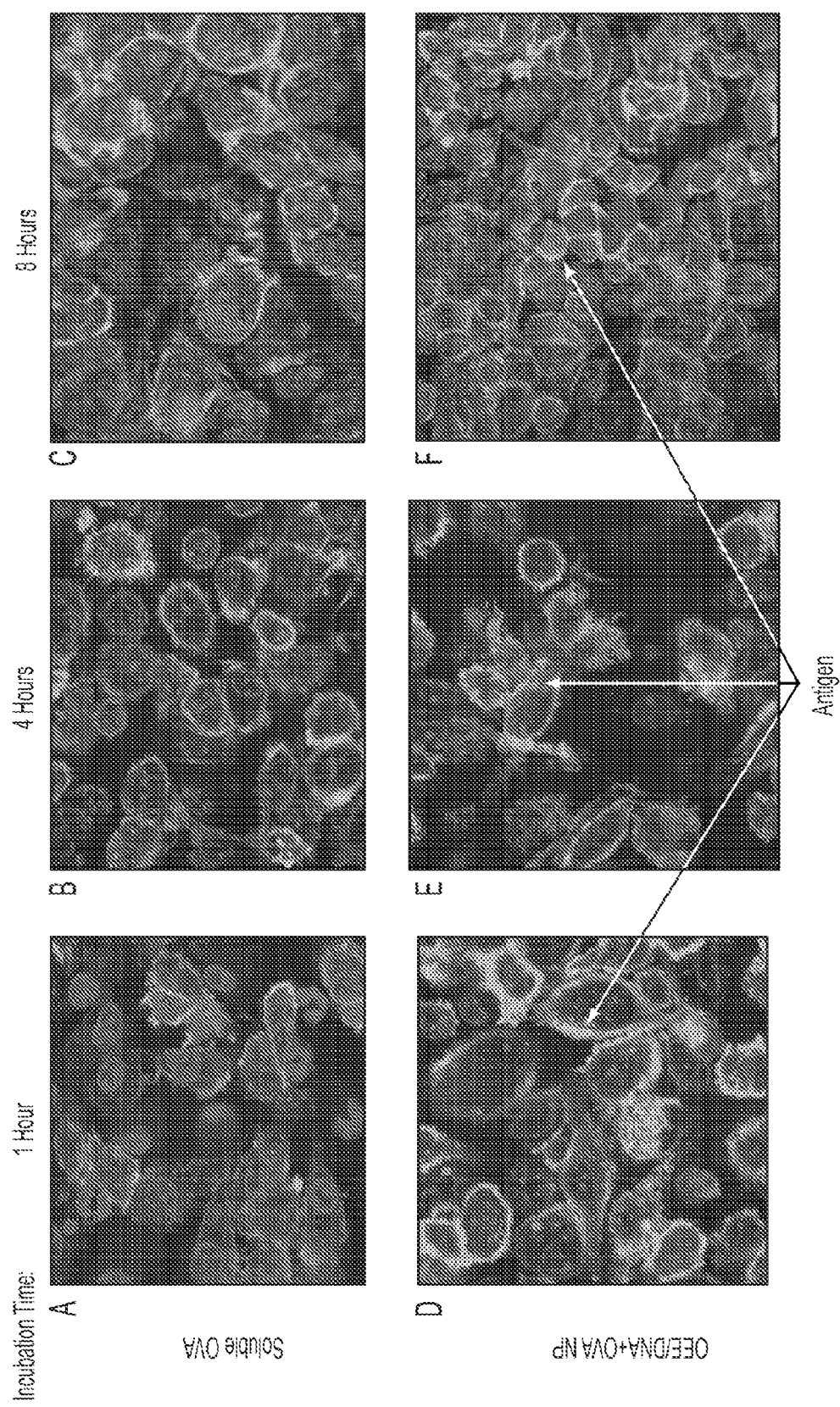
FIG. 25: shows exemplary confocal microscopy images of murine dendritic cell (DC) uptake of either soluble OVA (panels A, B and C) or OEE-coated nanoparticles containing *E coli* DNA and OVA (panels D, E, and F) after 1, 4 or 8 hours, respectively. Antigen administered in provided nanoparticles were observed inside DCs as early as 1 hour after administration (none observable in soluble OVA group) and significantly higher levels of antigen are found in DCs 8 hours after administration of provided nanoparticles as compared to administration of soluble OVA alone.
Figure 26:
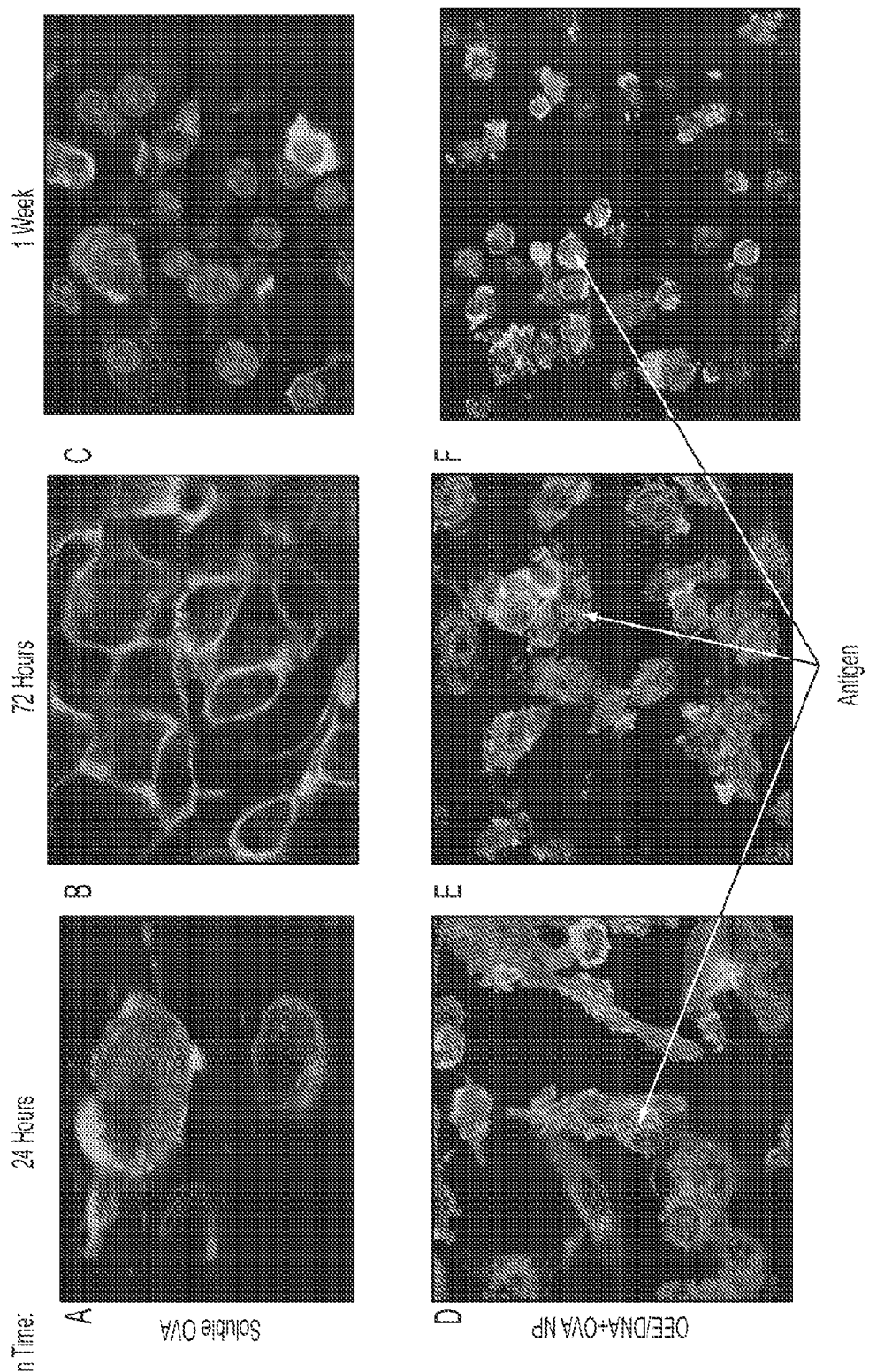
FIG. 26: shows exemplary confocal microscopy images of murine DC uptake of either soluble OVA (panels A, B, and C) or OEE-coated nanoparticles containing *E. coli* DNA and OVA (panels D, E, and F) after 24 hours, 72 hours, or 1 week, respectively. While similar levels of antigen appear present in both groups after 24 hours (panels A and D), soluble antigen is cleared by 72 hours (panels B and E) and by 1 week only encapsulated antigen in provided nanoparticles remain observable (panels C and F).

FIG. 24A shows the production of Interleukin-10 (IL-10), Interleukin-12 (IL-12), Interleukin-6 (IL-6), or tumor necrosis factor-α (TNFα) after exposure to one of the above described agents. As shown in FIG. 24A administration of each type of nanoparticle resulted in production of TNFα and IL-6 (with OEE/DNA+OVA also resulting in some production of IL-10), while administration of dead *E coli* containing OVA resulted in expression of IL-10, TNFα and the largest amount of IL-6 observed in the DC populations.

FIG. 24B shows the production of IL-10, Interleukin-13 (IL-13), Interleukin-5 (IL-5), or IFNγ after exposure to one of the above described treatments. As shown in FIG. 24B, each tested condition saw production of IFNγ, with the uncoated nanoparticles containing both *E coli* DNA and OVA showing the highest levels of IFNγ production. Interestingly, both the OEE/DNA+OVA nanoparticles and dead *E coli* containing OVA showed significantly more IL-10 production than the other groups, and the OEE/DNA+OVA nanoparticles also resulted in production of both IL-13 and IL-5.

As shown in FIGS. 24A and B, OEE/DNA+OVA induces significantly less IL-13 than uncoated nanoparticles containing DNA+OVA and, without wishing to be held to a particular theory, stimulating less IL-13 production may be considered an advantageous in some embodiments. In addition, OEE/DNA+OVA induces higher IL-10 production than uncoated DNA+OVA nanoparticles. Again, without wishing to be held to a particular theory, stimulating more IL-10 production may be considered advantageous in some embodiments.

Example 13: Evaluation of Antigen Delivery to Dendritic Cells

In this Example, the uptake of OVA antigen from OEE/DNA+OVA nanoparticles was compared to that of soluble OVA alone. Briefly, nanoparticles were incubated with C57/B16 mouse bone marrow-derived dendritic cells (BMDCs) for 1 hour, 4 hours, 8 hours, 24 hours, 72 hours, or 1 week. In this Example, and as shown in FIGS. 25A-F and 26A-F, provided nanoparticles were stained with Texas Red and BMDCs were stained with the F-actin stain phalloidin-AF488, In FIGS. 25 and 26, the nucleus was stained blue.

FIG. 25A-F show exemplary confocal microscopy images of dendritic cells exposed to either soluble OVA (panels A, B, and C) or OEE/DNA+OVA nanoparticles (panels D, E, and F) for 1, 4, or 8 hours, respectively. The bright outlines show the cellular cytoskeletons, with the nuclei being shown in dark blue and internalized antigen shown as lighter red spots (examples of antigen are noted with arrows). As shown in FIG. 25D, antigen is detected inside of dendritic cells exposed to OEE/DNA+OVA nanoparticles as early as 1 hour after administration, with increasing amounts of antigen present in the dendritic cells at 4 and 8 hours. In contrast, dendritic cells exposed to soluble OVA only show barely detectable levels of antigen loading even up to 8 hours after administration.

In addition to the effects of provided nanoparticles on dendritic cells after 1, 4 or 8 hours of incubation, longer time points of 24 hours, 72 hours, and 1 week were also examined. FIG. 26A-F show exemplary confocal microscopy images generated via the same methods as described above, unless otherwise specified. Panels A, B and C show dendritic cells exposed to soluble OVA for 24 hours, 72 hours, or 1 week, respectively. Panels D, E, and F show dendritic cells exposed to OEE/DNA+OVA for 24 hours, 72 hours, or 1 week, respectively. As shown in panels A and D, commensurate levels of OVA are observed in each treatment group after 24 hours, and by 72 hours, panels B and E show that soluble antigen has been cleared. Importantly, after 1 week, panel F shows that OVA encapsulated in provided nanoparticles remains present in dendritic cells while soluble OVA is no longer detectable.

This Example shows that encapsulation of antigen in provided nanoparticles results in more rapid uptake and a longer residence time in dendritic cells as compared to administration of soluble antigen alone.

Example 14: Lymph Node and Spleen Accumulation of Provided Nanoparticles

In this Example, the ability of provided nanoparticles to accumulate in specific tissues, here the lymph nodes and spleen, was confirmed. Specifically, the ability of OEE/DNA+OVA nanoparticles to accumulate in the lymph nodes and/or spleen was compared to both uncoated nanoparticles containing OVA and also to soluble OVA alone.

Briefly, C57/B16 mice were fed, via oral gavage, one of the following treatments: phosphate buffered saline (PBS), soluble OVA stained with Texas Red, uncoated nanoparticles containing Texas Red-labeled OVA, or organic *E coli* extract (OEE) coated nanoparticles containing *E coli* DNA and Texas Red labeled OVA (also referred to as "OEE/DNA+OVA" in this Example). Approximately 24 hours after administration, mice were sacrificed and lymph nodes and spleens were harvested from each animal and lymph nodes were pooled by type. Fluorescence was then read and divided by cell number, subtracting the fluorescence of phosphate buffered saline (PBS) mouse lymph node fluorescence as background.

Figure 27:
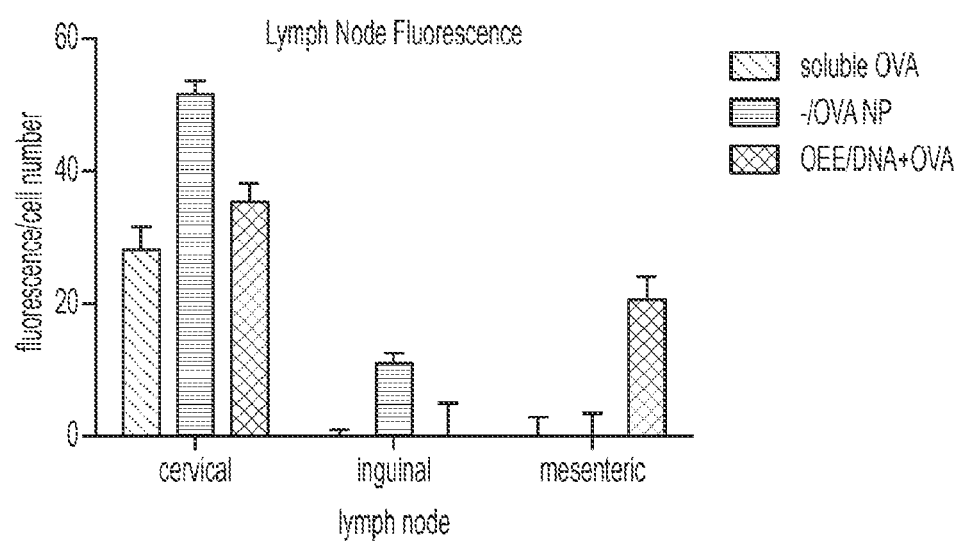
FIG. 27: shows an exemplary graph of antigen presentation in the cervical, inguinal and mesenteric lymph nodes of mice after administration of one of: soluble OVA, nanoparticles containing OVA, or nanoparticles coated with OEE and containing E. coli DNA and OVA.

FIG. 27 shows a graph of the fluorescence per cell number in each of the cervical, inguinal, and mesenteric lymph nodes in C57/B16 mice 24 hours after administration of provided nanoparticles or relevant control. As shown in FIG. 27, each treatment group showed accumulation in the cervical lymph node, with uncoated nanoparticles showing the greatest accumulation. Only uncoated nanoparticles showed appreciable accumulation in the inguinal lymph node. Interestingly only OEE/DNA+OVA nanoparticles showed accumulation in the mesenteric lymph node.

Figure 28:
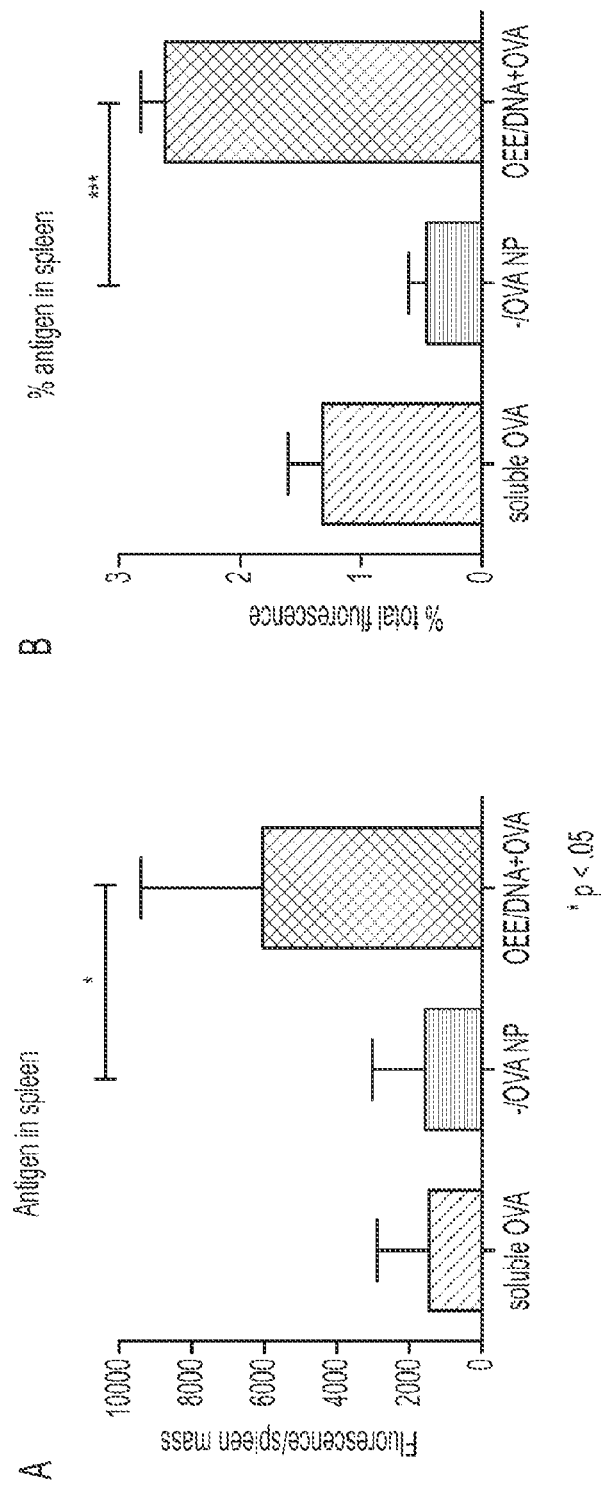
FIG. 28: shows exemplary graphs of relative amounts of antigen in the spleen of mice after exposure to one of: soluble OVA, nanoparticles containing OVA, or nanoparticles coated with OEE and containing E. coli DNA and OVA as measured through relative fluorescence of labeled OVA (normalized by organ mass). Encapsulating OVA inside provided nanoparticles results in significantly greater accumulation of antigen in the spleen as shown both by: A) relative fluorescence, and B) percent of overall fluorescence. *$p<0.05$, ***$p<0.01$

In addition to the lymph nodes, accumulation in the spleen was analyzed. Briefly, the spleens were harvested, normalized by organ mass, and the fluorescence was measured as described above. FIG. 28 shows the fluorescence/spleen mass for each of the tested groups. FIG. 28A shows the average OVA accumulation in the spleen, with OEE/DNA+OVA showing significantly more OVA accumulation in the spleen after 24 hours than the other two tested groups. FIG. 28B shows the percent OVA in the spleen per treatment group, which was normalized by total dosed fluorescence. As shown in FIG. 28B, approximately 2.5% of the dosed OVA in the OEE/DNA+OVA group goes to the spleen.

Example 15: Stimulation of Antigen-Specific CD4+ T Cell Response In Vivo

This Example confirms that provided nanoparticle compositions may be administered orally and exert a significant antigen-specific effect on the immune system in vivo. In this Example, the effect of provided compositions on CD4+ T Cells in vivo was confirmed after oral administration of a provided composition.

Specifically, in this Example, Thy1.1-OT-II CD4+ T cells were isolated and stained with Cell Trace Violet. Next, C57/B16 mice were injected intravenously with dyed CD4+ cells. Approximately 24 hours later, mice were dosed with either PBS (as a control) or nanoparticles coated with an organic extract of an *E. coli* cell culture (OEE) and encapsulating *E coli* DNA and ovalbumin (OVA) via oral gavage. Each dose or provided nanoparticles contained approximately the following: 4 mg nanoparticles, 69 µg OVA, 14 µg *E coli* DNA, and $3.18^{-11}$ EU endotoxin. Provided nanoparticles in this Example are referred to as "OEE/DNA+OVA" for convenience. Three days later, the mice were sacrificed, tissue from the spleen, inguinal lymph node, mesenteric lymph node, and cervical lymph node were isolated and stained for fluorescence-activated cell sorting (FACS). The Experimental design is shown below:

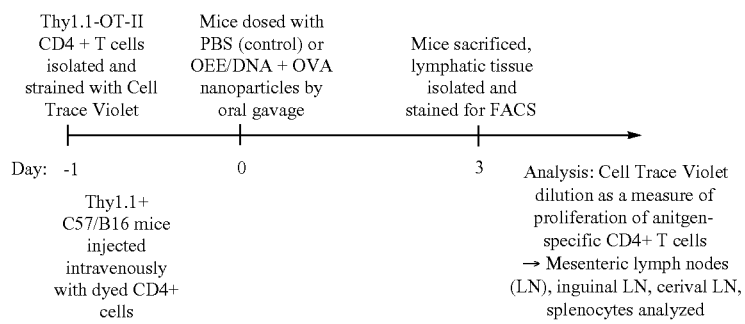

The Cell Trace Violet analysis was performed according to the manufacturers instructions. Briefly, Infused OT-II cells are freshly dyed, exhibiting maximum fluorescence. When the OT-II cells divide, such as in response to antigen-mediated stimulation, the dye is distributed among the daughter cells. As a result, each peak of decreasing fluorescence represents a new generation of cells. It is expected that the more divisions occur, the higher total of antigen-specific cell exist. Without wishing to be held to a particular theory, it is contemplated that an increase in the percent of divided cells means that provided nanoparticles were able to survive digestion and provide antigen to APCs in the mice.

Figure 29:
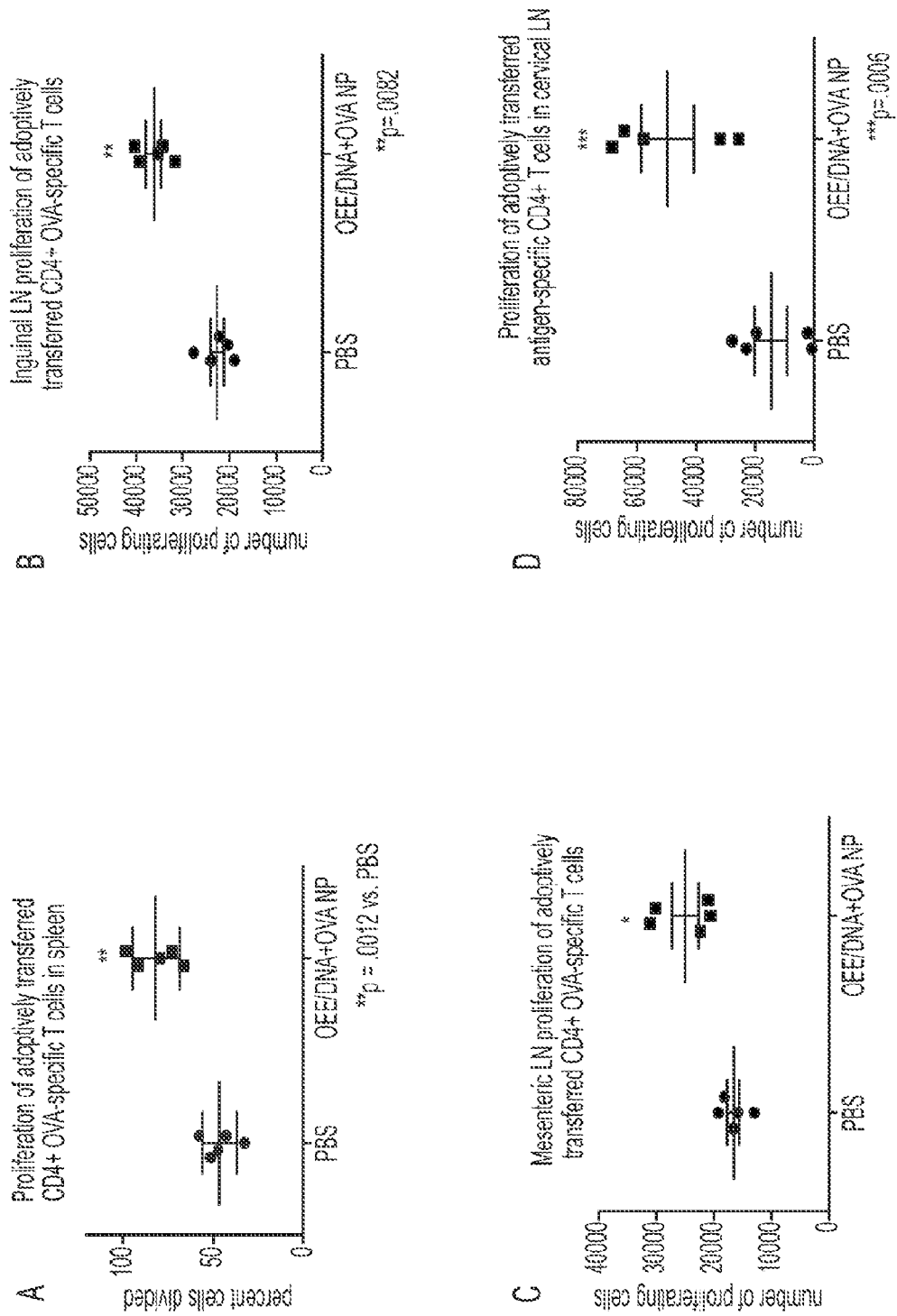
FIG. 29: shows exemplary graphs of CD4+ T cell proliferation in the A) spleen, B) inguinal lymph node, C) mesenteric lymph node, or D) cervical lymph nodes of mice treated with either PBS or nanoparticles coated with OEE and containing E. coli DNA and OVA, In all tested regions, mice treated with provided nanoparticles showed significantly higher levels of antigen-specific CD4+ T cell proliferation. *$p<0.05$, $p<0.01$, *$p<0.001$

As shown in FIG. 29A-D, a statistically significant increase in the OVA-specific T cell population was observed in each of the tissues analyzed. FIG. 29A shows an enhancement in CD4+ OVA-specific T cell number in the spleen, while FIGS. 29B, C and D show similar increases in each of the inguinal lymph node, mesenteric lymph node, and cervical lymph node, respectively.

This Example confirms that provided nanoparticle compositions may be administered orally and exhibit a significant and antigen-specific effect on the T cells of a subject in vivo.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A pharmaceutical composition comprising:
   (a) a plurality of nanoparticles, each of which is comprised of a biodegradable or biocompatible polymer arranged in a nanoparticle structure whose external surface-is coated with
      (i) a preparation comprising a crude hydrophobic bacterial extract; and
      (ii) a hydrophilic antigen encapsulated by the nanoparticle structure so that, when the nanoparticle composition is administered to a subject, the antigen is hidden from immune system components; and
   (b) at least one pharmaceutically acceptable excipient.

2. The pharmaceutical composition of claim 1, wherein the composition is formulated for intravenous, intradermal, transdermal, oral, subcutaneous, and/or transmucosal administration.

3. The pharmaceutical composition of claim 1, wherein the nanoparticles each further comprise a preparation comprising one or more hydrophilic cellular components.

4. The pharmaceutical composition of claim 1, wherein the nanoparticles each further comprise a second antigen, optionally also encapsulated by the nanoparticle structure so that, when the nanoparticle composition is administered to a subject, the antigen is hidden from immune system components.

5. The pharmaceutical composition of claim 1, wherein the antigen is selected from the group consisting of an allergic antigen, an anaphylactic antigen, an infectious antigen, an autoantigen, a disease-associated antigen, a food antigen, a microbial antigen, a viral antigen, a tumor antigen, and an environmental antigen.

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tccatgacgt tcctgacgtt 20

6. The pharmaceutical composition of claim 1, wherein the biodegradable or biocompatible polymer is poly(lactic-co-glycolic acid).

7. A method comprising:
treating a human subject suffering from or susceptible to at least two distinct allergic conditions by administering to a human subject in need thereof at least one nanoparticle composition comprising a plurality of nanoparticles, each of which is comprised of a biodegradable or biocompatible polymer arranged in a nanoparticle structure whose external surface is coated with a preparation comprising a crude hydrophobic bacterial extract; and
a hydrophilic antigen encapsulated by the nanoparticle structure so that, when the nanoparticle composition is administered to the human subject, the antigen is hidden from the subject's immune system components.

8. The method of claim 7, wherein the administration comprises at least two nanoparticle compositions, wherein each of the two nanoparticle compositions comprises a distinct antigen.

9. A nanoparticle composition comprising:
a plurality of nanoparticles, each of which is comprised of:
(a) poly(lactic-co-glycolic acid) arranged in a nanoparticle structure whose external surface-is coated with a preparation comprising a crude hydrophobic bacterial extract; and
(b) a hydrophilic antigen, which antigen is selected from the group consisting of: an allergic antigen, an anaphylactic antigen, an infectious antigen, an autoantigen, a disease-associated antigen, a food antigen, a microbial antigen, a viral antigen, a tumor antigen, and an environmental antigen, and
(c) one or more hydrophilic cellular components,
wherein the hydrophilic antigen and cellular components are encapsulated by the nanoparticle structure so that, when the nanoparticle composition is administered to a subject, the antigen is hidden from immune system components.

* * * * *